US00RE48510E

(19) United States
(12) Reissued Patent
Porosa et al.

(10) Patent Number: US RE48,510 E
(45) Date of Reissued Patent: Apr. 13, 2021

(54) PHOSPHORUS FUNCTIONAL ANTIMICROBIAL COATINGS FOR METAL SURFACES

(71) Applicant: NANO SAFE COATINGS INCORPORATED, Jupiter, FL (US)

(72) Inventors: Lukasz Porosa, Scarborough (CA); Gideon Wolfaardt, Mississauga (CA); Daniel Foucher, Toronto (CA)

(73) Assignee: Nano Safe Coatings Incorporated, Jupiter, FL (US)

(21) Appl. No.: 15/938,151

(22) Filed: Mar. 28, 2018

Related U.S. Patent Documents

Reissue of:
(64) Patent No.: 9,642,369
Issued: May 9, 2017
Appl. No.: 14/767,052
PCT Filed: Feb. 12, 2014
PCT No.: PCT/CA2014/000104
§ 371 (c)(1),
(2) Date: Aug. 11, 2015
PCT Pub. No.: WO2014/127451
PCT Pub. Date: Aug. 28, 2014

U.S. Applications:
(60) Provisional application No. 61/766,533, filed on Feb. 19, 2013.

(51) Int. Cl.

| | |
|---|---|
| ***A01N 57/20*** | (2006.01) |
| ***A01N 57/12*** | (2006.01) |
| ***B05D 3/02*** | (2006.01) |
| ***C07F 9/38*** | (2006.01) |
| ***C07F 9/40*** | (2006.01) |
| ***C07F 9/572*** | (2006.01) |
| ***C07F 9/655*** | (2006.01) |
| ***C09D 5/14*** | (2006.01) |
| ***C09D 5/16*** | (2006.01) |

(52) U.S. Cl.
CPC ..... *A01N 57/20* (2013.01); *A01N 57/12* (2013.01); *B05D 3/0272* (2013.01); *C07F 9/3808* (2013.01); *C07F 9/3817* (2013.01); *C07F 9/3873* (2013.01); *C07F 9/4006* (2013.01); *C07F 9/4009* (2013.01); *C07F 9/5728* (2013.01); *C07F 9/6552* (2013.01); *C09D 5/14* (2013.01); *C09D 5/1625* (2013.01)

(58) Field of Classification Search
CPC ..... A01N 57/20; A01N 57/12; C09D 5/1625; C09D 5/14; B05D 3/0272; C07F 9/4009; C07F 9/4006; C07F 9/3873; C07F 9/3817; C07F 9/3808; C07F 9/5728; C07F 9/6552
See application file for complete search history.

(56) References Cited

U.S. PATENT DOCUMENTS

| | | | | |
|---|---|---|---|---|
| 2,774,786 | A | 12/1956 | Erickson | |
| 3,454,677 | A | 7/1969 | Burpitt | |
| 3,507,937 | A | 4/1970 | Zimmerer | |
| 3,925,453 | A | 12/1975 | Clarke, III | |
| 4,208,401 | A | 6/1980 | Bauman | |
| 4,420,399 | A | 12/1983 | Redmore | |
| 5,753,634 | A | 5/1998 | Ebetino et al. | |
| 7,435,841 | B2 * | 10/2008 | Wo | C07F 9/4006 558/106 |
| 2008/0220037 | A1 | 9/2008 | Denizot et al. | |
| 2010/0121075 | A1 | 5/2010 | Nguyen et al. | |

FOREIGN PATENT DOCUMENTS

| | | | |
|---|---|---|---|
| CA | 2318733 | | 7/1999 |
| CA | 2318733 | A1 | 7/1999 |
| CA | 2636052 | A1 | 7/2008 |
| CA | 2858596 | A1 | 6/2013 |
| EP | 0279475 | A2 | 8/1988 |
| EP | 2282209 | A1 | 9/2011 |
| WO | 0125171 | A1 | 4/2001 |
| WO | 2012/160187 | A1 * | 11/2012 |
| WO | 2014127451 | A1 | 8/2014 |

OTHER PUBLICATIONS

Porosa, Lukasz M., et al., "Synthesis, structures and properties of self-assembling quatemary ammonium dansyl fluorescent tags for porous and non-porous surfaces", J. Mater. Chem. B, 2014, 2, 1509-1520.

Portet, David, et al., "Comparative Biodistribution of Thin-Coated Iron Oxide Nanoparticles TCION: Effect of Different Bisphosphonate Coatings", Drug Development Research 54: 173-181 (2001).

Brodersen, Nicolai, et al., "Synthesis of novel amphipilic conjugates with a biological recognition function for developing targeted triggered liposomal delivery systems", Tetrahedron 67 (2011) 7763-7774.

Takashi, Jin, "A New Fluorometric Method for the Deection of the Neurotransmitter Acetylcholine in Water Using Dansylcholine Complex with p-Sulfonated Calix[8]arene", Journal of inclusion Phenomena and Macrocyclic Chemistry 45: 196-201, 2003.

Karimi, Ali, et al., "Effect of chain length and electrical charge on properties of ammonium-bearing bisphosphonate-coated superparamagnetic iron oxide nanoparticles formulation and physicochemical studies", J. Nanopart Res (2010) 12:1239-1248.

Huang, Xiao-Jun, et al., "Surface Modification of Polyacrylonitrile-Based Membranes by Chemical Reactions to Generate Phospholipid Moieties", Langmuir 2005, 21, 2941-2947.

(Continued)

*Primary Examiner* — Jerry D Johnson
(74) *Attorney, Agent, or Firm* — Caesar Rivise, PC

(57) ABSTRACT

The invention relates to quaternary ammonium multi-dentate mono-, bis-, tris- and tetrakis-phosphonate compounds, processes for preparing quaternary ammonium multi-dentate mono-, bis-, tris- and tetrakis-phosphonate compounds, antimicrobial coating compositions comprising quaternary ammonium multi-dentate mono-, bis-, tris- and tetrakis-phosphonate compounds and method of treating a surface with said compositions to provide a durable, antimicrobial-treated surface.

11 Claims, 64 Drawing Sheets

(56) References Cited

OTHER PUBLICATIONS

Queffelec, Clemence, et al., "Surface Modification Using Phosphonic Acids and Esters", Chem. Rev. 2012, 112, 3777-3807.

Page, Kristopher, et al., "Antimicrobial surfaces and their potential in reducing the role of the inanimate environment in the incidence of hospital-acquired infections", J. Mater. Chem., 2009, 19, 3819-3831.

Kugel, Alex, et al., "Antimicrobial coatings produced by "tethering" biocides to the coating matrix, A comprehensive review", Progress in Organic Coatings 72 (2011) 222-252.

Boczula, Dorota, et al., "Structural and vibrational characteristics of amphiphillic phosphonate salts", Journal of Molecular Structure 1007 (2012) 220-226.

Banerjee, Indrani, et al., "Antifiouling Coatings: Recent Developments in the Design of Surfaces that Prevent Fouling by Proteins, Bacteria, and Marine Organisms", Adv. Mater 2011, 23, 690-718.

International Search Report for PCT/CA2014/000104 dated Jun. 12, 2014.

International Search Report for PCT/CA2014/050796 dated Dec. 23, 2014.

BR112016018532 English language published May 8, 2018, Abstract of corresponding document WO2014127451(a1).

Porosa, LM. et al. "Rapid Microwave-Assisted Synthesis of γ-Phosphonic Acid Quaternary Ammonium Antimicrobials for Biomedical Applications", Current Microwave Chemistry, vol. 2, No. 1, 2015, pp. 69-82(14).

* cited by examiner

PHOSPHORUS FUNCTIONAL ANTIMICROBIAL COATINGS FOR METAL SURFACES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

Bacterial infections in hospital environments are spread by two different ways: external contamination or in vivo contamination from implants. Patients can develop external infections through contact with surfaces such as door handles, pens, telephones, health care workers uniforms ("HCWU"), stethoscopes, or sterile packaging that have been colonized by microorganisms. Hospital-acquired infections ("HAI") from contact with pathogenic microorganisms affect approximately 2 million people and result in more than 100,000 deaths in the U.S.A. each year. Such infections require 10-20 days of additional patient hospitalization, costing the already strained U.S. health-care systems approximately $25,000-30,000 per infection totaling billions of dollars per year.

The second route for bacteria to infect patients is through hospital invasive support equipment such as intravascular lines and implanted medical devices such as artificial prosthetics, cardiovascular implants and urinary catheters. Implant associated infections ("IAI") occur in more than one million patients and cost an estimated $3 billion in the U.S. per year. For example, approximately 10-50% of patients with implanted catheters run the risk of developing urinary tract infections ("UTI") resulting in additional healthcare costs. The rise in the frequency and severity of HAI's and IAI's can be attributed to decreased antibiotic efficacy against drug-resistant strains of pathogens found in surface biofilms.

Biofilm formation involves three phases beginning with the initial reversible adhesion of bacteria on a surface through polysaccharides and adhesion proteins on the bacterial membrane (phase I). Under appropriate conditions, bacteria subsequently firmly attach to a surface (phase II), followed by the secretion of a protective polymeric matrix (biofilm, phase III) in which the bacteria typically show a marked increase in resistance to antibiotics, compared to none-adherent bacteria. As a result, once the infection occurs, it becomes difficult to treat. Thus, strategies that prevent bacterial contamination or destroy adsorbed microorganisms that lead to biofilm formation are actively sought.

In order to prevent the formation of biofilm, strategies have been employed in the past to make surfaces inhospitable to bacteria. For example, small molecule monolayers or polymer thin films either "grafted to" or "grown from" a surface have been widely used to prepare antimicrobial surfaces and clothing. These prior art monolayers or polymer coatings include, for example, non-biofouling coatings which are passive strategies that rely on preventing bacterial adhesion with hydrophobic or zwitterionic thin films, but do not kill the approaching bacteria. A second class of antibacterial thin films kills microbes on contact either by releasing a biocidal agent or immobilizing a biocidal agent. A third class of antibacterial thin films utilize a combination strategy of including a non-biofouling and biocidal component into the coating.

Organophosphorus Antimicrobial Surfaces Based on Monolayers

The first quaternary ammonium phosphonate compounds (phosphonate quats) were disclosed in the early 1950's in U.S. Pat. No. 2,774,786 and Dutch patent NL 79189 for use as synthetic detergents. In the patents syntheses, the final product could only be isolated as a sodium salt of the phosphobetaine after hydrolysis of the phosphonate ester with HCl followed by treatment with $NaHCO_3$. In a similar synthesis Germanaud et al., (Bulletin de la Societe Chimique de France, 1988, 4, 699-704) published the isolation of the phosphonate quats as betaines by purification on an anion exchange resin. The products disclosed in the patents were not spectrally characterized and were used as is, while Germanaud's purification was costly and the product wasn't isolated as a phosphonic acid.

Phosphonate monolayers for the antimicrobial treatment of surfaces have been shown to be advantageous over self-assembled monolayers (SAMs) of thiols and silanes in terms of durability, long-term stability and surface coverage, especially on titanium and stainless steel. Thiol-based SAM's lack substrate specificity (mainly reserved for gold surfaces) and long-term stability needed for biomedical applications, (i.e. implants). Over time, the thiol-based SAM's become oxidized to sulfonates, which lack affinity for gold and become displaced from the surface.

In comparison to silane based SAM's on metal oxide surfaces, phosphonate based SAM's are advantageous because they resist hydrolysis under physiological conditions and higher surface coverage can be obtained without harsh acid surface pretreatment (to increase the OH content). Siloxanes are also known to be unstable and are easily hydrolyzed under physiological conditions.

Both active and passive strategies to prevent biofilm formation have been described with both mono- and bisphosphonate monolayers. Examples for active surfaces include contact killing monolayers employing immobilized quaternary ammonium salts and the antibiotic daptomycin. Passive strategies have been described employing hydrophobic perfluorinated bisphosphonates on stainless steel, silicon, and titanium oxidize surfaces for anticorrosion applications.

U.S. Pat. No. 4,101,654 teaches phosphonate-pendant nitrogen heterocyclic compounds that are quaternized by alkyl halides and their use as corrosion inhibitor compounds.

U.S. Pat. No. 4,420,399 teaches phosphonate-quaternary ammonium compounds having a methylene group linking the phosphorus and nitrogen atoms and their use as corrosion inhibitor compounds.

U.S. Pat. No. 4,962,073 teaches porous surfaces treated with phosphoric acid esters.

U.S. Pat. No. 5,770,586 teaches phosphonate/phosphoric acid-quaternary ammonium compounds for use as dental care ingredients and for bone density treatment.

U.S. Pat. No. 5,888,405 teaches methods of inhibiting bacteria from adhering to submerged surfaces using aminophosphonic acid compounds.

U.S. Patent Application Publication No. 2002/0023573 teaches phosphonate, phosphate and phosphinate compounds linked to mineral oxide surfaces through the oxygen atoms of the phosphorus moieties.

U.S. Patent Application Publication No. 2002/0128150 teaches phosphonate, phosphate and phosphinate sulfur compounds linked to mineral oxide surfaces through the oxygen atoms of the phosphorus moieties.

PCT Application Publication WO 2007/080291 teaches bisphosphonate-amines and quaternary ammonium compounds, their preparation and attachment to metal and metal-oxide surfaces and testing for antibacterial activity.

PCT Application Publication WO 2008/017721 teaches bisphosphonate-amines and quaternary ammonium compounds, their preparation and attachment to silicon and metal surfaces and cell proliferation testing.

U.S. Patent Application Publication No. 2008/0220037 teaches bisphosphonic acid compounds having pendant oxygen, sulfur or at least two quaternary ammonium functional groups, their preparation and treatment of mineral and metal surfaces and antibacterial or biofilm formation testing.

Guerro G et al., Pathologic Biologie, 2009, 57, 36-43 teaches surfaces modified with materials such as phosphonate quaternary ammonium compounds and phosphonate silver coatings, and their bacterial adhesion and inhibition properties.

Queffelec C et al., Chemical Reviews, 2012, 112(7), 3777-3807 teaches phosphonic acids and esters, their synthesis and modification of surfaces using functionalized phosphonic acids and esters. The functional groups include heterocycles, amino groups and larger organic molecules.

Thus, there has been a long-felt need for a durable and environmentally safe antimicrobial metal or mineral surface treatment and a process to manufacture the same.

SUMMARY OF THE INVENTION

According to one aspect of the invention there is provided a quaternary ammonium mono-phosphonate compound of formula (I) and a process for preparing a compound of formula (I)

(I)

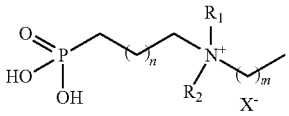

wherein $R_1$ and $R_2$ are independently lower alkyl groups preferably saturated hydrocarbon chains being one, two or three carbon atoms in length, more preferably selected from methyl, ethyl, isopropyl or n-propyl groups, even more preferably methyl groups, m is 15, 16, 17, 18 or 19, n is 0, 1, 2, 3, 4, 5 or 6, and X is chloro, bromo or iodo, comprising the steps of (a) reacting a compound of formula (II)

(II)

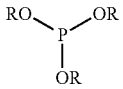

where R is independently methyl, ethyl, isopropyl, n-butyl or phenyl, preferably the same, more preferably ethyl, with an alkyl halide of formula (III)

(III)

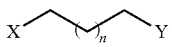

where X and n are as above and Y is a halogen selected from chloro or bromo, more preferably bromo to give a compound of formula (IV)

(IV)

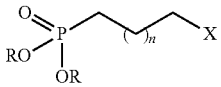

(b) reacting the compound of formula (IV) with a compound of formula (V)

(V)

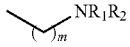

wherein $R_1$ and $R_2$ are each independently a lower alkyl group, preferably saturated hydrocarbon chains being one, two or three carbon atoms in length, more preferably selected from methyl, ethyl, isopropyl or n-propyl groups, even more preferably methyl groups, and m is 15, 16, 17, 18 or 19, to give a compound of formula (VI)

(VI)

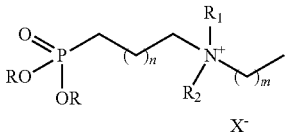

and (c) reacting a compound of formula (VI) with $SiR_3R_4R_5Z$ wherein $R_3$, $R_4$ and $R_5$ are independently methyl or ethyl and Z is chloro, bromo, iodo or triflate, or a mineral acid selected from HCl, HBr or HI, to give a compound of formula (I). In a preferred embodiment the process may take place neat or in a polar, protic reaction solvent, preferably a lower alkanol selected from methanol, ethanol and isopropanol. The process may be carried out at the refluxing temperature of the reaction solvent. The process is considered complete when the compound of formula (VI) is no longer observable via thin-layer chromatography. Optionally the compound of formula (I) may be purified, preferably by chromatography or recrystallization.

According to another aspect of the invention there is provided a quaternary ammonium bis-phosphonate compound of formula (VII) and a process for preparing a compound of formula (VII)

(VII)

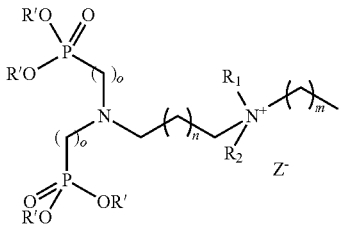

wherein R' is independently hydrogen, methyl, ethyl, isopropyl, n-butyl or phenyl, preferably the same, more preferably ethyl, and Z is chloro, bromo or hydroxy, preferably bromo, $R_1$ and $R_2$ are each independently a lower alkyl group, preferably saturated hydrocarbon chains being one, two or three carbon atoms in length, more preferably methyl, m is 15, 16, 17, 18 or 19, n is 0, 1, 2, 3, 4, 5, or 6, and o is 1, 2 or 3, comprising the steps of (a) reacting, preferably at least two equivalents of compound of formula (IX)

(IX)

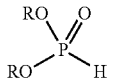

wherein R is independently methyl, ethyl, isopropyl, n-butyl or phenyl, preferably the same, more preferably ethyl, per equivalent of a compound of formula (X)

(X)

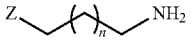

to give a compound of formula (XI)

(XI)

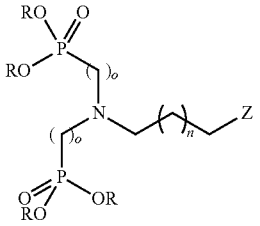

which is then reacted with a compound of formula (V)

(V)

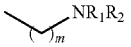

where R, $R_1$, $R_2$, m, n and Z are as defined above, to give a compound of formula (VII).

According to another aspect of the invention there is provided a quaternary ammonium bis-phosphonate compound of formula (VII) and a process for preparing a compound of formula (VII) wherein R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, more preferably methyl groups, m is 15, 16, 17, 18 or 19 and Z is chloro, bromo or hydroxyl, preferably bromo, comprising the steps of:

(a) reacting a compound of formula (XI)

(XI)

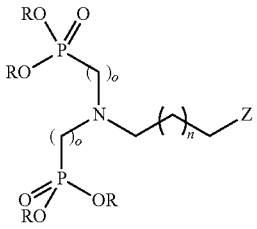

where R is independently methyl, ethyl, isopropyl, n-butyl or phenyl, preferably the same, more preferably ethyl, n is 0, 1, 2, 3, 4, 5, or 6, o is 1, 2 or 3 and Z is selected from chloro, bromo or hydroxyl, preferably bromo, with p-toluenesulfonyl chloride, trimethyl ammonium chloride, trimethylamine in a polar, aprotic solvent preferably acetonitrile, dimethylformamide or dichloromethane, more preferably dichloromethane, (b) adding a compound $R_1R_2NH$ where $R_1$ and $R_2$ are each independently a lower alkyl group, preferably saturated hydrocarbon chains being one, two or three carbon atoms in length, more preferably methyl, in a polar, protic solvent selected from methanol, ethanol or isopropanol optionally in the presence of water, to give a compound of formula (XII)

(XII)

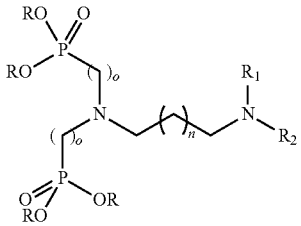

and (c) reacting the compound of formula (XII) with a compound of formula (XIII)

(XIII)

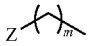

where m is 15, 16, 17, 18 or 19, and Z is chloro, bromo or hydroxyl, preferably bromo, to give a compound of formula (VII).

According to another aspect of the invention there is provided a quaternary ammonium bis-phosphonate of formula (XIV) and a process for preparing a compound of formula (XIV)

(XIV)

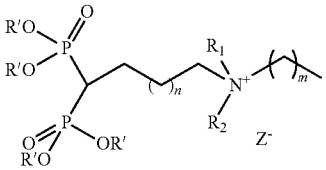

where R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, more preferably methyl groups, m is 15, 16, 17, 18 or 19, n is 0, 1, 2, 3, 4, 5, or 6, and Z is selected from chloro or bromo, preferably bromo, comprising the steps of (a) reacting a compound of formula (XV) wherein R is defined as above (XV)

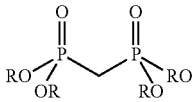

wherein R is independently methyl, ethyl, isopropyl, n-butyl or phenyl, preferably the same, more preferably ethyl, with a compound of formula (XVI)

(XVI)

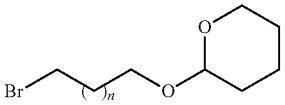

to give a compound of formula (XVII)

(XVII)

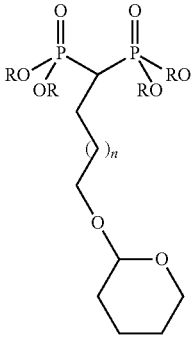

which is treated with p-toluenesulfonic acid, methanesulfonyl chloride, triethylamine, and $R_1R_2NH$ where $R_1$ and $R_2$ are defined as above, and a compound of formula (XIII)

(XIII)

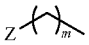

where Z is chloro or bromo, preferably bromo to give a compound of formula (XIV), or (c) reacting a compound of formula (XVIII)

(XVIII)

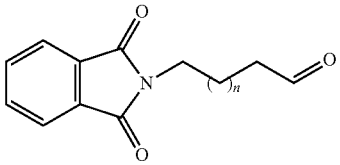

where n is as defined above with at least one equivalent of $O{=}PH(OR)_2$ where R is independently methyl, ethyl, isopropyl, n-butyl or phenyl, preferably the same, more preferably ethyl, in the presence of an alkali metal carbonate, preferably potassium carbonate, methanesulfonyl chloride and an organic amine base, and further reacted with sodium hydride and at least a second equivalent of $O{=}PH(OR)_2$ to give a compound of formula (XIX)

(XIX)

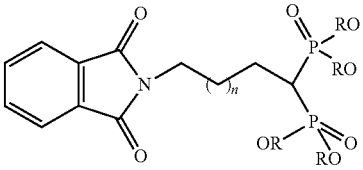

where R is as defined above and (d) reacting the compound of formula (XIX) with hydrazine, and an aldehyde selected from formaldehyde or acetaldehyde in the presence of zinc metal, and a compound of formula (XIII)

(XIII)

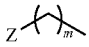

where Z is chloro or bromo, preferably bromo, and m is 15, 16, 17, 18 or 19, to give a compound of formula (XIV).

According to another aspect of the invention there is provided a bis-phosphonate compound of formula (XVII) and a process for preparing a compound of formula (XVII)

(XVII)

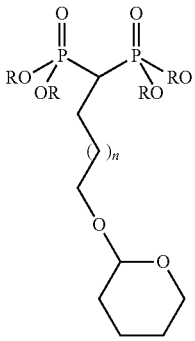

where R is independently hydrogen, methyl, ethyl, isopropyl, n-butyl or phenyl, preferably the same, more preferably ethyl, and n is 0, 1, 2, 3, 4, 5 or 6, comprising the steps of reacting a compound of formula (XX)

(XX)

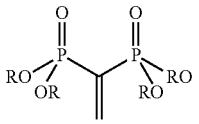

where R is as defined above, with a compound of formula (XXI)

(XXI)

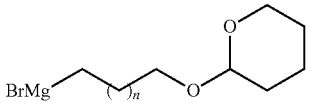

to give a compound of formula (XVII).

According to another aspect of the invention there is provided a bis-phosphonate compound of formula (XXII) and a process for preparing a compound of formula (XXII)

(XXII)

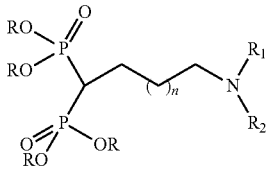

where R is methyl, ethyl, isopropyl, n-butyl or phenyl, preferably the same, more preferably ethyl, $R_1$ and $R_2$ are each independently a lower alkyl group preferably saturated hydrocarbon chains being one, two or three carbon atoms in length, more preferably methyl groups, and n is 0, 1, 2, 3, 4, 5 or 6, comprising reacting a compound of formula (XXIII)

(XXIII)

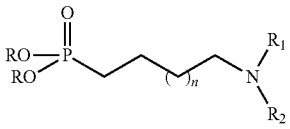

with $O{=}P(OR)_2Cl$ where n and R are as defined above, in the presence of lithium diisopropylamide in a polar, aprotic solvent to give a compound of formula (XXII) which optionally can be reacted with an alkyl halide of formula (XIII) to give a quaternary ammonium bis-phosphonate of formula (XIV) where R, $R_1$, $R_2$ and m are as defined above.

According to another aspect of the invention there is provided a bis-phosphonate compound of formula (XXIV) and a process for preparing a compound of formula (XXIV) where R is hydrogen, methyl, ethyl, isopropyl, n-butyl or phenyl, preferably the same, more preferably ethyl, and n is 0, 1, 2, 3, 4, 5 or 6, (XXIV)

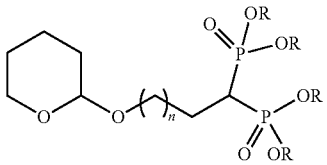

comprising reacting a compound of formula (XXV)

(XXV)

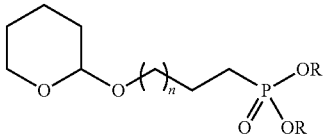

with $O{=}P(OR)_2Cl$ where R and n are as defined above, in the presence of lithium diisopropylamide in a polar, aprotic solvent to give a compound of formula (XXIV).

According to another aspect of the invention there is provided a quaternary ammonium bis-phosphonate compound of formula (XXVI) and a process for preparing a compound of formula (XXVI)

(XXVI)

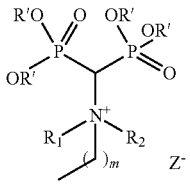

where R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, more preferably methyl groups, m is 15, 16, 17, 18 or 19 and Z is selected from chloro or bromo, preferably bromo, comprising the steps of (a) reacting oxalyl chloride with

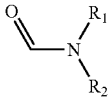

in chilled dichloromethane in the presence of a compound of formula (II) to give a compound of formula (XXVII)

(XXVII)

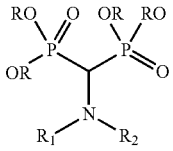

wherein R is independently methyl, ethyl, isopropyl, n-butyl or phenyl, preferably the same, more preferably ethyl, and $R_1$ and $R_2$ are as defined above, and (b) reacting the compound of formula (XXVII) with a compound of formula (XIII)

(XIII)

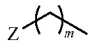

to give a compound of formula (XXVI) where R', $R_1$, $R_2$, m and Z are as defined above.

According to yet another aspect of the invention there is provided a quaternary ammonium mono-phosphonate compound of formula (XXVIII) and a process for preparing a compound of formula (XXVIII)

(XXVIII)

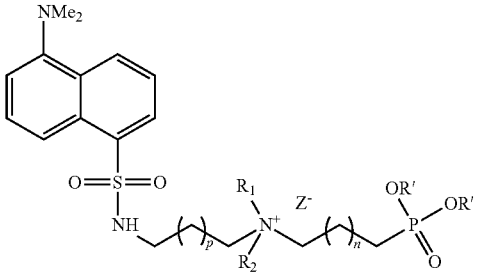

where R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, more preferably methyl groups, n is 0, 1, 2, 3, 4, 5 or 6, p is 0, 1, 2, 3, 4, 5 or 6, and Z is selected from chloro or bromo, preferably bromo, comprising the steps of (a) reacting a compound of (XXIX)

(XXIX)

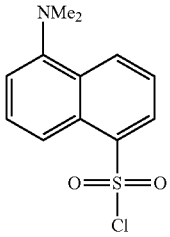

with a compound of formula (XXX)

(XXX)

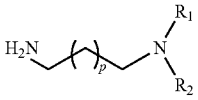

where $R_1$, $R_2$ and p are as defined above, in a polar, aprotic solvent in the presence of an organic amine base to give a compound of formula (XXXI)

(XXXI)

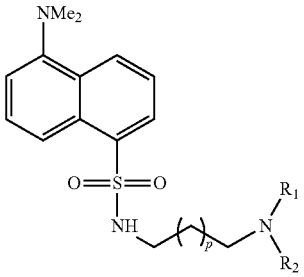

and (b) reacting a compound of formula (XXXI) with a compound of formula (XXXII)

(XXXII)

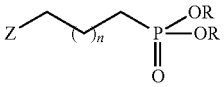

wherein R is independently methyl, ethyl, isopropyl, n-butyl or phenyl, preferably the same, more preferably ethyl, and n and Z are as defined above, in a polar, aprotic solvent to give a compound of formula (XXVIII).

In preferred embodiments, for chemical reactions involving reagents that are sensitive to protons, the processes may take place neat or in polar, aprotic reaction solvents, for example but not limited to dichloromethane, acetonitrile and dimethylformamide. For chemical reactions involving reagents that are not sensitive to protons, the processes may take place in a lower alkanol preferably methanol, ethanol and isopropanol. The processes may be carried out at temperatures from about −80° C. to about 150° C. The process is considered complete when the starting material is no longer observable via thin-layer chromatography. The final products optionally may be purified, preferably by chromatography or recrystallization.

According to yet another aspect of the invention, there is provided quaternary ammonium multidentate tri- and tetra-substituted phosphonate compounds of formula (XXXIII), (XXXIV), (XXXV), (XXXVI) and (XXXVII) and processes for preparing the compounds of formula (XXXIII), (XXXIV), (XXXV), (XXXVI) and (XXXVII)

(XXXIII)

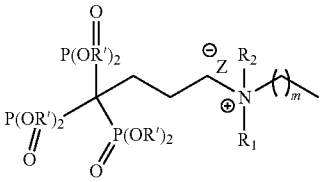

-continued (XXXIV)

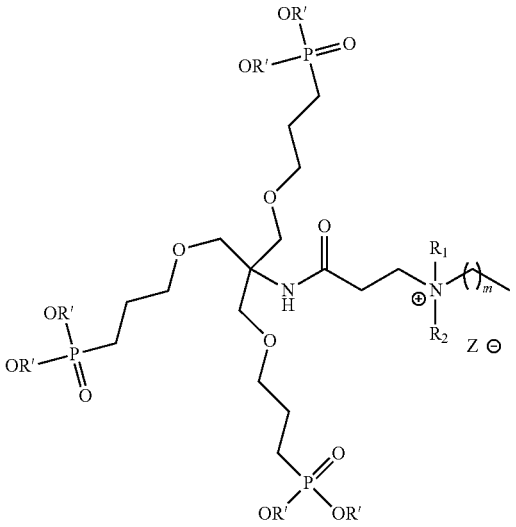

(XXXV)

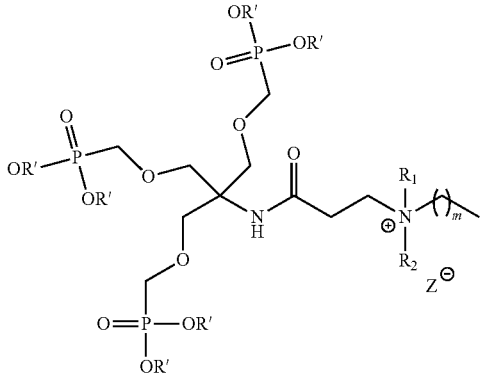

(XXXVI)

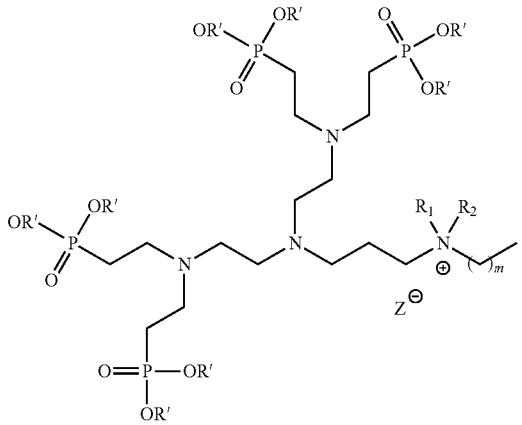

-continued (XXXVII)

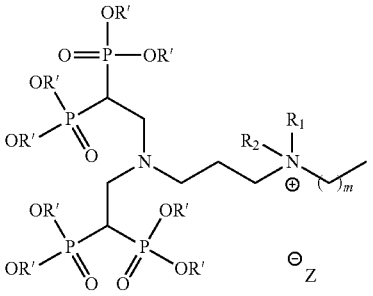

where R' is independently hydrogen, methyl, ethyl, isopropyl, n-butyl or phenyl, preferably the same, more preferably ethyl or hydrogen and even more preferably hydrogen, m is 15, 16, 17, 18 or 19 and Z is selected from chloro or bromo, preferably bromo, comprising the steps of:

a) alkylating a tetralkyl methylenebisphosphonate (TAMBP) compound, mono-deprotecting TAMBP followed by mono alkylation to lead to alpha (C—H) bisphosphonates, and performing a second deprotonation/alkylation with dialkyl chlorophosphate to provide trisphosphonates;

b) Michael addition of dialkyl vinylphosphite to provide beta aminobisphosphonates and further deprotonation and phosphorylation with dialkyl chlorophosphate to provide tetraphosphonates; or c) Lewis acid-mediated Abrzov addition of trialkylphosphite three times to three reactive bromoacteylTRISBOC and the radical addition of dialkyl phosphite to terminal vinyl groups on the TRIS BOC scaffold to give trisphosphonates.

According to yet another aspect of the invention there is provided an antimicrobial composition comprising any one of a compound of formulae (I), (VII), (XIV), (XXVI), (XXVIII), (XXXIII), (XXXIV), (XXXV), (XXXVI) and (XXXVII) and a process for treating a surface with an antimicrobial coating comprising the steps of contacting the surface with a composition comprising any one of a compound of formulae (I), (VII), (XIV), (XXVI), (XXVIII), (XXXIII), (XXXIV), (XXXV), (XXXVI) and (XXXVII).

According to yet another aspect of the invention, there is provided a phosphonate antimicrobial coating composition for treating surfaces to give a stable and durable phosphonate antimicrobial coating surface treatment, said composition comprising any one of a compound of formulae (I), (VII), (XIV), (XXVI), (XXVIII), (XXXIII), (XXXIV), (XXXV), (XXXVI) or (XXXVII) in a suitable carrier. In one embodiment said suitable carrier is an environmentally friendly carrier comprising a lower alkanol selected from the group consisting of methanol, ethanol, n-propanol and i-propanol, water or a mixture thereof depending on the solubility of the phosphonate compound in the carrier. The phosphonate antimicrobial coating can be applied onto a given surface preferably by dip coating, painting or with aerosol spraying with an about 1 to an about 20 mM solution of the phosphonate compound for a length of time so as to completely coat the surface. In one embodiment, the coating process may be repeated to apply additional layers of the phosphonate antimicrobial coating. Preferably the stable and durable phosphonate antimicrobial coatings may be coated onto various material surfaces such as, but not limited to, metal oxides or metal alloys of aluminum, copper, iron, steel, titanium, zirconium and silicon (silica). Even more preferably, phosphonate antimicrobial coating strength and stability may be further enhanced by subjecting the uncoated surface to a pretreatment oxidation step known as passivation (Min, S. L., Smiley, K. J. & Gawalt, E. S. J. Am. Chem. Soc. 193-204 (2011)). Without being bound by any theory, passivation creates a metal hydroxide layer that provides additional binding sites for the phosphonate compounds of the phosphonate antimicrobial coating to bind to. Passivation can be accomplished known processes in the art such as thermal annealing (subjecting the uncoated surface to temperatures of about 100-140° C. for about 18 hours) or reduced pressure annealing (subjecting the uncoated surface to pressures of about 0.05 to about 0.3 Torr, more preferably 0.1 Torr) (Raman, A., Dubey, M., Gouzman, I. & Gawalt, E. S. Formation of Self-Assembled Monolayers of Alkylphosphonic Acid on the Native Oxide Surface of SS316L. Langmuir 22, 6469-6472 (2006); Lecollinet, G. et al. Self-Assembled Monolayers of Bisphosphonates: Influence of Side Chain Steric Hindrance. Langmuir 25, 7828-7835 (2009)).

Further and other aspects will be appreciated by the skilled reader.

DETAILED DESCRIPTION OF THE INVENTION

Figure 1:
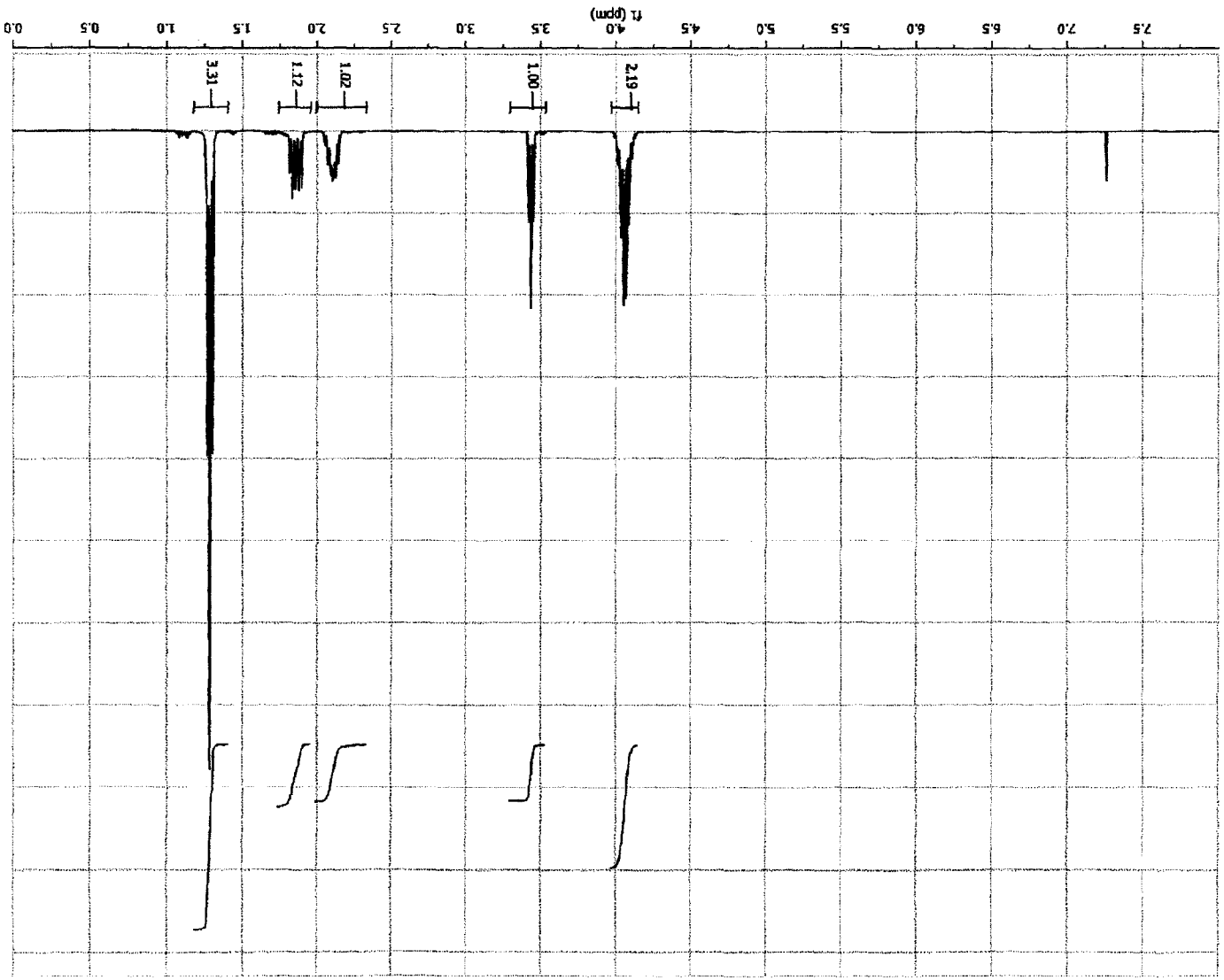
FIG. 1 shows the $^{1}$H NMR of compound (1) of Referential Example 1
Figure 2:
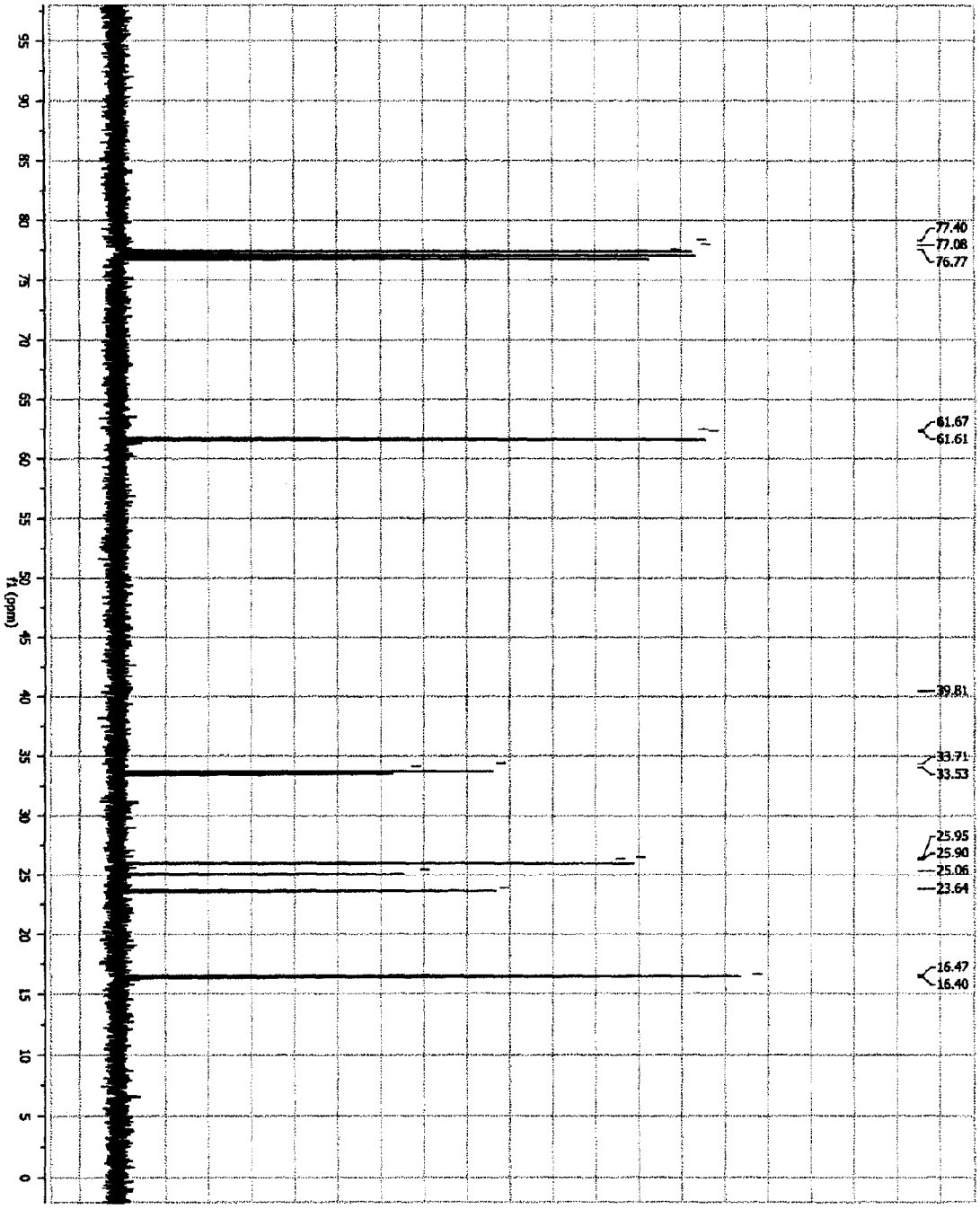
FIG. 2 shows the $^{13}$C NMR of compound (1) of Referential Example 1
Figure 3:
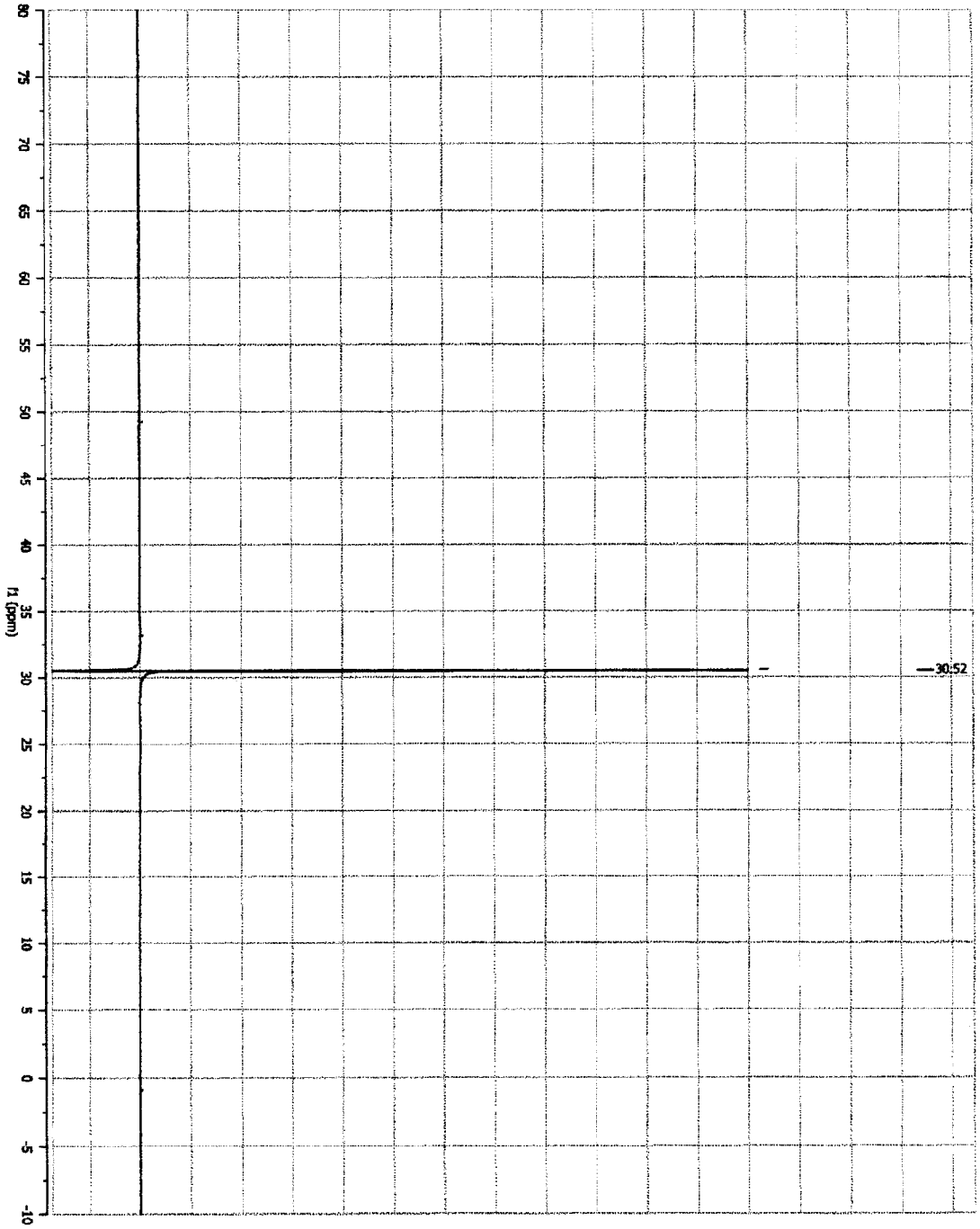
FIG. 3 shows the $^{31}$P NMR of compound (1) of Referential Example 1
Figure 4:
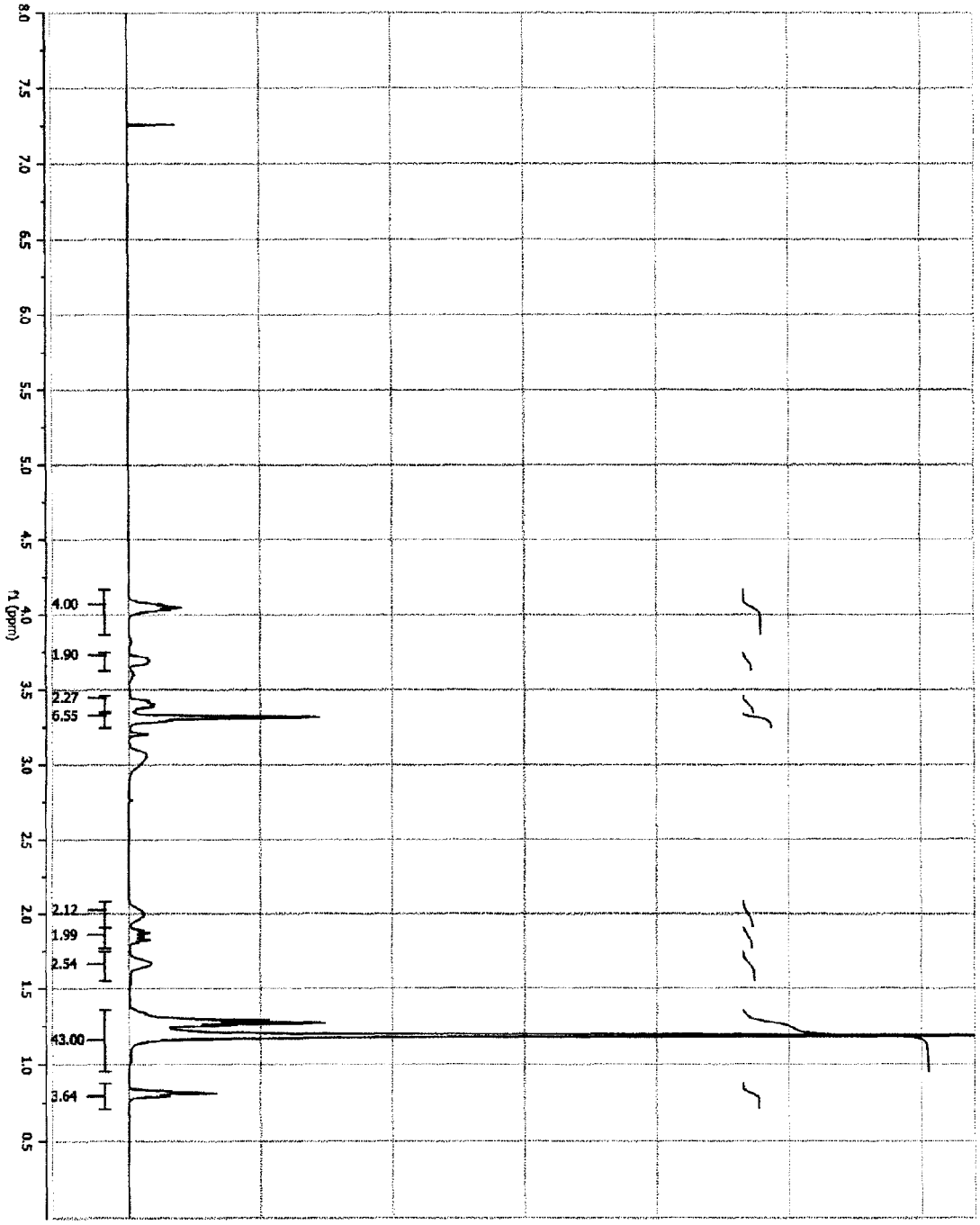
FIG. 4 shows the $^{1}$H NMR of compound (2) of Example 1
Figure 5:
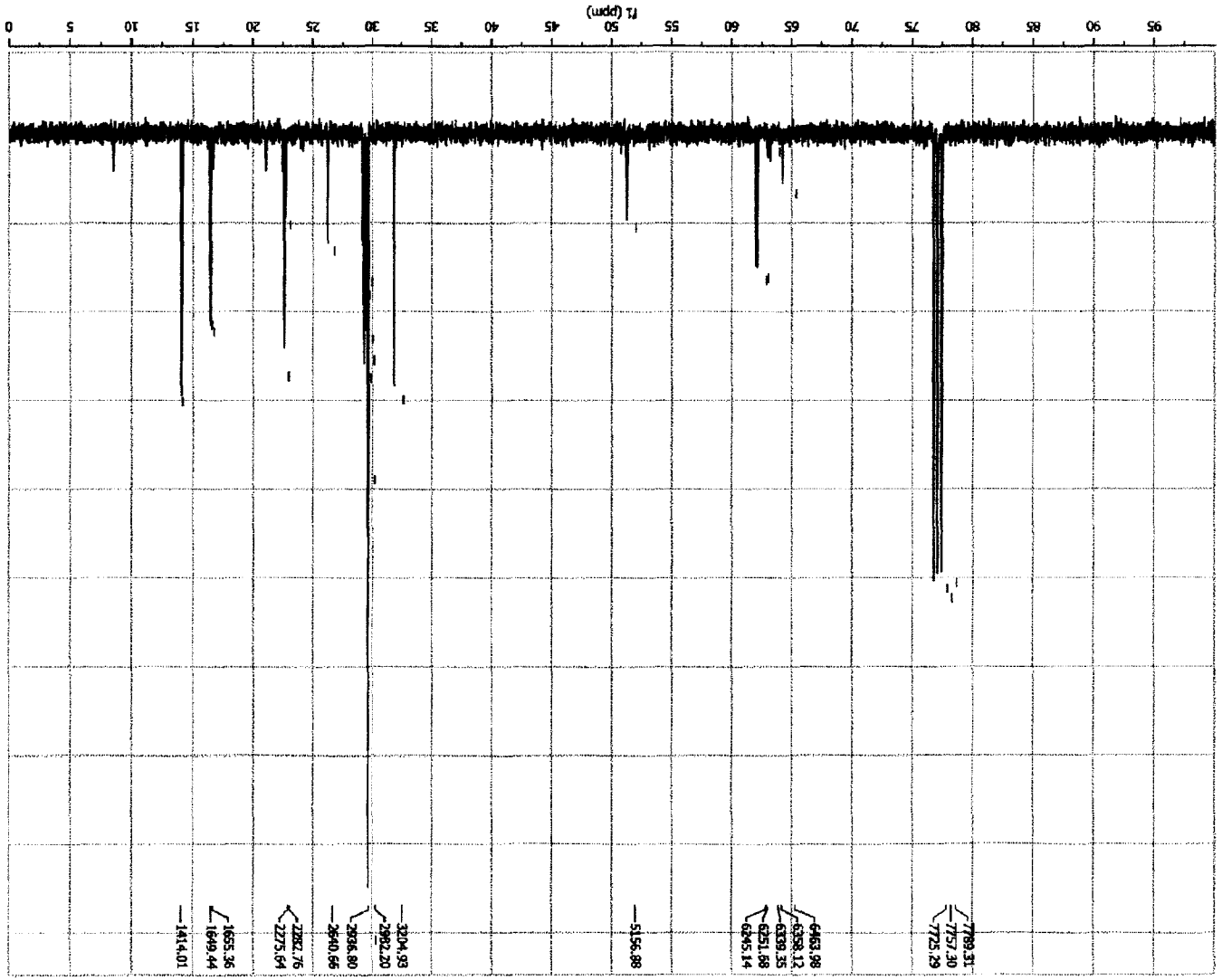
FIG. 5 shows the $^{13}$C NMR of compound (2) of Example 1
Figure 6:
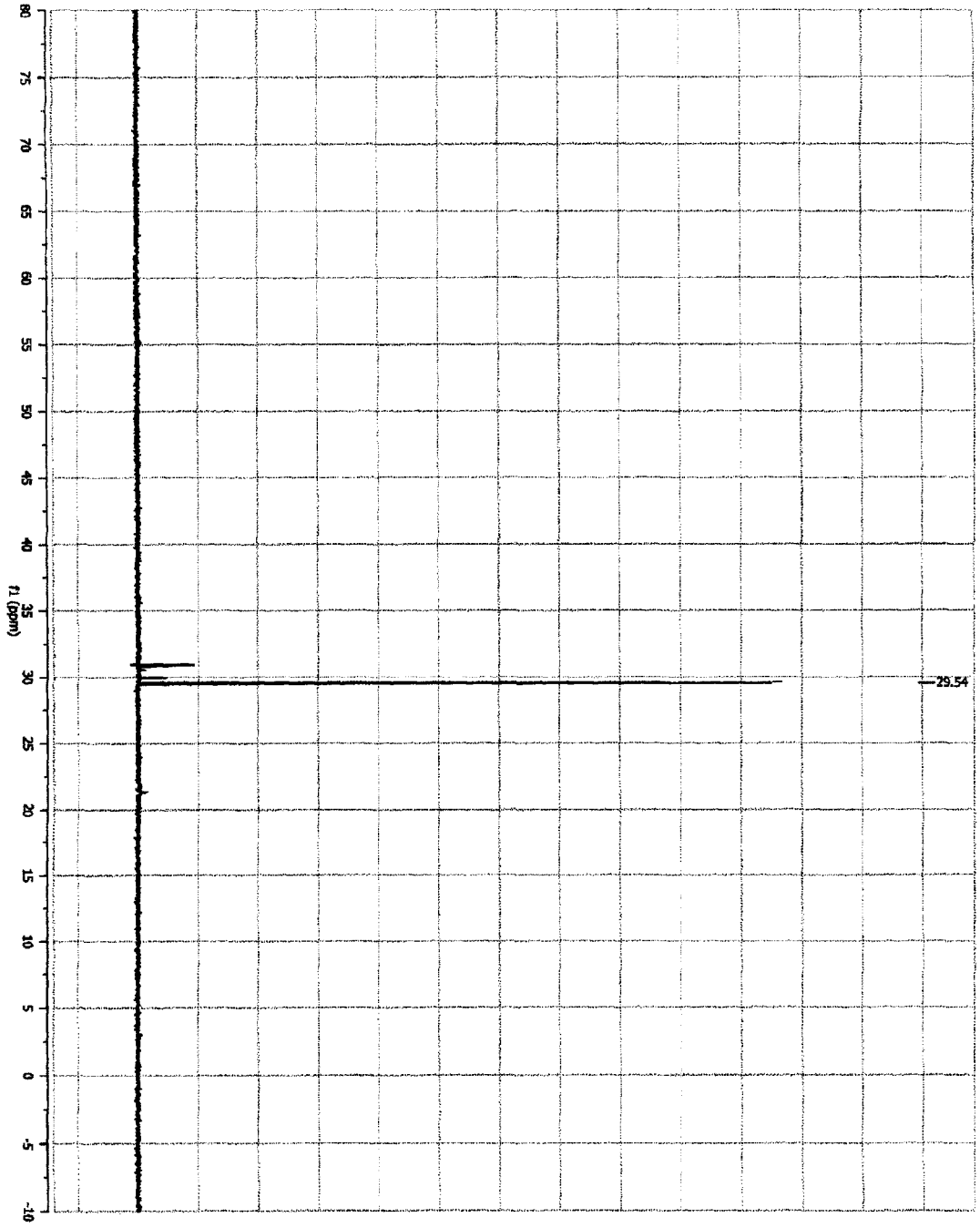
FIG. 6 shows the $^{31}$P NMR of compound (2) of Example 1
Figure 7:
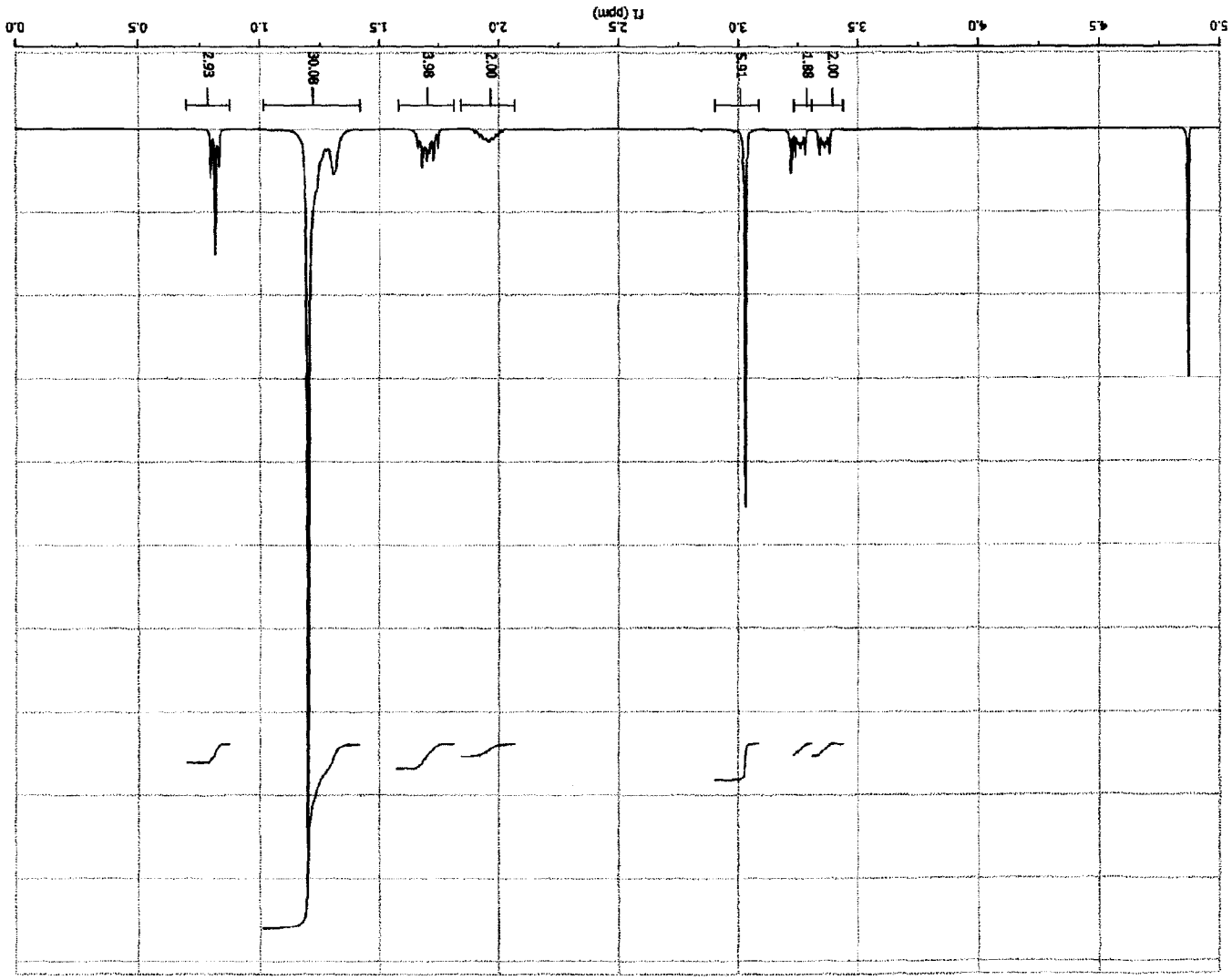
FIG. 7 shows the $^{1}$H NMR of compound (3) of Example 2
Figure 8:
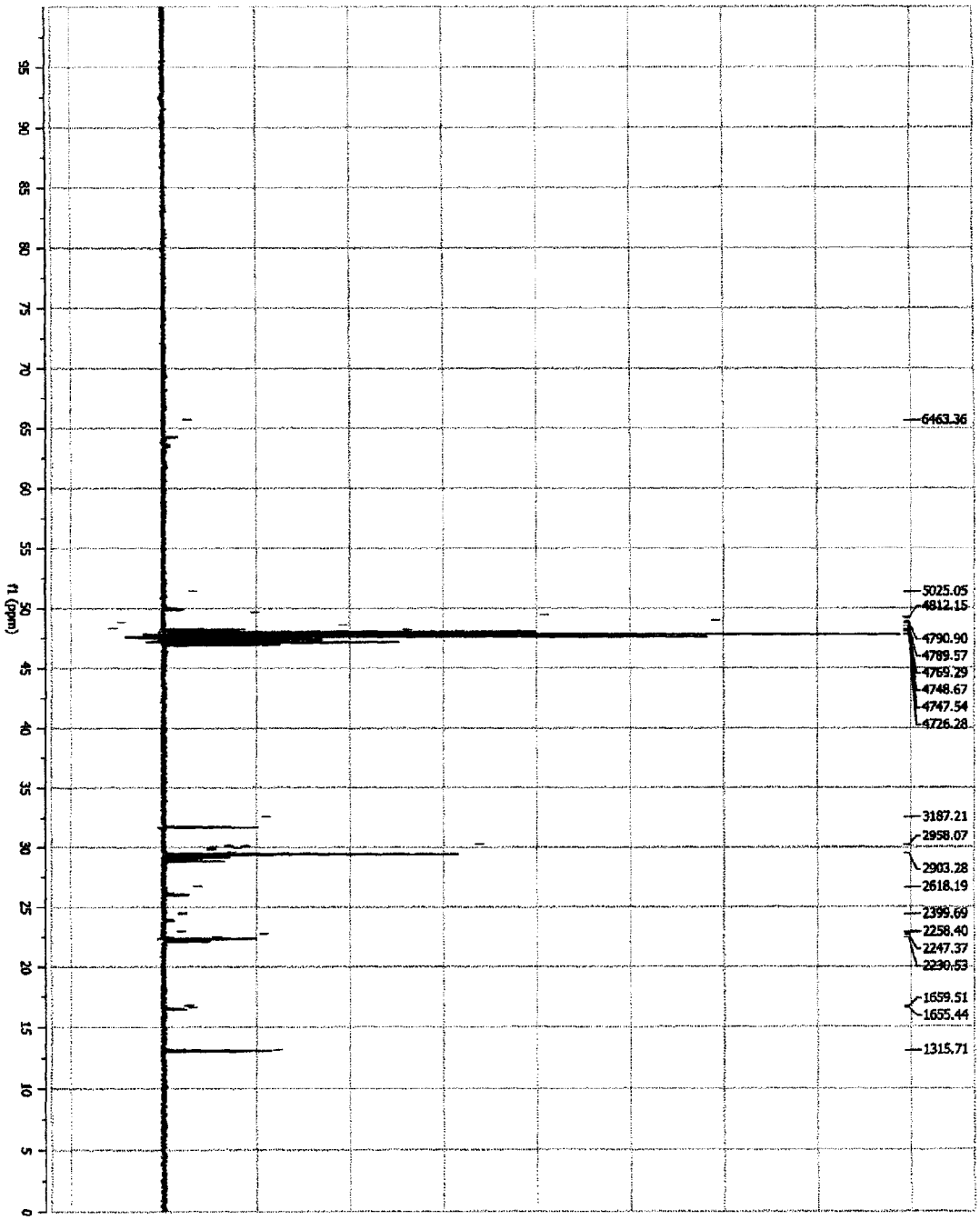
FIG. 8 shows the $^{13}$C NMR of compound (3) of Example 2
Figure 9:
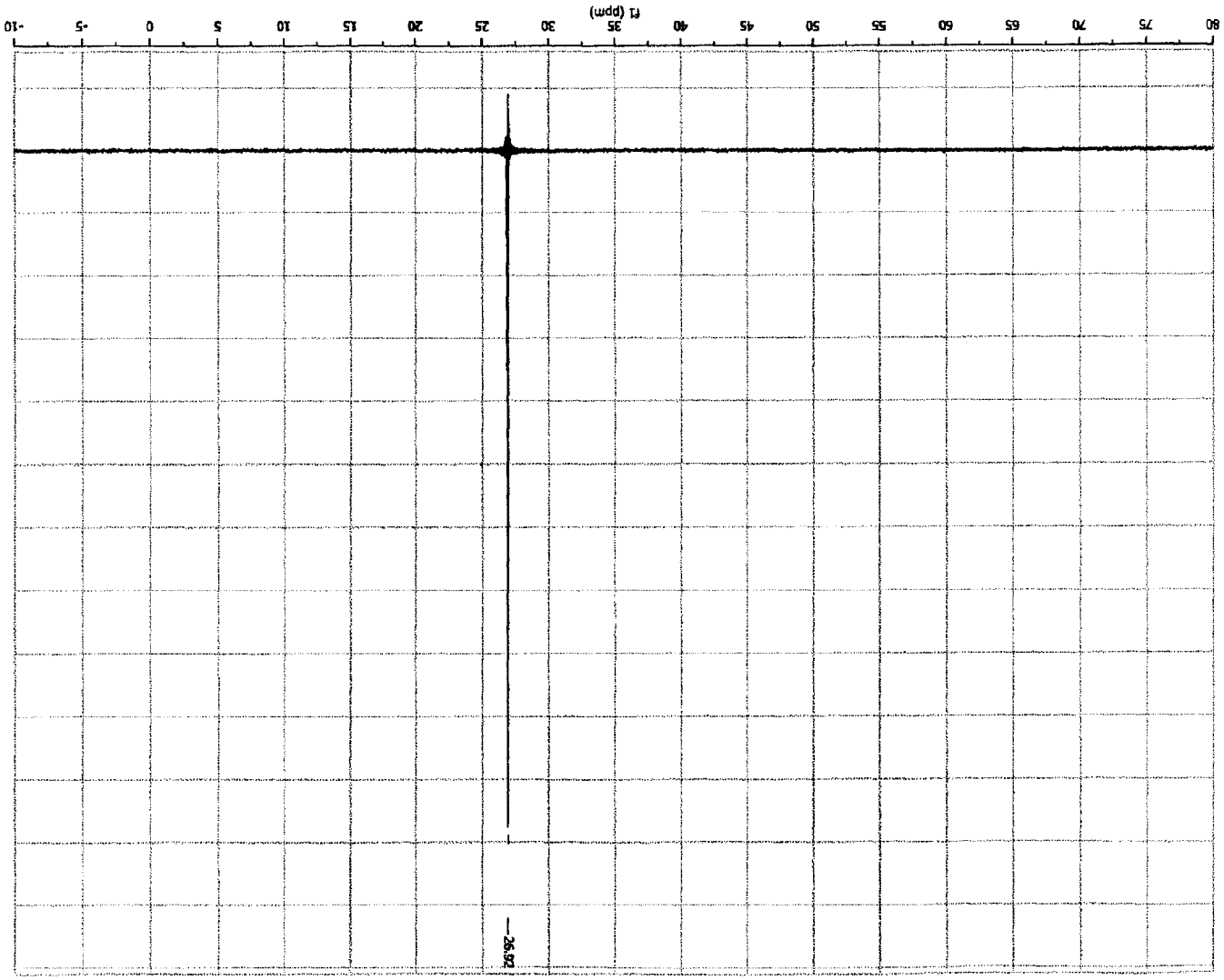
FIG. 9 shows the $^{31}$P NMR of compound (3) of Example 2
Figure 10:
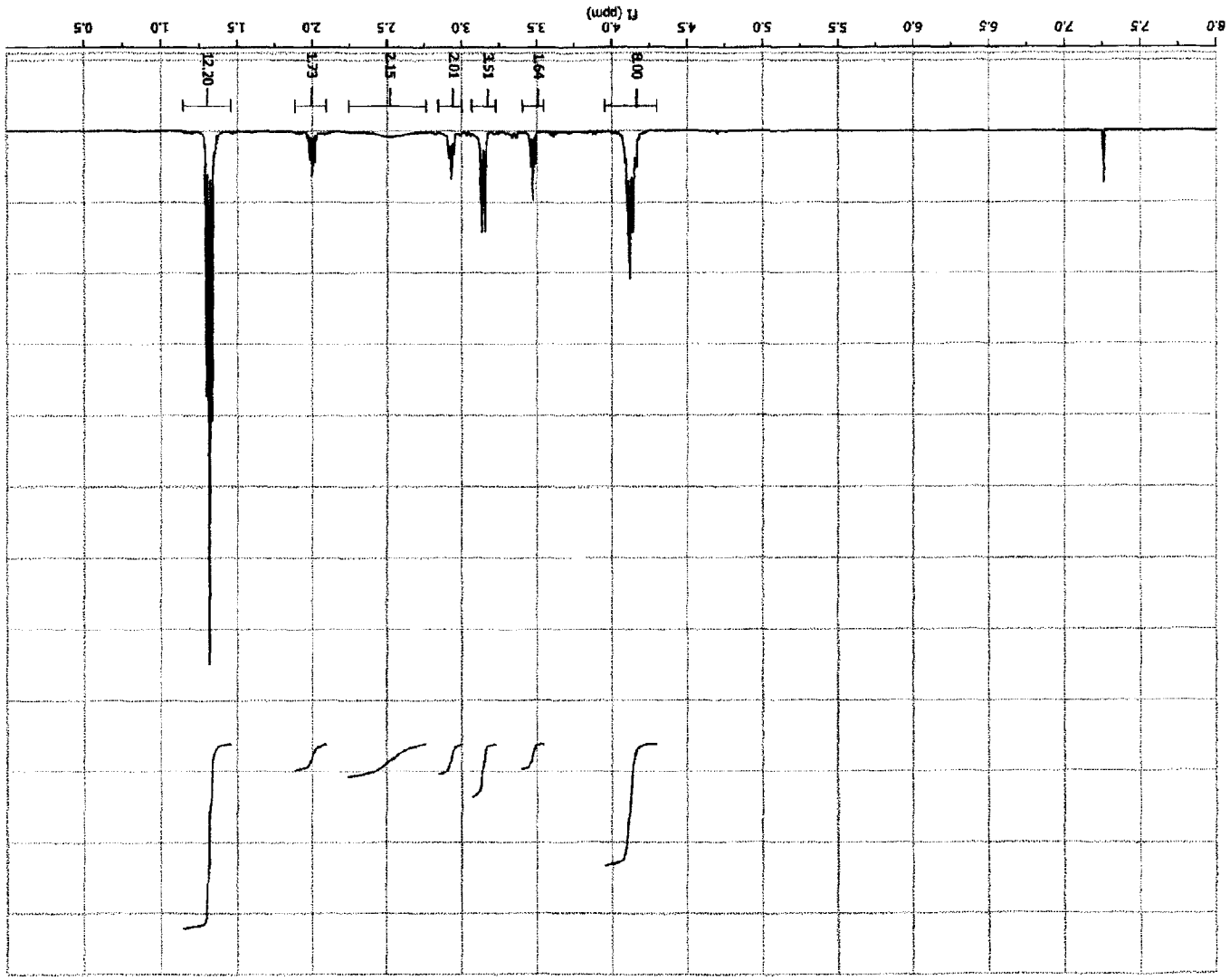
FIG. 10 shows the $^{1}$H NMR of compound (4) of Example 3
Figure 11:
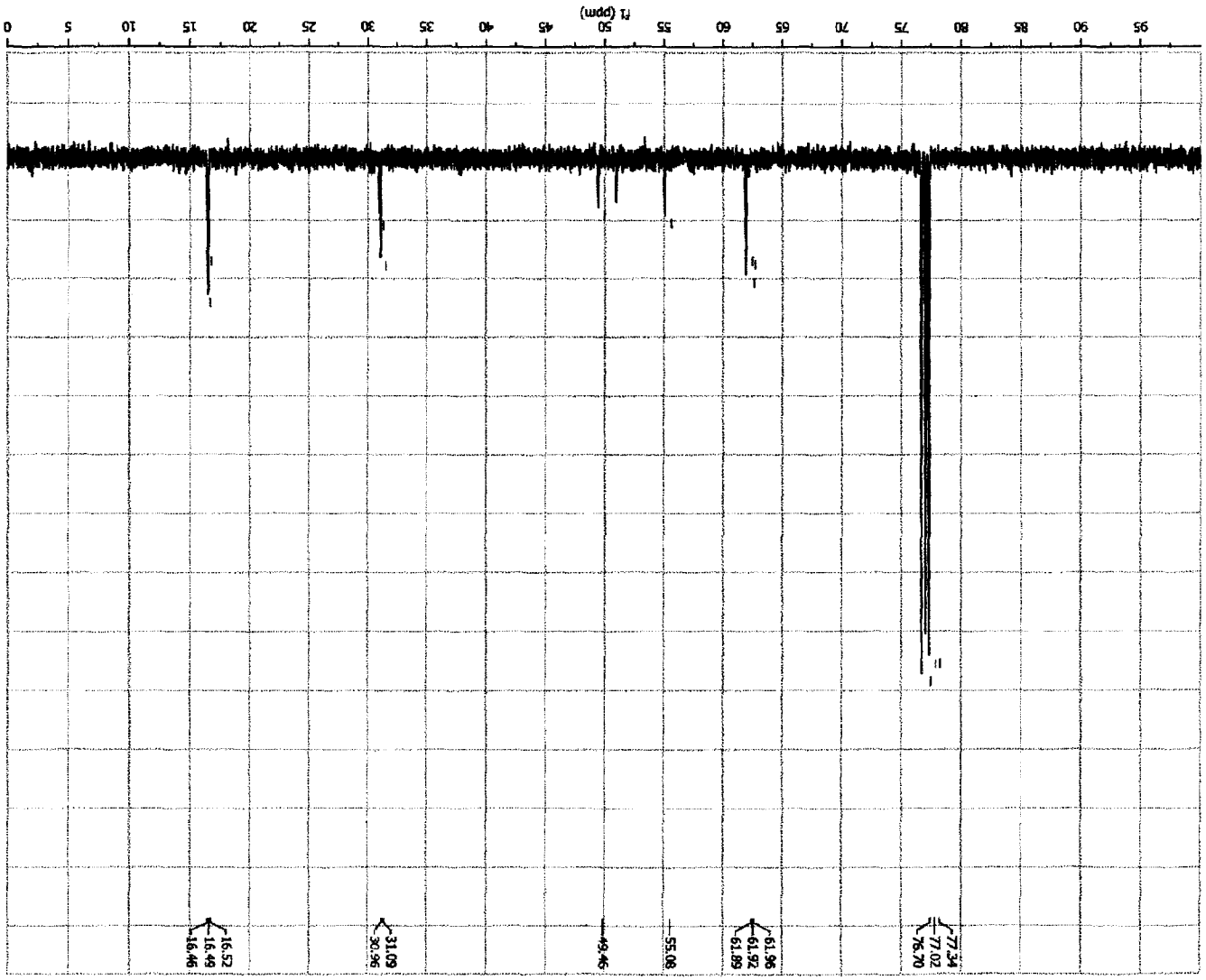
FIG. 11 shows the $^{13}$C NMR of compound (4) of Example 3
Figure 12:
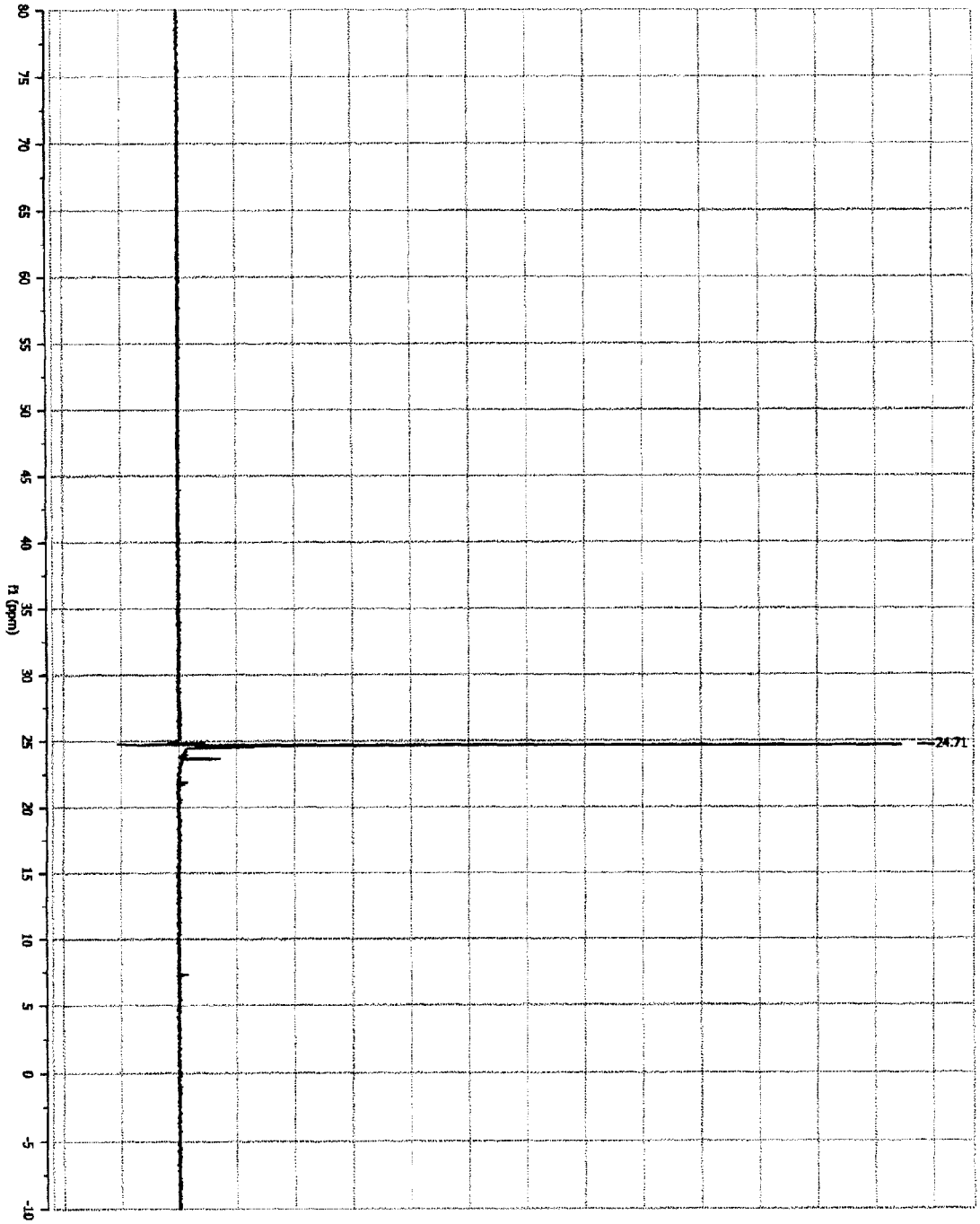
FIG. 12 shows the $^{31}$P NMR of compound (4) of Example 3
Figure 13:
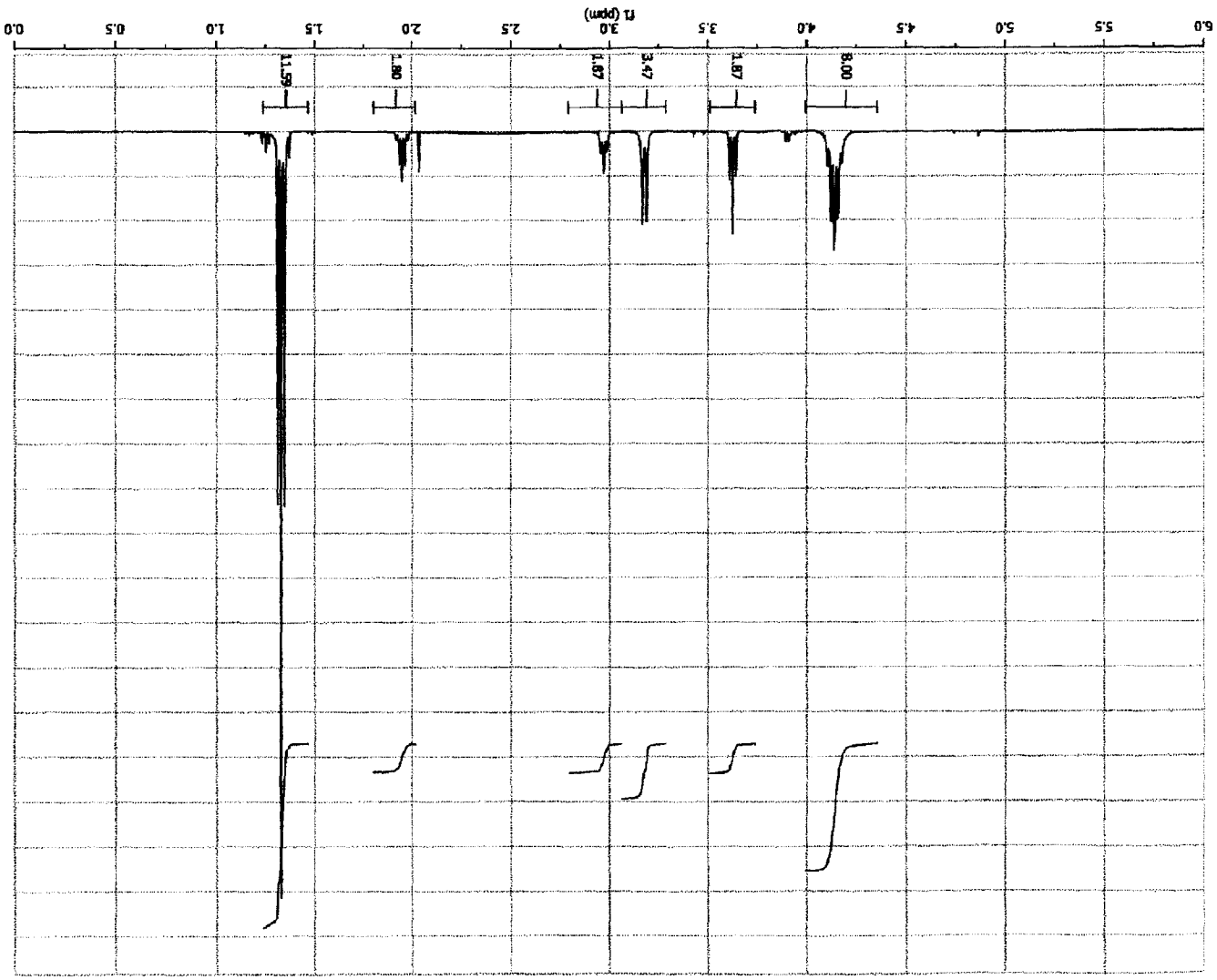
FIG. 13 shows the $^{1}$H NMR of compound (5) of Example 4
Figure 14:
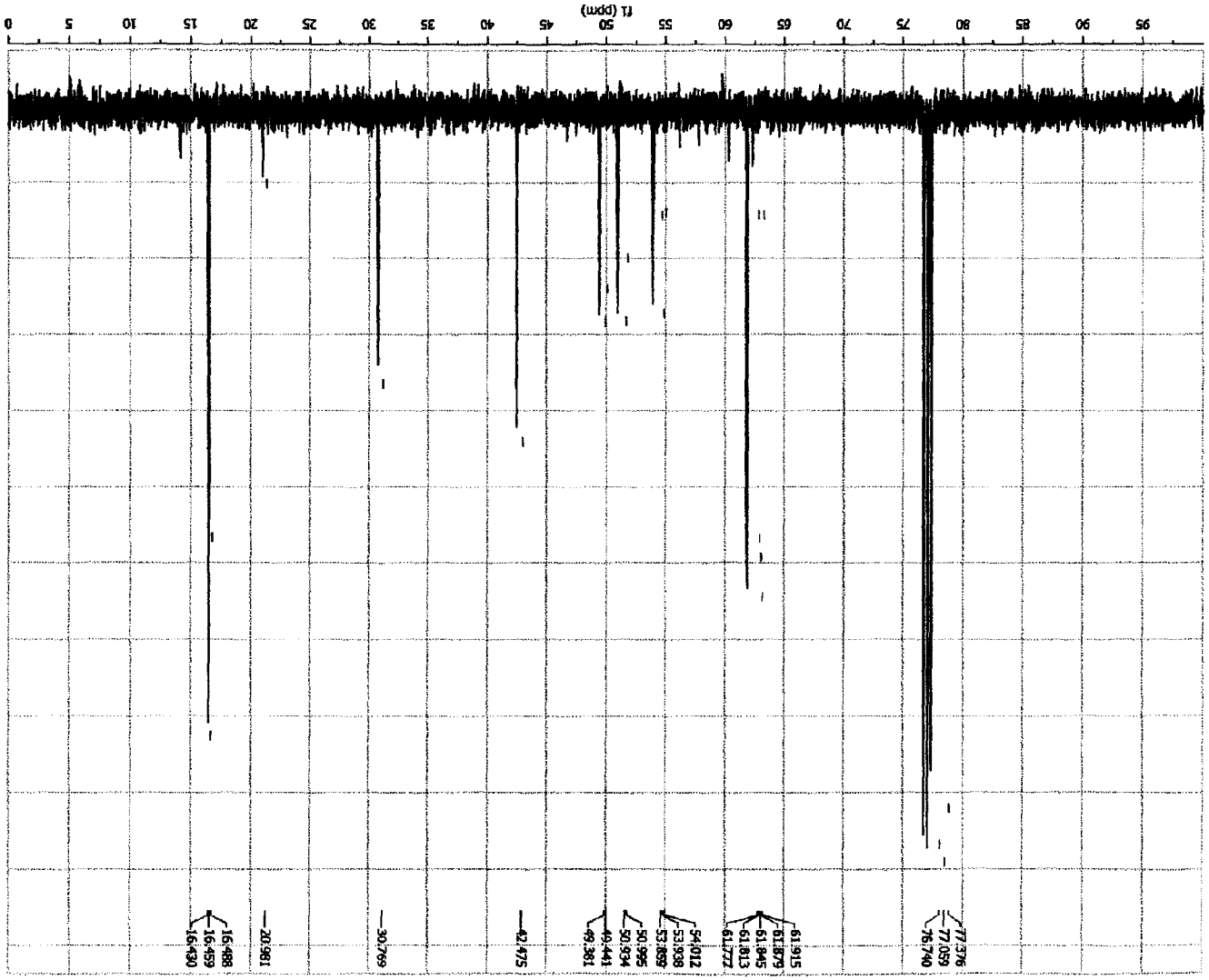
FIG. 14 shows the $^{13}$C NMR of compound (5) of Example 4
Figure 15:
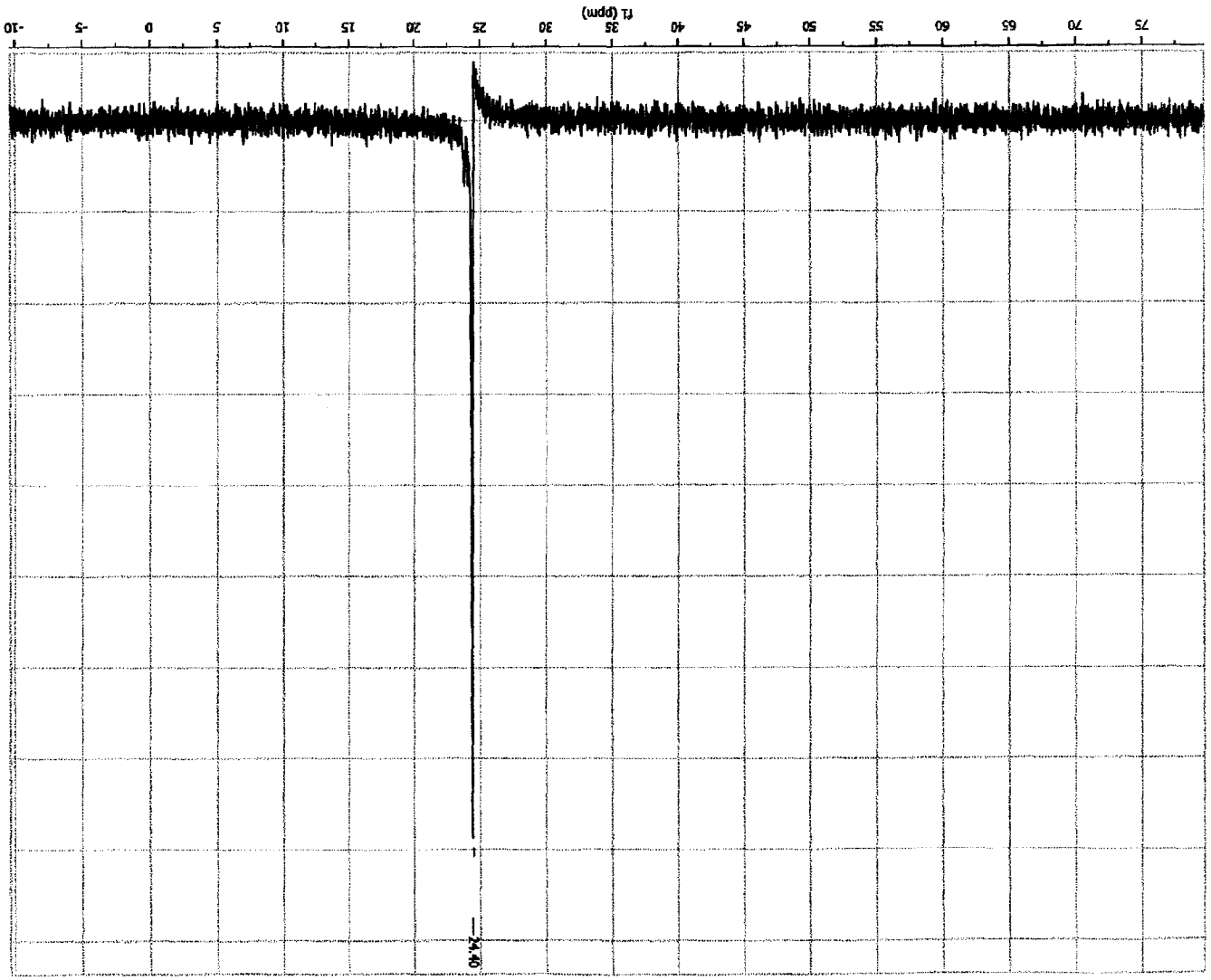
FIG. 15 shows the $^{31}$P NMR of compound (5) of Example 4
Figure 16:
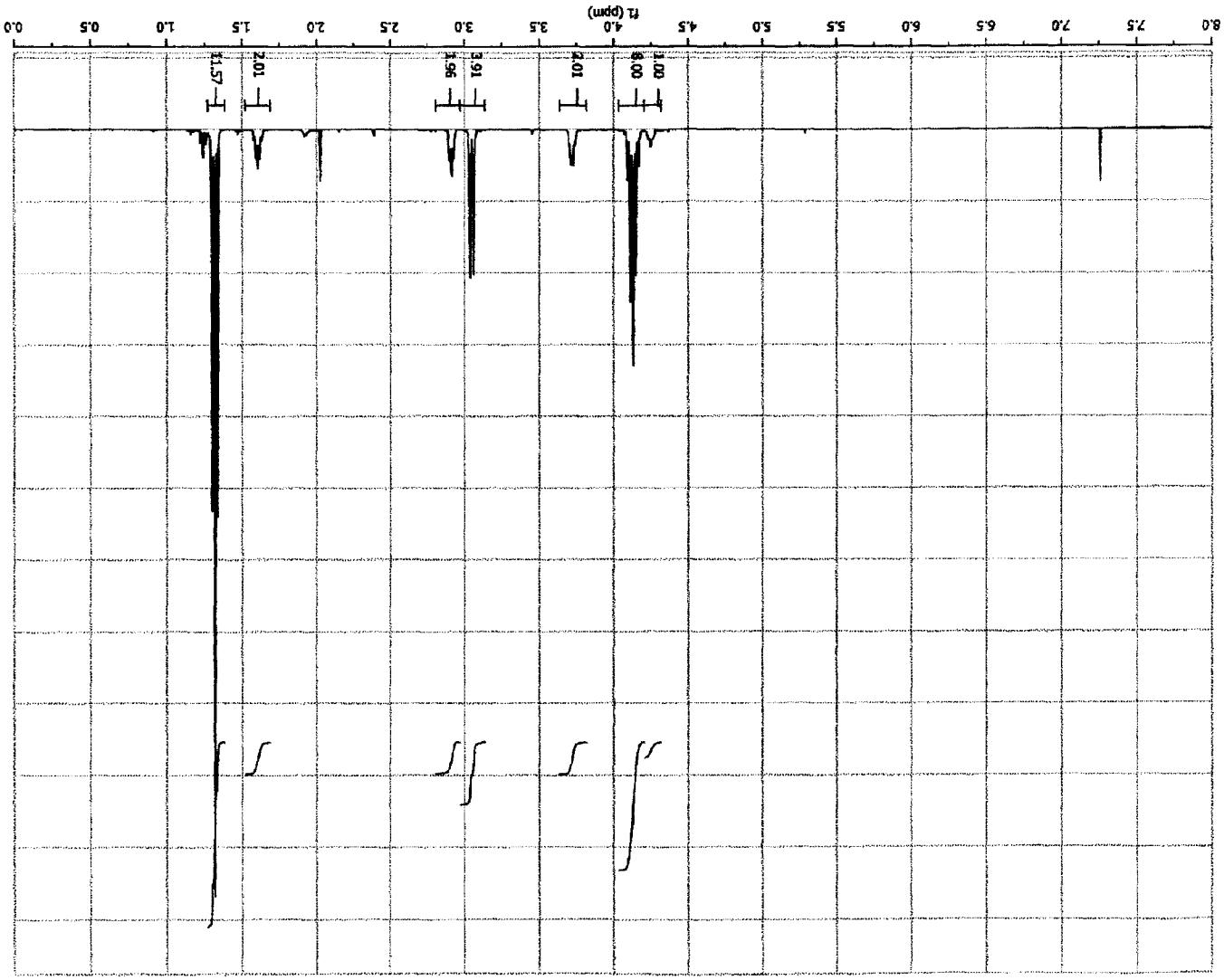
FIG. 16 shows the $^{1}$H NMR of compound (6) of Example 5
Figure 17:
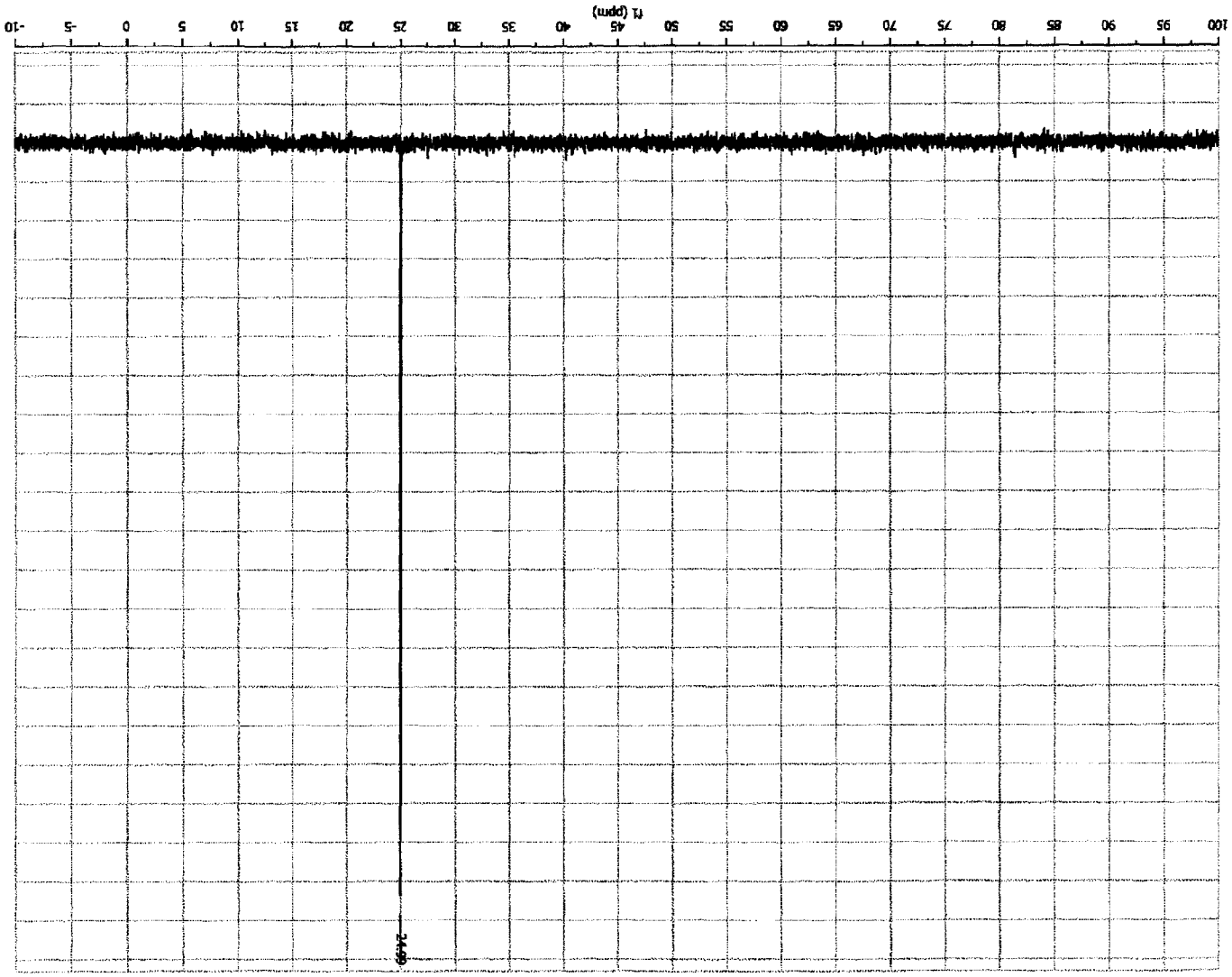
FIG. 17 shows the $^{31}$P NMR of compound (6) of Example 5
Figure 18:
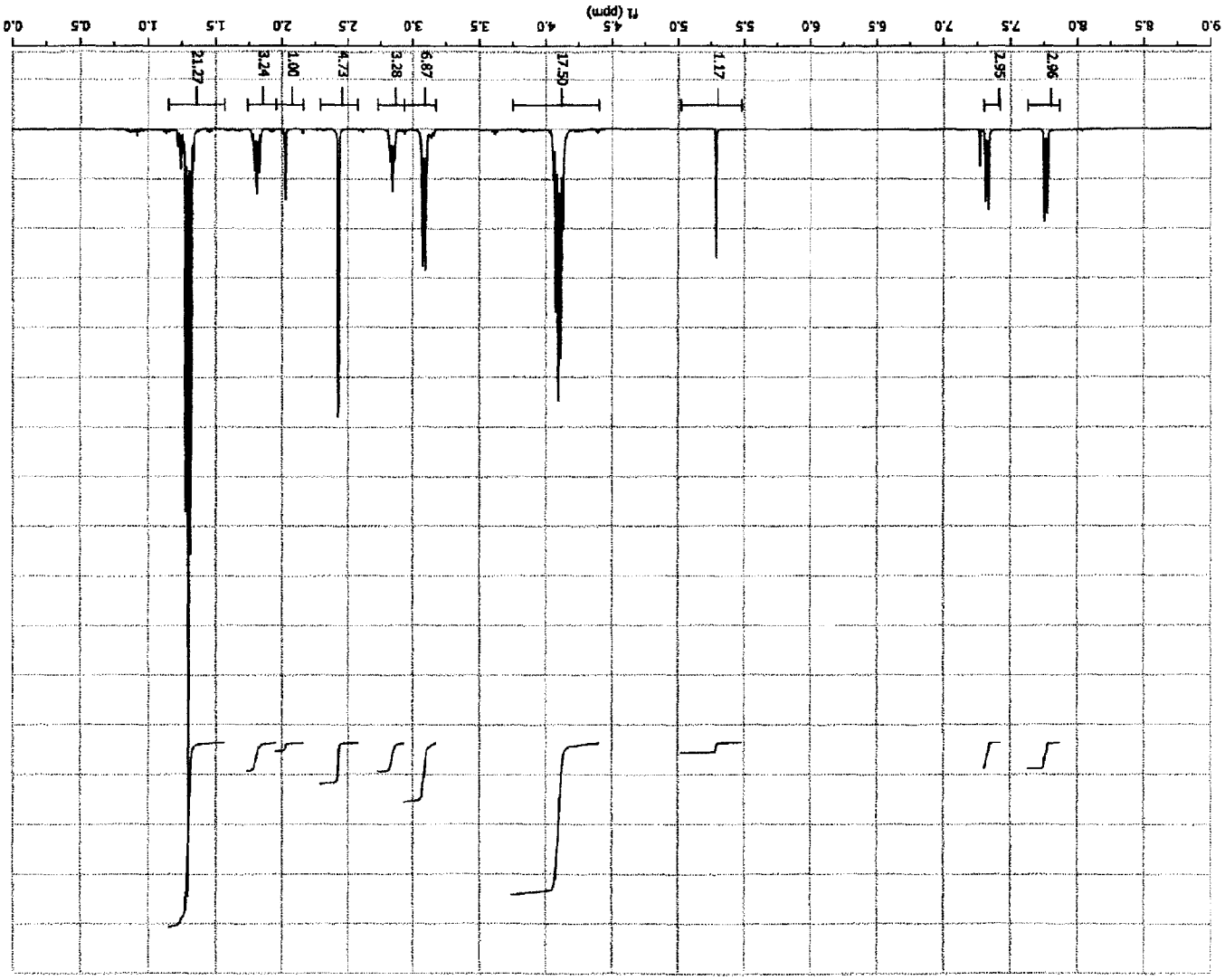
FIG. 18 shows the $^{1}$H NMR of compound (7) of Example 6
Figure 19:
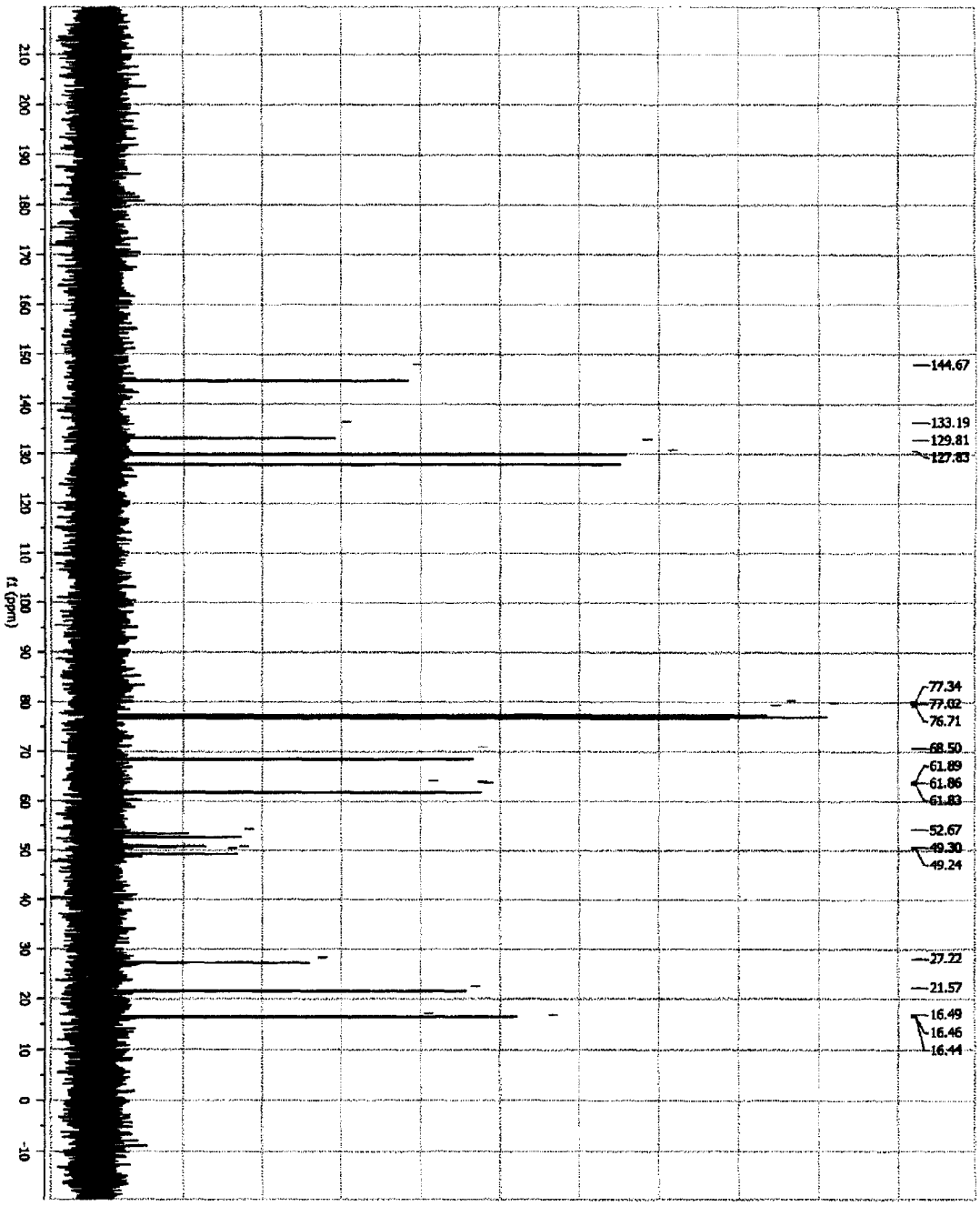
FIG. 19 shows the $^{13}$C NMR of compound (7) of Example 6
Figure 20:
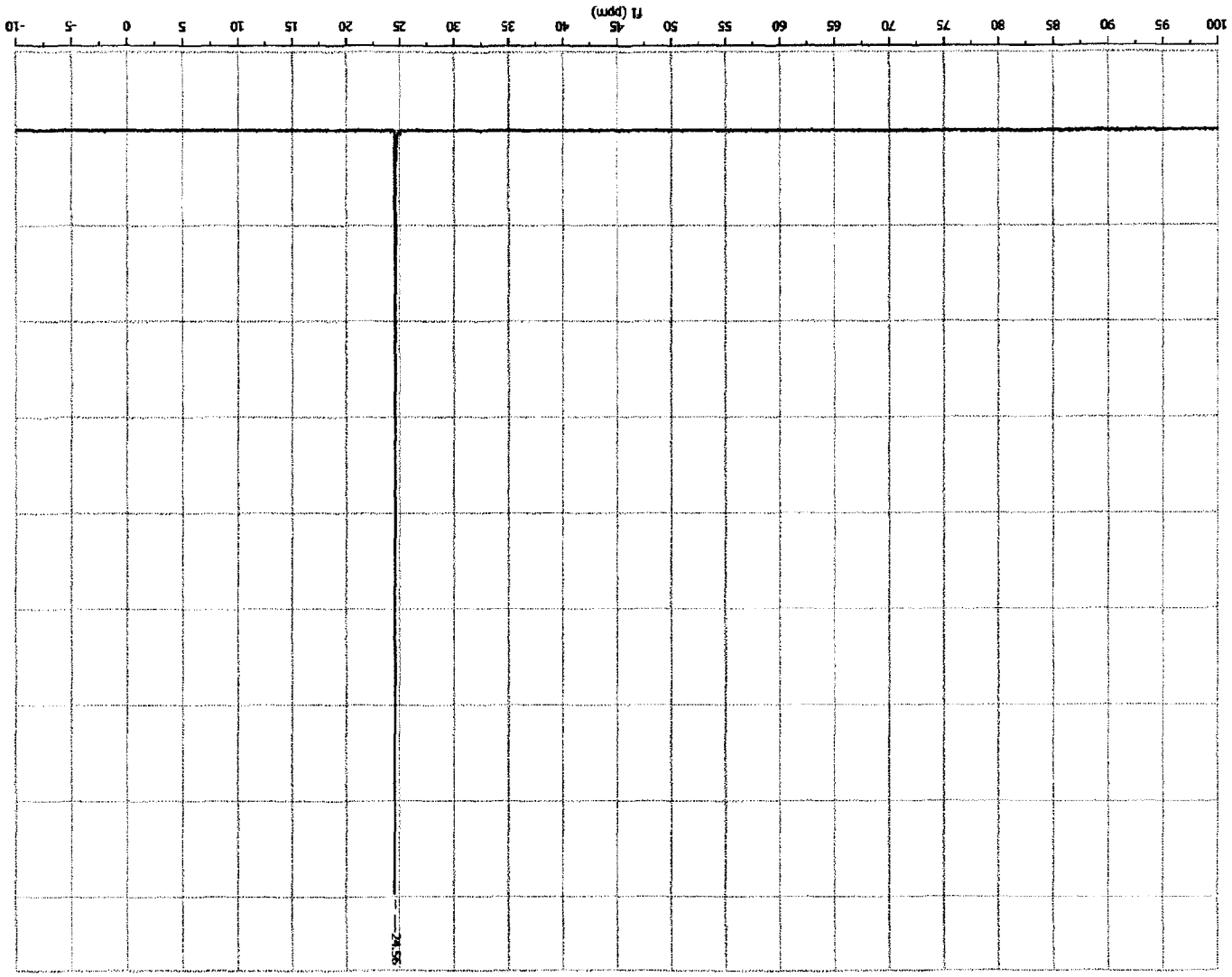
FIG. 20 shows the $^{31}$P NMR of compound (7) of Example 6
Figure 21:
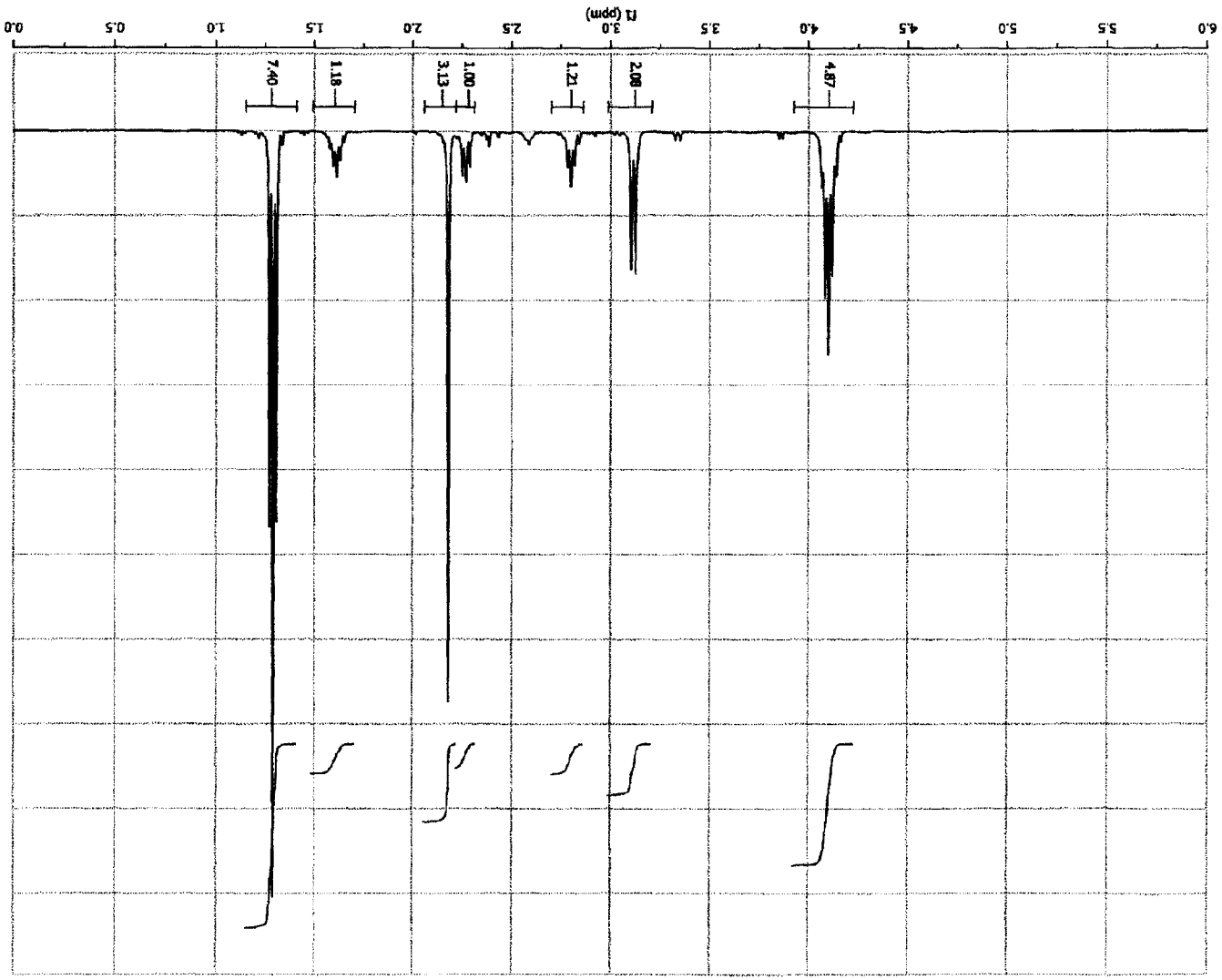
FIG. 21 shows the $^{1}$H NMR of compound (8) of Example 7
Figure 22:
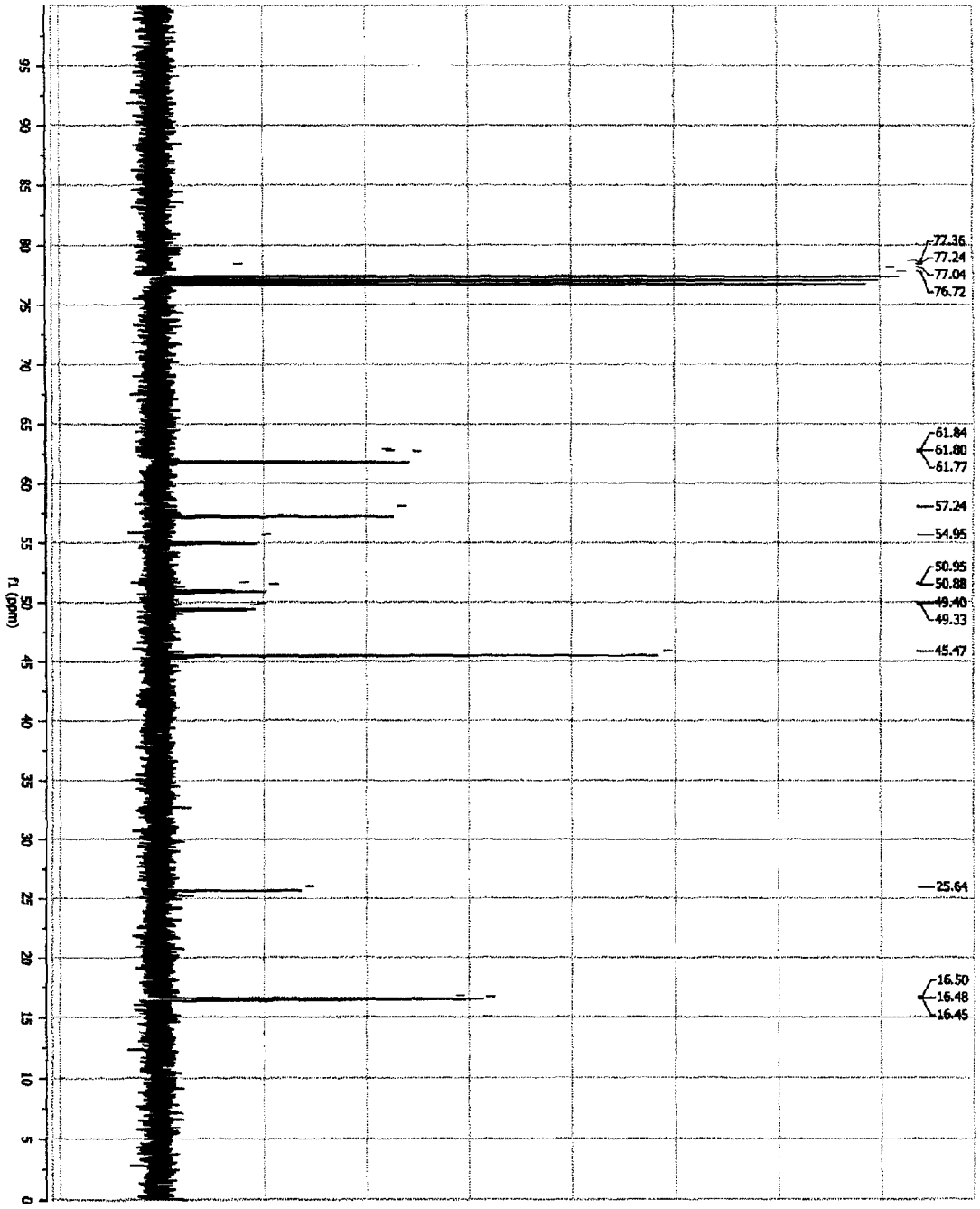
FIG. 22 shows the $^{13}$C NMR of compound (8) of Example 7
Figure 23:
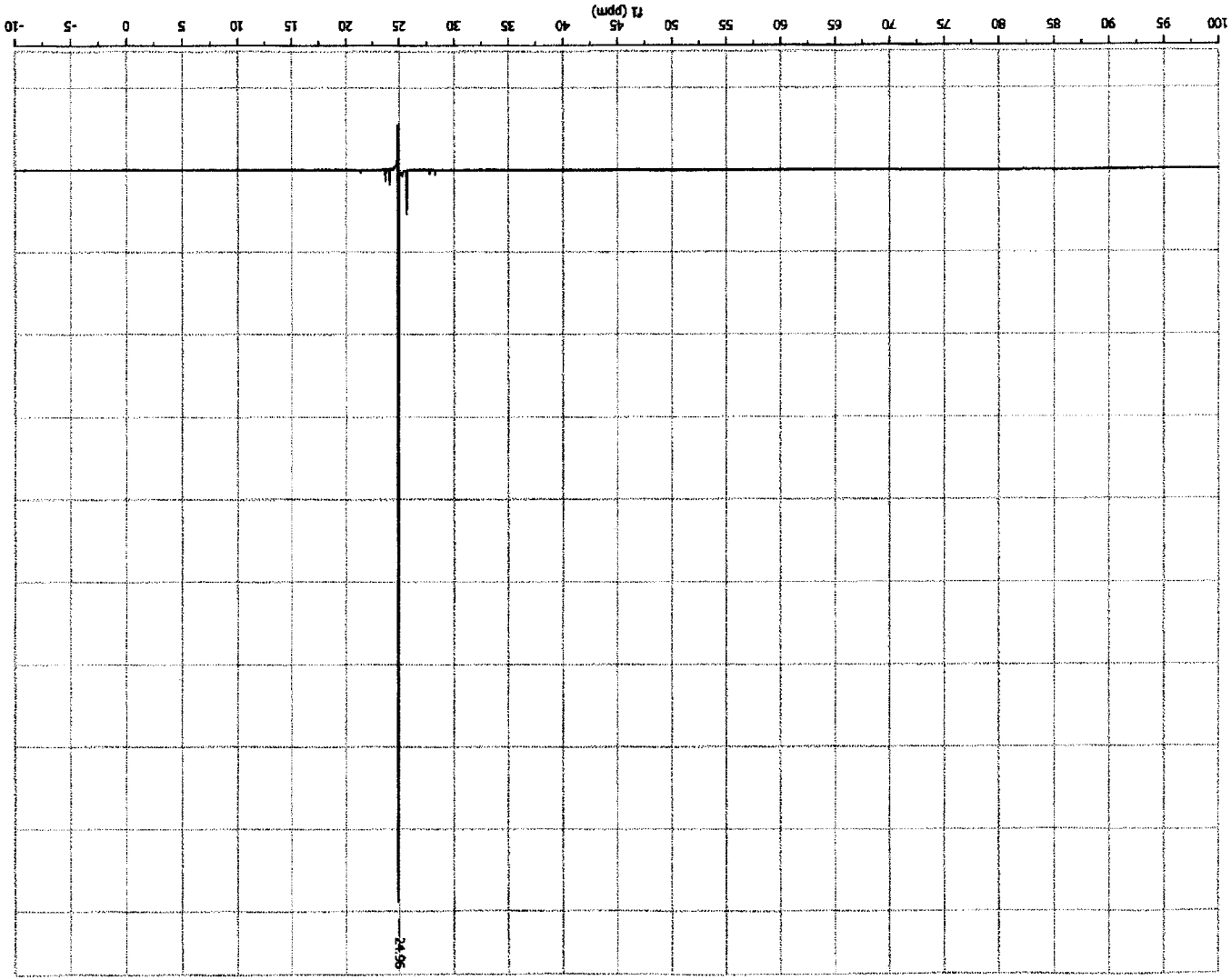
FIG. 23 shows the $^{31}$P NMR of compound (8) of Example 7
Figure 24:
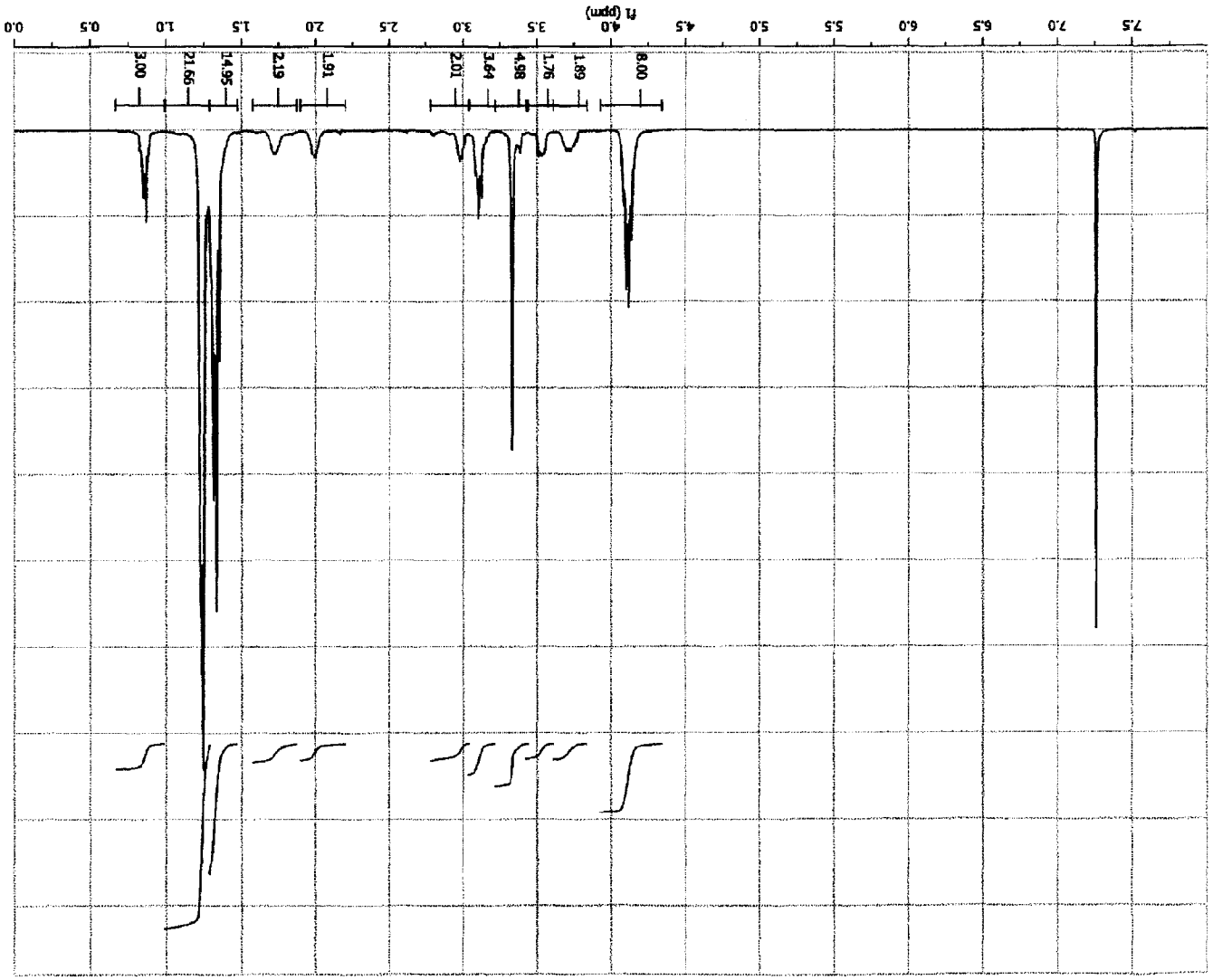
FIG. 24 shows the $^{1}$H NMR of compound (9) of Example 8
Figure 25:
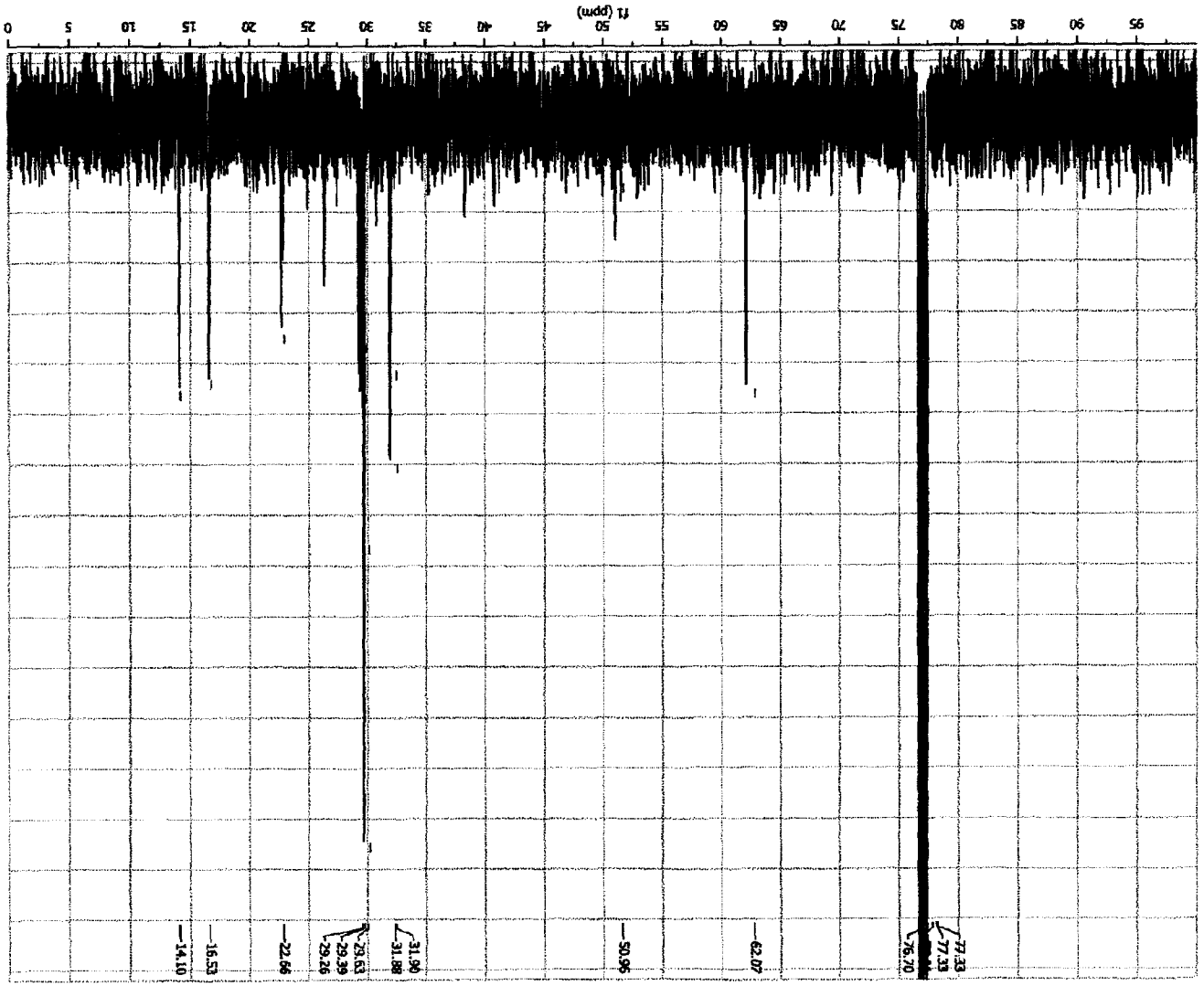
FIG. 25 shows the $^{13}$C NMR of compound (9) of Example 8
Figure 26:
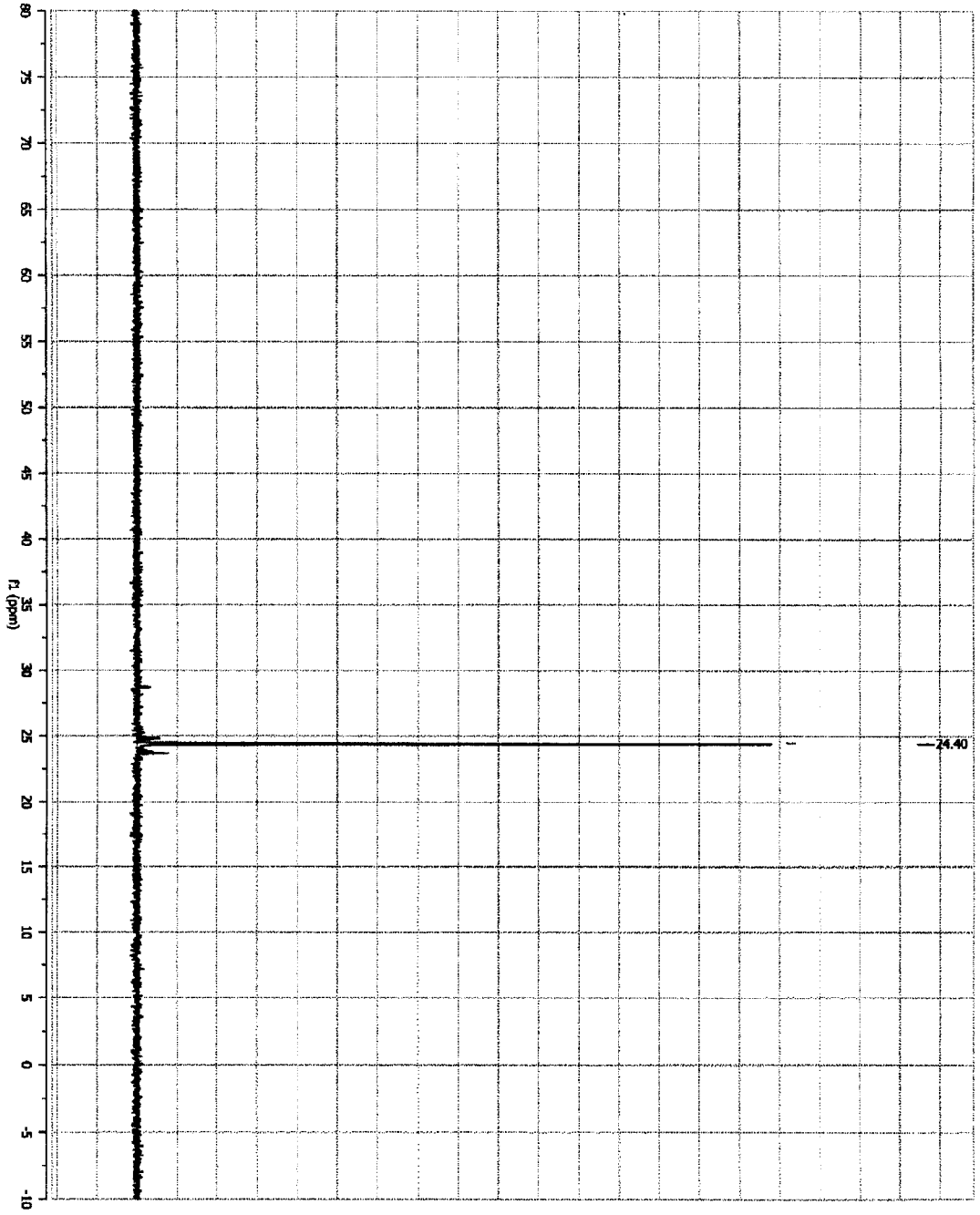
FIG. 26 shows the $^{31}$P NMR of compound (9) of Example 8
Figure 27:
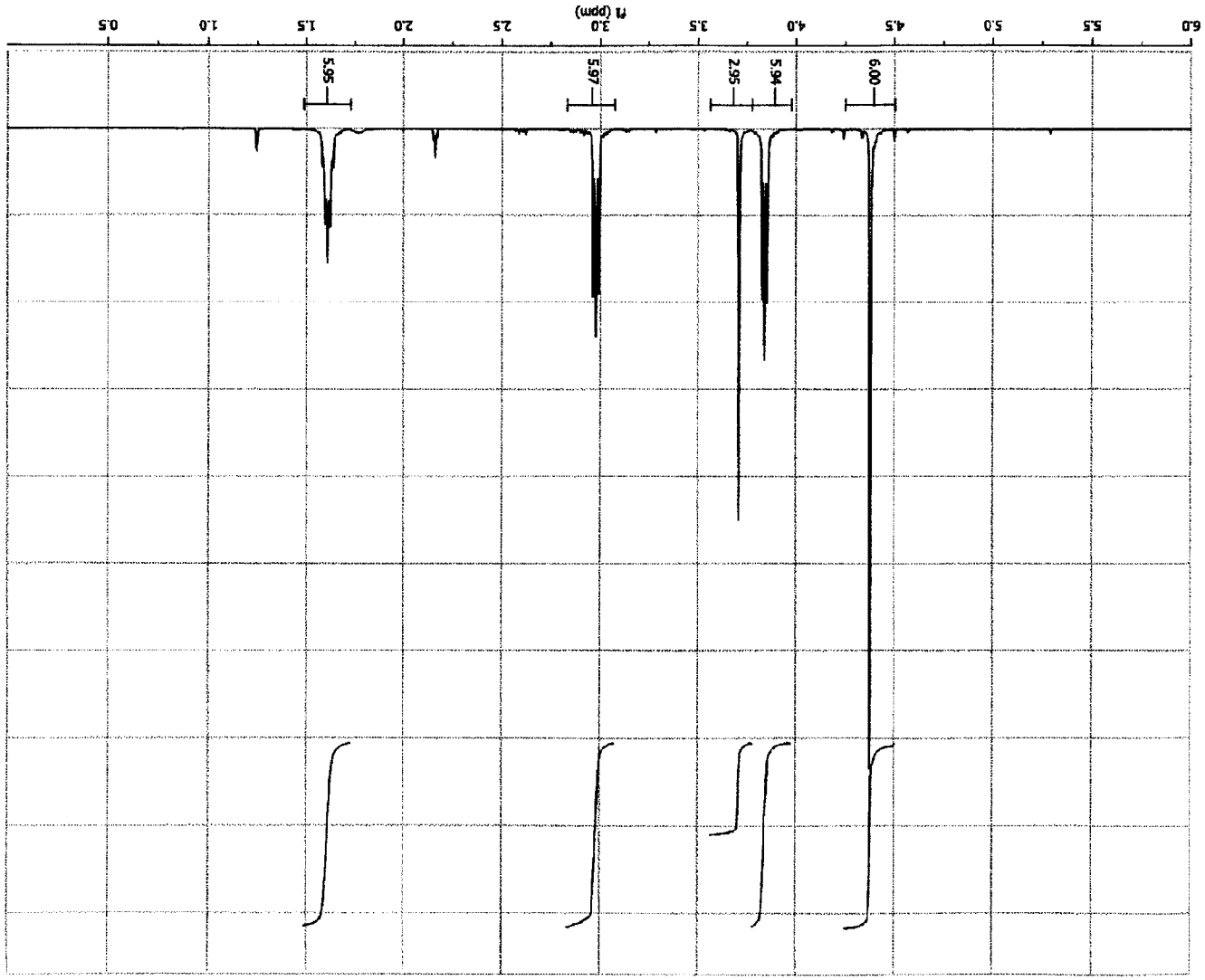
FIG. 27 shows the $^{1}$H NMR of compound (10) of Example 9
Figure 28:
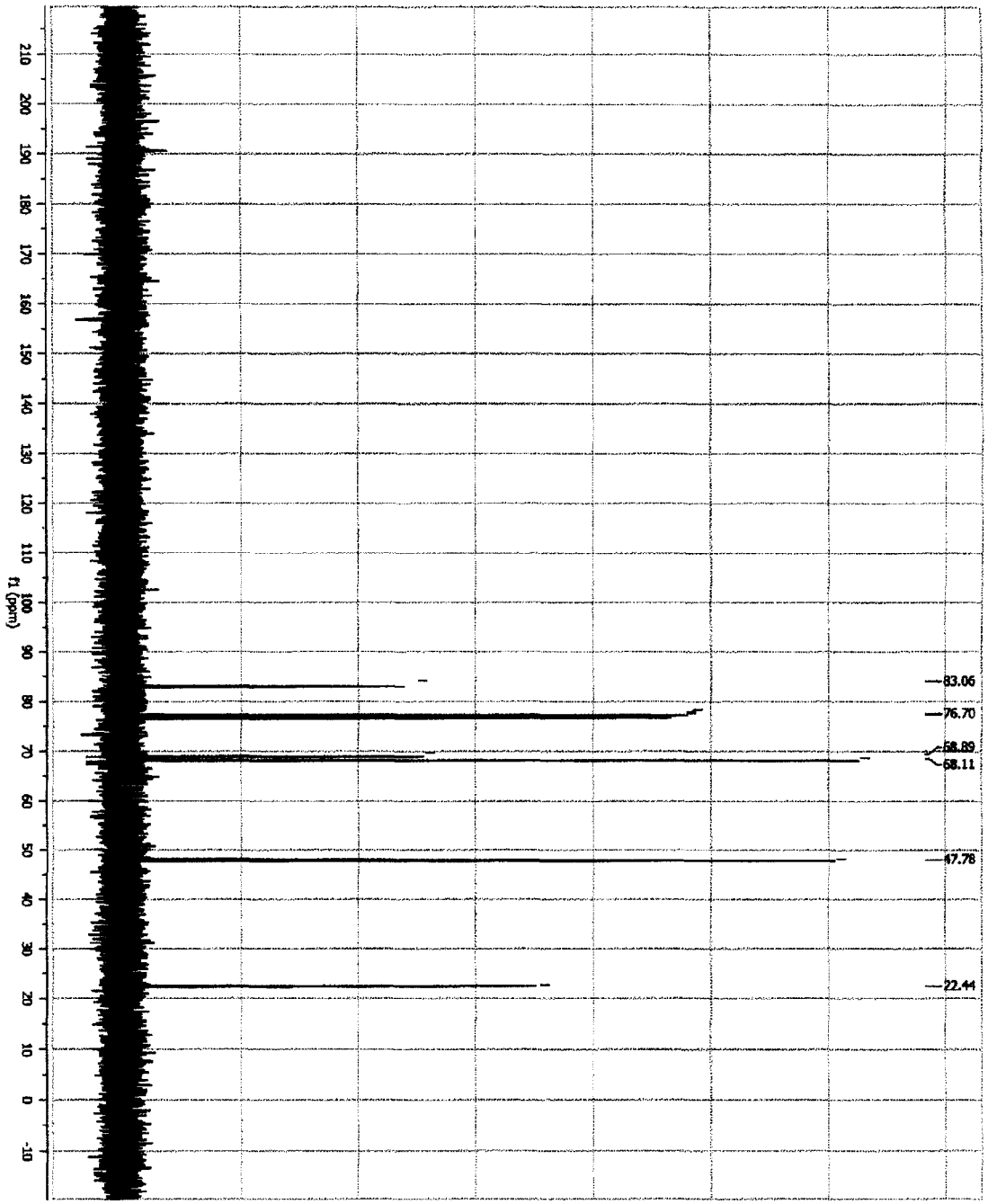
FIG. 28 shows the $^{13}$C NMR of compound (10) of Example 9
Figure 29:
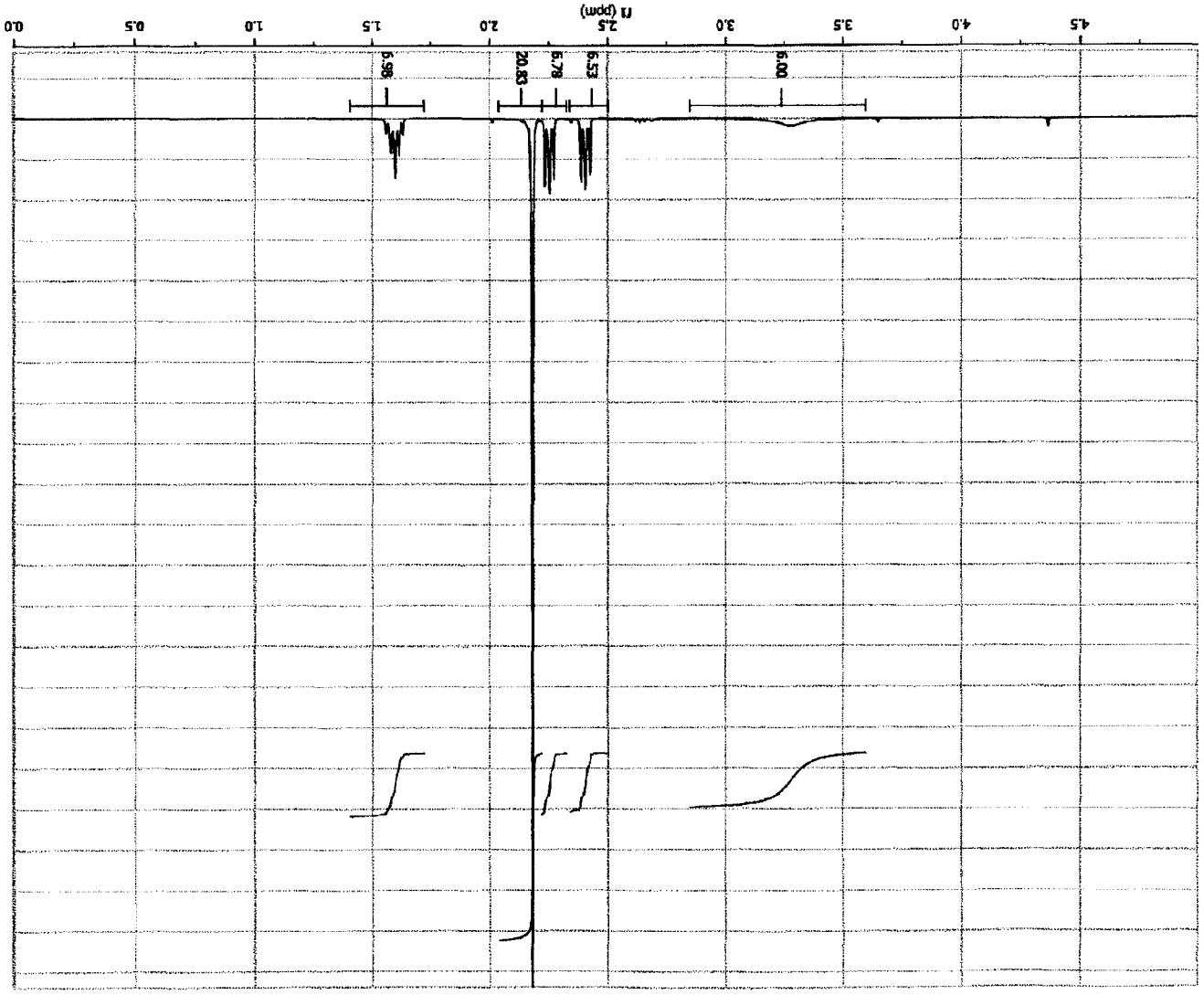
FIG. 29 shows the $^{1}$H NMR of compound (11) of Example 10
Figure 30:
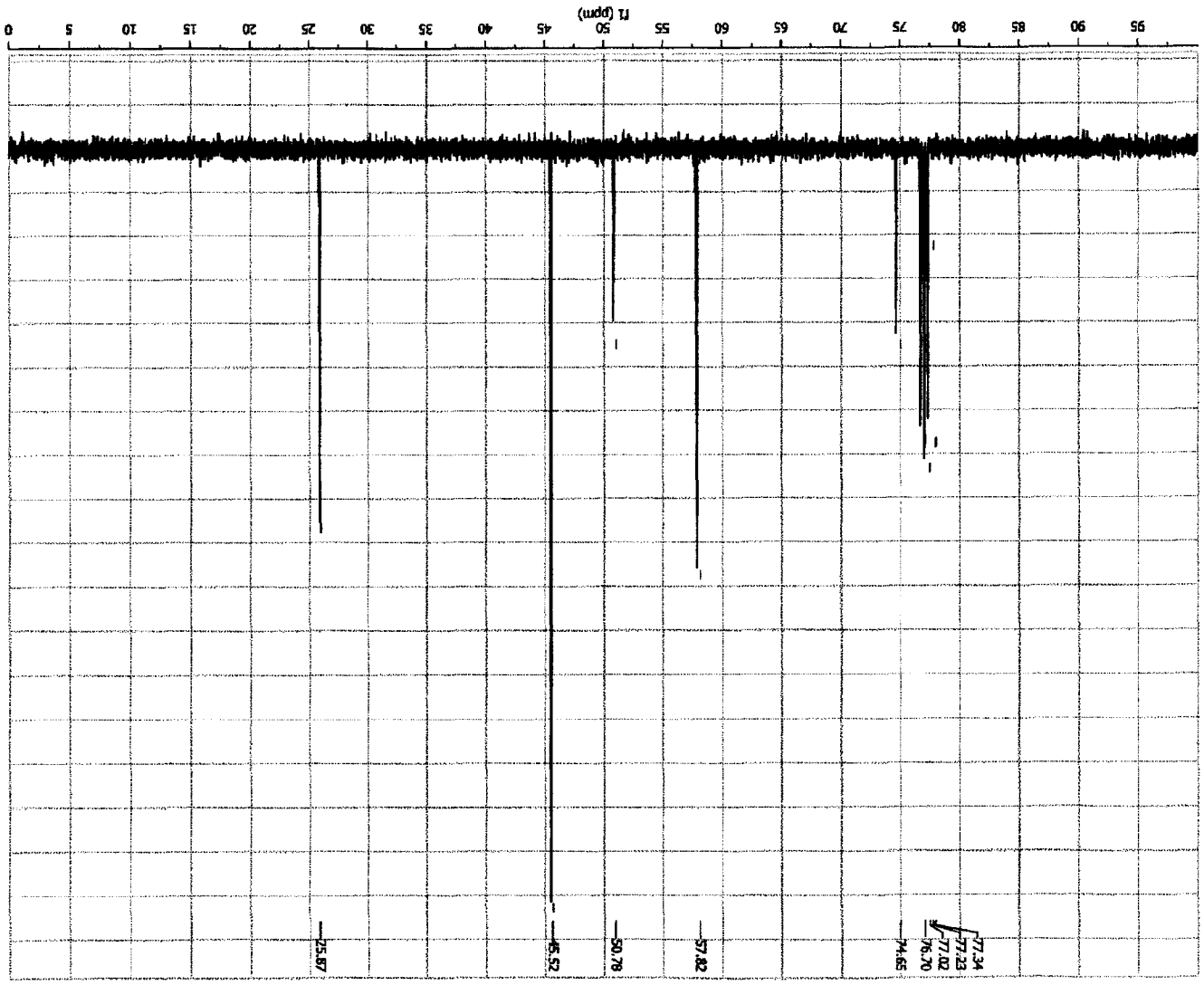
FIG. 30 shows the $^{13}$C NMR of compound (11) of Example 10
Figure 31:
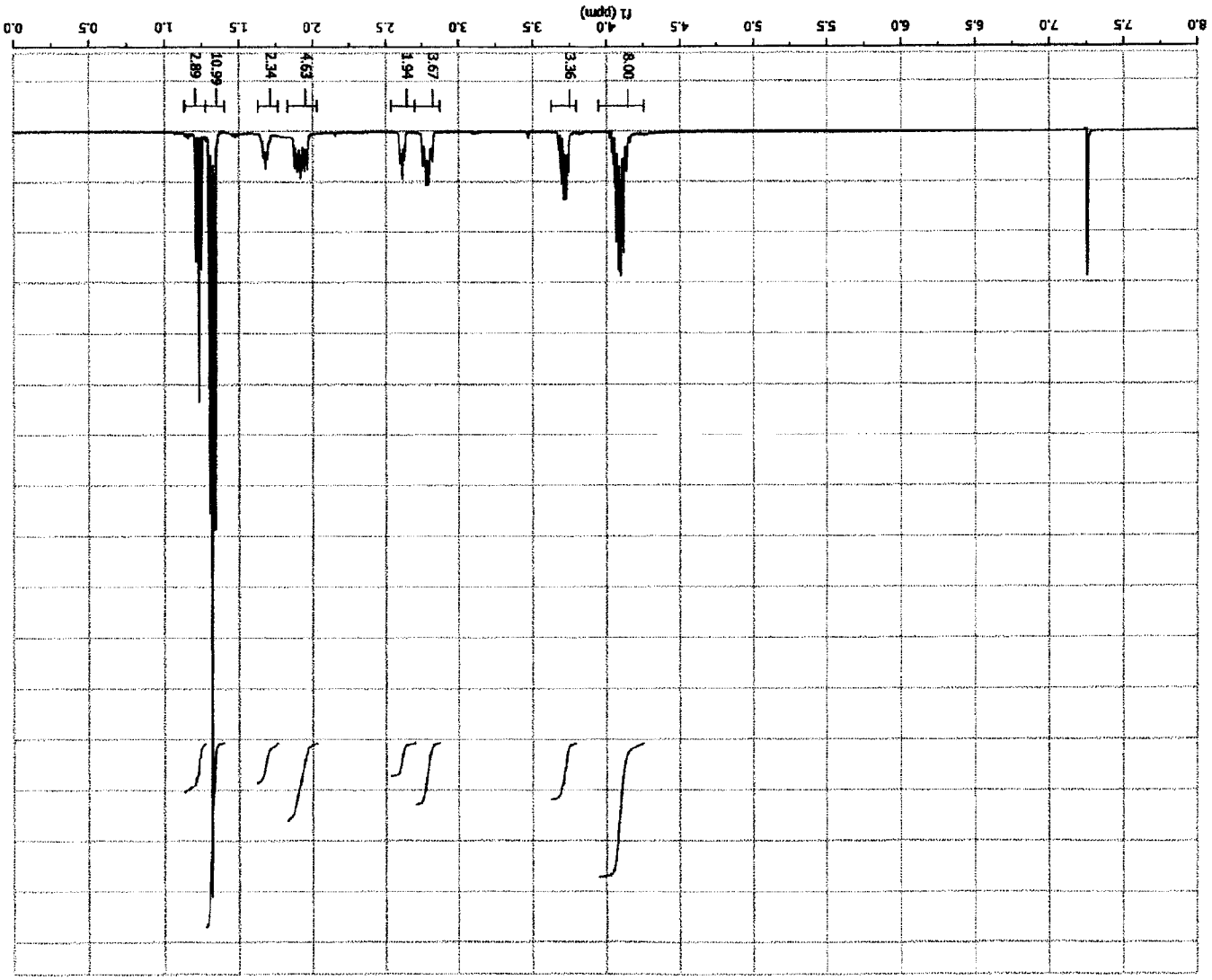
FIG. 31 shows the $^{1}$H NMR of compound (12) of Example 11
Figure 32:
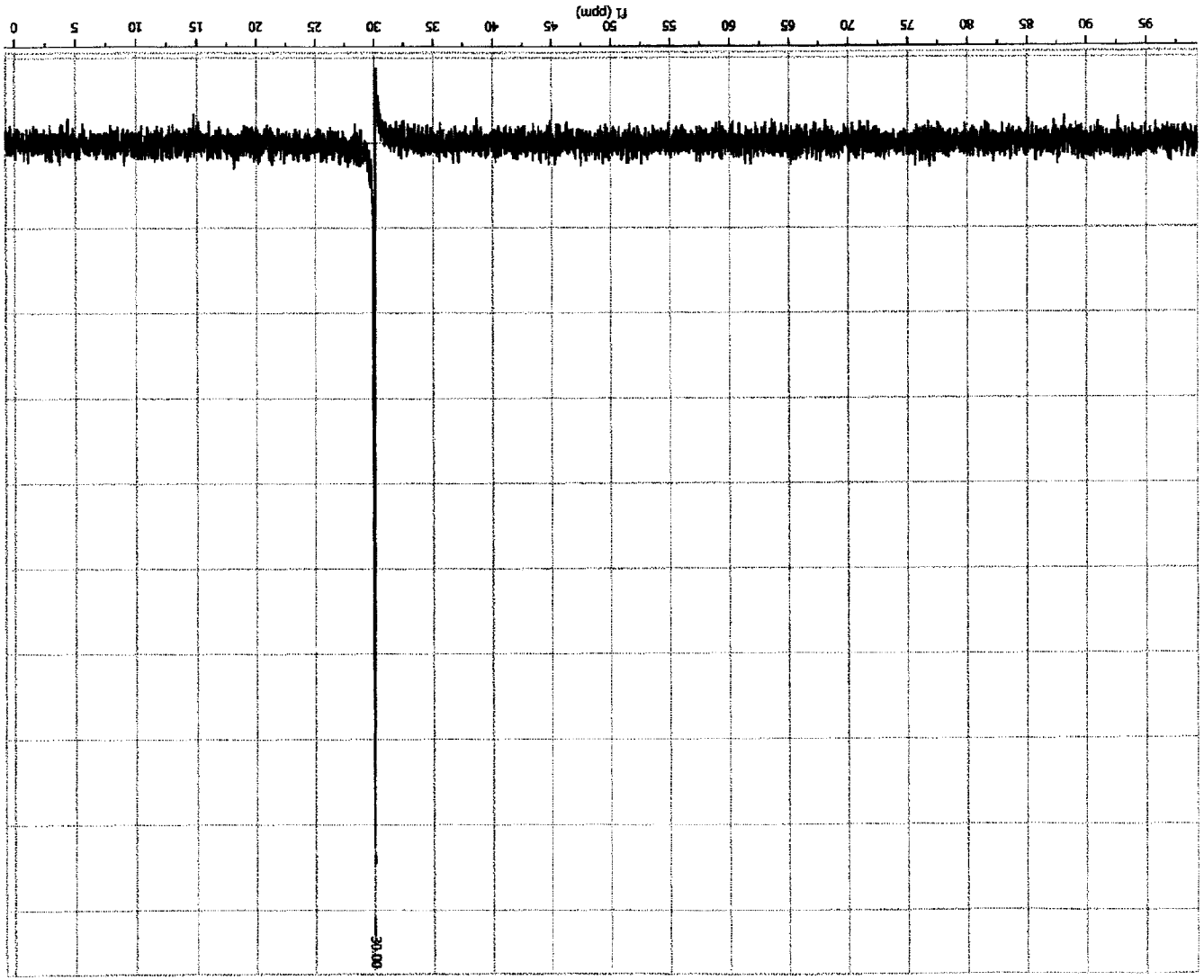
FIG. 32 shows the $^{31}$P NMR of compound (12) of Example 11
Figure 33:
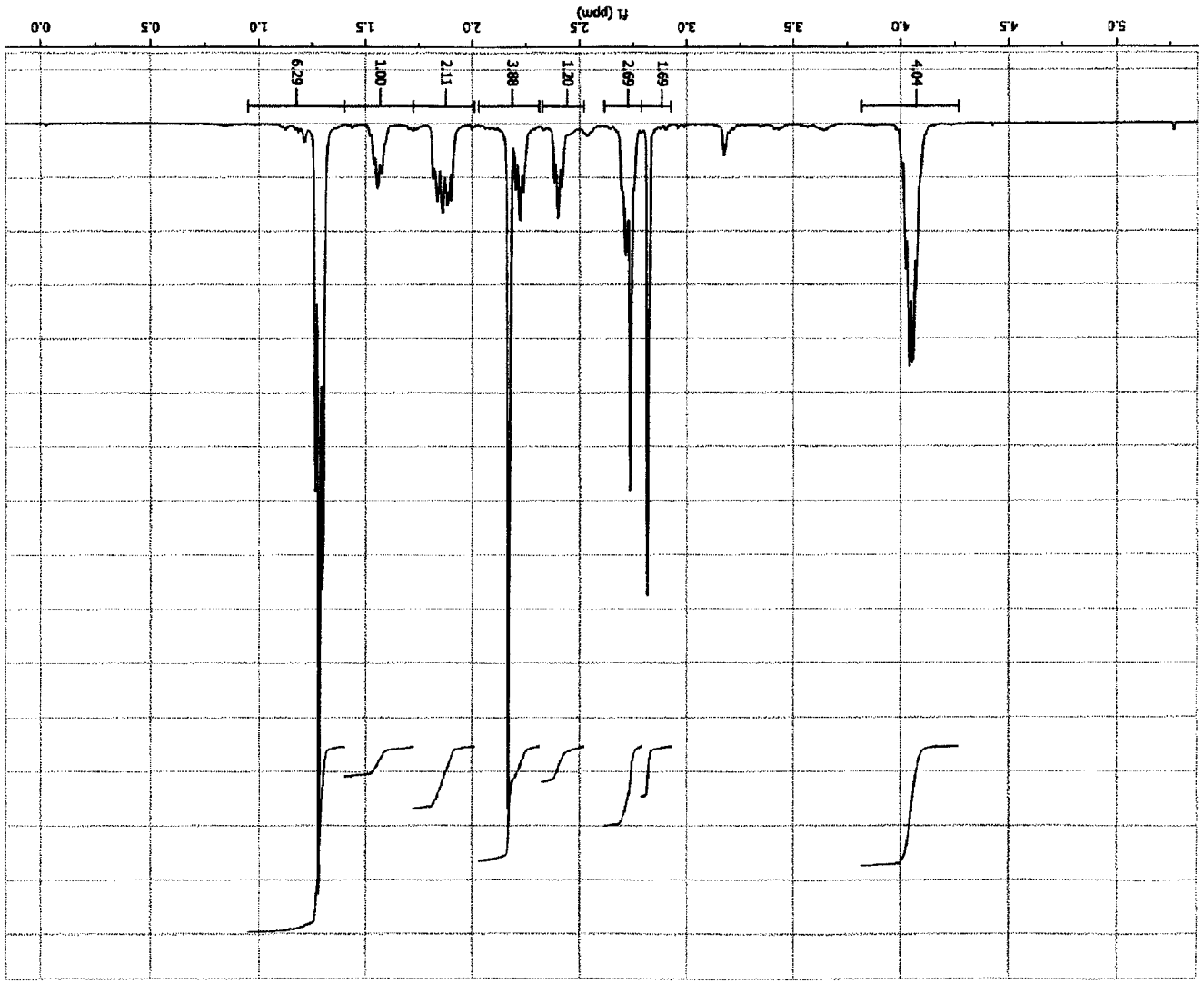
FIG. 33 shows the $^{1}$H NMR of compound (13) of Example 12
Figure 34:
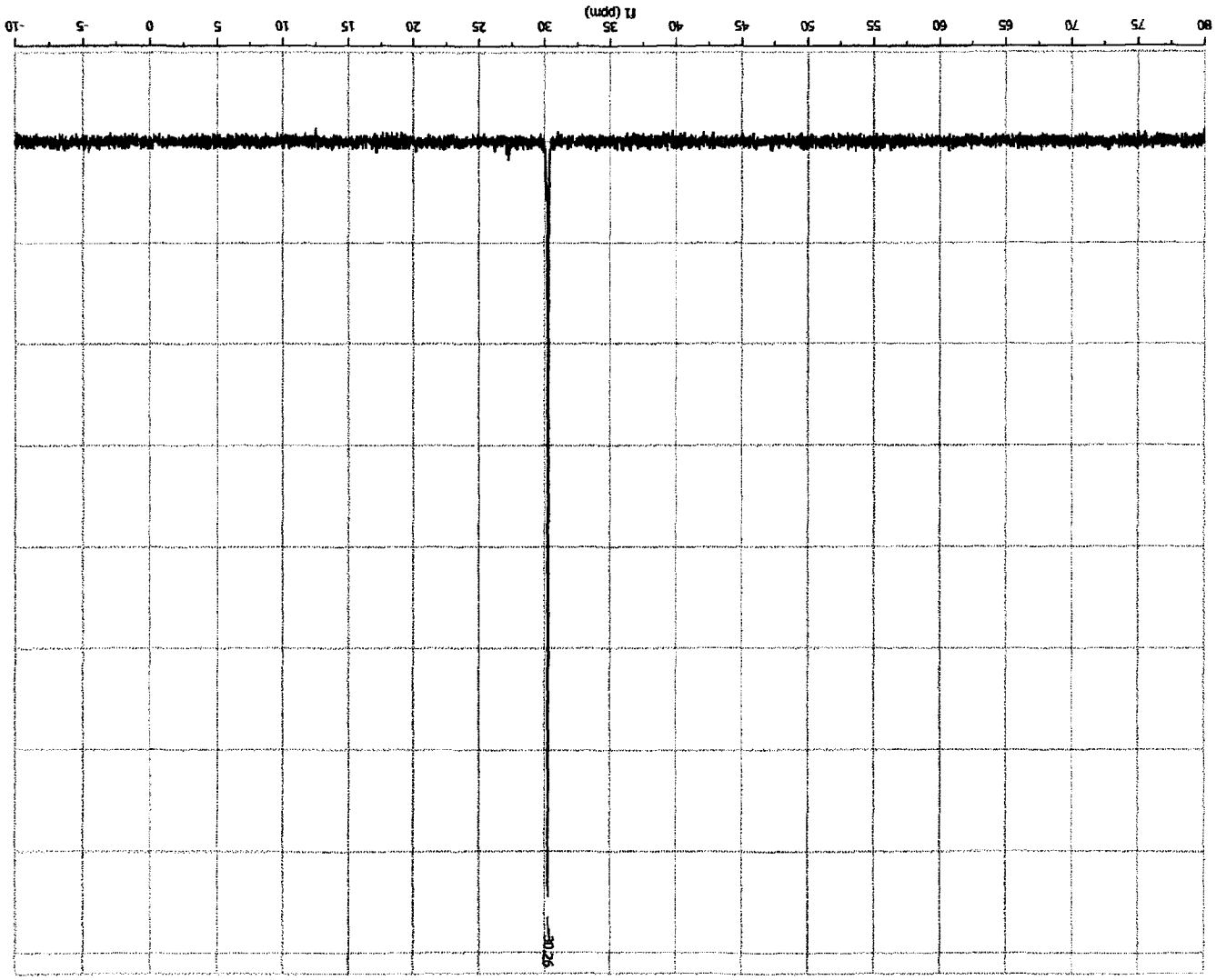
FIG. 34 shows the $^{31}$P NMR of compound (13) of Example 12
Figure 35:
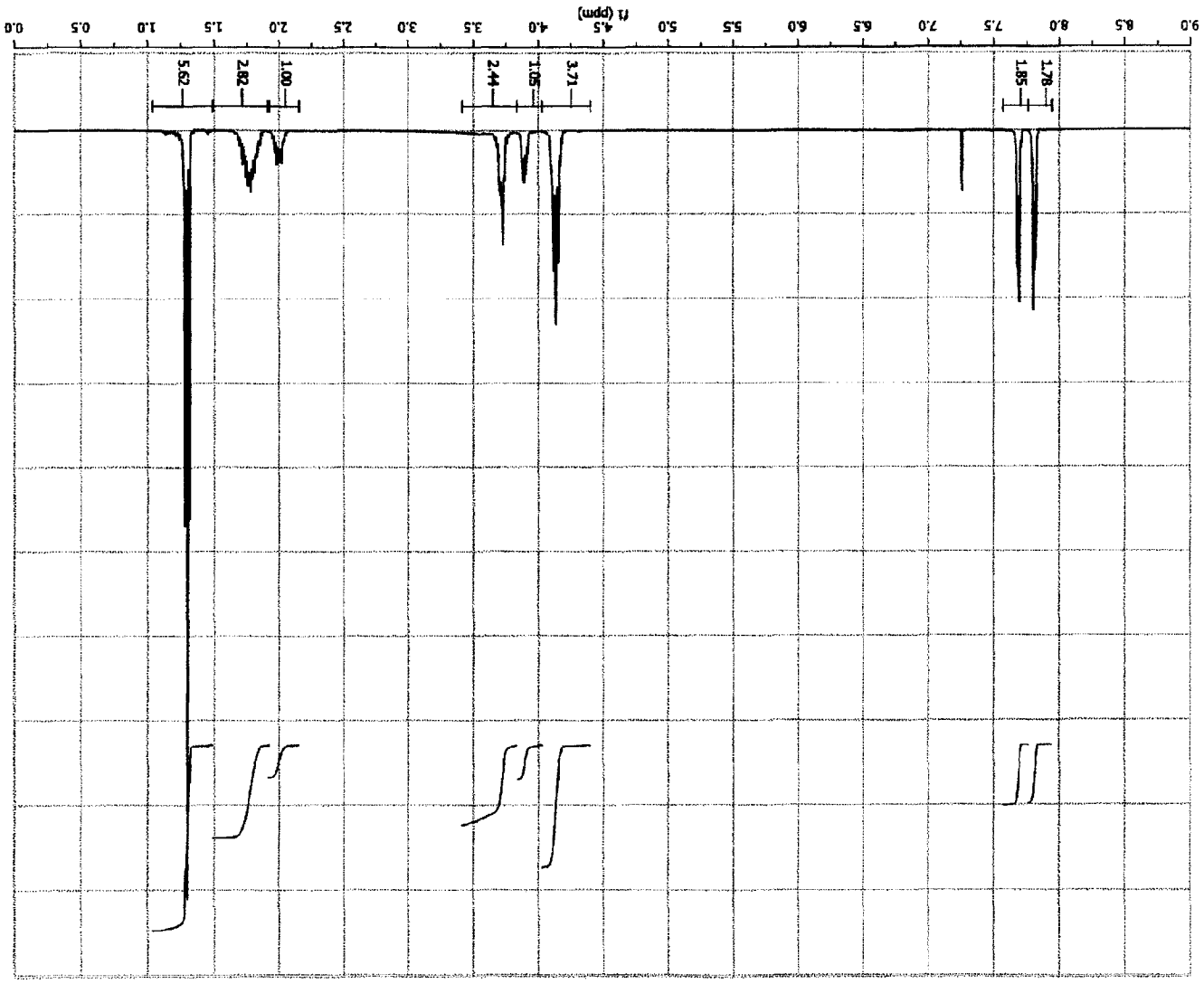
FIG. 35 shows the $^{1}$H NMR of compound (14) of Example 13
Figure 36:
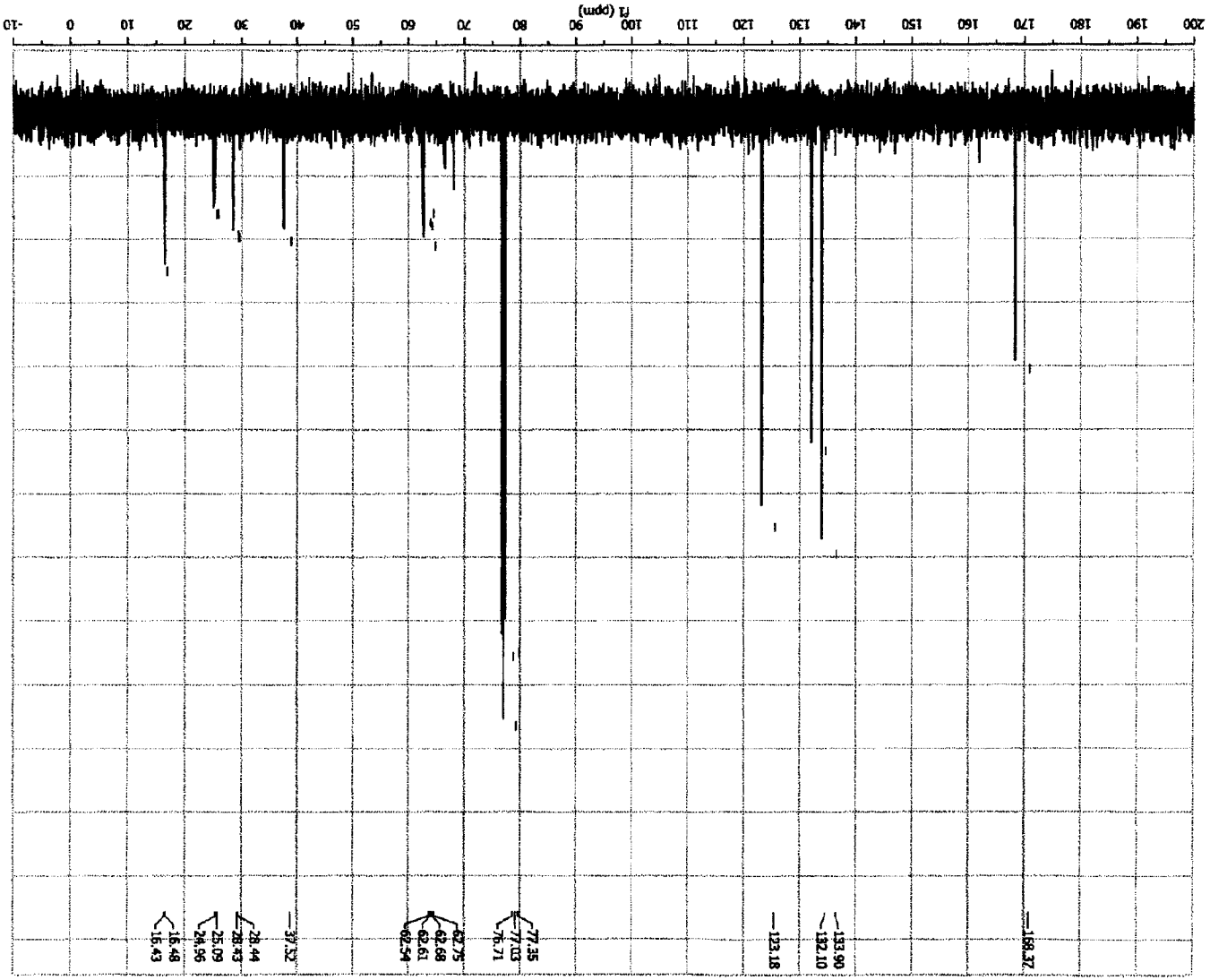
FIG. 36 shows the $^{13}$C NMR of compound (14) of Example 13
Figure 37:
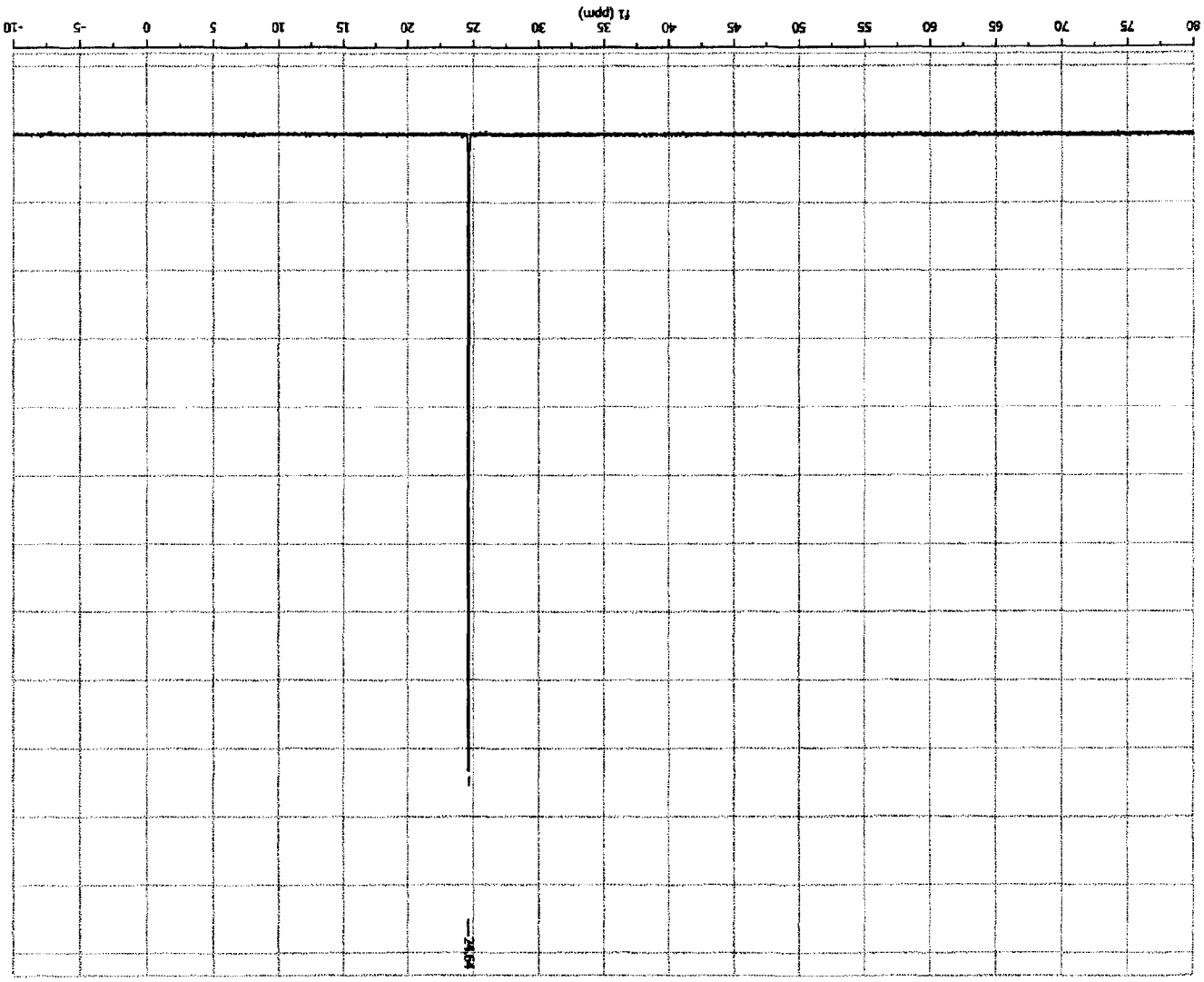
FIG. 37 shows the $^{31}$P NMR of compound (14) of Example 13
Figure 38:
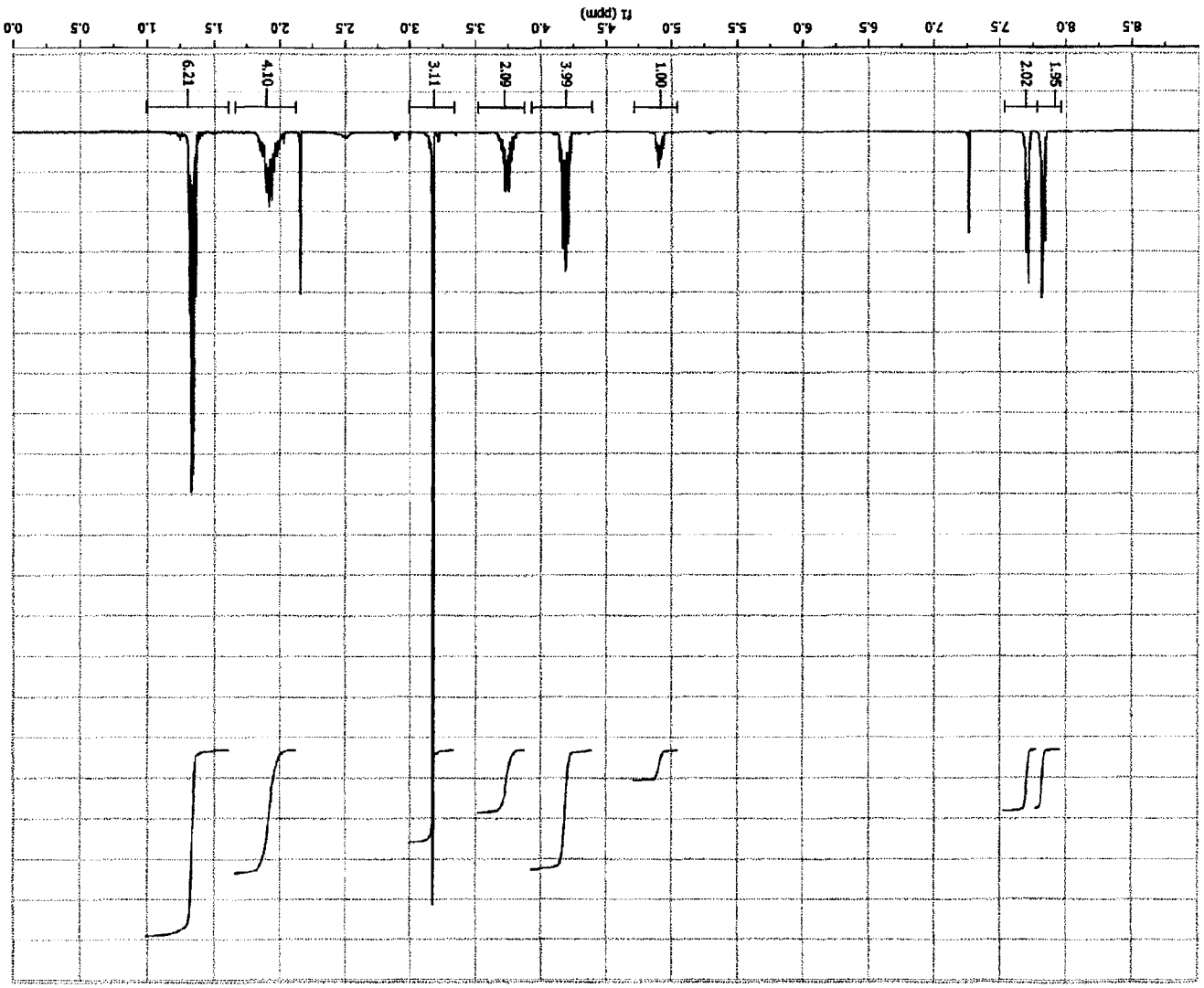
FIG. 38 shows the $^{1}$H NMR of compound (15) of Example 14
Figure 39:
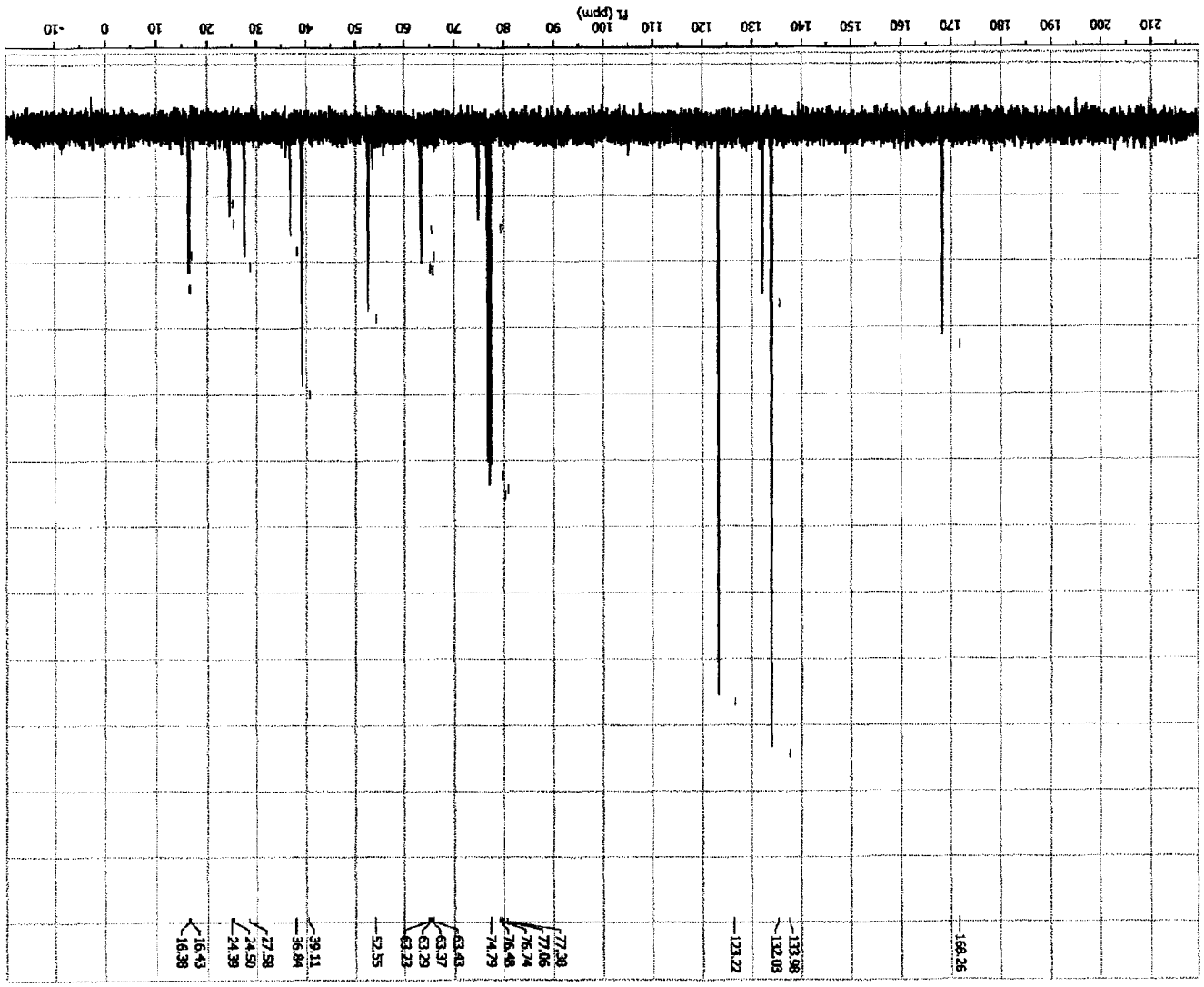
FIG. 39 shows the $^{13}$C NMR of compound (15) of Example 14
Figure 40:
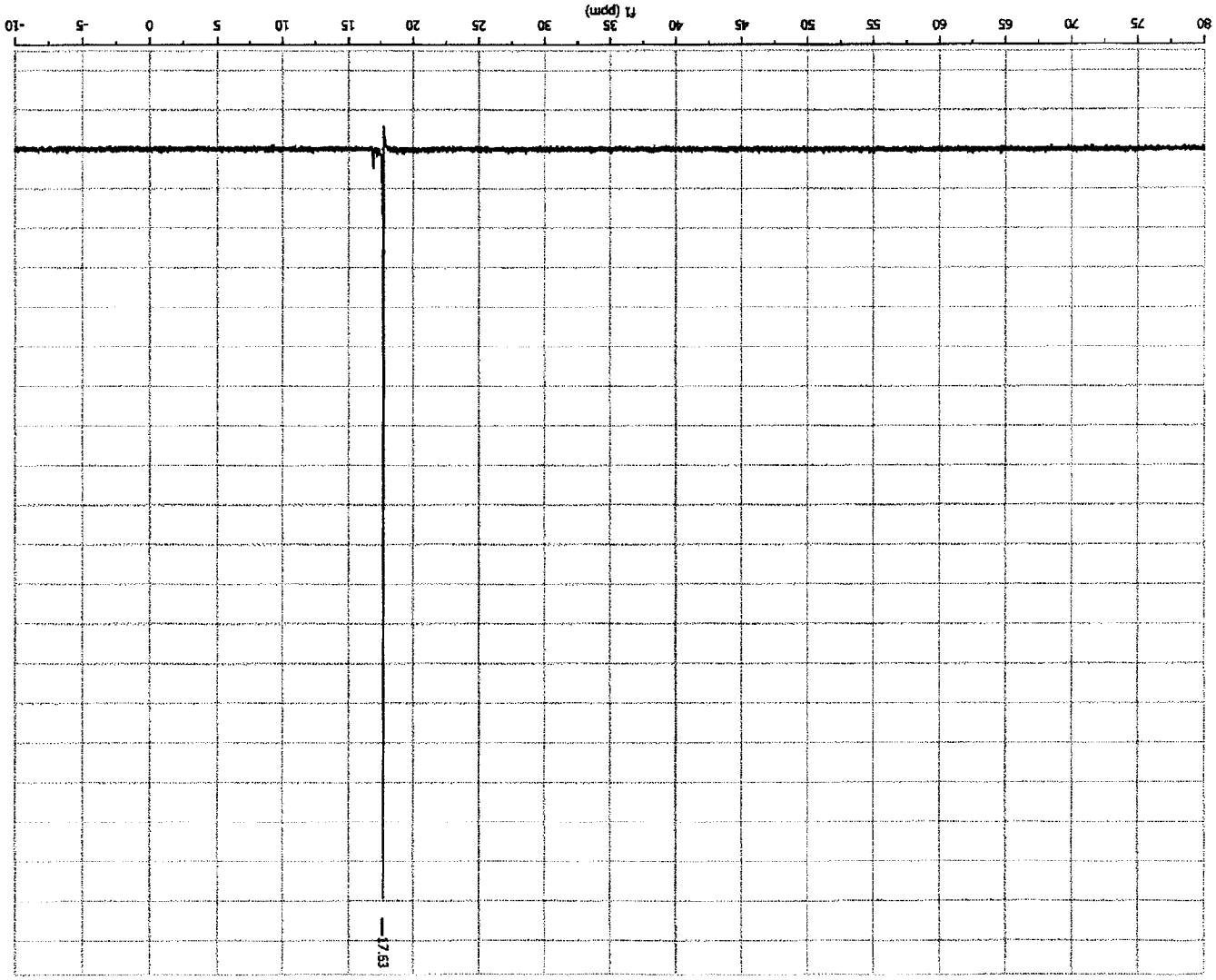
FIG. 40 shows the $^{31}$P NMR of compound (15) of Example 14
Figure 41:
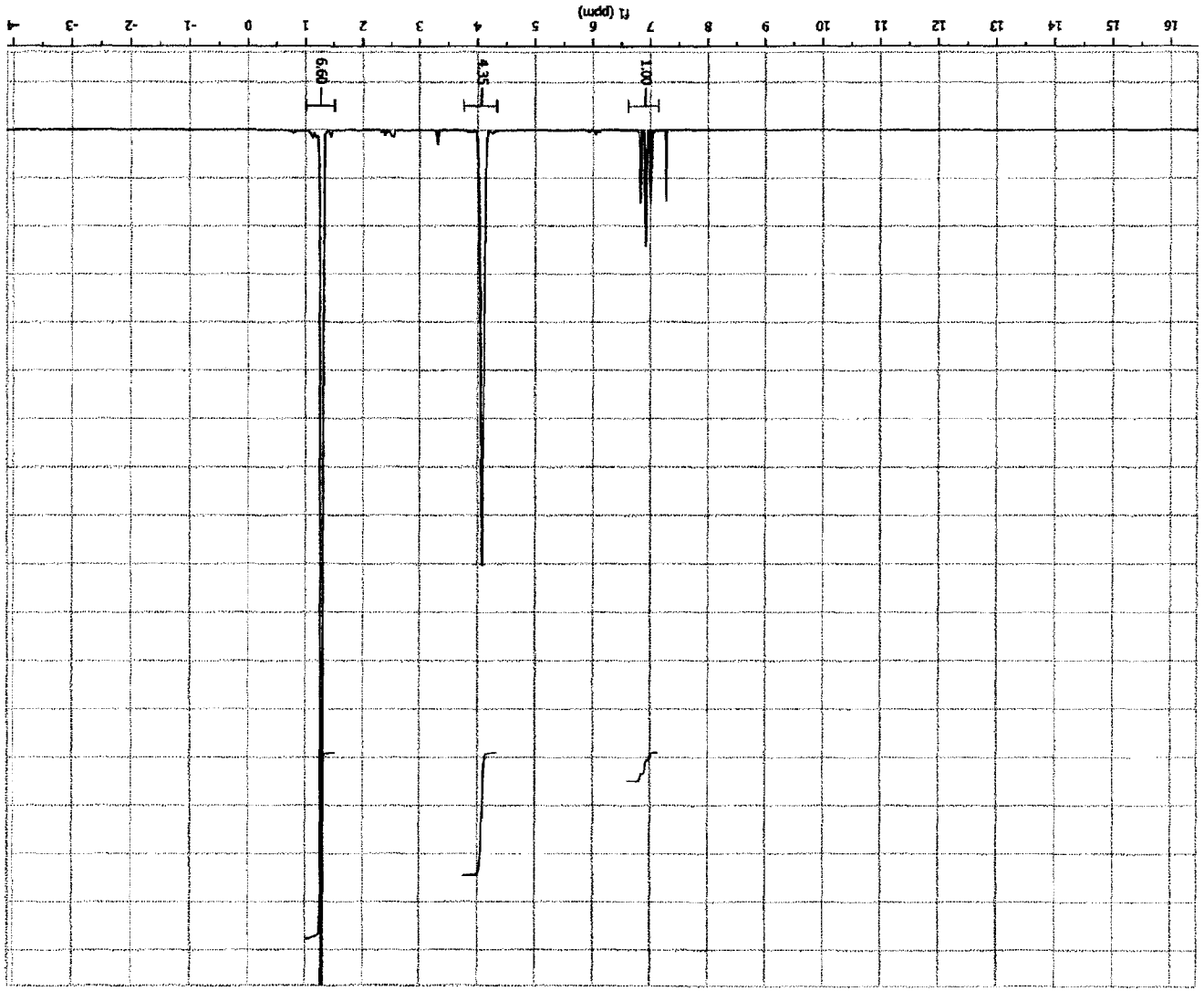
FIG. 41 shows the $^{1}$H NMR of compound (16) of Example 15
Figure 42:
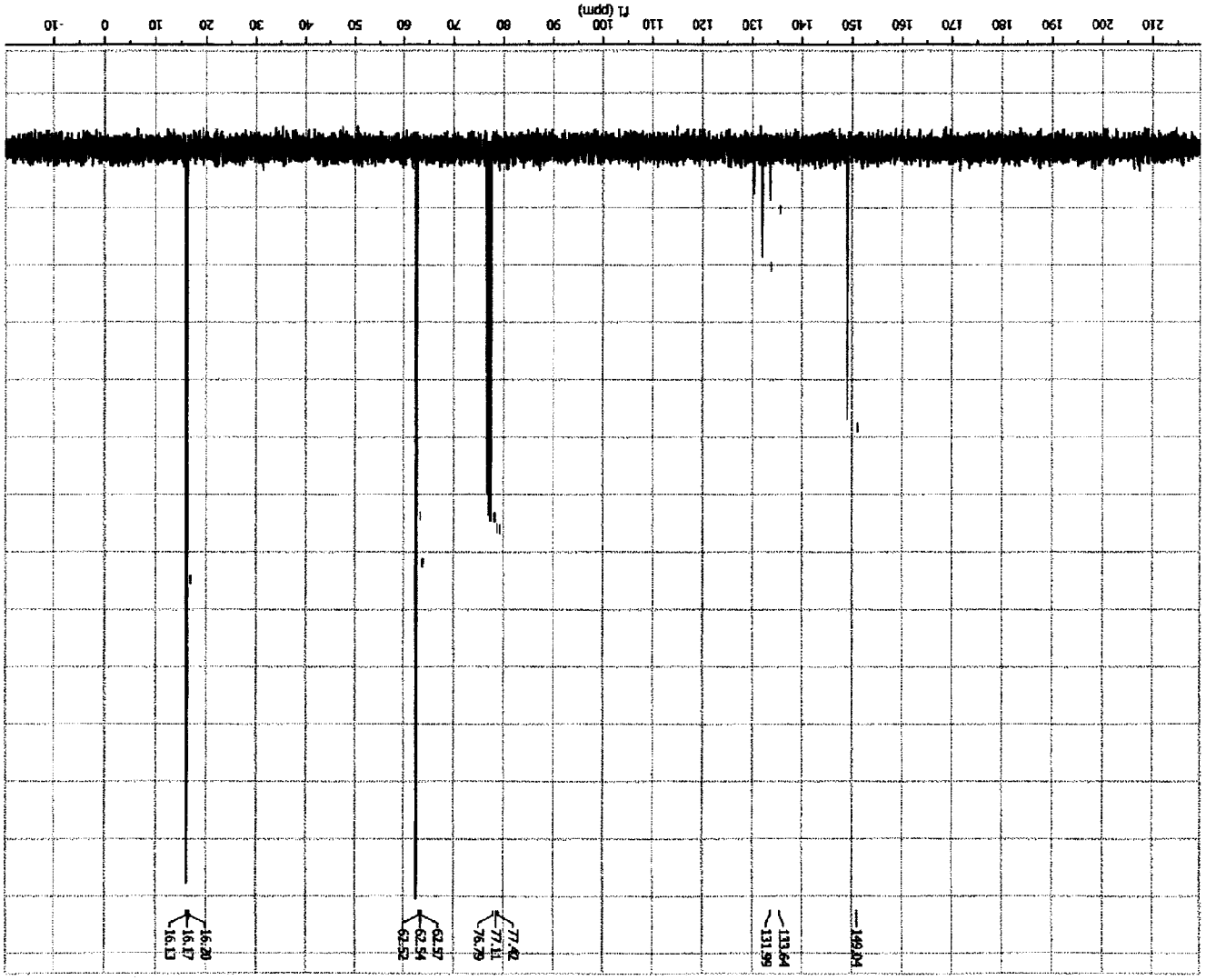
FIG. 42 shows the $^{13}$C NMR of compound (16) of Example 15
Figure 43:
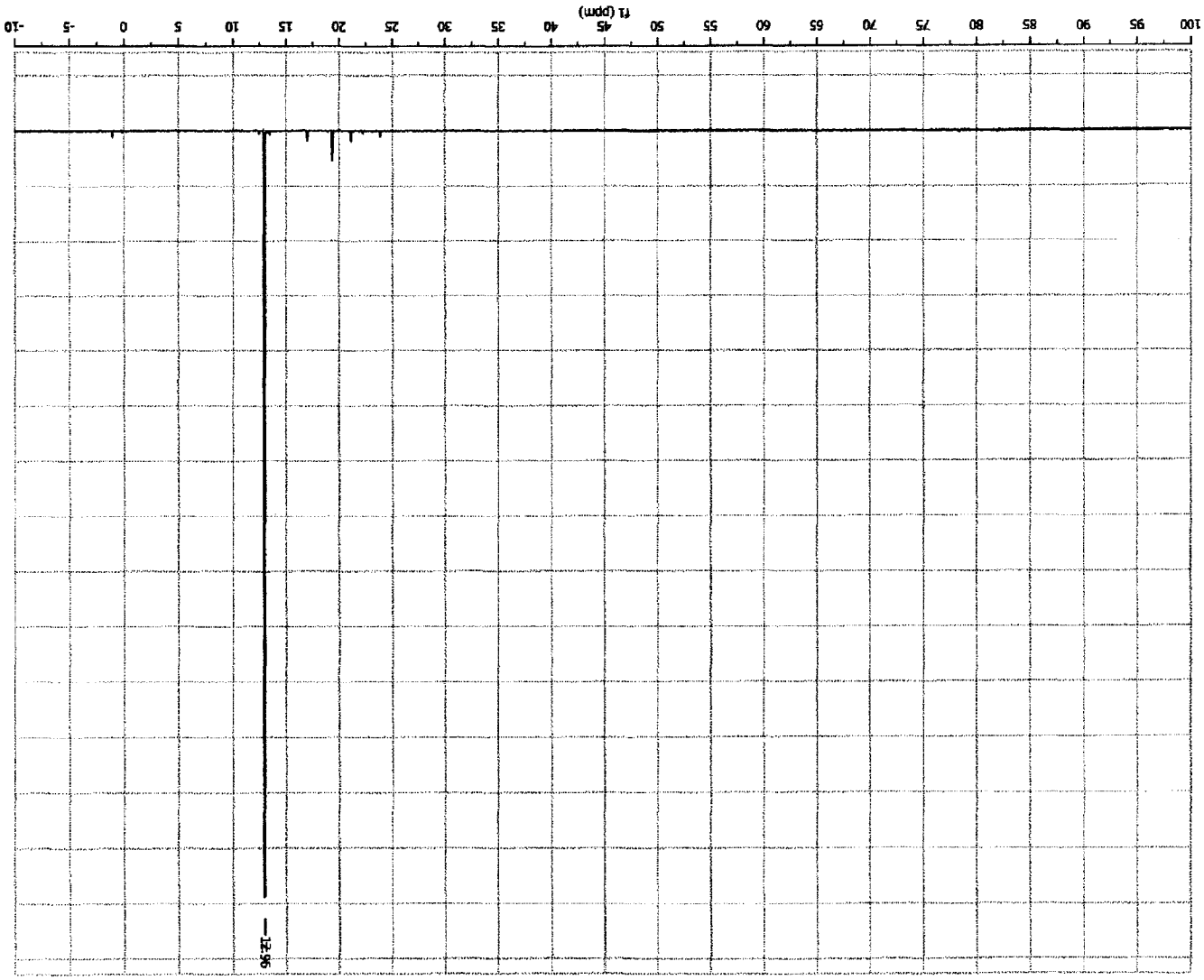
FIG. 43 shows the $^{31}$P NMR of compound (16) of Example 15
Figure 44:
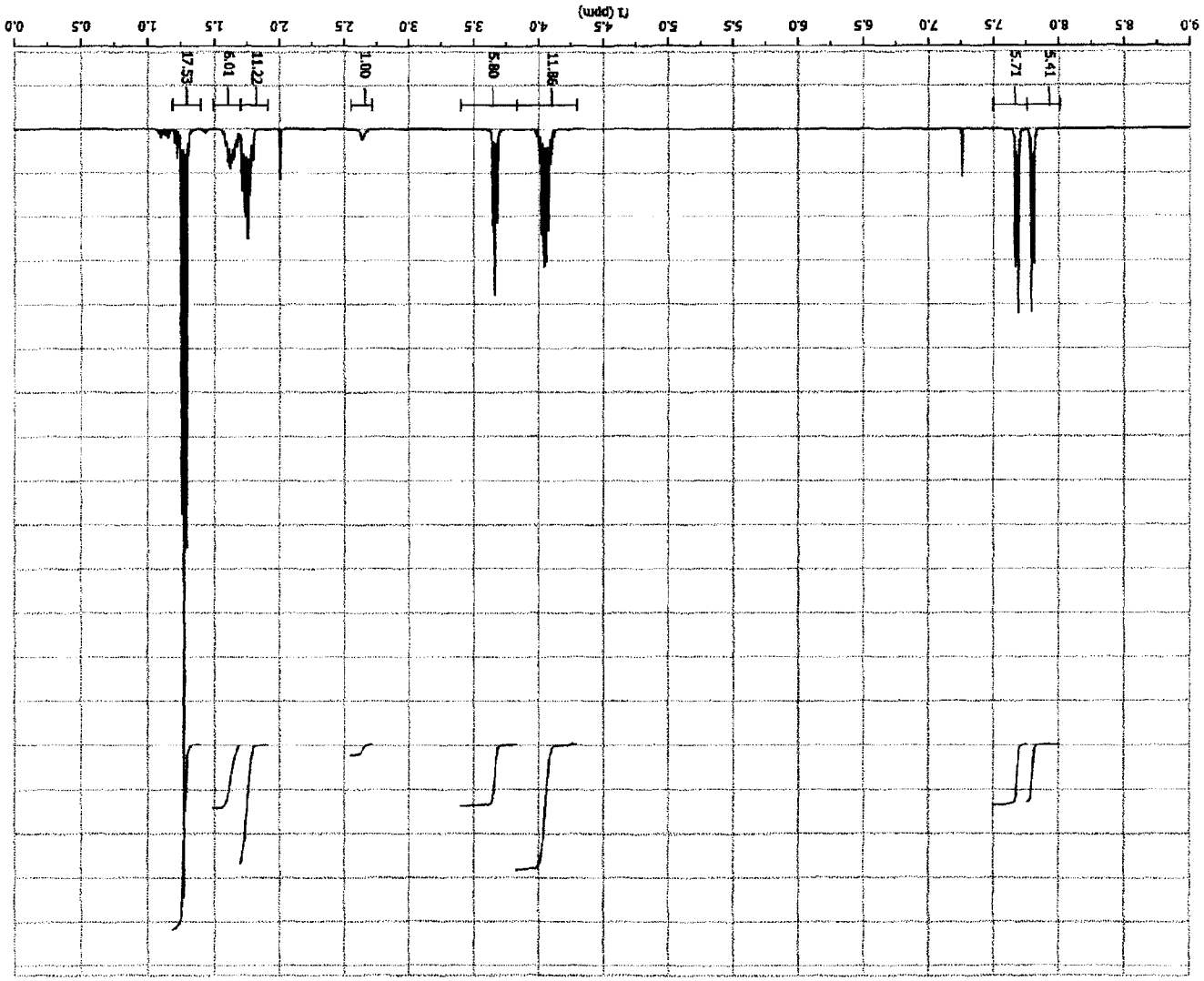
FIG. 44 shows the $^{1}$H NMR of compound (17) of Example 16
Figure 45:
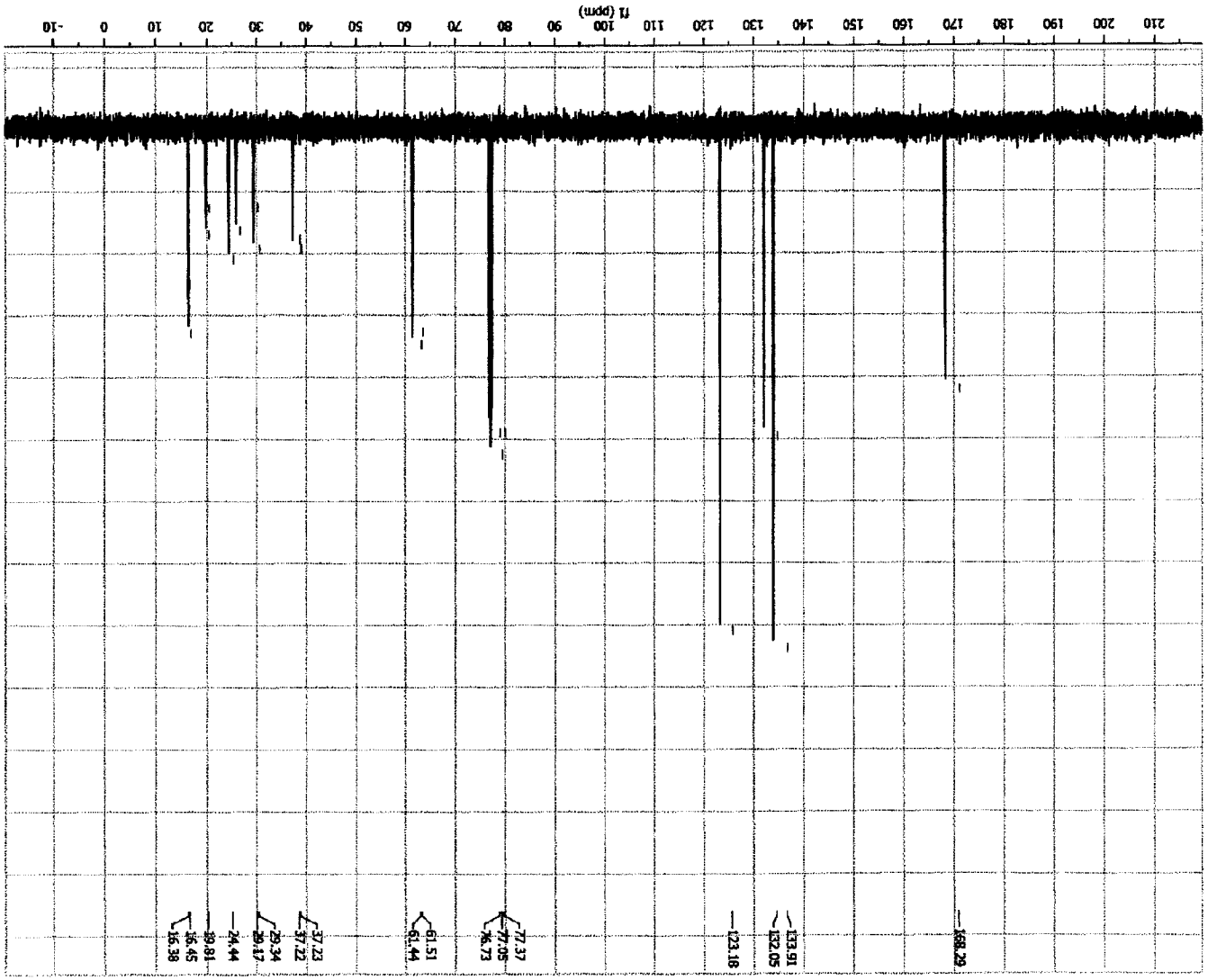
FIG. 45 shows the $^{13}$C NMR of compound (17) of Example 16
Figure 46:
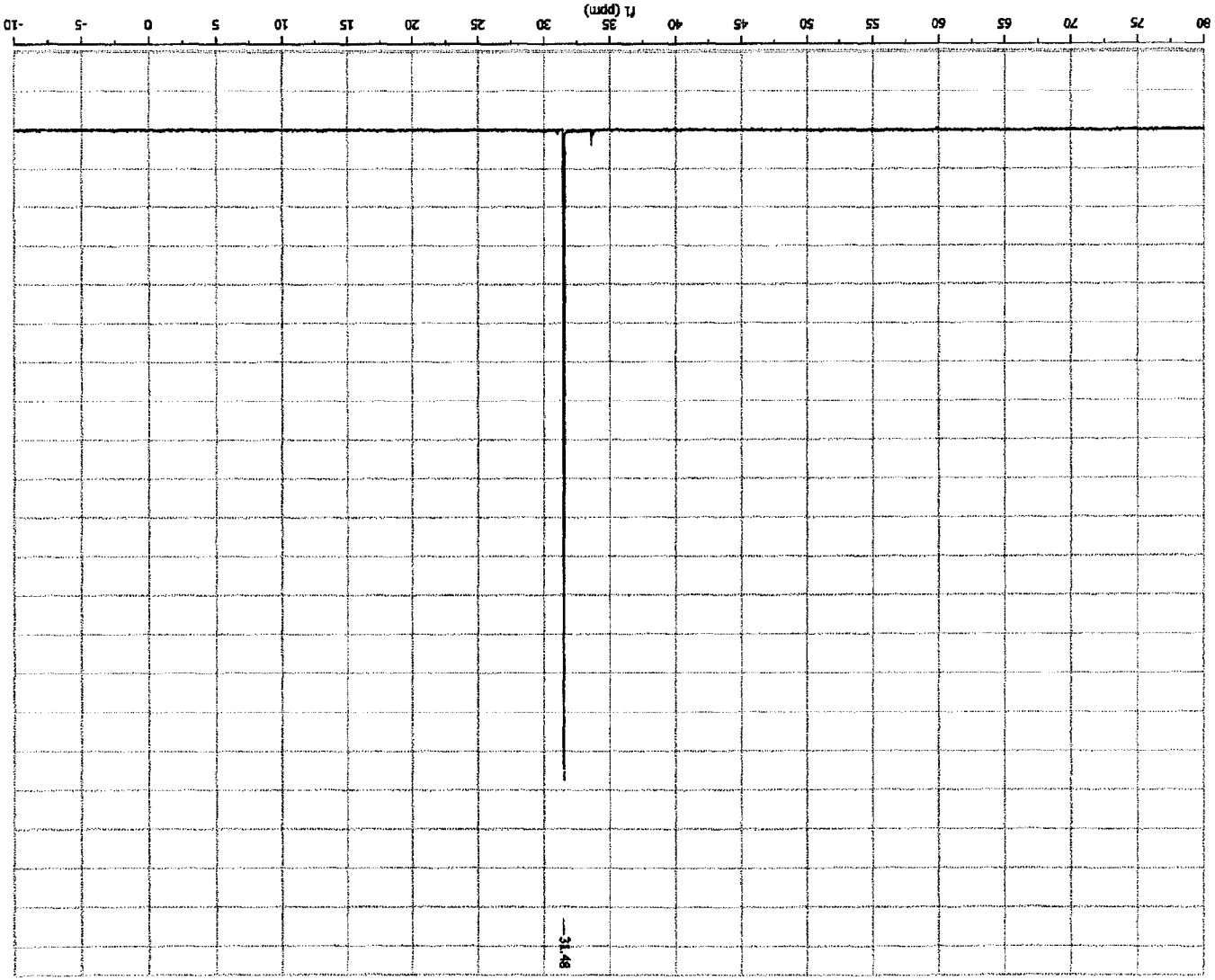
FIG. 46 shows the $^{31}$P NMR of compound (17) of Example 16
Figure 47:
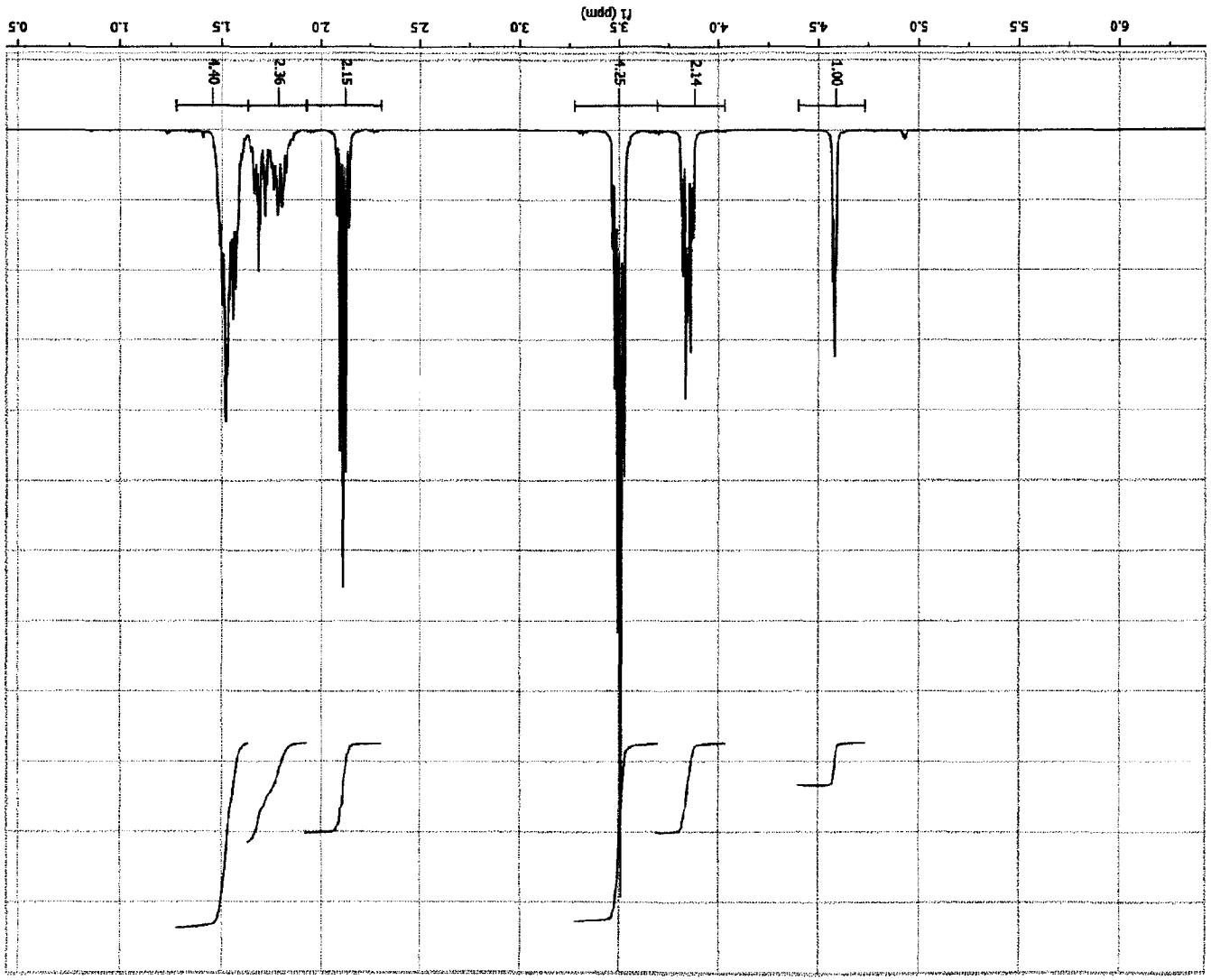
FIG. 47 shows the $^{1}$H NMR of compound (18) of Example 17
Figure 48:
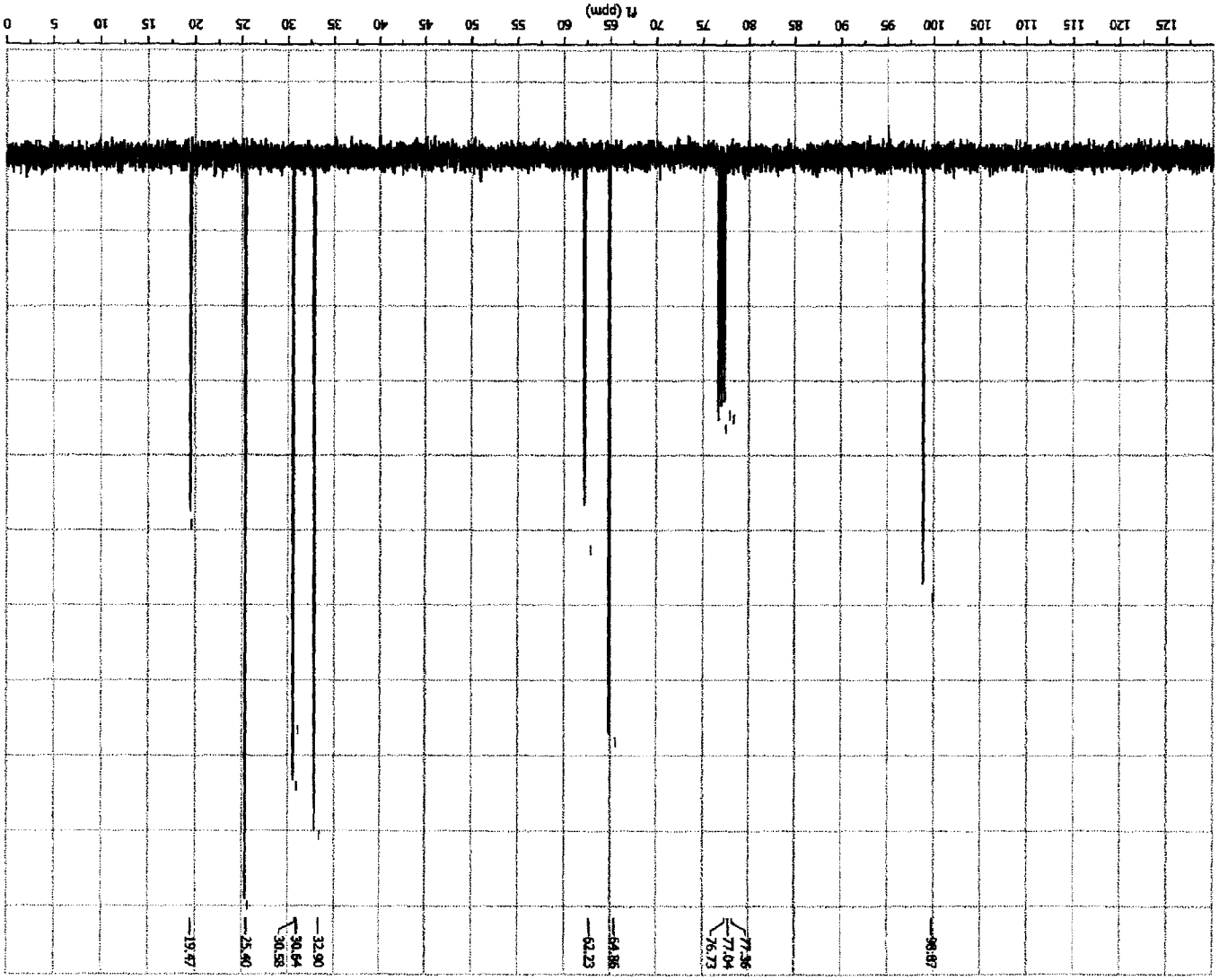
FIG. 48 shows the $^{13}$C NMR of compound (18) of Example 17
Figure 49:
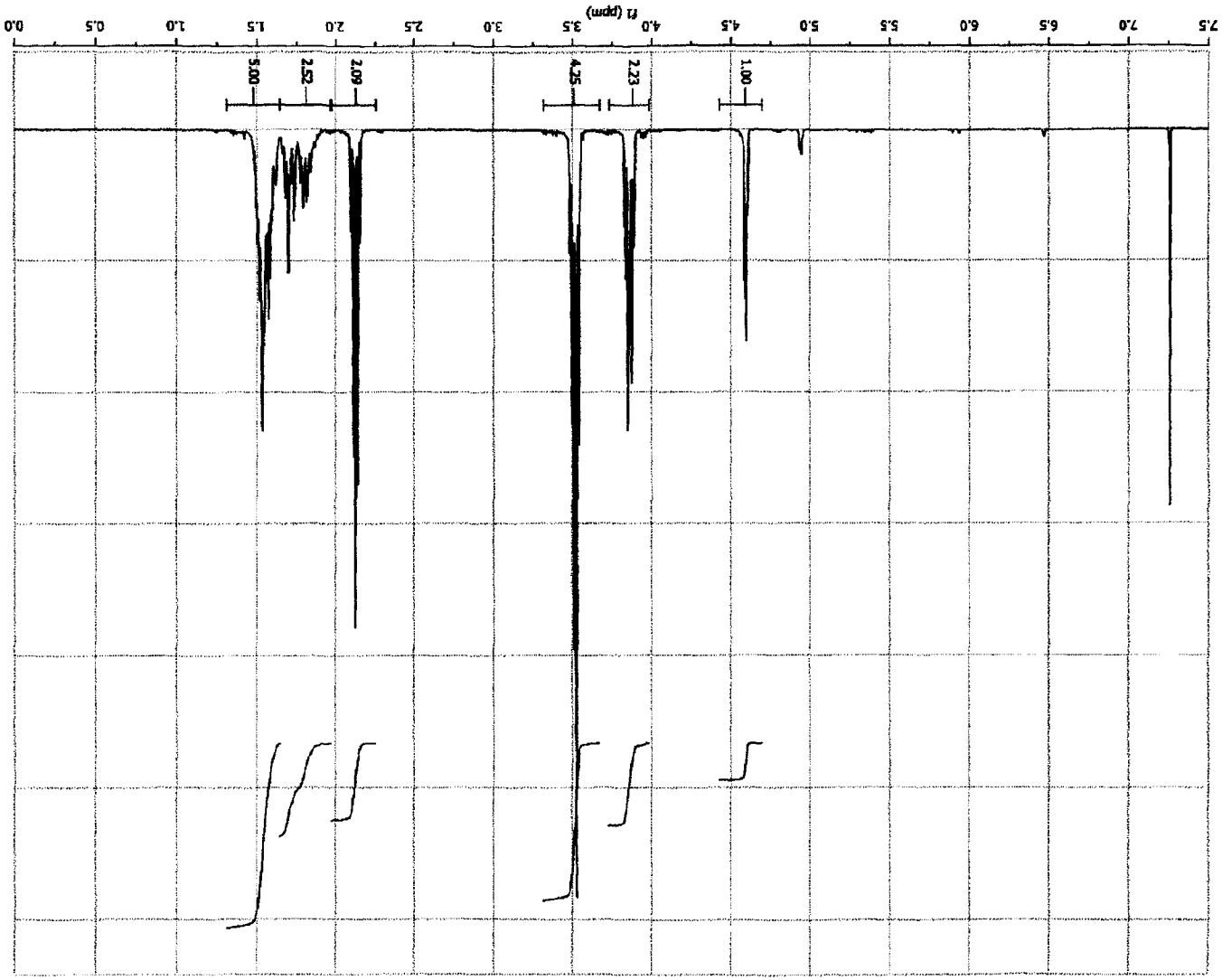
FIG. 49 shows the $^{1}$H NMR of compound (19) of Example 18
Figure 50:
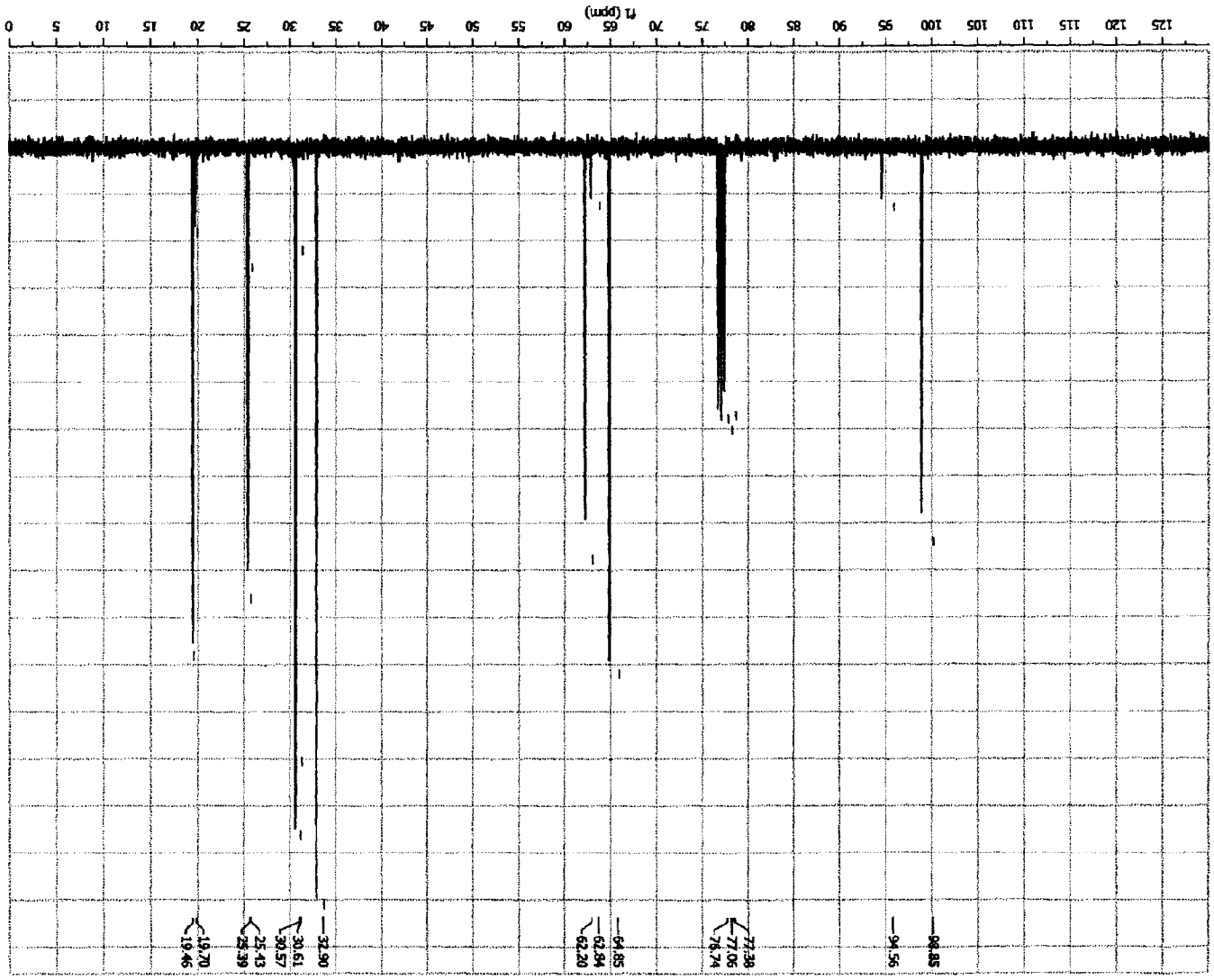
FIG. 50 shows the $^{13}$C NMR of compound (19) of Example 18
Figure 51:
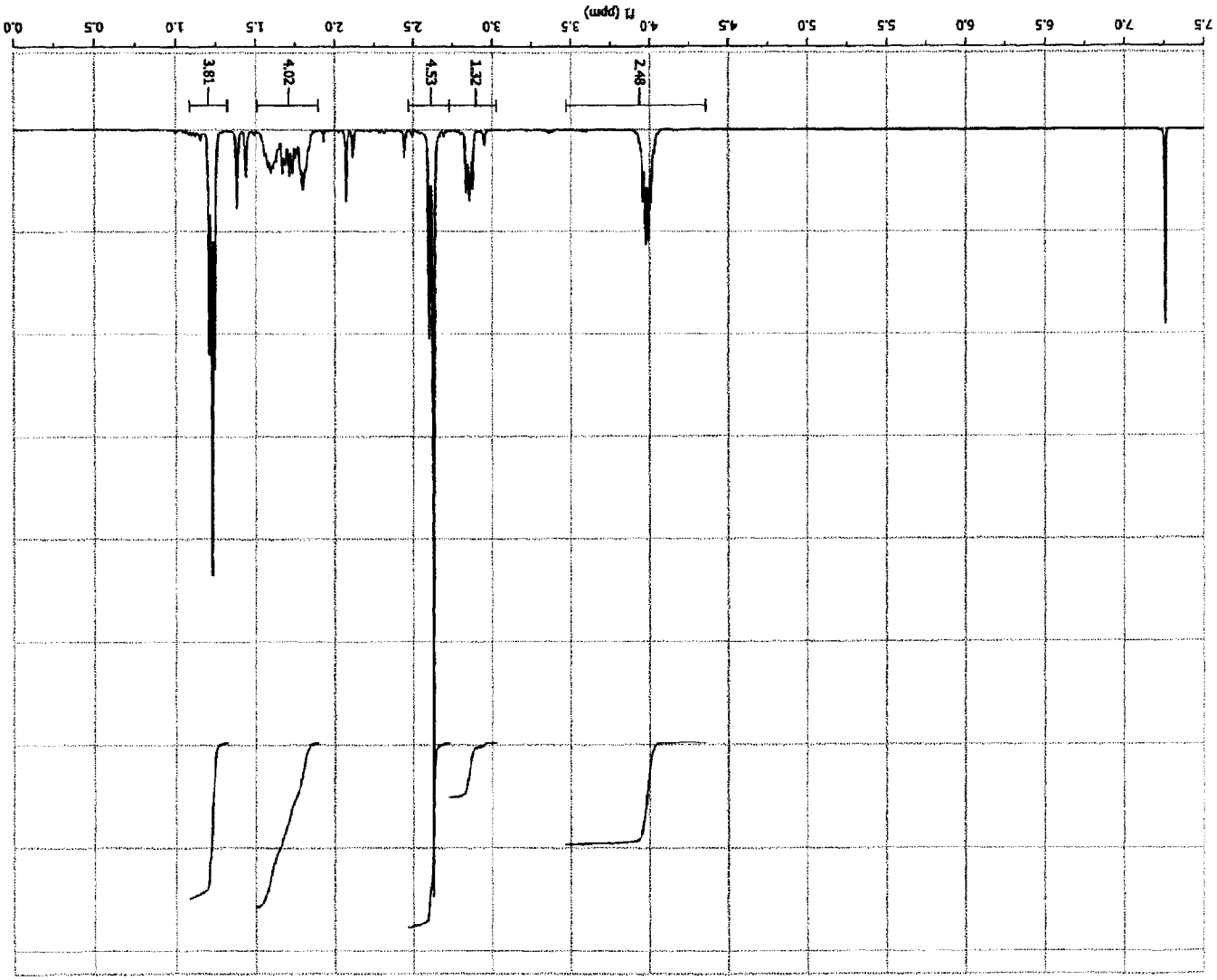
FIG. 51 shows the $^{1}$H NMR of compound (20) of Example 19
Figure 52:
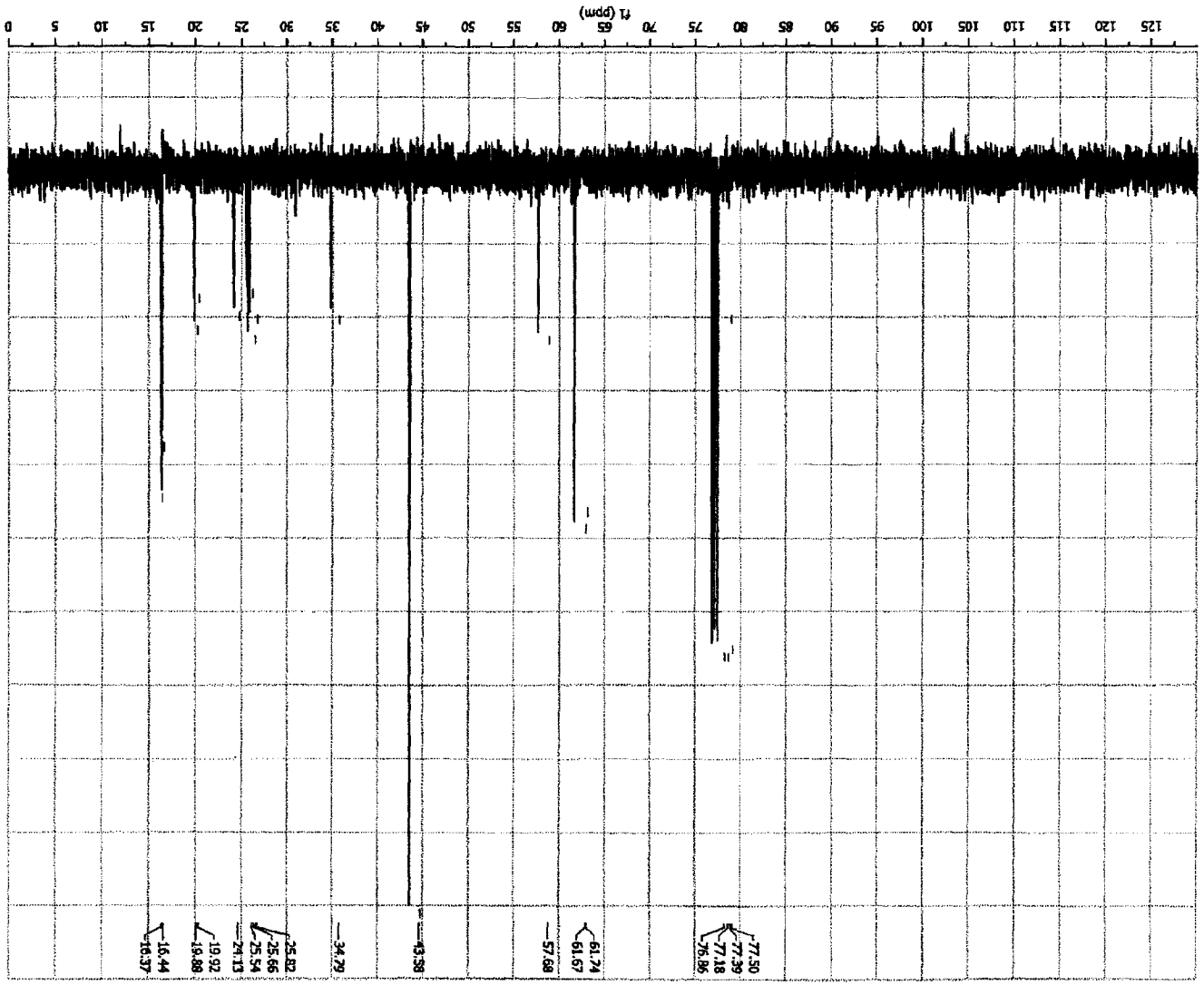
FIG. 52 shows the $^{13}$C NMR of compound (20) of Example 19
Figure 53:
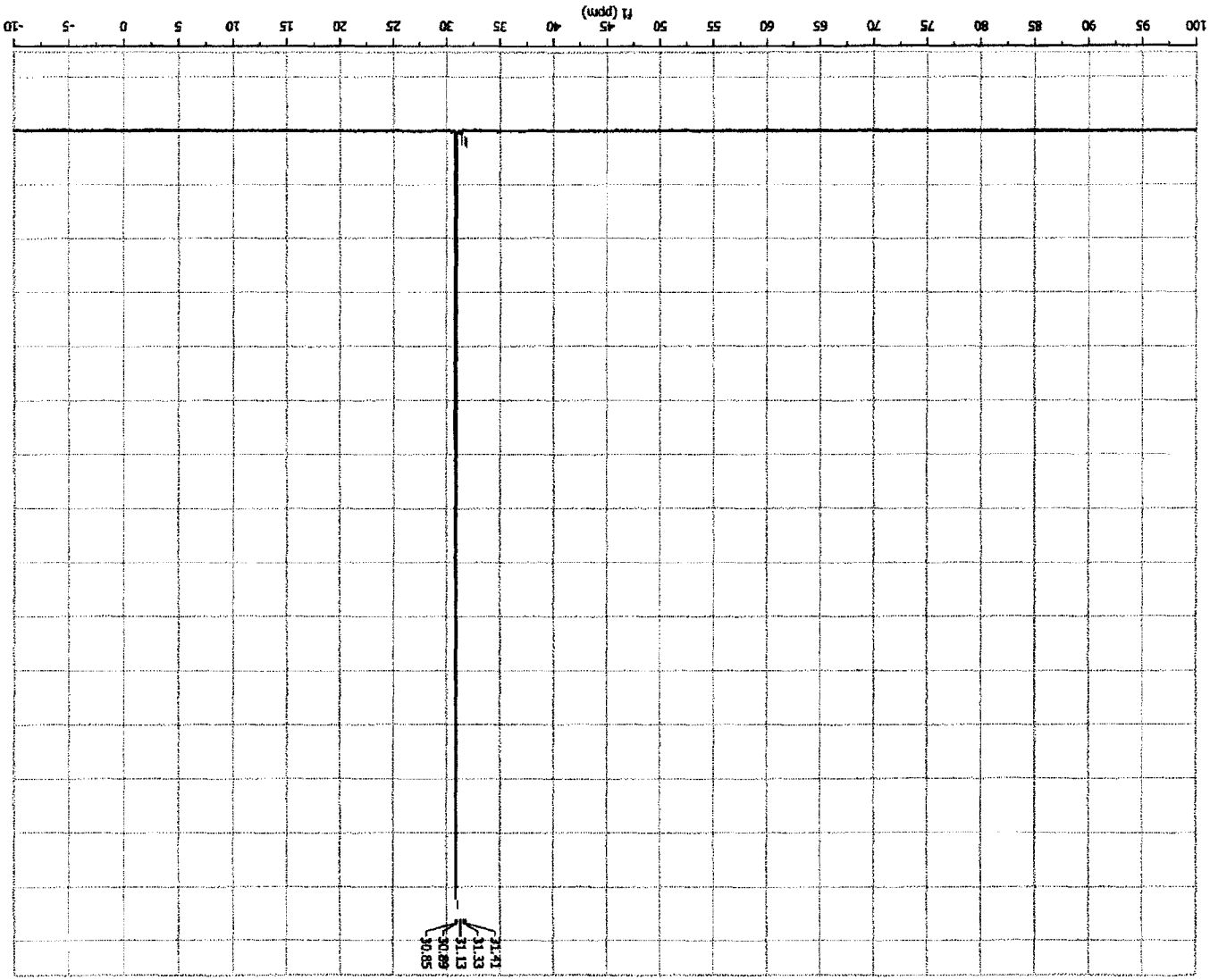
FIG. 53 shows the $^{31}$P NMR of compound (20) of Example 19
Figure 54:
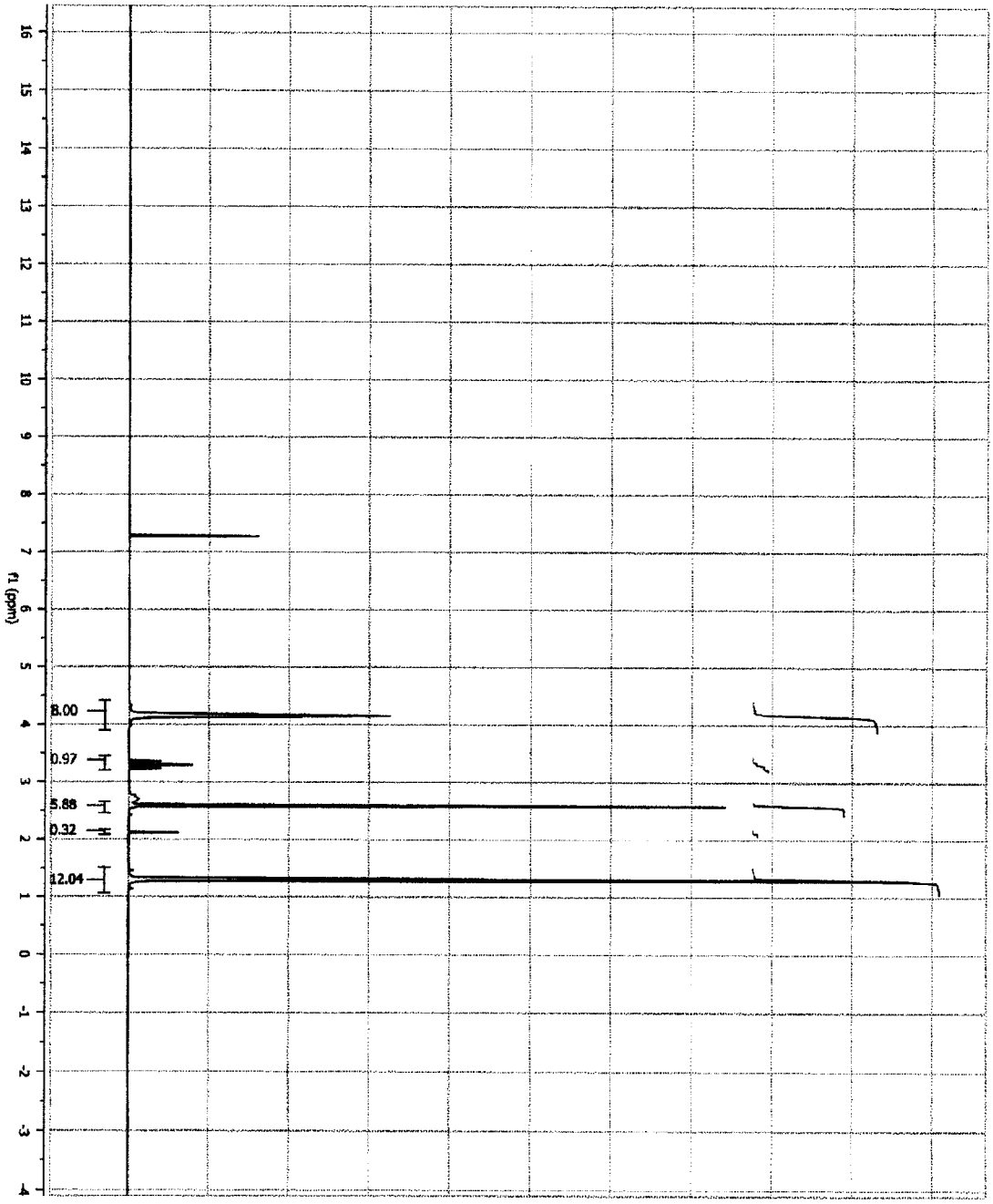
FIG. 54 shows the $^{1}H$ NMR of compound (21) of Example 20
Figure 55:
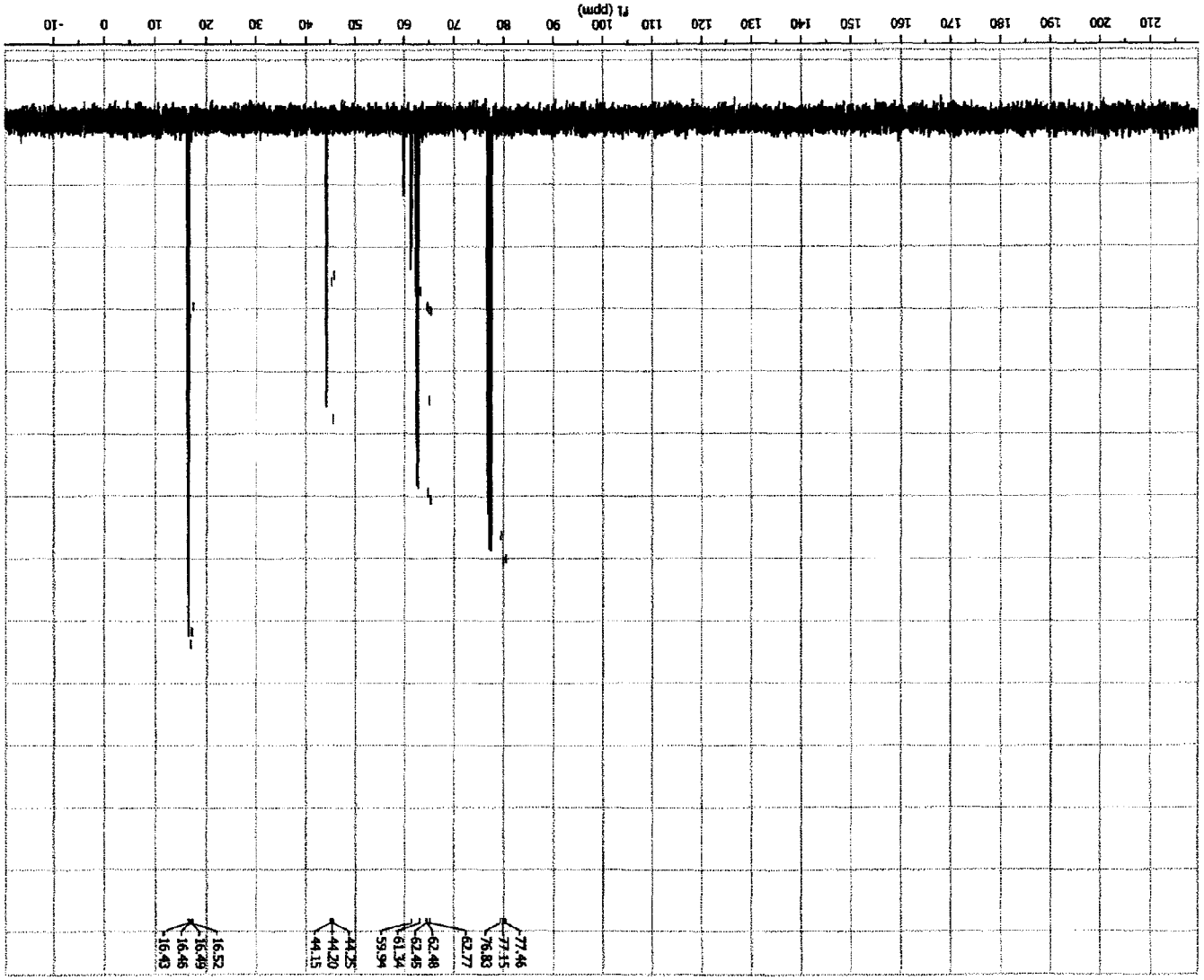
FIG. 55 shows the $^{13}C$ NMR of compound (21) of Example 20
Figure 56:
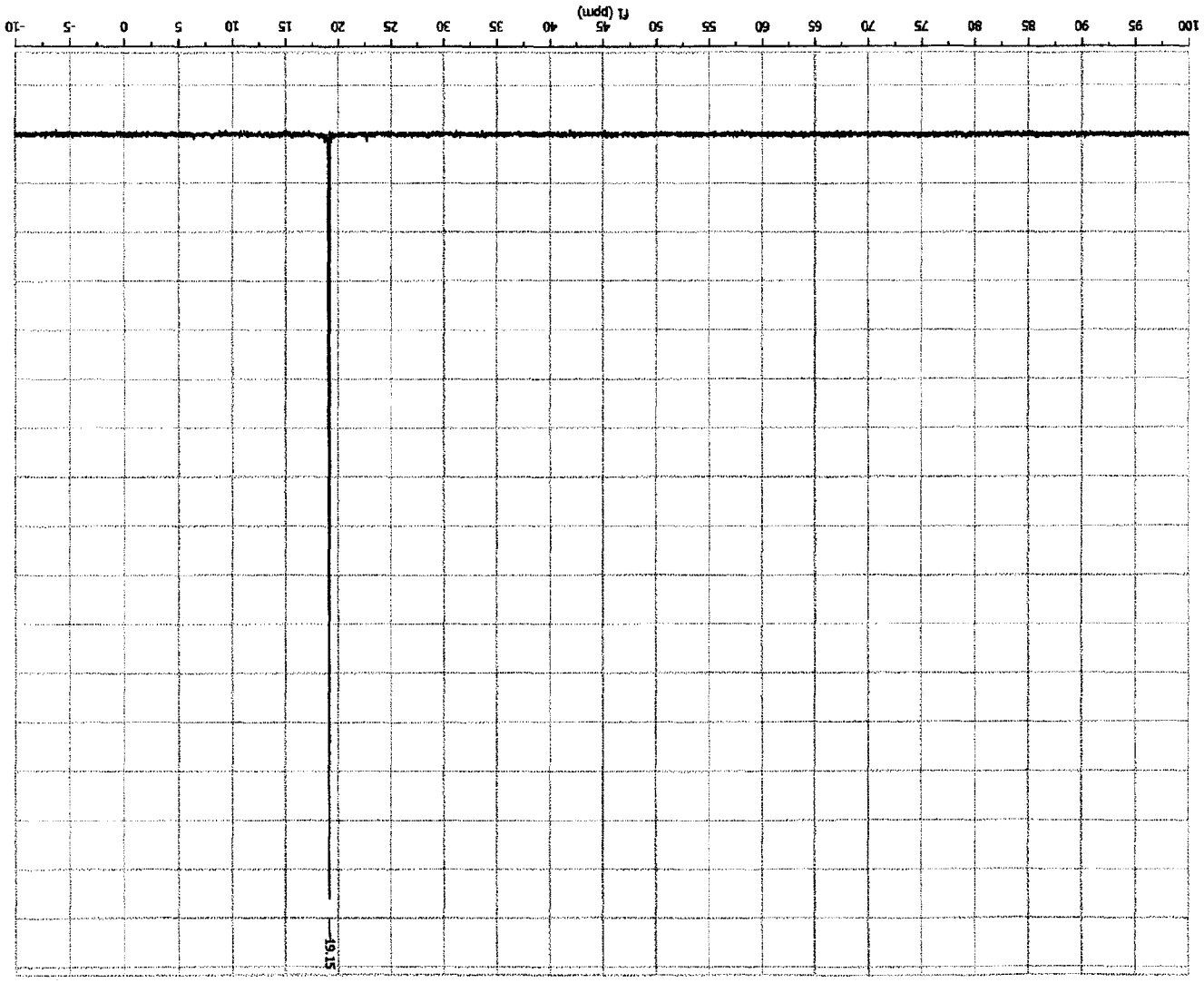
FIG. 56 shows the $^{31}P$ NMR of compound (21) of Example 20
Figure 57:
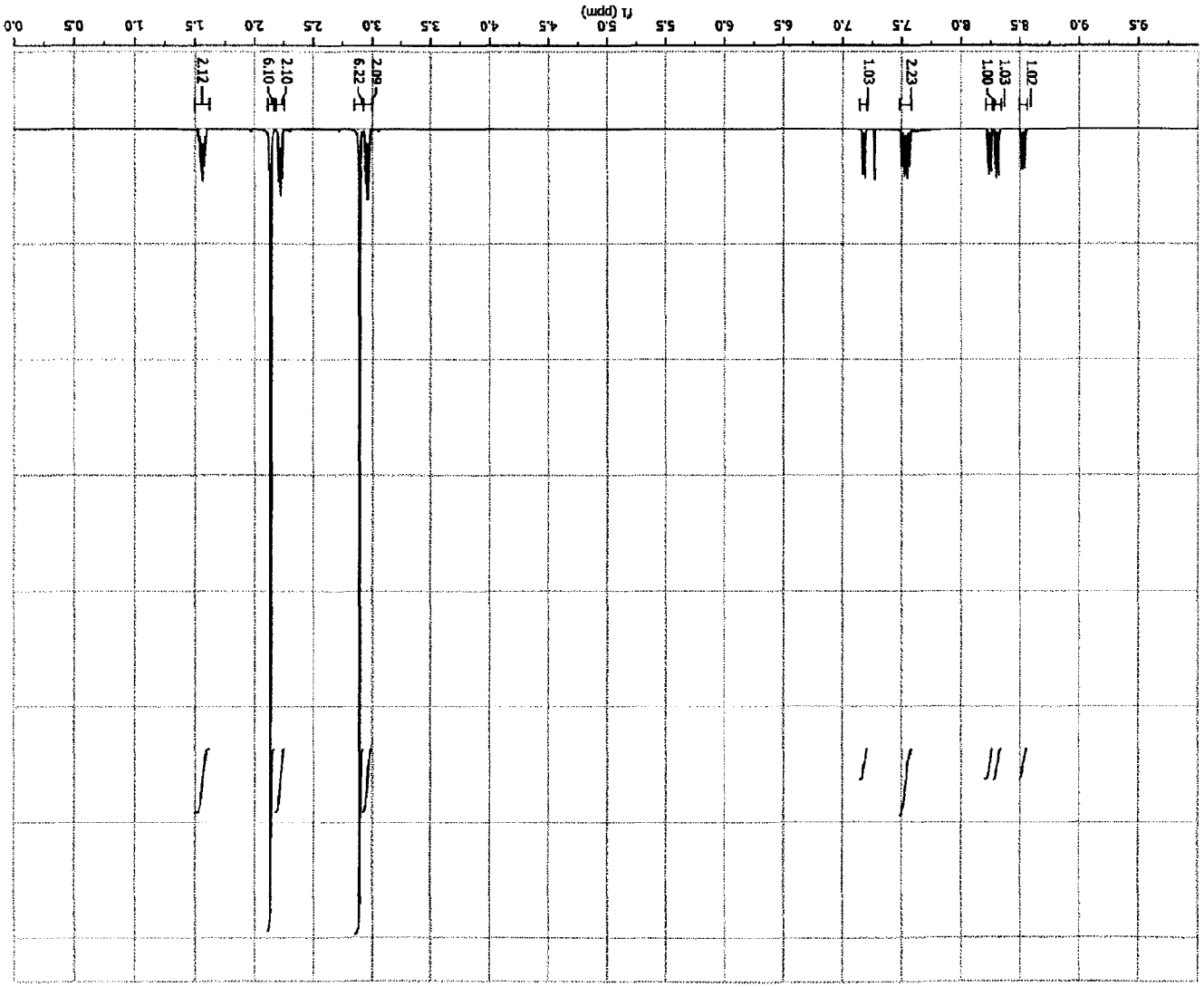
FIG. 57 shows the $^{1}H$ NMR of compound (30) of Example 21
Figure 58:
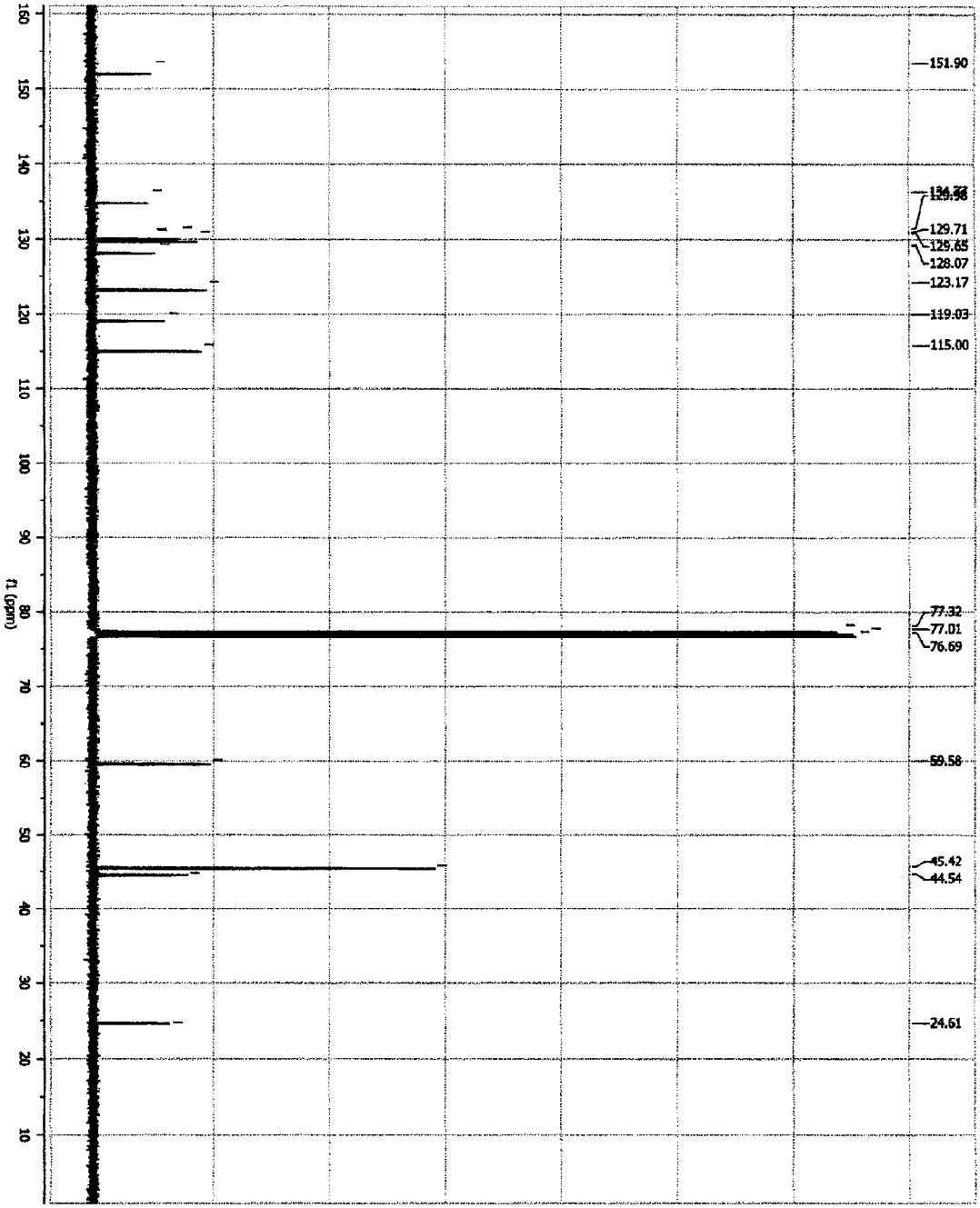
FIG. 58 shows the $^{13}C$ NMR of compound (30) of Example 21
Figure 59:
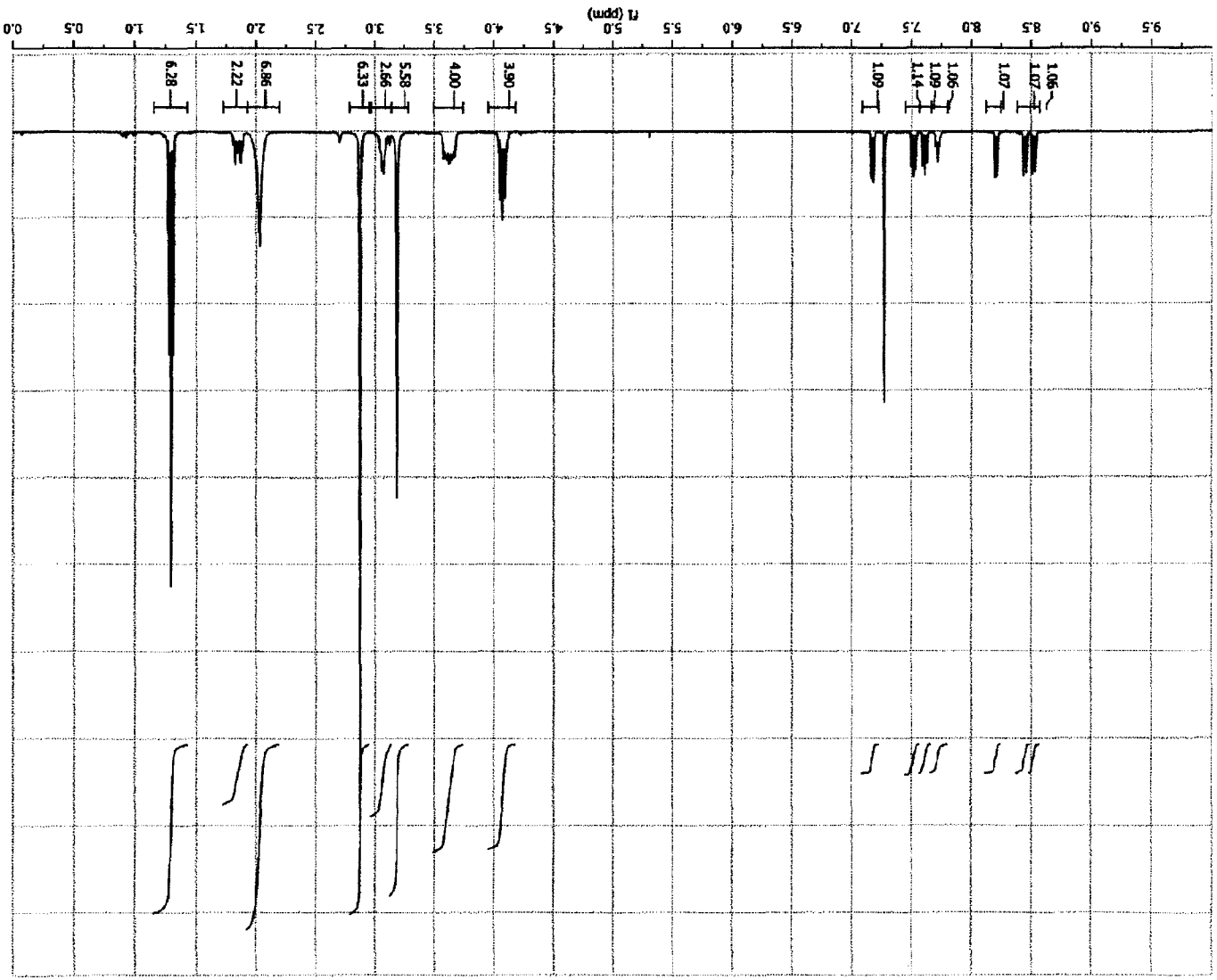
FIG. 59 shows the $^{1}H$ NMR of compound (31) of Example 22
Figure 60:
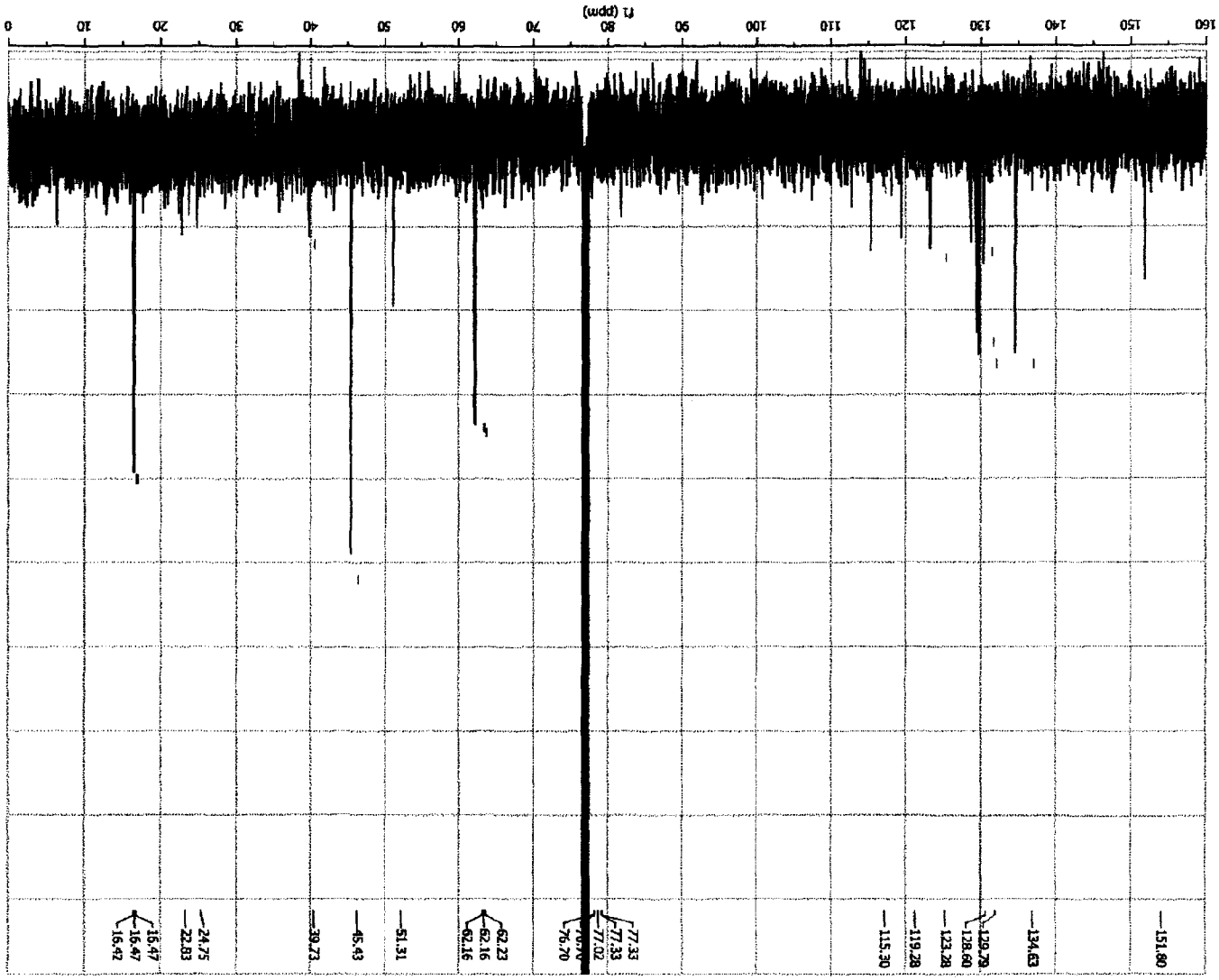
FIG. 60 shows the $^{13}C$ NMR of compound (31) of Example 22
Figure 61:
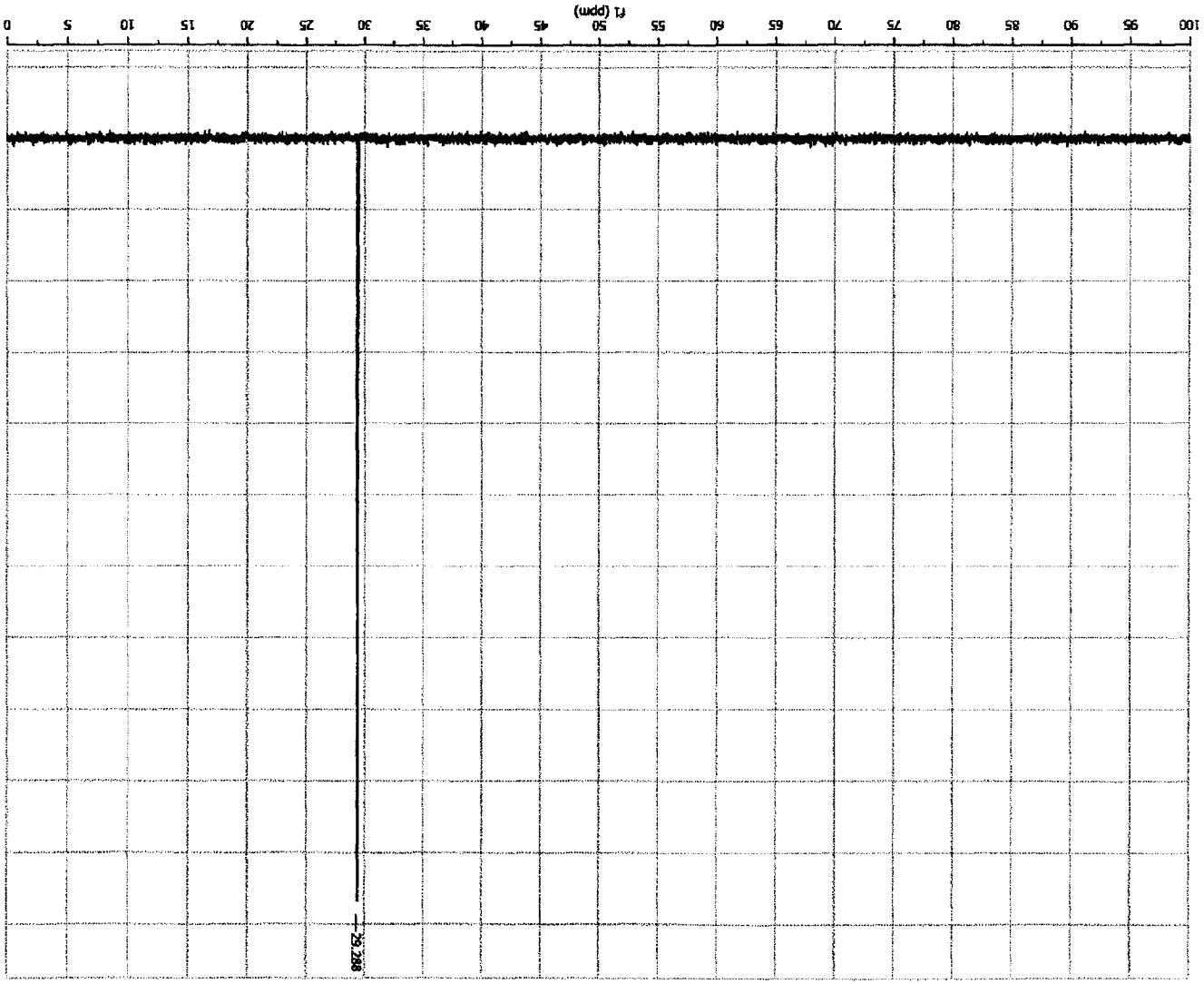
FIG. 61 shows the $^{31}P$ NMR of compound (31) of Example 22
Figure 62:
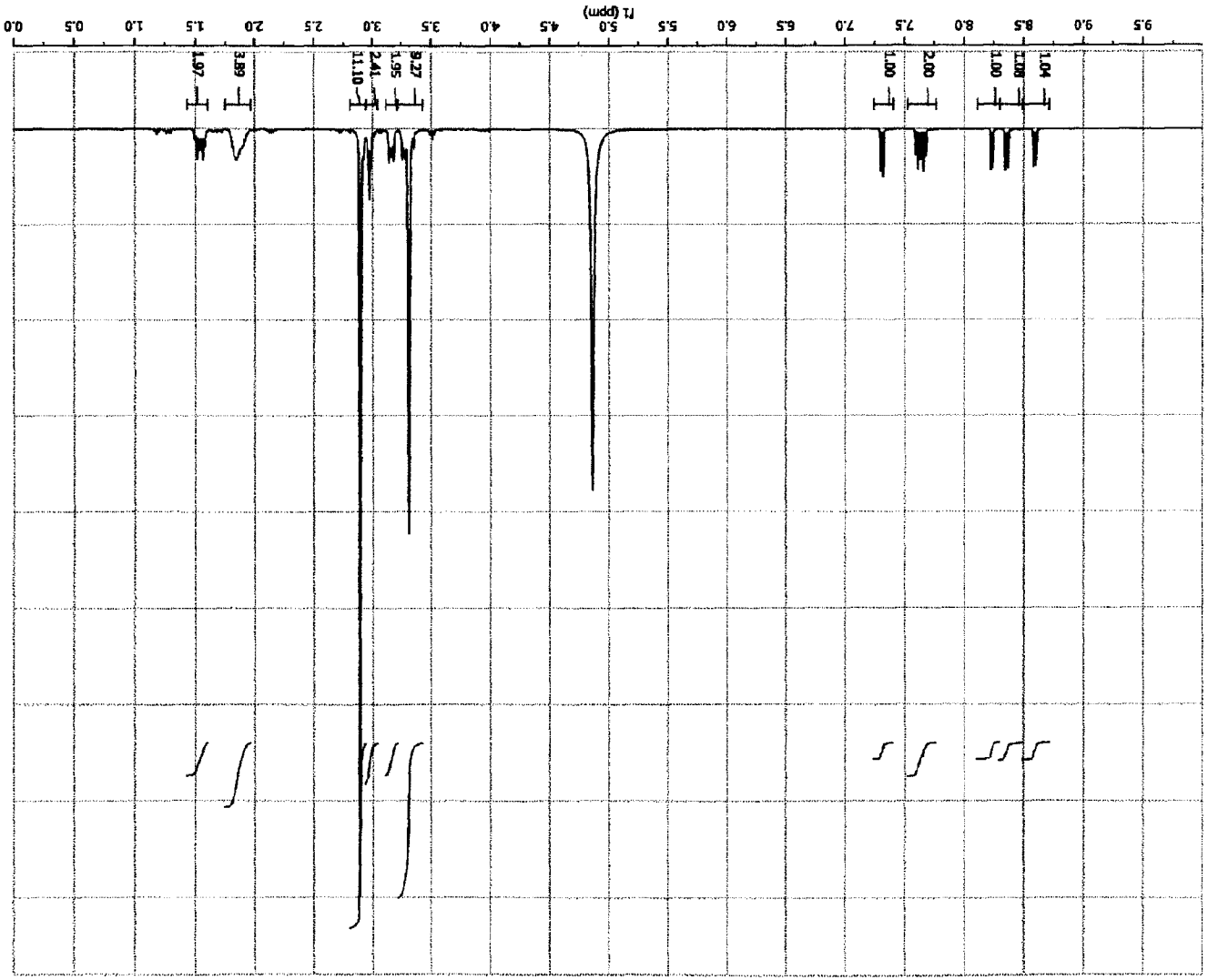
FIG. 62 shows the $^{1}H$ NMR of compound (32) of Example 23
Figure 63:
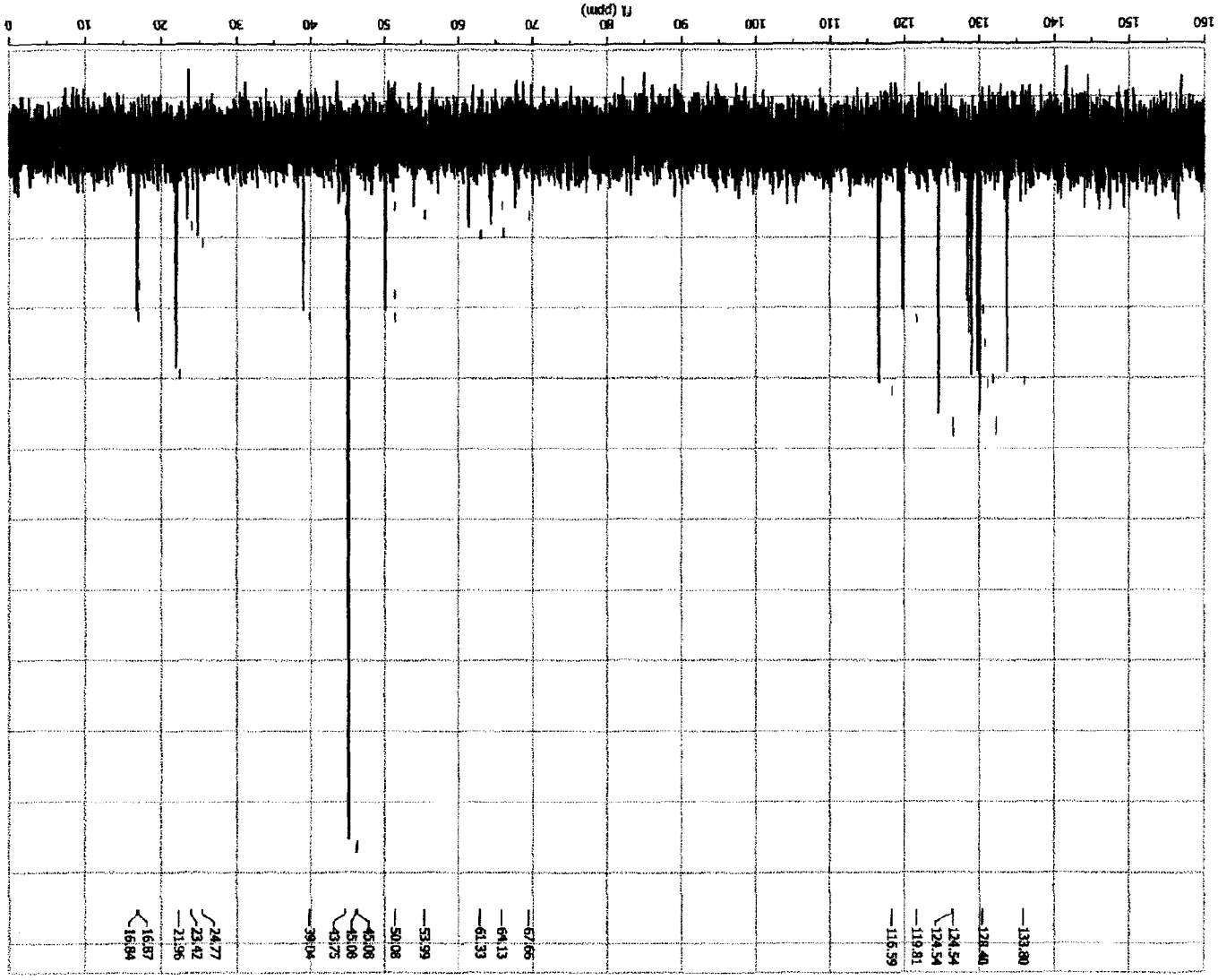
FIG. 63 shows the $^{13}C$ NMR of compound (32) of Example 23
Figure 64:
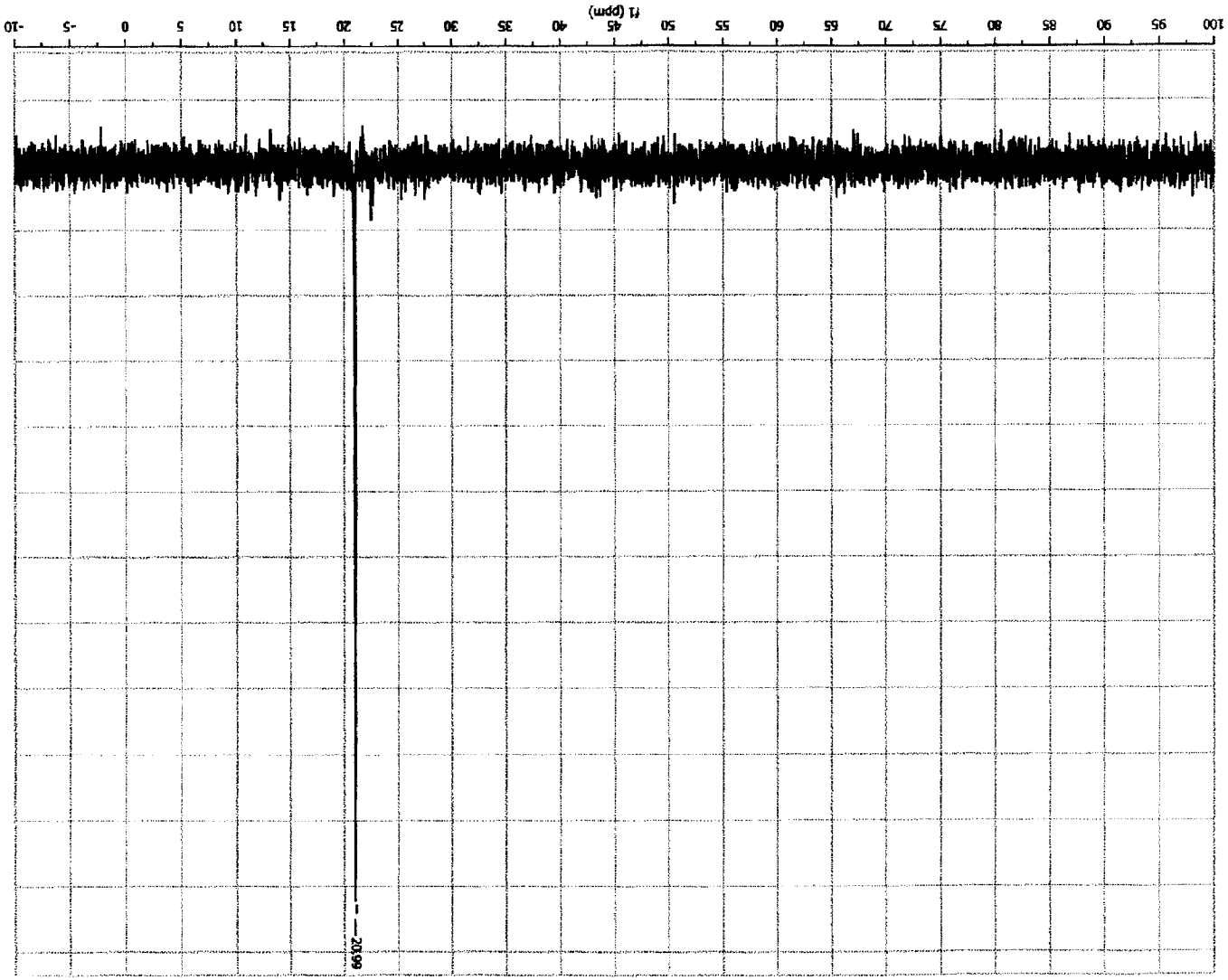
FIG. 64 shows the $^{31}P$ NMR of compound (32) of Example 23

The present invention is directed to quaternary ammonium mono- and multidentate-phosphonate compounds, methods for manufacturing the compounds, compositions comprising said compounds and methods for treating surfaces and/or articles with the compounds to provide a durable, antimicrobial-treated article.

The term quaternary ammonium mono-phosphonate refers to quaternary ammonium compounds that have been substituted with a single phosphonate group $O{=}P(OR)_2$ where R is selected from methyl, ethyl, isopropyl, n-butyl or phenyl or hydrogen, preferably ethyl or hydrogen and even more preferably hydrogen, and the phosphonate group can be linked to the quaternary ammonium nitrogen centre by a one, two, three or four carbon atom chain, preferably a saturated chain. The term quaternary ammonium multidentate-phosphonate refers to quaternary ammonium compound that have been substituted with two or more phosphonate groups $O{=}P(OR)_2$ where R is as above.

The term polar, aprotic solvent means a solvent that has a dipole moment but does not have an acidic hydrogen. Non-limiting examples include acetonitrile, dimethylformamide, dimethylsulfoxide and dichloromethane.

The term polar, protic solvent means a solvent that has a dipole moment and has an acidic hydrogen. Non-limiting examples including lower alkanols, carboxylic acids and water.

The term surface means any metallic or non-metallic article surface that is capable of forming phosphorus-oxygen bonds. Non-limiting examples include steel, stainless steel, titanium, silica glass and clays.

The term neat means without the use of solvents, specifically directed to chemical reactions that do not involve the use of solvents.

All microwave reactions were performed in sealed glass reaction tube utilizing the Biotage® Initiator Microwave Synthesizer at the indicated temperature and time The quaternary ammonium mono- and bis-phosphonate compounds of the present invention can be prepared via one of several processes. In one embodiment, a quaternary ammonium mono-phosphonate compound of formula (I)

(I)

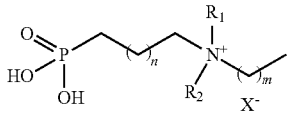

wherein $R_1$ and $R_2$ are each independently a lower alkyl group preferably saturated hydrocarbon chains being one, two or three carbon atoms in length, more preferably methyl groups, m is 15, 16, 17, 18 or 19, n is 0, 1, 2, 3, 4, 5 or 6, and X is chloro, bromo or iodo, can be prepared by a process comprising the steps of (a) reacting a compound of formula (II)

(II)

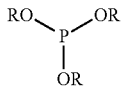

where R is independently methyl, ethyl, isopropyl, n-butyl or phenyl, preferably the same and more preferably ethyl, with an alkyl halide of formula (III)

(III)

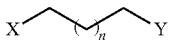

where n and X are as above and Y is a halogen selected from chloro or bromo, more preferably bromo to give a compound of formula (IV)

(IV)

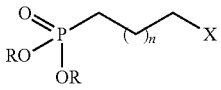

(b) reacting the compound of formula (IV) with a compound of formula (V)

(V)

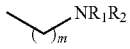

wherein $R_1$ and $R_2$ are each independently a lower alkyl group, preferably saturated hydrocarbon chains being one, two or three carbon atoms in length, more preferably methyl groups, and m is 15, 16, 17, 18 or 19, to give a compound of formula (VI)

(VI)

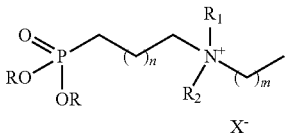

and (c) reacting a compound of formula (VI) with $SiR_3R_4R_5Z$ wherein $R_3$, $R_4$ and $R_5$ are independently methyl or ethyl and Z is chloro, bromo, iodo or triflate, or a mineral acid selected from HCl, HBr or HI, to give a compound of formula (I). The process may take place neat or in a polar, protic reaction solvent, preferably a lower alkanol selected from methanol, ethanol and isopropanol. The process may be carried out at the refluxing temperature of the reaction solvent. The process is considered complete when the compound of formula (VI) is no longer observable via thin-layer chromatography. The final product optionally may be purified, preferably by chromatography or recrystallization.

In another embodiment, a quaternary ammonium bis-phosphonate compound of formula (VII)

(VII)

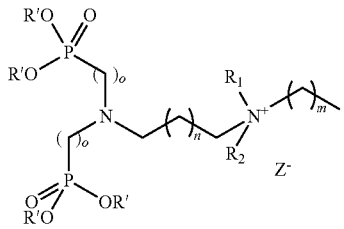

wherein R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, more preferably methyl groups, m is 15, 16, 17, 18 or 19, n is 0, 1, 2, 3, 4, 5 or 6, o is 1, 2 or 3, and Z is chloro, bromo or hydroxy, preferably bromo, is prepared by a process comprising the steps of (a) reacting at least two equivalents of compound of formula (IX)

(IX)

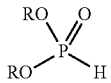

where R is independently methyl, ethyl, isopropyl, n-butyl or phenyl, preferably the same, more preferably ethyl, with per equivalent of a compound of formula (X)

(X)

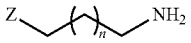

where n is 0, 1, 2, 3, 4, 5 or 6, and Z is selected from chloro, bromo or hydroxyl, preferably bromo, to give a compound of formula (XI)

(XI)

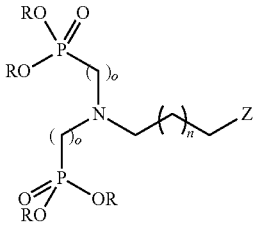

where n, o, R and Z are as defined above. which is reacted with a compound of formula (V)

(V)

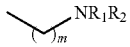

where $R_1$ and $R_2$ are independently lower alkyl groups preferably saturated hydrocarbon chains being one, two or three carbon atoms in length, preferably methyl groups, and m is 15, 16, 17, 18 or 19, to give a compound of formula (VII) where R', $R_1$, $R_2$, m, n, o and Z are as defined above. The process for preparing the compound of formula (XI) can take place in a polar, aprotic solvent selected from but not limited to acetonitrile or dichloromethane, or neat, preferably neat, at a temperature from about −5° C. to about 10° C. then warmed to about 90° C. to about 140° C. for about one hour. The product of formula (XI) can be isolated by extraction and optionally purified, preferably by chromatography. The process alternatively can take place in the presence of microwave radiation at a temperature of about 120° C. to about 140° C., preferably 130° C., for about five minutes. The microwave radiation has a frequency of about 2500 MHz.

The process for preparing the compound of formula (VII) from the compound of formula (XI) can take place in a neat mixture of a compound of formula (XI) and a compound of formula (V) where R, $R_1$, $R_2$ and Z are as defined above. The process can take place in the absence of reaction solvent at a temperature of about 90° C. to about 110° C., preferably 100° C., for about one hour, or alternatively, in the presence of microwave radiation at a temperature of about 140° C. to about 160° C., preferably 150° C., for about one to three minutes, preferably about two minutes. The microwave radiation has a frequency of about 2500 MHz.

In an alternative embodiment, the quaternary ammonium bis-phosphonate compound of formula (VII) is prepared by a process comprising the steps of (a) reacting a compound of formula (XI)

(XI)

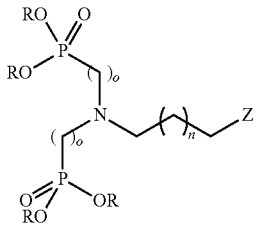

where R is independently methyl, ethyl, isopropyl, n-butyl or phenyl, preferably the same, more preferably ethyl, $R_1$ and $R_2$ are each independently a lower alkyl group, preferably saturated hydrocarbon chains being one, two or three carbon atoms in length, more preferably methyl groups, n is 0, 1, 2, 3, 4, 5 or 6, o is 1, 2 or 3, and Z is selected from chloro, bromo or hydroxyl, preferably bromo, with p-toluenesulfonyl chloride, trimethyl ammonium chloride, an organic amine, preferably triethylamine, in a polar, aprotic solvent selected from but not limited to acetonitrile, dimethylformamide or dichloromethane, preferably dichloromethane, (b) adding a compound $R_1R_2NH$ where $R_1$ and $R_2$ are defined as above, in a polar, protic solvent selected from but not limited to methanol, ethanol or isopropanol, optionally in the presence of water, to give a compound of formula (XII)

(XII)

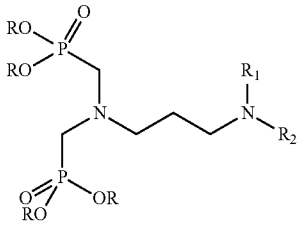

and (c) reacting the compound of formula (XII) with a compound of formula (XIII)

(XIII)

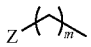

where m is 15, 16, 17, 18 or 19, and Z is chloro, bromo or hydroxyl, preferably bromo, to give a compound of formula (VII). The process of step (a) can take place at a temperature of about 20° C. to about 30° C. The process of step (b) can take place at a temperature of about 90° C. to about 115° C., preferably 100° C., and for a reaction time of about one hour. Alternatively, the process of step (b) can take place in the presence of microwave radiation at a temperature of about 100° C. to about 120° C., preferably 110° C., for about five minutes. The microwave radiation has a frequency of about 2500 MHz. The process of step (c) can take place neat at a temperature of about 90° C. to about 115° C. for about one hour or, alternatively, in the presence of microwave radiation at a temperature of about 140° C. to about 160° C., preferably 150° C., for about two minutes. The microwave radiation has a frequency of about 2500 MHz.

In another embodiment, the quaternary ammonium bisphosphonate compound of formula (XIV)

(XIV)

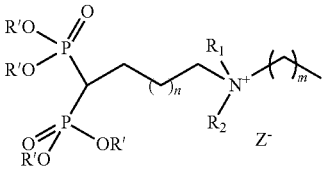

where R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, more preferably methyl groups, m is 15, 16, 17, 18 or 19, n is 0, 1, 2, 3, 4, 5 or 6, and Z is selected from chloro or bromo, preferably bromo, is prepared by a process comprising the steps of (a) reacting a compound of formula (XV)

(XV)

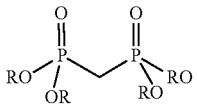

wherein R is independently methyl, ethyl, isopropyl, n-butyl or phenyl, preferably the same, more preferably ethyl, with a compound of formula (XVI)

(XVI)

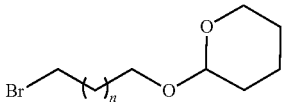

to give a compound of formula (XVII)

(XVII)

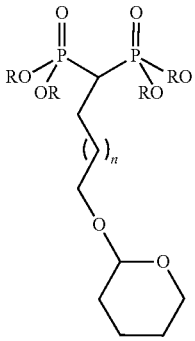

where n and R are as defined above, which is preferably not isolated and used in the next step, and (b) treating a compound of formula (XVII) with p-toluenesulfonic acid, methanesulfonyl chloride, triethylamine and $R_1R_2NH$ where $R_1$ and $R_2$ are defined as above, and a compound of formula (XIII)

(XIII)

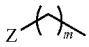

where m is as defined above and Z is chloro or bromo, preferably bromo to give a compound of formula (XIV), or alternatively (c) reacting a compound of formula (XVIII)

(XVIII)

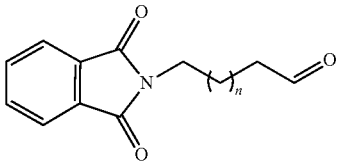

wherein n is 0, 1, 2, 3, 4, 5, or 6, with one equivalent of $O{=}PH(OR)_2$ where R is independently methyl, ethyl, isopropyl, n-butyl or phenyl, preferably the same, more preferably ethyl, in the presence of an alkali metal carbonate, preferably potassium carbonate, methanesulfonyl chloride and an organic amine base, preferably triethylamine, and further reacted with sodium hydride and a second equivalent of O═PH(OR)$_2$ to give a compound of formula (XIX)

(XIX)

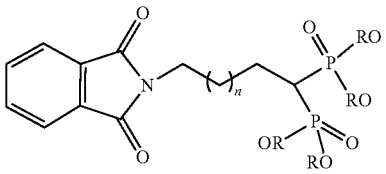

where n and R are as defined above and (d) reacting the compound of formula (XIX) with hydrazine, an aldehyde selected from formaldehyde or acetaldehyde in the presence of zinc metal, and a compound of formula (XIII)

(XIII)

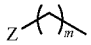

where Z is chloro or bromo, preferably bromo, and m is 15, 16, 17, 18 or 19, to give a compound of formula (XIV). The process of step (c) can take place in a polar, aprotic solvent selected from but not limited to acetonitrile, tetrahydrofuran or dioxane, preferably acetonitrile or dioxane, at a temperature of about 25° C. to about 75° C., preferably 60° C.

In another embodiment, the bis-phosphonate compound of formula (XVII)

(XVII)

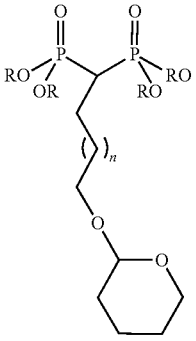

where n is 0, 1, 2, 3, 4, 5, or 6, and R is independently methyl, ethyl, isopropyl, n-butyl or phenyl, preferably the same, more preferably ethyl, is prepared by a process comprising the step of reacting a compound of formula (XX)

(XX)

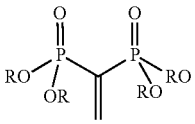

where R is as defined above, with a compound of formula (XXI)

(XXI)

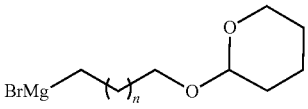

to give a compound of formula (XVII).

In another embodiment of preparing a compound of formula (XIV), the bis-phosphonate compound of formula (XXII)

(XXII)

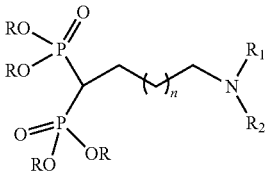

where n is 0, 1, 2, 3, 4, 5 or 6, R is independently methyl, ethyl, isopropyl, n-butyl or phenyl, preferably the same, more preferably ethyl, $R_1$ and $R_2$ are each independently a lower alkyl group, preferably saturated hydrocarbon chains being one, two or three carbon atoms in length, more preferably methyl, is prepared by a process comprising reacting a compound of formula (XXIII)

(XXIII)

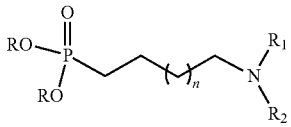

with O═P(OR)$_2$Cl where n, R, $R_1$ and $R_2$ are as defined above, in the presence of lithium diisopropylamide in a polar, aprotic solvent to give a compound of formula (XXII) which optionally is reacted with an alkyl halide of formula (XIII) to give a quaternary ammonium bis-phosphonate of formula (XIV) where R, $R_1$, $R_2$, Z, m and n are as defined above.

In another embodiment, the compound of formula (XXIV)

(XXIV)

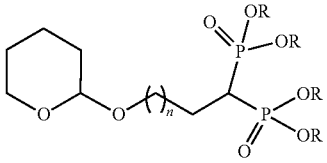

where n is 0, 1, 2, 3, 4, 5 or 6, and R is independently methyl, ethyl, isopropyl, n-butyl or phenyl, preferably the same, more preferably ethyl, is prepared by a process comprising reacting a compound of formula (XXV)

(XXV)

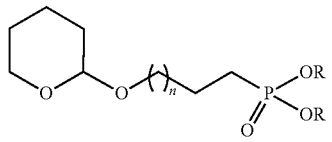

with $O{=}P(OR)_2Cl$ in the presence of lithium diisopropylamide in a polar, aprotic solvent to give a compound of formula (XXIV) where R is independently methyl, ethyl, isopropyl, n-butyl or phenyl, preferably the same, more preferably ethyl.

In another embodiment, the quaternary ammonium bisphosphonate compound of formula (XXVI)

(XXVI)

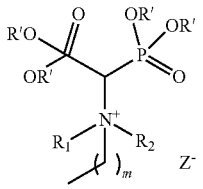

where R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, preferably methyl groups, m is 15, 16, 17, 18 or 19 and Z is selected from chloro or bromo, preferably bromo, is prepared by the process comprising the steps of (a) reacting oxalyl chloride with

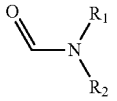

in chilled dichloromethane in the presence of a compound of formula (II) to give a compound of formula (XXVII)

(XXVII)

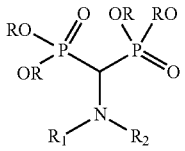

wherein R is independently methyl, ethyl, isopropyl, n-butyl or phenyl, preferably the same, more preferably ethyl, and (b) reacting the compound of formula (XXVII) with a compound of formula (XIII) to give a compound of formula (XXVI).

The process of step (a) can take place in a polar, aprotic solvent selected from but not limited to acetonitrile or dichloromethane, preferably dichloromethane, and the term chilled means a temperature from about −5° C. to about 10° C., rising to about 20° C. to about 30° C. for about one hour.

In another embodiment of the present invention, a quaternary ammonium mono-phosphonate compound of formula (XXVIII)

(XXVIII)

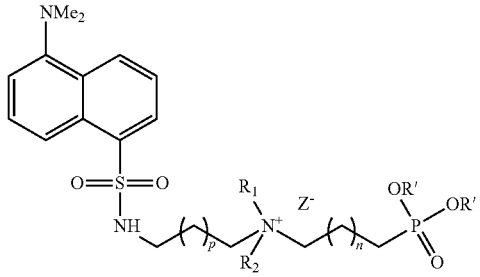

where n is 0, 1, 2, 3, 4, 5 or 6, p is 0, 1, 2, 3, 4, 5 or 6, R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, preferably methyl groups, m is 15, 16, 17, 18 or 19 and Z is selected from chloro, bromo, iodo or mesyl, preferably bromo, is prepared by a process comprising the steps of (a) reacting a compound of (XXIX)

(XXIX)

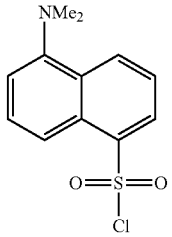

with a compound of formula (XXX)

(XXX)

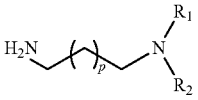

where p, $R_1$ and $R_2$ are as defined above, in a polar, aprotic solvent in the presence of an organic amine base to give a compound of formula (XXXI)

(XXXI)

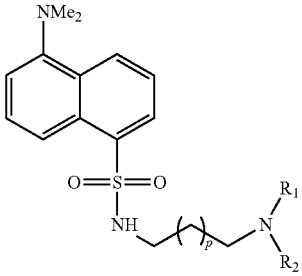

and (b) reacting a compound of formula (XXXI) with a compound of formula (XXXII)

(XXXII)

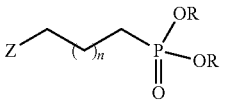

wherein R is independently methyl, ethyl, isopropyl, n-butyl or phenyl, preferably the same, more preferably ethyl, and n and Z are as defined above, in a polar, aprotic solvent to give a compound of formula (XXVIII). The dansyl group

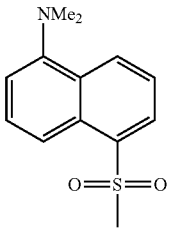

is used as a UV fluorescing marker to indicate the presence of the quaternary ammonium mono-phosphate compound after a compound of formula (XXVIII) has been applied to a surface.

In another embodiment of the present invention, quaternary ammonium multidentate tri- and tetra-substituted phosphonate compounds of formula (XXXIII), (XXXIV), (XXXV), (XXXVI) and (XXXVII)

(XXXIII)

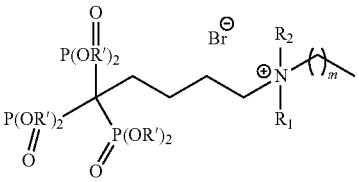

(XXXIV)

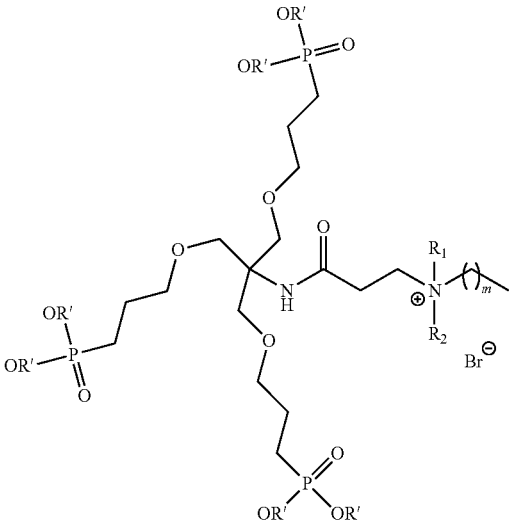

-continued (XXXV)

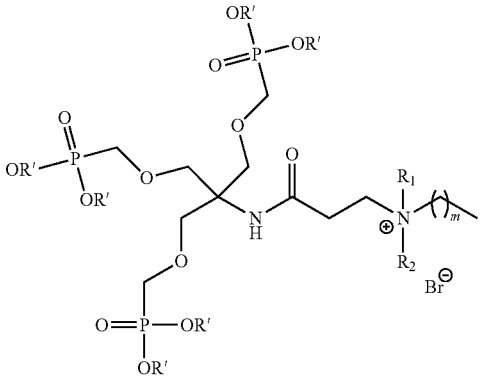

(XXXVI)

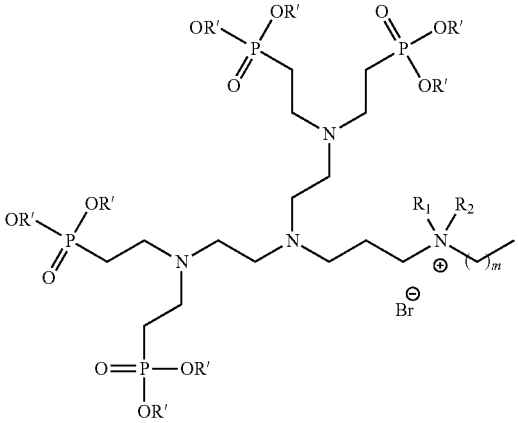

(XXXVII)

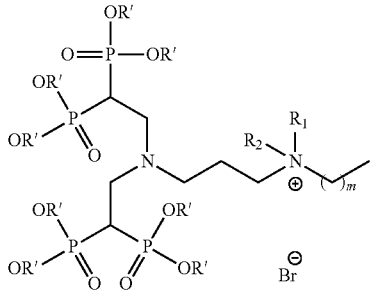

are prepared where R' is independently hydrogen, methyl, ethyl, isopropyl, n-butyl or phenyl, preferably the same, more preferably ethyl or hydrogen and even more preferably hydrogen, $R_1$ and $R_2$ are each independently a lower alkyl group, preferably saturated hydrocarbon chains being one, two or three carbon atoms in length, preferably methyl groups, m is 15, 16, 17, 18 or 19 and Z is selected from chloro or bromo, preferably bromo. Multidentate phosphonic acid antimicrobials may generally be prepared by introduction of the bis-, tris- or tetraphosphonate anchor prior to quaternization and dealkylation with trimethylbromosilane (TMBr). The most direct way to synthesize bisphosphonates is through the alkylation of tetralkyl methylenebisphosphonate (TAMBP). Monodeprotonation of TAMBP followed by mono alkylation leads to alpha (C—H) bisphosphonates whereas a second deprotonation/alkylation with dialkyl chlorophosphate provides trisphosphonates. A second method for the synthesis of bisphosphonates is through Michael addition of dialkyl vinylphosphite to provide beta aminobisphosphonates. Further deprotonation and phosphorylation with dialkyl chlorophosphate provides tetraphosphonates. Alternatively the TRIS BOC scaffold containing three reactive groups may be turned into trisphosphonates via established synthetic routes used to prepare monophosphonates. Two examples include the lewis acid-mediated Abrzov addition of trialkylphosphite three times to three reactive bromoacteylTRISBOC and the radical addition of dialkyl phosphite to terminal vinyl groups on TRISBOC. General schemes for producing quaternary ammonium bis-, tris- and tetraphosphonate compounds are as follows:

General Scheme 1: Quarternary Ammonium Bisphosphonic Acids via direct alkylation

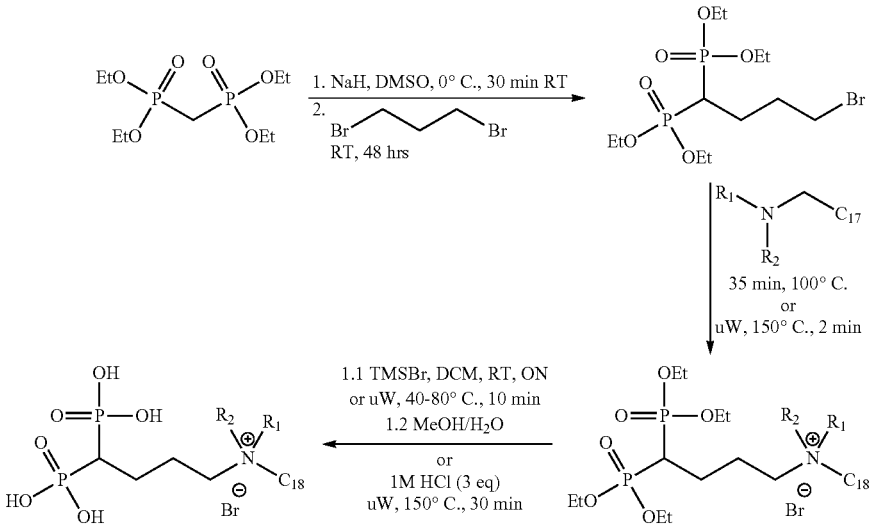

wherein $R_1$ and $R_2$ are independently lower alkyl groups, preferably methyl.

General Scheme 2: Quaternary Ammonium Bisphosphonic Acids via Michael addition of dialkyl vinylphosphonate:

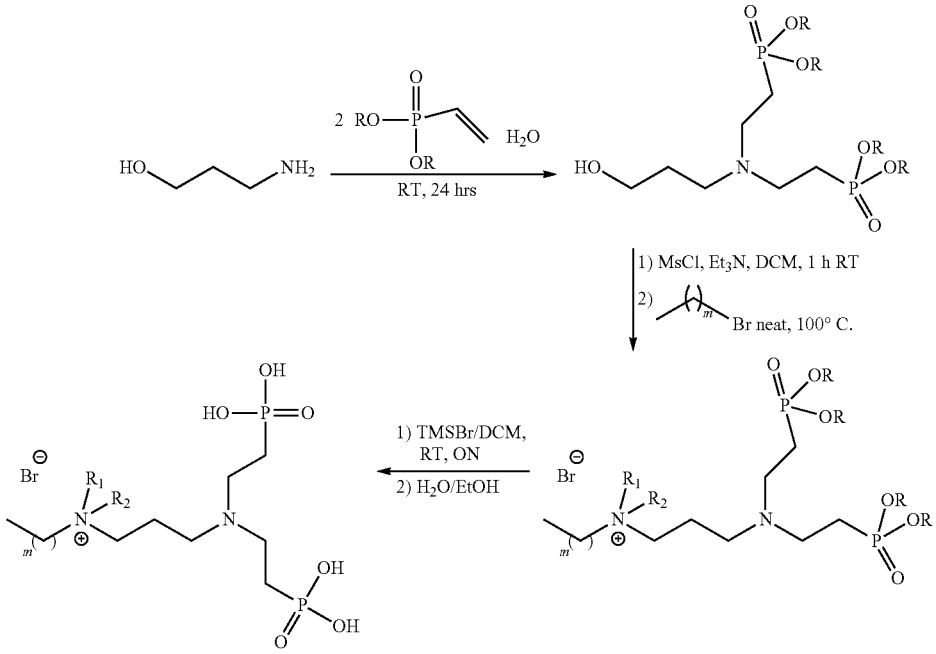

wherein R is independently methyl, ethyl, isopropyl, n-butyl or phenyl, preferably the same, more preferably ethyl, $R_1$ and $R_2$ are independently lower alkyl groups, preferably methyl and m is 15, 16, 17, 18 or 19.

General Scheme 3: Quaternary Ammonium Trisphosphonic Acid compounds via addition of dialkyl chlorophosphite

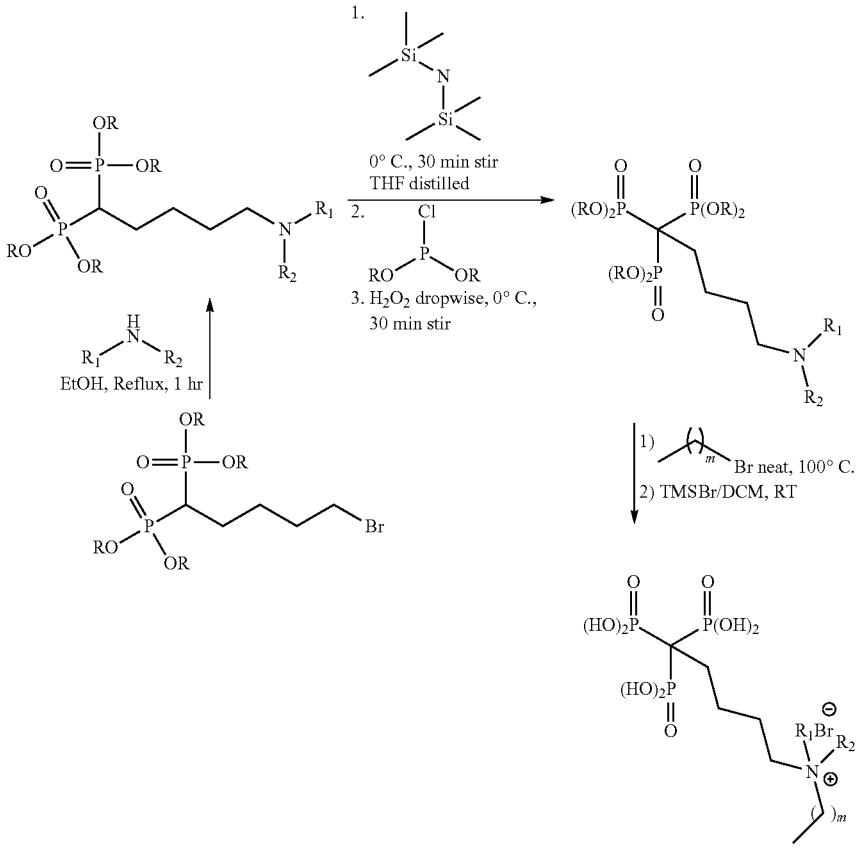

wherein R is independently methyl, ethyl, isopropyl, n-butyl or phenyl, preferably the same, more preferably ethyl, $R_1$ and $R_2$ are independently lower alkyl groups, preferably methyl and m is 15, 16, 17, 18 or 19.

General Scheme 4: Quarternary Ammonium Triphosphonic Acid compounds via TrisBOC

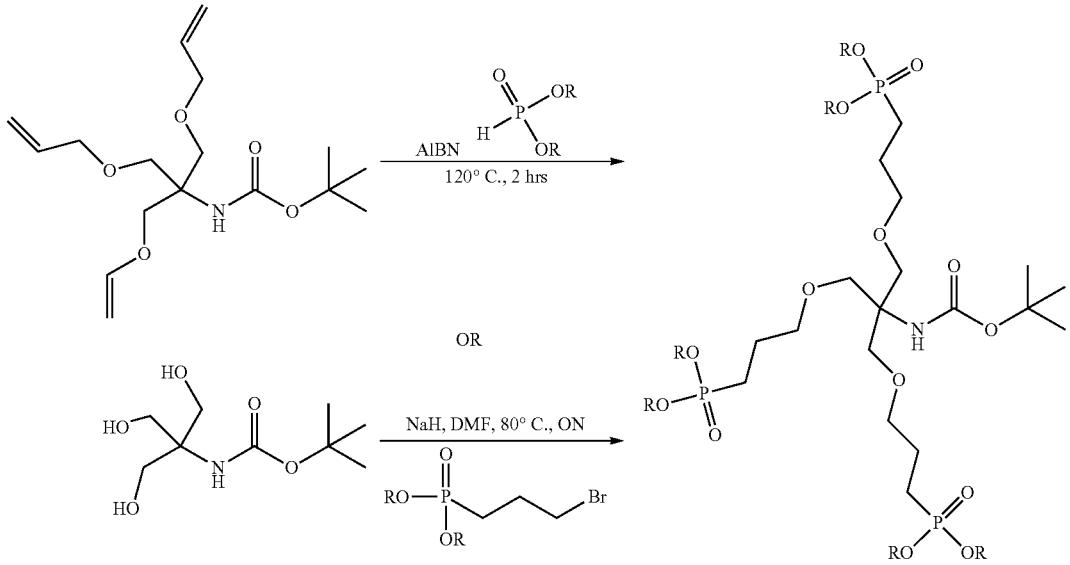

-continued

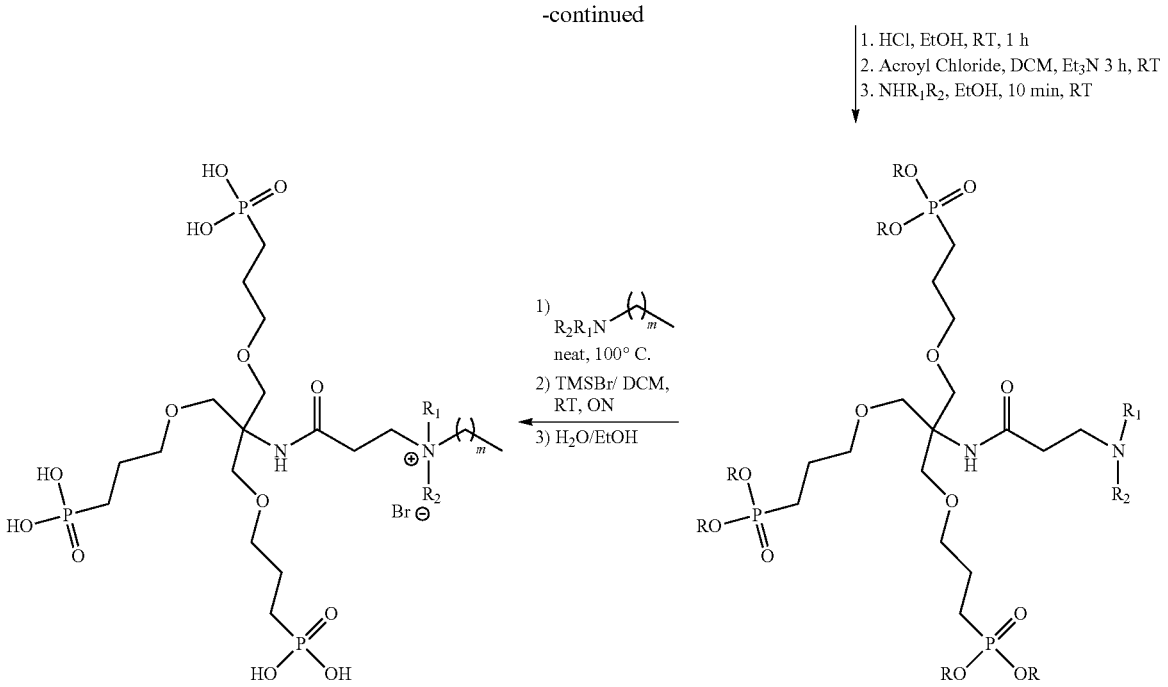

wherein R is independently methyl, ethyl, isopropyl, n-butyl or phenyl, preferably the same, more preferably ethyl, $R_1$ and $R_2$ are independently lower alkyl groups, preferably methyl and m is 15, 16, 17, 18 or 19.

General Scheme 5: Quaternary Ammonium Tetraphosphonic Acid compounds via Michael addition of dialkyl vinylphosphonate followed by phosphorylation with dialkyl chlorophosphate

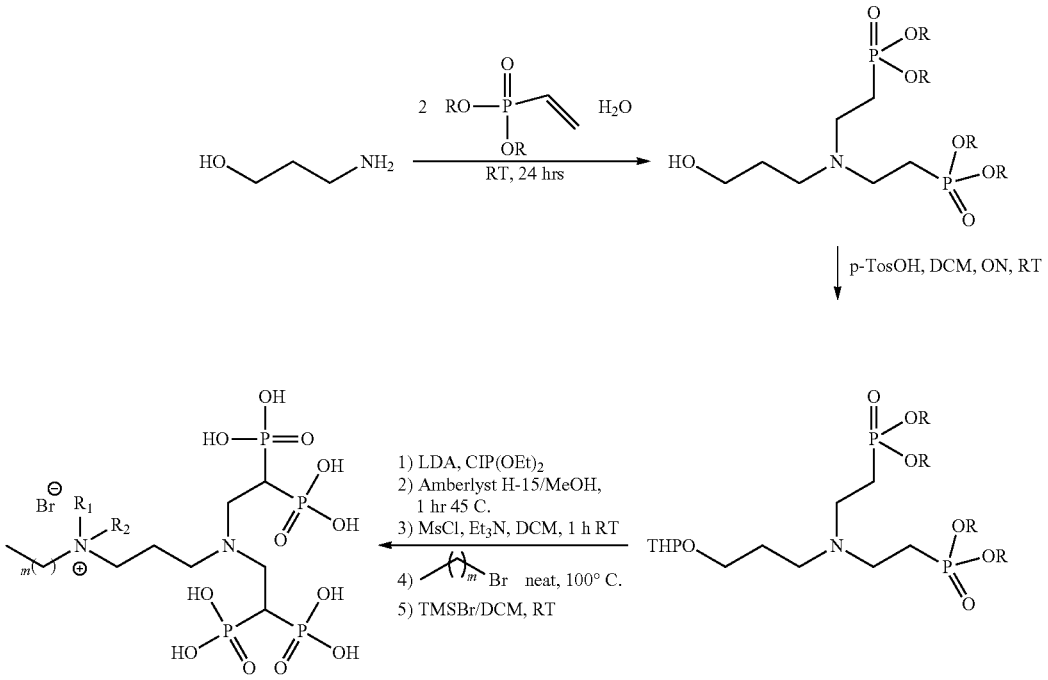

wherein R is independently methyl, ethyl, isopropyl, n-butyl or phenyl, preferably the same, more preferably ethyl, and m is 15, 16, 17, 18 or 19.

General Scheme 6: Quarternary Ammonium Tetraphosphonic Acid compounds via Michael addition of dialkyl vinylphosphonate

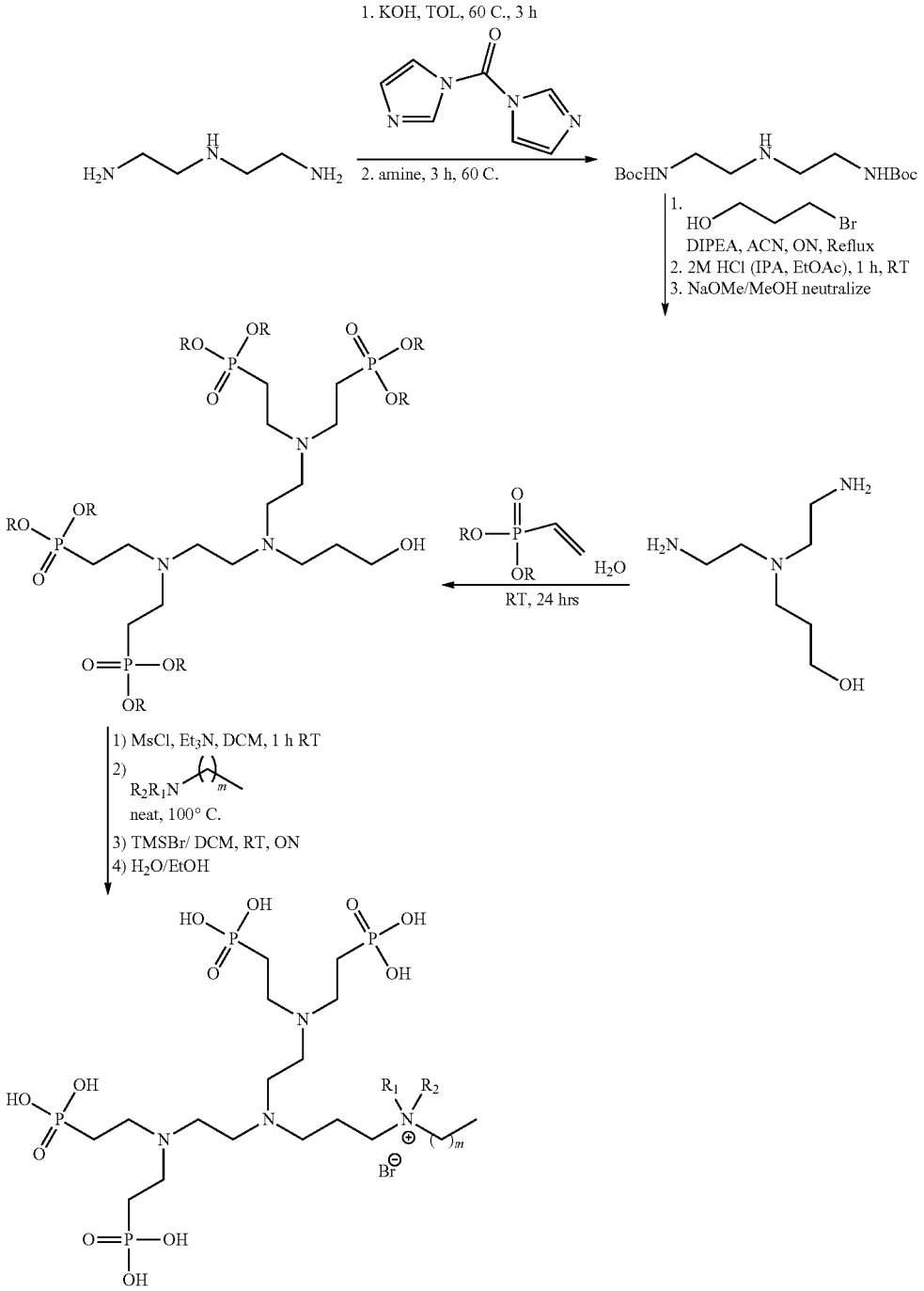

wherein R is independently methyl, ethyl, isopropyl, n-butyl or phenyl, preferably the same, more preferably ethyl, $R_1$ and $R_2$ are independently lower alkyl groups, preferably methyl and m is 15, 16, 17, 18 or 19.

In another embodiment, the quaternary ammonium mono- and bis-phosphonate and multidentate tri- and tetra-substituted phosphonate compounds of the present invention may be used to antimicrobially treat hard surfaces. A surface may be an inner surface and/or an outer surface. Specifically, there is provided a phosphonate antimicrobial coating composition for treating surfaces to give a stable and durable phosphonate antimicrobial coating surface treatment, said composition comprising any one of a compound of formulae (I), (VII), (XIV), (XXVI), (XXVIII), (XXXIII), (XXXIV), (XXXV), (XXXVI) or (XXXVII) in a suitable carrier. In one embodiment said suitable carrier is an environmentally friendly carrier comprising a lower alkanol selected from the group consisting of methanol, ethanol, n-propanol and i-propanol, water or a mixture thereof depending on the solubility of the phosphonate compound in the carrier. The phosphonate antimicrobial coating may be applied onto a given surface preferably by dip coating, painting or with aerosol spraying with an about 1 to an about 20 mM solution of the phosphonate compound for a length of time so as to completely coat the surface. In one embodiment, the coating process may be repeated to apply additional layers of the phosphonate antimicrobial coating. Preferably the stable and durable phosphonate antimicrobial coatings may be coated onto various material surfaces such as, but not limited to, metal oxides or metal alloys of aluminum, copper, iron, steel, titanium, zirconium and silicon (silica). Even more preferably, phosphonate antimicrobial coating strength and stability may be further enhanced by subjecting the uncoated surface to a pretreatment oxidation step known as passivation. Without being bound by any theory, passivation creates a metal hydroxide layer that provides additional binding sites for the phosphonate compounds of the phosphonate antimicrobial coating to bind to. Passivation is accomplished by known processes in the art such as thermal annealing (subjecting the uncoated surface to temperatures of about 100-140° C. for about 18 hours) or reduced pressure annealing (subjecting the uncoated surface to pressures of about 0.05 to about 0.3 Torr, more preferably 0.1 Torr).

The following non-limiting examples are provided.

ACRONYMS

AIBN—Azobisisobutyronitrile

ACN—acetonitrile

DCM—dichloromethane

DMF—dimethylformamide

Hrs—hours

LDA—lithiumdiisopropylamide

NaH—sodium hydride

MsCl—mesylchloride

ON—overnight

RT—room temperature

TMSBr—trimethylsilylbromide

TosCl—tosyl chloride

TOL—toluene

ST—sealed tube uW—microwave

Monophosphonic Acid Quaternary Ammonium Antimicrobials (MPQ).

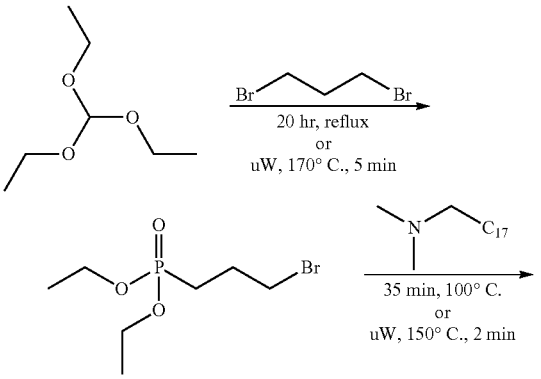

-continued

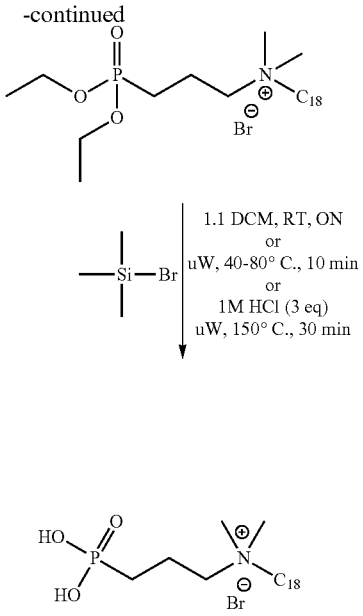

Synthesis of Monophosphonic Acid Quats.

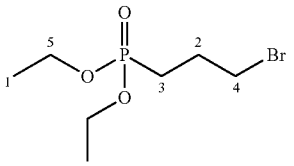

Referential Example 1

Diethyl (3-bromopropyl)phosphonate (1)

According to a general procedure reported in Li, F. et al. Photopolymerization of Self-Assembled Monolayers of Diacetylenic Alkylphosphonic Acids on Group-III Nitride Substrates. Langmuir 26, 10725-10730 (2010), to a flame dried 250 mL round bottom flask equipped with a reflux condenser connected to an inert atmosphere manifold, was added 1,3-dibromopropane (40 mL, 394 mmol, 4 eq.) followed by triethylphosphite (13 mL, 75.8 mmol). The flask was evacuated (2 min), backfilled with $N_2$ and the reaction mixture refluxed overnight (175° C.) using a sand bath. The solution was then cooled to room temperature and excess 1,3-dibromopropane was vacuum distilled ($1\times10^{-2}$ mm Hg) using a shortpath distillation head attached to a Schlenk line. Once all of the excess 1,3-dibromopropane was removed as judged by TLC, the title compound was vacuum distilled utilizing an oil bath (150° C.) to afford a clear, colourless liquid. Yield: 79% (15.54 g). TLC (50% EtOAc:hexanes, $KMnO_4$ stain), $R_f$=0.60; $^1$H NMR (400 MHz, $CDCl_3$, δ): 4.12-4.00 (m, 4H, H5), 3.43 (t, 2H, J=4.3 Hz, H4), 2.16-2.05 (m, 2H, H3), 1.90-1.81 (m, 2H, H2), 1.28 (t, J=7.0 Hz, 6H, H1) ppm; $^{13}$C NMR (100 MHz, $CDCl_3$, δ): 61.6 (d, $^2J_{C-P}$=6.5 Hz, C5), 33.71 (C4), 25.92 (d, $^2J_{C-P}$=4.4 Hz, C2), 23.64 (s, C3), 16.4 (d, $^2J_{C-P}$=6.2 Hz, C1) ppm; $^{31}$P NMR (121.45 MHz, $CDCl_3$, δ): 30.2 ppm.

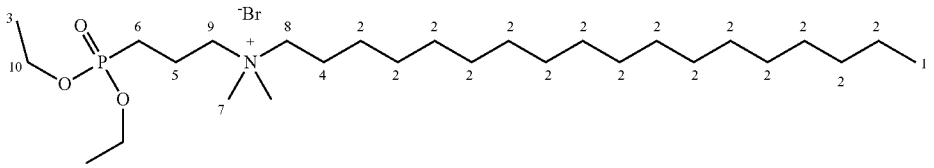

Example 1

N-(3-diethoxyphosphorylpropyl)-N,N-dimethyloctadecan-1-ammonium bromide (2)

The compound has been previously reported in: Brunet, S., Germanaud, L., Le, P., Pierre & Sillion, B. Neutral phosphobetaines, their preparation, and their use in petroleum recovery. Fr. Demande, 33 (1986); Chevalier, Y. et al. Zwitterionic amphiphiles: synthesis and physical properties. Commun. Journ. Com. Esp. Deterg. 18, 231-45 (1987); Gallot, B., Germanaud, L., Chevalier, Y. & Le, P., P. Mesomorphic structure of neutral amphiphilic phosphotobetaines having different interionic distances I. Ethylphosphonatobetaines. J. Colloid Interface Sci. 121, 514-21 (1988); Germanaud, L., Brunel, S., Le, P., P. & Sillion, B. Surfactant properties of neutral phosphobetaines with a modulated intercharge distance. Rev Inst Fr Pet 41, 773-85 (1986); and Germanaud, L., Brunel, S., Chevalier, Y. & Le, P., Pierre. Synthesis of neutral amphiphilic phosphobetaines with variable interionic distances. Bull. Soc. Chim. Fr., 699-704 (1988). To a flame dried and evacuated 20 mL screw cap vial was added dimethyl (3-bromopropyl)phosphonate (1.264 g, 4.88 mmol) followed by N,N-dimethyloctadecylamine (DMOA) by pasteur pipette (1.7075 g, 5.1 mmol, 1.1 eq.) and the closed vial placed in a 100° C. sand bath for 35 min until it solidified. The mixture was then cooled to room temperature, centrifuged from hexanes (15 mL), and recrystallized from 20 mL ethyl acetate/hexanes (1:5) to afford N-(3-(diethoxyphosphoryl)propyl)-N,N-dimethyloctadecan-1-ammonium bromide as a white waxy solid. Yield: 67% (1.82 g). Mp=54-55° C.; $^{1}$H NMR (400 MHz, $CDCl_3$, δ): 4.09-4.01 (m, 2H, H10), 3.66-3.22 (m, 2H, H9) 3.43-3.38 (m, 2H, H8), 3.31 (s, 6H, H7), 2.03 (brs, 2H, H6), 1.84-1.80 (m, 2H, H5), 1.67 (brs, 2H, H4), 1.33-1.25 (m, 6H, H3), 1.19 (brs, 30H, H2), 0.83-0.79 (m, 3H, H1) ppm; $^{13}$C NMR (100 MHz, $CDCl_3$, δ): 64.45 (C8), 63.09 (d, $^{3}J_{C-P}$=6.54 Hz C9), 62.97 (d, $^{2}$J=6.54 Hz, C10), 51.25 (C7), 31.86 (C2 overlap), 29.64-29.19 (C2 overlap), 22.69 (C4), 22.62 (C5), 16.45-16.39 (C6, C3), 14.05 (C1) ppm; $^{31}$P NMR (121.45 MHz, $CDCl_3$, δ): 29.54 ppm. HRMS-DART (m/z): [M$^{+}$] calculated for $C_{33}H_{73}N_2O_6P_2$, 476.4227. found, 476.4240.

Example 2

N,N-dimethyl-N-(3-phosphonopropyl)octadecan-1-ammonium bromide (3)

The internal salt of this compound has been previously reported in: Martinelli, M. J. & Pollack, S. R. Bromotrimethylsilane, John Wiley & Sons Ltd, 2011); and Conibear, A. C., Lobb, K. A. & Kaye, P. T. 31P NMR kinetic study of the tandem cleavage of phosphonate esters by bromotrimethylsilane. Tetrahedron 66, 8446-8449 (2010). Inside a flame dried and evacuated 20 mL screw cap vial N-(3-(diethoxyphosphoryl)propyl)-N,N-dimethyloctadecan-1-ammonium bromide (0.2768 g, 0.46 mmol) was dissolved in anhydrous DCM (5 mL). To the clear stirred solution was added TMSBr (0.25 mL, 1.9 mmol, 4.0 eq.) through a rubber septum via syringe and the reaction was stirred at room temperature overnight. Completion of the reaction was followed by $^{31}$P after which the reaction was quenched with EtOH (10 mL) and stirred for 1 h followed by addition of $H_2O$ (1 mL). Volatiles were removed with a rotovap connected to a high vacuum Schlenk line and the crude product was centrifuged with $Et_2O$ (2×10 mL) to remove brown colored impurities (0.9422 g, 94%). A small portion of the title compound was recrystallized from EtOAc/IPA for MS & X-ray analysis. Clear, long needles. Mp=118-120° C.; $^{1}$H NMR (400 MHz, MeOD, δ): 3.38-3.33 (m, 2H, H8), 3.28-3.23 (m, 2H, H7), 3.02 (s, 6H, H6), 2.02-1.90 (m, 2H, H5), 1.75-1.65 (m, 4H, H4, H3), 1.20 (brs, 30H, H3), 0.82 (t, J=6.9 Hz, 3H, H1), ppm; $^{13}$C NMR ($CDCl_3$, 100 MHz, δ): 64.26 (C7) 63.57 (C8), 49.94 (C6), 31.68 (C2 overlap), 29.41-28.86 (C2 overlap), 26.03 (C2 overlap), 22.45-22.17 (C3, C4), 16.47 (d, $^{1}J_{C-P}$=4.07 Hz, C5), 13.08 (C1) ppm; $^{31}$P NMR (121.45 MHz, $CDCl_3$, δ): 26.92 ppm; HRMS-DART (m/z): [M$^{+}$]+ calculated for $C_{23}H_{51}NO_3P$, 420.3601. found, 420.3608.

α-Amino Bisphosphonic Acid Antimicrobials (α-ABPQ).

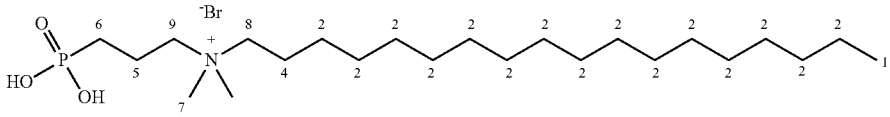

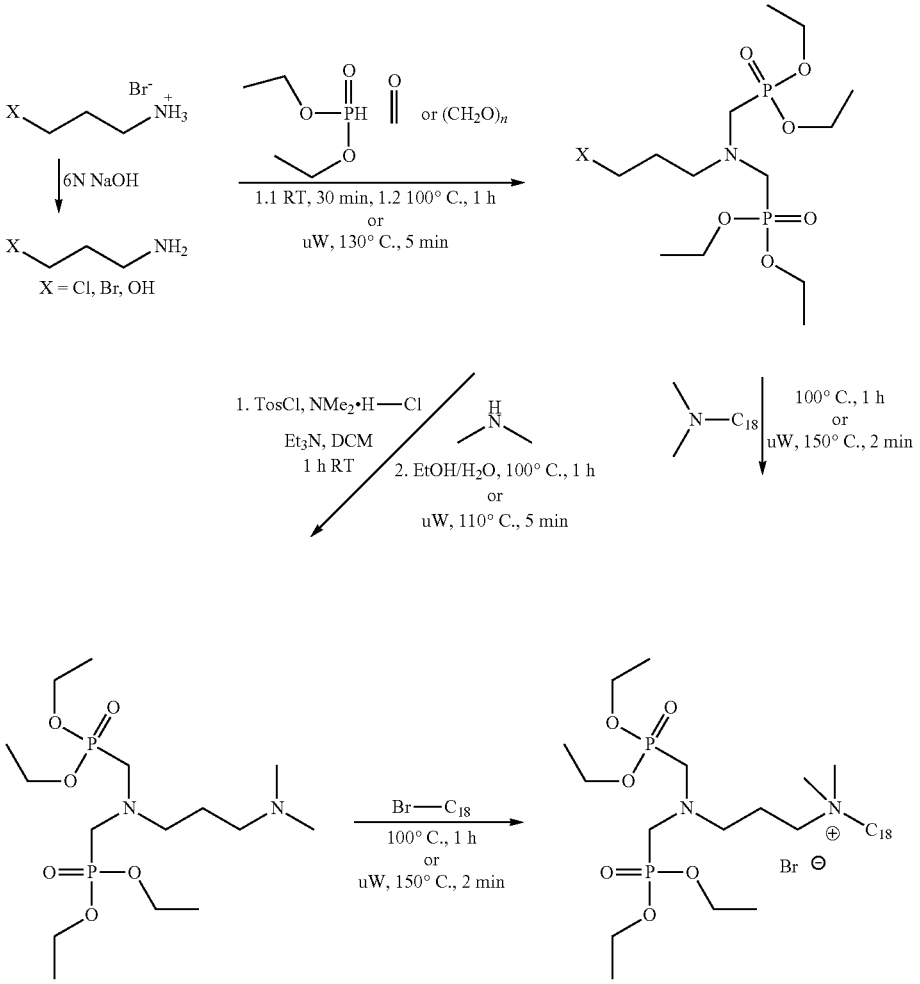

Synthesis of α-Amino Bisphosphonic Quats-Via Double Kabachnik Fields Reaction.

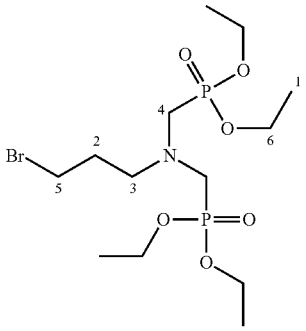

Example 3

Tetraethyl (((3-bromopropyl)azanediyl)bis(methylene))bis(phosphonate) (4)

To a 20 mL glass screw cap vial, equipped with a magnetic stir bar was added diethylphosphite (2.77 mL, 21.56 mmol, 2.2 eq.) and the vial was placed on ice meanwhile 3-aminopropyl-1-bromide hydrobromide (~2.5 g, ~11 mmol) was treated with KOH (6N, 6 g in 20 mL) and stirred at 0° C. until a yellow oil appeared (~5 min). The mixture was then extracted without solvent, collecting the upper yellow layer of the free base aminopropyl-1-bromide (incompletely dry by NMR, 50% water present). The amine (1.350 g, 9.78 mmol) was added to the vial containing diethyl phosphite and cooled at 0-5° C. (ice bath). To the chilled, stirred solution was added formalin, dropwise (37%, 2.12 mL, 25.43 mmol, 2.6 eq.) over 10 min while maintaining the reaction temp under 10° C., then warming the mixture to room temperature for 30 min, and finally to 100° C. for 1 h. The reaction was diluted with 0.2N NaOH (~300 mg in 40 mL) and extracted with $CHCl_3$ (1×30 mL, 1×10 mL), the organic layer was separated, washed with brine (1×20 mL) and dried over anhydrous $MgSO_4$ filtered and concentrated to afford a yellow oil. The title compound was in poor yield, however analysis by $^1H$ NMR revealed >98% purity and required no further purification. Yield 20.9% (0.7658 g); TLC (5% MeOH in EtOAc), $R_f$=0.48; $^1H$ NMR (400 MHz, $CDCl_3$, δ): 4.17-4.07 (m, 8H, H6), 3.47 (t, 2H, J=6.7 Hz, H5), 3.14 (d, 4H, J=8.5 Hz, H4), 2.93 (t, 2H, J=6.6 Hz, H3), 2.00 (q, 2H, J=6.58 Hz, H2), 1.31 (t, 12H, J=7.1 Hz, H1); $^{13}C$ NMR (100 MHz, $CDCl_3$, δ): 61.9 (t, $^2J_{C-P}$=3.36 Hz, C6), 55.08 (C3), 49.43 (C4), 31.09 (C5), 30.96 (C2), 16.49 (t, $^3J_{C-P}$=2.94 Hz, C1); $^{31}P$ NMR (121.45 MHz, $CDCl_3$, δ): 24.60 ppm.

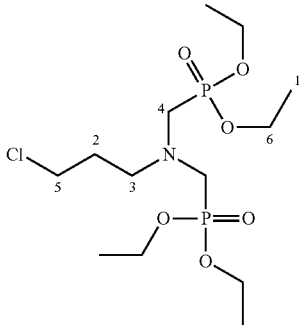

Example 4

Tetraethyl (((3-chloropropyl)azanediyl)bis(methylene))bis(phosphonate) (5)

To a 20 mL glass screw cap vial, equipped with a magnetic stir bar was added diethylphosphite (2.86 g, 20.74 mmol, 2.0 eq.). The vial was placed on ice to cool. In a separate beaker, 3-aminopropyl-1-chloride hydrochloride (2.0 g, 11.4 mmol) was treated with NaOH (~12 N, 2 g in 5 mL) and stirred at 0° C. until a yellow oil appeared (~5 min). The mixture was then extracted without solvent, adding the upper yellow layer of the free base 3-aminopropyl-1-chloride to the vial containing diethyl phosphite cooled to 0-5° C. (ice bath). To the chilled solution was added formalin, dropwise, via syringe (37%, 2.15 mL, 25.79 mmol, 2.5 eq.) over 10 min maintaining the reaction temp under 10° C. The mixture was then warmed, with stirring, to room temperature for 10 min, then heated to 100° C. for 30 min. Excess formaldehyde and water via rotovap and the crude material purified by Dry Column Vacuum Chromatography (DCVC) on silica gel (20 g silica, 3.5 cm×4.5 cm) eluting with 80 mL EtOAc and collecting 50 mL (20% MeOH/EtOAc). Yield 50% (2.03 g); TLC (10% MeOH in EtOAc), $R_f$=0.70; $^1$H NMR (400 MHz, $CDCl_3$, δ): 4.18-4.09 (m, 8H, H6), 3.62 (t, 2H, J=6.6 Hz, H5), 3.17 (d, 4H, J=8.6 Hz, H4), 2.97 (t, 2H, J=6.6 Hz, H3), 2.00 (p, 2H, J=6.64 Hz, H2), 1.33 (t, 12H, J=7.1 Hz, H1); $^{13}$C NMR (100 MHz, $CDCl_3$, δ): 61.84 (p, $^2J_{C-P}$=3.58 Hz, C6), 53.93 (t, $^3J_{C-P}$=7.44 Hz, C5), 50.18 (dd, $^1J_{1C-P}$=6.08 Hz, $^1J_{1C-P}$=6.00 Hz, C4), 42.47 (C3), 30.77 (C2), 16.45 (t, $^3J_{C-P}$=2.94 Hz, C1); $^{31}$P NMR (121.45 MHz, $CDCl_3$, δ): 24.40 ppm.

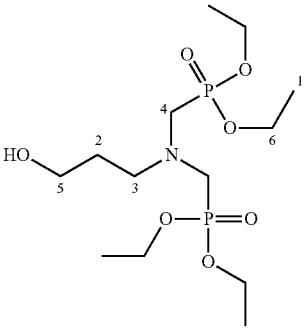

Example 5

Tetraethyl (((3-hydroxypropyl)azanediyl)bis(methylene))bis(phosphonate) (6)

This compound has been previously reported in: Cavero, E., Zablocka, M., Caminade, A. & Majoral, J. P. Design of Bisphosphonate-Terminated Dendrimers. Eur. J. Org. Chem., 2759-2767 (2010); Chougrani, K., Boutevin, B., David, G., Seabrook, S. & Loubat, C. Acrylate based anti-corrosion films using novel bis-phosphonic methacrylates. J. Polym. Sci., Part A: Polym. Chem. 46, 7972-7984 (2008); and Chougrani, K., Boutevin, B., David, G. & Boutevin, G. New N,N-amino-diphosphonate-containing methacrylic derivatives, their syntheses and radical copolymerizations with MMA. Eur. Polym. J. 44, 1771-1781 (2008). To a 20 mL glass screw cap vial, equipped with a magnetic stir bar was added diethylphosphite (2.86 g, 20.74 mmol, 2.0 eq.) and 3-amino-1-propanol (0.768 g, 10.24 mmol,) and the mixture cooled to 0-5° C. (ice bath). To the chilled solution was added formalin, dropwise, via syringe (37%, 2.15 mL, 25.79 mmol, 2.5 eq.) over 10 min maintaining the reaction temp under 10° C. The mixture was warmed, with stirring, to room temperature for 30 min, then heated to 100° C. for 60 min. Excess formaldehyde and water were removed via rotovap and the crude material purified by Dry Column Vacuum Chromatography (DCVC) on silica gel (20 g silica, 3.5 cm×4.5 cm) eluting with 100 mL EtOAc (20% MeOH/EtOAc). Yield 50% (2.03 g); TLC (10% MeOH in EtOAc), $R_f$=0.50; $^1$H NMR (400 MHz, $CDCl_3$, δ): 4.18-4.09 (m, 8H, H6), 3.62 (t, 2H, J=6.6 Hz, H5), 3.17 (d, 4H, J=8.6 Hz, H4), 2.97 (t, 2H, J=6.6 Hz, H3), 1.61 (p, 2H, J=5.56 Hz, H2), 1.32 (t, 12H, J=7.1 Hz, H1) ppm; $^{31}$P NMR (121.45 MHz, $CDCl_3$, δ): 25.0 ppm.

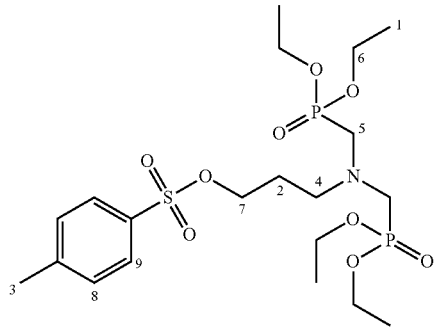

Example 6

3-(bis((diethoxyphosphoryl)methyl)amino)propyl 4-methylbenzenesulfonate (7)

To a flame dried and evacuated 25 mL round bottom flask, equipped with a magnetic stir bar was added sequentially trimethylamine hydrochloride (0.045 g, 0.24 mmol, 0.24 eq.), DCM (1 mL), triethylamine (0.58 mL, 2.5 mmol, 2.5 eq) the alcohol (0.375 g, 1 mmol) and the solution cooled to 0° C. in an ice bath. To the chilled, stirred solution was added, dropwise, tosyl chloride, anhydrous DCM (2 mL) and the cloudy yellow mixture was stirred for 1 hr at room temperature at which point TLC showed disappearance of the starting amine (5% MeOH in EtOAc, 10 mL). The reaction was diluted with water (1×15 mL) and extracted with DCM (10 mL total), the aqueous layer was re-extracted with EtOAC (15 mL) and the combined organic layers were dried over $MgSO_4$, filtered and evaporated to give a yellow oil. The crude material was purified by flash chromatography on silica gel (20 g silica, 1.5 cm i.d) with gradient elution: 100% EtOAc (35 mL) then 5% MeOH:EtOAc (90 mL) to obtain the title compound as a yellow oil. Yield 56.7% (0.3003 g); TLC (5% MeOH in EtOAc), $R_f$=0.42; $^1$H NMR (400 MHz, $CDCl_3$, δ): 7.76 (d, 2H, J=8.24 Hz, H9), 7.32 (d, 2H, J=8.04 Hz, H8), 4.13-4.05 (m, 10H, H7+H6), 3.08 (d, 4H, J=8.40 Hz, H5), 2.83 (t, 2H, J=6.70 Hz, H4), 2.42 (s, 3H, H3), 1.81 (t, 2H, J=6.65 Hz, H2), 1.30 (t, 12H, J=7.08 Hz, H1); $^{13}$C NMR (100 MHz, $CDCl_3$, δ): 44.67 (C11), 133.19 (C10), 129.81 (C8), 127.83 (C9), 68.50 (C7), 61.86 (t, $^2J_{C\text{-}P}$=3.19 Hz, C6), 52.67 (dd, $^1J_{C\text{-}P}$=6.02 Hz, C5), 52.67 (C4), 27.22 (C2), 21.57 (C3), 16.46 (t, $^3J_{C\text{-}P}$=2.78 Hz, C1) ppm; $^{31}$P NMR (121.45 MHz, $CDCl_3$, δ): 24.56 ppm.

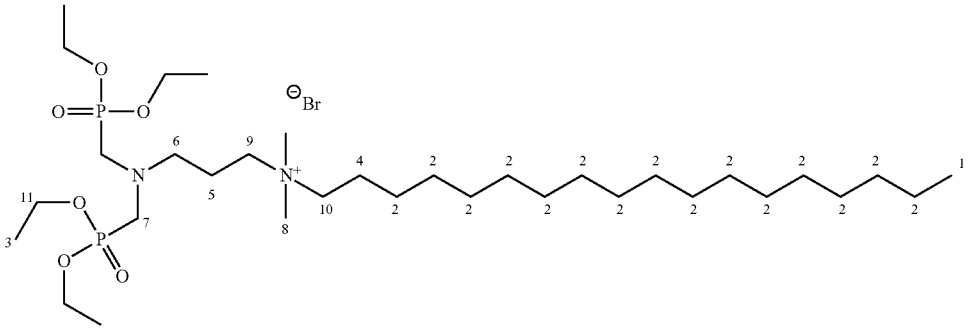

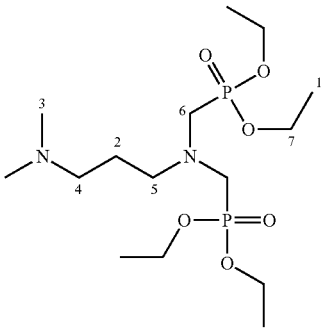

Example 7

Tetraethyl (((3-(dimethylamino)propyl)azanediyl)bis(methylene))bis(phosphonate) (8)

To a 20 mL glass screw cap vial equipped with a magnetic stir bar containing the bromo amino bisphosphonate (0.954 g, 1.8 mmol) was added $NHMe_2$ (5.6 M in EtOH, 2.5 mL, excess) followed by $H_2O$ (0.5 mL) and the clear mixture was stirred at reflux sealed for 1.5 hr, at which point TLC showed disappearance of the starting material (1% $NH_4^+OH^-$ in Acetone, 10 mL, $R_f$=0.95). The cooled yellow reaction diluted with water (1×20 mL, pH was 11) and extracted with $CHCl_3$ (2×30 mL), dried over $MgSO_4$, filtered and evaporated to give an orange oil. The title compound was isolated >98% purity ($^1$H and $^{31}$P NMR) and required no further purification. Yield 62% (0.4461 g); TLC (1% $NH_4^+OH^-$ in Acetone, 10 mL) or (20% MeOH (6% NaBr): MeCN, $R_f$=0.47; $^1$H NMR (400 MHz, $CDCl_3$, δ): 4.15-4.06 (m, 8H, H7), 3.11 (d, 4H, J=8.9 Hz, H6), 2.80 (t, 2H, J=6.8 Hz, H5), 2.27 (t, 211, J=7.5 Hz, H4), 2.18 (s, 6H, H3), 1.61 (p, 2H, J=7.15 Hz, H2), 1.28 (t, 12H, J=7.0 Hz, H1) ppm; $^{13}$C NMR (100 MHz, $CDCl_3$, δ): 61.8 (t, $^2J_{CP}$=3.3 Hz, C7), 57.24 (C4), 55.03 (C5), 50.92 (dd, $^1J_{CP}$=7.1 Hz, C6), 49.36 (dd, $^1J_{CP}$=6.7 Hz, C6), 45.48 (C3), 25.65 (C2), 16.48 (t, $^3J_{CP}$=2.8 Hz, C1) ppm; $^{31}$P NMR (121.45 MHz, $CDCl_3$, δ): 24.89 ppm.

Example 8

N-(3-(bis((diethoxyphosphoryl)methyl)amino)propyl)-N,N-dimethyloctadecan-1-aminium (9)

To a flame dried and evacuated 20 mL screw cap vial, equipped with a magnetic stir bar was added a mixture of bromoaminobisphosphonate (0.2 g, 0.51 mmol) and DMOA (0.143 g, 0.6 mmol, 1.19 eq.) was which was sealed and heated to 100° C. on a sand batch. After 1 hr, TLC showed the disappearance of the starting amine (5% MeOH in EtOAc, 10 mL). The mixture was partitioned between hexanes (~7 mL) and MeOH/$H_2O$ (4:1, 5 mL), the bottom yellow methanolic layer was separated and concentrated (2×5 mL ACN to azeotrope excess water) to afford a yellow oily solid (0.3082 g). The crude material was purified by Dry Column Vacuum Chromatography (DCVC) on silica gel (20 g silica, 3.5 cm×4.5 cm) pre-washed with 60 mL 20% MeOH (NaBr 6%): ACN then eluting with the same eluent (1st 40 mL removed upper $R_f$ impurity, product was obtained in the next 7 fractions total 95 mL) as a yellow oil after filtering off NaBr through a pad of Celite washing with $CHCl_3$. Yield 46.1% (0.162 g). TLC (20% MeOH (NaBr 6%): ACN), $R_f$=0.5; $^1$H NMR (400 MHz, $CDCl_3$, δ) 4.15-4.08 (m, 8H, H11), 3.72-3.69 (m, 2H, H10), 3.55-3.51 (m, 2H, H9), 3.33 (s, 6H, H8), 3.12-3.08 (m, 4H, H7), 2.99-2.97 (m, 2H, H6), 2.0-1.98 (m, 2H, H5), 1.74-1.71 (m, 2H, H4), 1.24-1.20 (br m, 42H, H2, H3, overlap) 0.88-0.83 (m, 3H, H1) ppm; $^{13}$C NMR (100 MHz, $CDCl_3$, δ): 62.15-62.0 (overlap, C7, C9, C10, C11), 51.1 (C6, C8 overlap), 31.91 (C2 overlap), 29.67-29.27 (C2 overlap), 22.84 (C4), 22.67 (C5), 16.58-16.50 (m, $J_{CP}$=unresolved, C3), 14.10 (C1) ppm; $^{31}$P NMR (121.45 MHz, $CDCl_3$, δ) 24.40 ppm. HRMS-DART (m/z): [$M^+$] calculated for $C_{33}H_{73}N_2O_6P_2$, 655.4937. found, 655.4938.

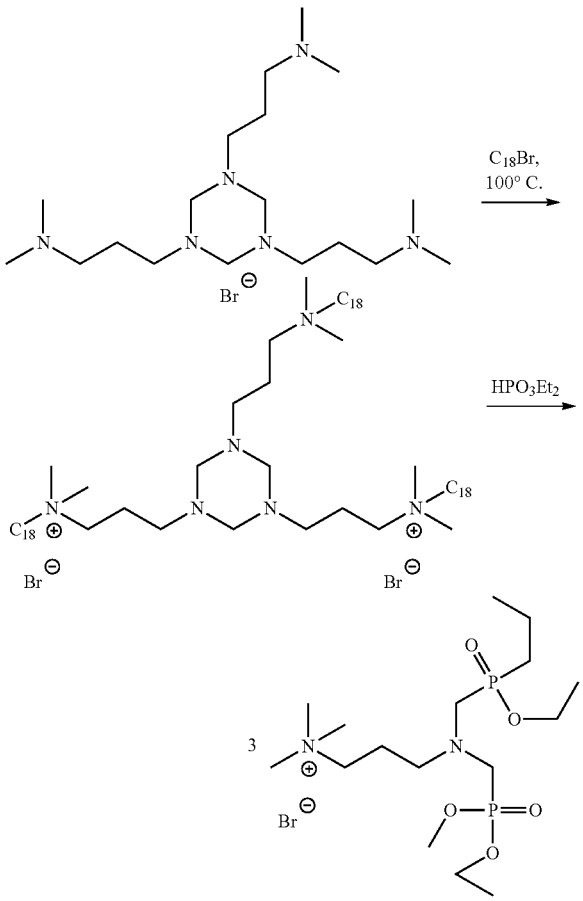

Synthesis of α-Amino Bisphosphonic Quats-Via Triazinane Intermediate.

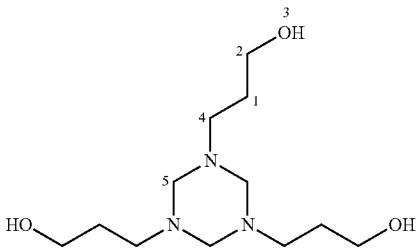

Example 9

3,3',3"-(1,3,5-triazinane-1,3,5-triyl)tris(propan-1-ol) (10)

To a 125 mL round bottom flasks, formalin (0.813 mL, 10 mmol) was added to a solution of 3-amino-1-propanol (0.751 g, 10 mmol) in MeCN (10 mL). The reaction was stirred at room temperature overnight. Evaporation of volatiles followed by (DCVC) on silica gel (20 g silica, 3.5 cm×4.5 cm) eluting with 5% $NH_4^+OH^-$ in acetone (50 mL) then collecting (150 mL) provided pure product. Yield 92% (0.8 g). TLC (5% $NH_4^+OH^-$ in acetone, 10 mL), $R_f$=0.3; $^1H$ NMR (400 MHz, $CDCl_3$, δ): 4.37 (s, 6H, H5), 3.84 (t, 6H, J=7.0 Hz, H4), 3.71 (s, 3H, H3), 2.97 (t, 6H, J=5.6 Hz, H2), 1.60 (q, 6H, J=5.40 Hz, H1) ppm; $^{13}C$ NMR (100 MHz, $CDCl_3$, δ): 83.06 (C4), 68.12 (C3), 47.78 (C2), 22.45 (C1) ppm.

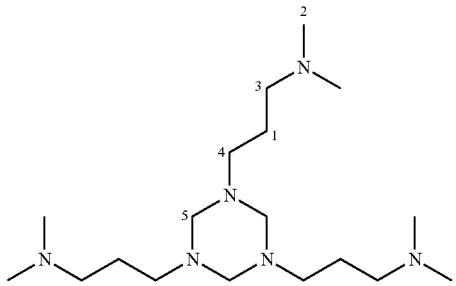

Example 10

3,3',3"-(1,3,5-triazinane-1,3,5-triyl)tris(N,N-dimethylpropan-1-amine) (11)

To a 125 mL round bottom flask, paraformaldehyde (1.652 g, 55 mmol, 1.1 eq.) was added to a solution of N,N-dimethylpropane-1,3-diamine (6.29 mL, 50 mmol) in toluene (15 mL). The reaction was refluxed using a dean-stark trap for 1.5 hr. Toluene was evaporated and a portion of the residue (1.9757 g) was partitioned between $CHCl_3$ (15 mL) and water (5 mL). The organic layer was separated, dried with $MgSO_4$ and concentrated to give a clear oil. Yield 66% (1.3067 g). TLC (20% MeOH in EtOAc, 10 mL), $R_f$=0.05; $^1H$ NMR (400 MHz, $CDCl_3$, δ): 3.29 (brs, 6H, H5), 2.40 (t, 6H, J=7.5 Hz, H4), 2.25 (t, 6H, J=7.5 Hz, H3), 2.18 (s, 18H, H2), 1.59 (p, 6H, J=7.5 Hz, H1) ppm; $^{13}C$ NMR (100 MHz, $CDCl_3$, δ): 74.65 (C5), 57.83 (C3), 50.78 (C4), 45.54 (C2), 25.88 (C1) ppm.

β-Amino Bisphosphonic Acid Antimicrobials (β-ABPQ)

Scheme 3.0 Synthesis of β-Amino Bisphosphonic Quats.

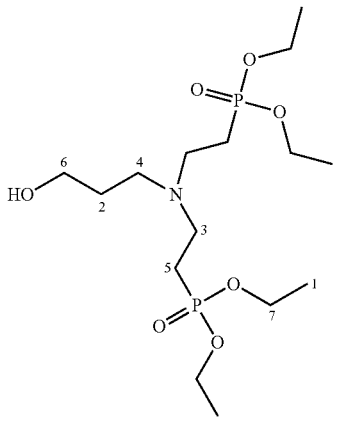

Example 11

Tetraethyl (((3-hydroxypropyl)azanediyl)bis(ethane-2,1-diyl))bis(phosphonate) (12)

This compound has been previously reported in: Pothayee, N. et al. Synthesis of 'ready-to-adsorb' polymeric nanoshells for magnetic iron oxide nanoparticles via atom transfer radical polymerization. Polymer 52, 1356-1366 (2011). To a 25 mL round bottom flask equipped with a magnetic stir bar, was added a stirred solution of the primary amine (0.448 g, 5.9 mmol) in distilled water (5 ml) at room temperature. Two equivalents of diethyl vinylphosphonate (1.637 g, 12.03 mmol, 2.01 eq.) was then added and the reaction stirred at room temperature overnight. The reaction was transferred to a 125 mL round bottom flask along with 30 mL MeCN and evaporated to a clear oil (2.1446 g, containing ≈7% starting material by $^{31}$P NMR). The crude material was purified by Dry Column Vacuum Chromatography (DCVC) on silica gel (20 g silica, 3.5 cm×4.5 cm) eluting with 30% MeOH:EtOAc (240 mL). The fractions containing the title compound were filtered through a pad of Celite evaporated to obtain the title compound as a clear oil. Yield 95% (1.9687 g); TLC (30% MeOH:EtOAc), $R_f$=0.33; $^1$H NMR (400 MHz, $CDCl_3$, δ): 4.16-4.03 (m, 8H, H7), 3.75-3.67 (m, 3H, H6), 2.83-2.75 (m, 4H, H5), 2.64-2.59 (m, 2H, H4), 1.97-1.86 (m, 4H, 1H), 1.68 (q, 2H, J=5.58 Hz, H2), 1.31 (t, 12H, J=7.06 Hz, H1) ppm; $^{31}$P NMR (121.45 MHz, $CDCl_3$, δ): 30.00 ppm.

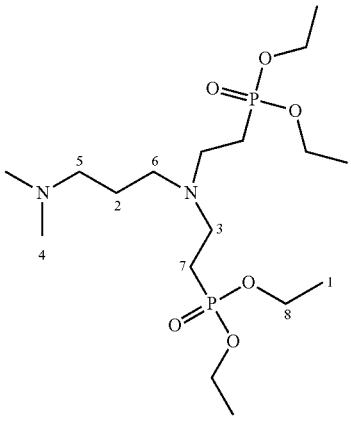

Example 12

Tetraethyl (((3-(dimethylamino)propyl)azanediyl)bis (ethane-2,1-diyl))bis(phosphonate) (13)

Synthesized from alcohol via mesylate and dimethylamine, see Tetraethyl (((3-(dimethylamino)propyl)azanediyl) bis(methylene))bis(phosphonate) procedure; $^1$H NMR (400 MHz, $CDCl_3$, δ): 4.11-3.99 (m, 8H, H8), 2.76-2.69 (m, 4H, H7), 2.40 (t, 2H, J=7.12 Hz, H6), 2.22 (t, H5, J=7.14 Hz, H5), 2.16 (s, 6H, H4), 1.91-1.81 (m, 4H, H3), 1.60-1.53 (m, H2, 2H), 1.28 (t, H1, J=7.04 Hz) ppm; $^{31}$P NMR (121.45 MHz, $CDCl_3$, δ): 30.57 ppm.

Bisphosphonic Acid Antimicrobials (BPQ).

Syntheses of Bisphosphonic Quats—Direct Alkylation of Tetraethylmethylene Bisphosphonate.

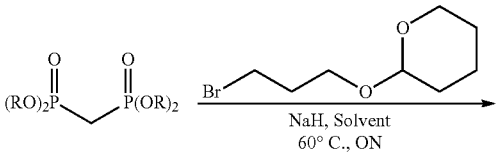

-continued

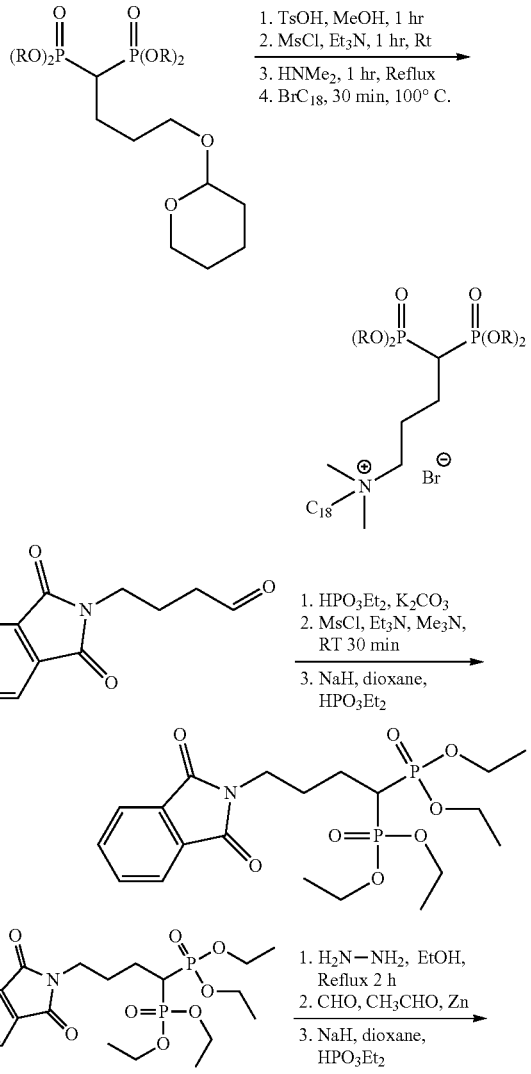

Syntheses of Bisphosphonic Quats—Via α-Mesylate.

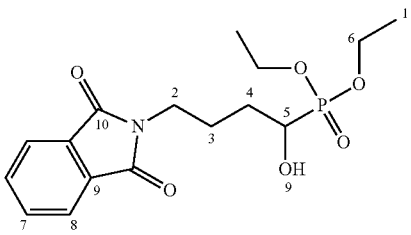

Example 13

Diethyl (4-(1,3-dioxoisoindolin-2-yl)-1-hydroxybutyl)phosphonate (14)

A 25 mL round bottom flask, equipped with a magnetic stir bar and a condenser was charged with the aldehyde (2.281 g, 10.5 mmol), diethylphosphonate (1.523 g, 11.03 mmol, 1.05 eq.), $K_2CO_3$ (0.073 g, 0.53 mmol, 0.05 eq.) and MeCN (5 mL). The heterogeneous solution was stirred at 60° C. for 15 min at which point TLC showed disappearance of the starting aldehyde (60% EtOAc in hexanes, 10 mL). The reaction was cooled to 0° C., filtered and evaporated. The resulting yellow oil solidified under high vacuum (10 min) and was recrystallized from hot EtOAc (5 mL) after cooling for 20 min at 0° C. Yield 69.1% (2.5787 g); TLC (60% EtOAc in hexanes), $R_f$=0.2; $^1$H NMR (400 MHz, $CDCl_3$, δ): 7.83-7.79 (m, 4H, H8), 7.71-7.64 (m, 4H, H7), 4.18-4.07 (m, 4H, H6), 3.89 (quintet, J=4.59 Hz, 1H, H5), 3.77-3.66 (m, 2H, H4), 2.05-1.95 (m, 2H, H3), 1.87-1.68 (m, 2H, H2), 1.29 (t, J=7.08 Hz, 6H, H1) ppm; $^{13}$C NMR (100 MHz, $CDCl_3$, δ): 168.37 (C10), 133.90 (C9), 132.10 (C7), 123.18 (C8), 68.12 (C5), 62.65 (q $^2J_{C-P}$=7.3 Hz, C6), 37.52 (C2), 28.43 (d, $^1J_{C-P}$=1.45 Hz, C5), 25.02 (C3), 24.96 (C4), 16.46 (d, $^3J_{C-P}$=5.20 Hz, C1) ppm; $^{31}$P NMR (121.45 MHz, $CDCl_3$, δ): 24.64 ppm.

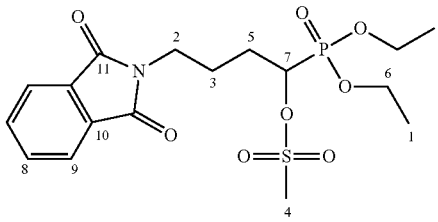

Example 14

1-(diethoxyphosphoryl)-4-(1,3-dioxoisoindolin-2-yl) butyl methanesulfonate (15)

To a flame dried and evacuated 50 mL round bottom flask, equipped with a magnetic stir bar was added sequentially trimethylamine hydrochloride (0.062 g, 0.62 mmol, 0.20 eq.), DCM (2 mL), triethylamine (0.65 mL, 4.63 mmol, 1.5 eq.) and the alcohol (1.097 g, 3.09 mmol) and the solution was cooled to 0° C. in an ice bath. To the chilled stirred solution was added, dropwise, mesyl chloride (0.25 mL, 3.70 mmol, 1.2 eq.) in anhydrous DCM (2 mL) and the cloudy yellow mixture was stirred for 20 min at room temperature at which point TLC showed disappearance of the starting amine (10% MeOH in EtOAc, 10 mL). The reaction was diluted with water (1×10 mL) and extracted with DCM (2×5 mL total), the combined organic layers were dried over $MgSO_4$, filtered and evaporated to give a yellow oil. The crude product (1.409 g) containing traces of DCM and excess mesyl chloride by $^1$H NMR, was placed under high vacuum at 60° C. for 1 hr. Yield 93% (1.2013 g); TLC (10% MeOH in EtOAc), $R_f$=0.5; $^1$H NMR (400 MHz, $CDCl_3$, δ): 7.85-7.81 (m, 2H, H9), 7.73-7.70 (m, 2H, H8), 4.94-4.88 (m, 1H, H7), 4.20-4.15 (m, 4H, H6), 3.77-3.70 (m, 2H, H5), 3.15 (s, 3H, H4), 1.95-1.82 (m, 4H, H2, H3), 1.41-1.25 (m, 6H, H1) ppm; $^{13}$C NMR (100 MHz, $CDCl_3$, δ): 168.26 (C11), 133.98 (C10), 132.08 (C9), 123.22 (C8), 74.79 (C7), 63.31 (q, $^2J_{C-P}$=7.3 Hz, C6), 52.56 (C2), 39.11 (C4), 27.58 (C3), 24.45 (d, $^2J_{C-P}$=11.67 Hz C5), 16.45 ($^2J_{C-P}$=5.20 Hz, C1) ppm; $^{31}$P NMR (121.45 MHz, $CDCl_3$, δ): 17.63 ppm.

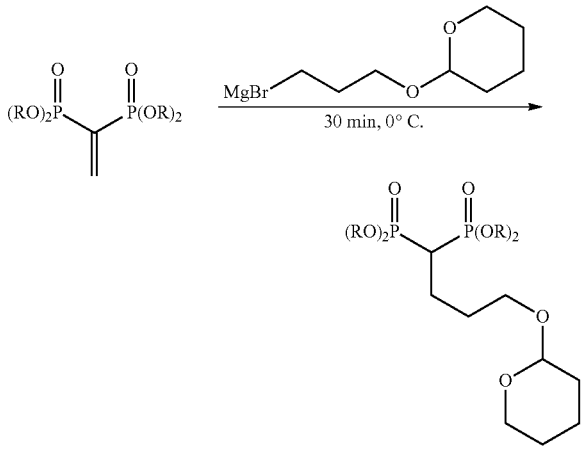

Syntheses of Bisphosphonic Quats—Via Michael Addition to a Vinylbisphosphonate.

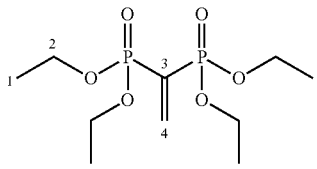

Example 15

Tetraethyl ethene-1,1-diylbis(phosphonate) (16)

This compound has been previously reported in: Gebbia, N., Simoni, D., Dieli, F., Tolomeo, M. & Invidiata, F. P. Geminal bisphosphonates, their preparation and their use in the field of oncology. PCT Int. Appl., 38 (2009); and Simoni, D. et al. Design, Synthesis, and Biological Evaluation of Novel Aminobisphosphonates Possessing an in Vivo Antitumor Activity Through a T Lymphocytes-Mediated Activation Mechanism. J. Med. Chem. 51, 6800-6807 (2008). A 50 mL round bottom flask was charged with paraformaldehyde (6.3 g, 200 mmol, 4.0 eq.) and diethylamine (5.2 mL, 50 mmol, 1 eq.) in methanol (125 mL) and the mixture was stirred under reflux until a clear solution was obtained (~5 min). Tetraethylmethylene bisphosphonate was added via syringe (12.4 mL, 50 mmol, 1.0 eq.) and the solution was refluxed overnight (24 hr). The clear solution was concentrated in vacuo and then re-evaporated from toluene (2×10 mL) completely removing residual MeOH to give the intermediate methyl ether as a clear oil. The residue was dissolved in toluene (100 mL), treated with p-toluenesulphonic acid (38 mg, 0.02 mmol), and refluxed through a Dean-Stark trap overnight. The orange solution was concentrated in vacuo, dissolved in chloroform (50 mL), washed with water (2×10 mL), dried over $MgSO_4$, and concentrated in vacuo. A portion of the orange oil (6 g) was further distilled under high vacuum. Yield 90% (5.4 g); TLC (EtOAc), $R_f$=0.2; $^1$H NMR (400 MHz, $CDCl_3$, δ): 7.02-6.86 (m, H3, 2H), 4.10-

4.05 (m, H2, 8H), 1.34-1.21 (m, H1, 12H) ppm; $^{13}C$ NMR (100 MHz, $CDCl_3$, δ): 149.04 (m, C4), 133.77-129.71 (m, C3), 62.54 (t, $^2J_{C-P}$=2.88 Hz, C2), 16.17 (t, $^3J_{C-P}$=3.15 Hz, C1) ppm; $^{31}P$ NMR (121.45 MHz, $CDCl_3$, δ): 21.0 ppm.

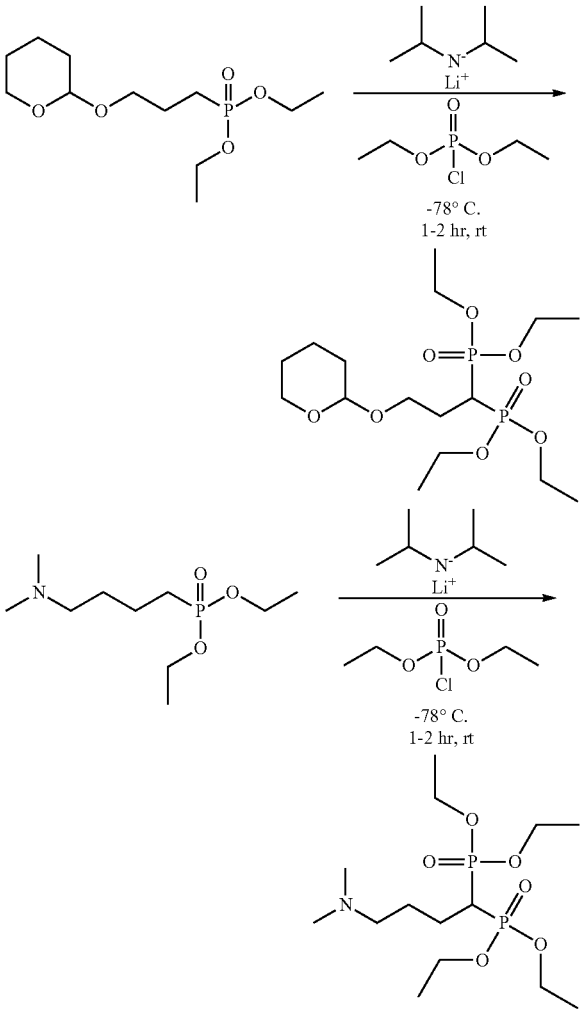

Syntheses of Bisphosphonic Quats—Via Phosphorylation of a Mono-Phosphonate.

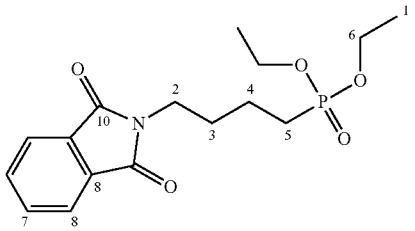

Example 16

Diethyl
(4-(1,3-dioxoisoindolin-2-yl)butyl)phosphonate (17)

This compound has been previously reported in Hara, T., Durell, S. R., Myers, M. C. & Appella, D. H. Probing the Structural Requirements of Peptoids That Inhibit HDM2-p53 Interactions. J. Am. Chem. Soc. 128, 1995-2004 (2006). To a flame dried 50 mL round bottom flask equipped with a reflux condenser was added N-(4-Bromobutyl)-phthalimide (5 g, 17.7 mmol, 1.0 eq.) followed by triethylphosphite (18.24 mL, 106.3 mmol, 6 eq.) and the mixture was refluxed overnight (175° C.) using a sand bath. The reaction was then cooled to room temperature and excess triethylphosphite was vacuum distilled using a shortpath distillation head attached to a Schlenk line. Once all of the excess triethylphosphite stopped distilling, the title compound was placed under high vacuum (~30 min) until it solidified. Further recrystallization from EtOAc (5 mL) at −20° C. provided pure product. Colourless crystals. Yield: 90% (5.4263 g). TLC (5% MeOH: EtOAc), $R_f$=0.90; $^1H$ NMR (400 MHz, $CDCl_3$, δ): 7.82-7.77 (m, 2H, H8), 7.70-7.66 (m, 2H, H7), 4.11-3.98 (m, 4H, H6), 3.66 (m, J=7.0 Hz, 2H, H5), 1.81-1.71 (m, 4H, H4, H3), 1.67-1.56 (m, 2H, H2), 1.27 (t, J=7.1 Hz, H1) ppm; $^{13}C$ NMR (100 MHz, $CDCl_3$, δ): 168.29 (C10), 133.91 (C9), 132.06 (C7), 123.18 (C8), 61.48 (d, $^2J_{C-P}$=6.5 Hz, C6), 37.23 (d, $^1J_{C-P}$=1.33 Hz, C5), 29.25 (d, $^2J_{C-P}$=16.77 Hz C4), 24.44 (C2), 19.81 (d, $^3J_{C-P}$=5.01 Hz, C3), 16.42 (d, $^3J_{C-P}$=6.01 Hz, C1) ppm; $^{31}P$ NMR (121.45 MHz, $CDCl_3$, δ): 31.48 ppm.

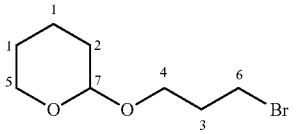

Example 17

2-(3-bromopropoxy)tetrahydro-2H-pyran (18)

This compound has been previously reported in: Pinchuk, A. N. et al. Synthesis and Structure-Activity Relationship Effects on the Tumor Avidity of Radioiodinated Phospholipid Ether Analogues. J. Med. Chem. 49, 2155-2165 (2006). To a stirred solution inside a 125 mL round bottom flask containing 3-bromo-1-propanol (6.95 g, 50 mmol, 1 eq.) in DCM (25 mL) was added 3,4-dihydropyran (5.93 mL, 65 mmol, 1.3 eq.). The mixture was stirred overnight at room temperature at which point TLC showed disappearance of 3-bromo-1-propanol (20% EtOAc in hexanes, 10 mL, $KMnO_4$). The reaction was evaporated and the crude material was purified by flash chromatography on silica gel (20 g silica, 1.5 cm i.d) eluting with 10% EtOAc: hexanes (100 mL) to obtain the title compound as a clear oil. Yield 86.4% (9.637 g); TLC (20% EtOAc in hexanes), $R_f$=0.85; $^1H$ NMR (400 MHz, $CDCl_3$, δ): 4.59 (t, 1H, J=3.52 Hz, H7), 3.90-3.81 (m, 2H, H6), 3.55-3.47 (m, 4H, H4+H5), 2.16-2.08 (m, 2H, H3), 1.90-1.64 (m, 2H, H2), 1.57-1.50 (m, 4H, H1) ppm; $^{13}C$ NMR (100 MHz, $CDCl_3$, δ): 98.90 (C7), 64.88 (C6), 62.26 (C5), 32.90 (C3), 30.59 (d, $^2J$=6.04 Hz, C4), 25.41 (C2), 19.48 (C1) ppm.

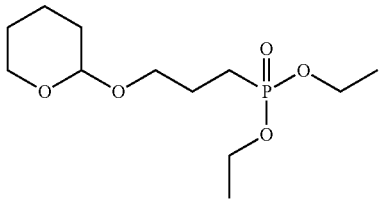

Example 18

Diethyl (3-((tetrahydro-2H-pyran-2-yl)oxy)propyl) phosphonate (19)

This compound has been previously reported in: Voigt, M. et al. Surface Functionalization of ZnO Nanorods with C60 Derivatives Carrying Phosphonic Acid Functionalities. J. Phys. Chem. C 115, 5561-5565 (2011). To a 20 mL conical round bottom flask was added the THP protected bromopropylalcohol (4.55 g, ~20 mmol) followed by excess triethyl phosphite (10.0 mL, 60.0 mmol, 3.0 eq.). The reaction was heated at reflux (175° C.) overnight. Excess triethyl phosphite was vacuum distilled at reduced pressure providing the pure product as a clear, viscous oil. Yield 89% (5 g). $^{1}$H NMR (400 MHz, $CDCl_3$, δ): 4.57 (t, 2H, J=3.54 Hz, H8), 4.17-4.04 (m, 4H, H7), 3.86-3.72 (m, 2H, H6), 3.52-3.40 (m, 2H, H5), 1.93-1.77 (m, 4H, H4+H3), 1.73-1.67 (m, 4H, H2), 1.31 (t, 6H, J=7.04 Hz, H1) ppm; $^{13}$C NMR (100 MHz, $CDCl_3$, δ): 98.86 (C8), 64.85 (C6), 62.21 (C5), 32.90 (C3), 30.66 (C4), 25.43 (C2), 19.71 (C1) ppm.

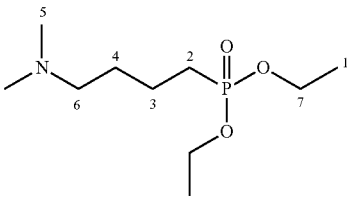

Example 19

Diethyl (4-(dimethylamino)butyl)phosphonate (20)

A mixture of diethyl (4-bromobutyl)phosphonate (5.0 g, 18.3 mmol) with $NHMe_2$ (5.6 M in EtOH, 10 mL, excess) was placed, with a magnetic stirring bar, into a 20 ml glass reaction tube and sealed. The reaction mixture was heated in the Biotage® Initiator Microwave Synthesizer at 110° C. (5 min). Volatiles were removed on a rotovap and the crude material was purified by Dry Column Vacuum Chromatography (DCVC) on silica gel (50 g silica, 3.5 cm×5.5 cm) eluting first with 150 mL (10% MeOH/acetone) collecting 250 mL (10% MeOH/10% $NH_4^+OH^-$/80% acetone). Yield 81% (3.55 g); TLC (20% $NH_4^+OH^-$/acetone), Rf=0.50; $^{1}$H NMR (400 MHz, $CDCl_3$, δ): 4.06-3.92 (m, 4H, H7), 2.85 (t, 2H, J=7.96 Hz, H6), 2.62 (s, 6H, H5), 1.83-1.53 (m, 6H, H4-H2 overlap), 1.22 (t, 6H, J=7.04 Hz, H1) ppm; $^{13}$C NMR (100 MHz, $CDCl_3$, δ): 61.71 (d, $^{2}J_{CP}$=6.60 Hz, C7), 57.68 (C6), 43.58 (C5), 25.68 (t, $^{1}J_{CP}$=14.07 Hz, C2), 24.13 (C4), 19.90 (d, $^{2}J_{CP}$=4.60 Hz, C3), 16.41 (d, $^{3}J_{CP}$=6.22 Hz, C1) ppm; $^{31}$P NMR (121.45 MHz, $CDCl_3$, δ): 30.89 ppm.

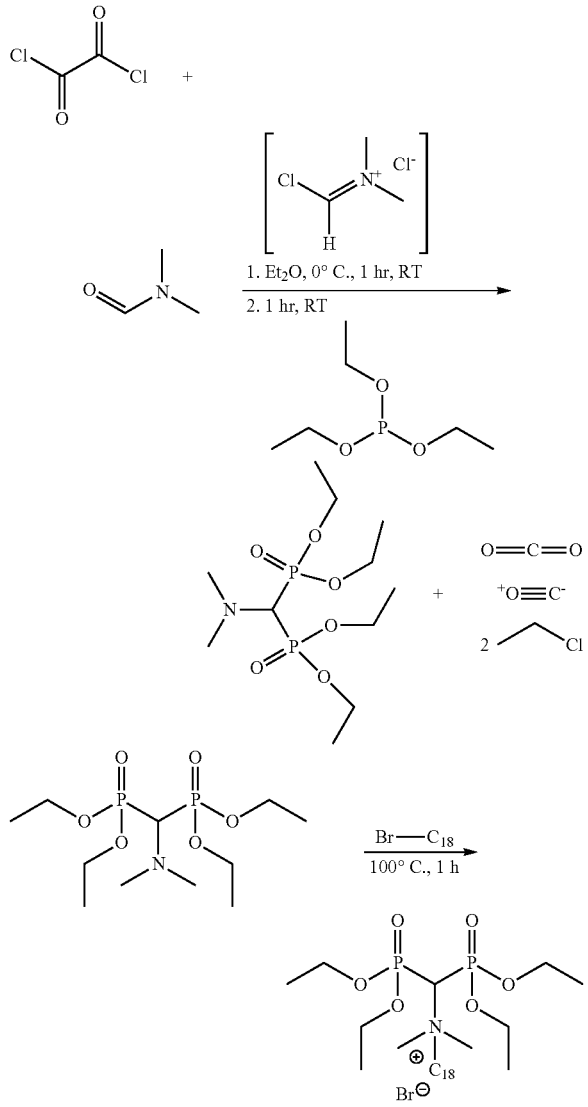

Syntheses of Bisphosphonic Quats—Via Triethylorthoformate.

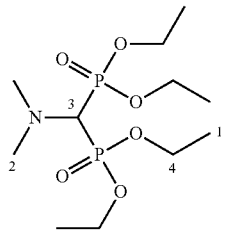

Example 20

Tetraethyl dimethylaminomethylenediphosphonate (21)

This compound has been previously reported in: O'Boyle, N. M. et al. Synthesis, evaluation and structural studies of antiproliferative tubulin-targeting azetidin-2-ones. Bioorg.

Med. Chem. 19, 2306-2325 (2011). To a chilled solution of dimethylformamide (3.87 mL, 50 mmol) in DCM (75 mL) was added dropwise with stirring a solution of oxalyl chloride (25 mL, 2M in DCM, 50 mmol). Following addition, the mixture was allowed to warm to room temperature and stirred for 1 h. Triethyl phosphite (18.77 mL, 109.5 mmol, 2.19 eq.) was then added dropwise with stirring. After 1 hr the mixture was concentrated under reduced pressure. The product was obtained as a yellow oil in 75.5% yield. $^{1}$H NMR (400 MHz, $CDCl_3$, δ): 4.21-4.14 (m, 8H, H4), 3.22 (dt, 1H, $^{1}$J=24.98 Hz, $^{2}$J=24.98 Hz, H3), 2.58 (s, 6H, H2), 3.18 (dt, 12H, J=7.07 Hz, J=7.06 Hz, 1H) ppm; $^{13}$C NMR (100 MHz, $CDCl_3$, δ): 62.70 (t, $^{1}J_{C\text{-}P}$=3.05 Hz, C3), 62.40 (t, $^{2}J_{C\text{-}P}$=3.61 Hz, C4), 44.11 (t, $^{3}J_{C\text{-}P}$=4.71 Hz, C2), 16.39 (q, $^{3}J_{C\text{-}P}$=3.01 Hz, C1) ppm; $^{31}$P NMR (121.45 MHz, $CDCl_3$, δ): 19.15 ppm.

Multidentate Phosphonic Acid Antimicrobial Structures

Bisphosphonic Acid Antimicrobials:

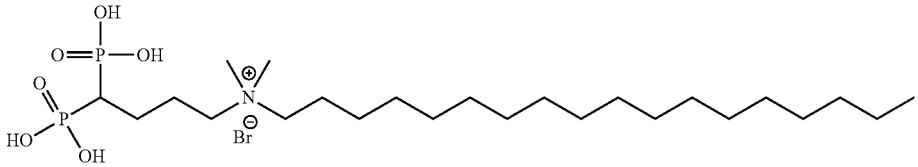

N-(4,4-diphosphonobutyl)-N,N-dimethyloctadecan-1-aminium bromide. (22)

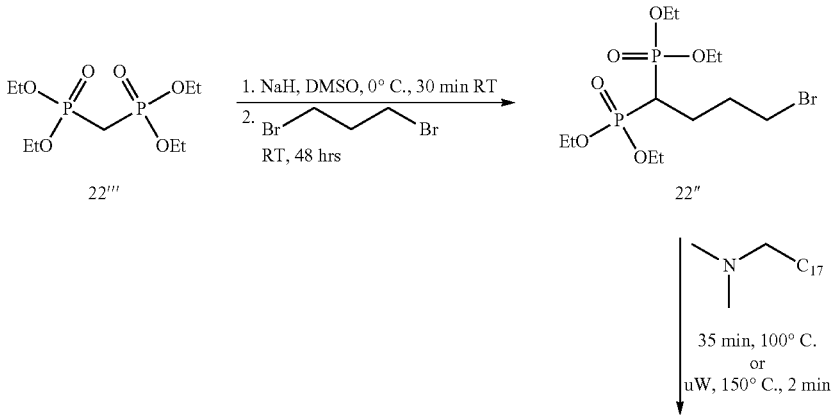

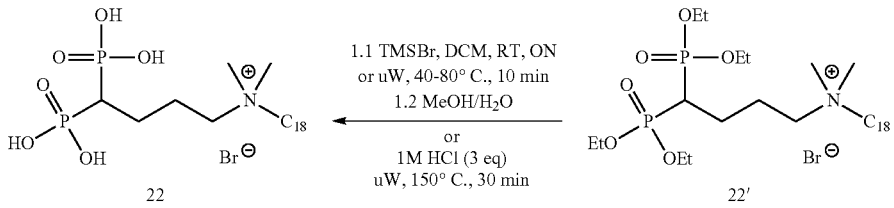

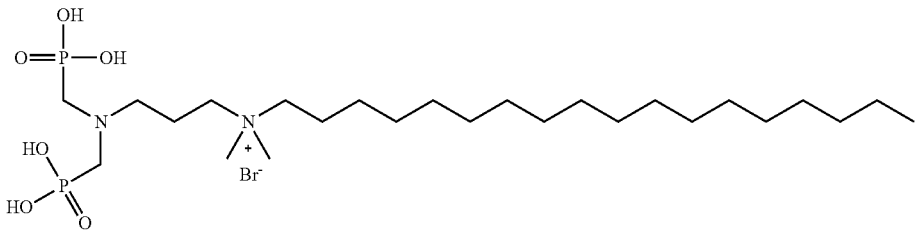

N-(3-(bis(phosphonomethyl)amino)propyl)-N,N-dimethyloctadecan-1-aminium bromide (23)
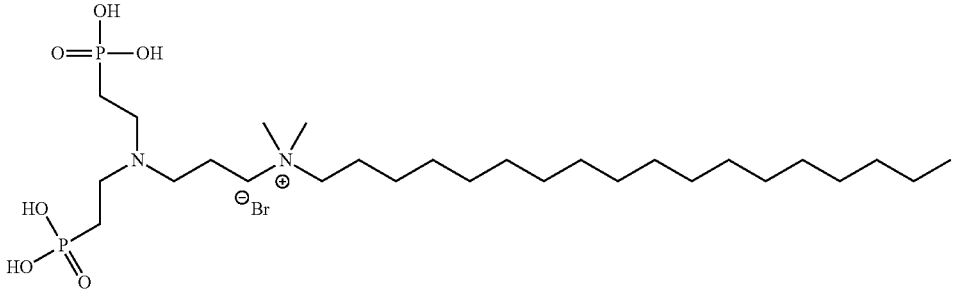
N-(3-(bis(2-phosphonoethyl)amino)propyl)-N,N-dimethyloctadecan-1-aminium bromide (24)
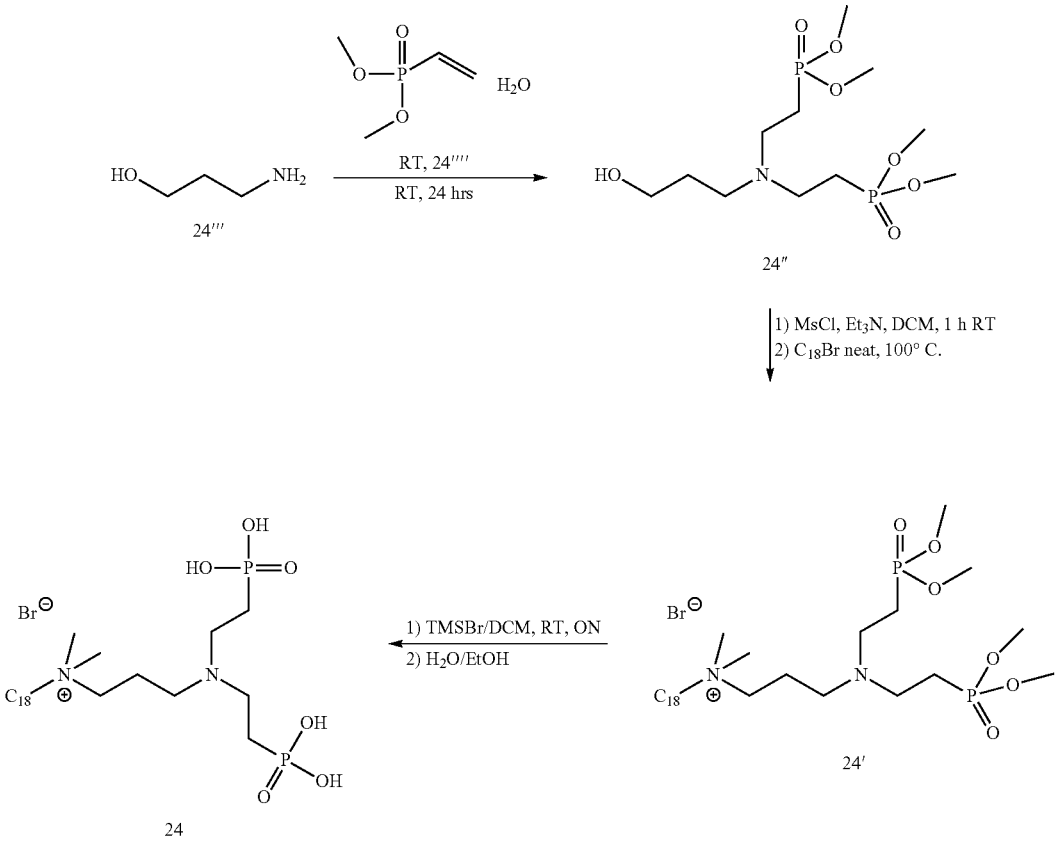
Trisphosphonic Acid Antimicrobials:
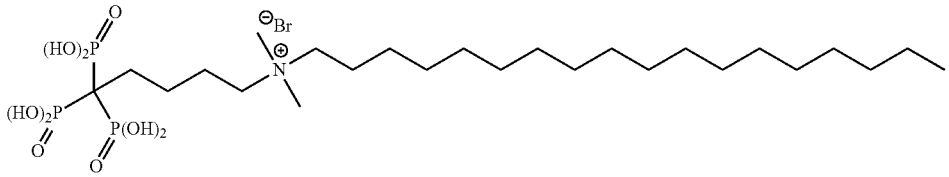

N,N-dimethyl-N-(4,4,4-triphosphonobutyl)octadecan-1-aminium bromide (25)
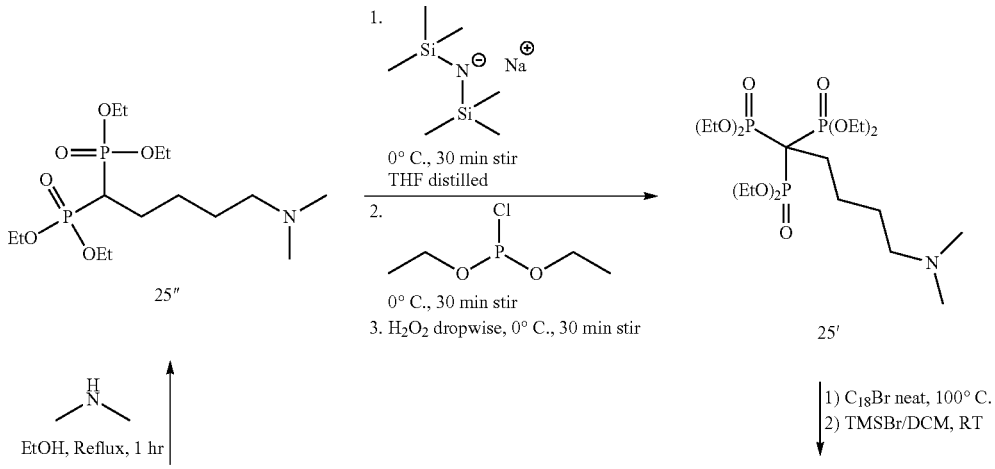
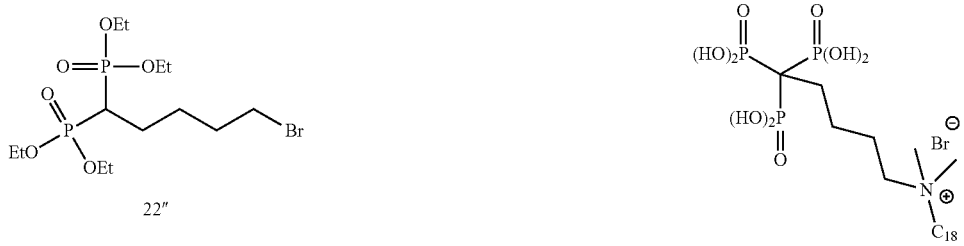
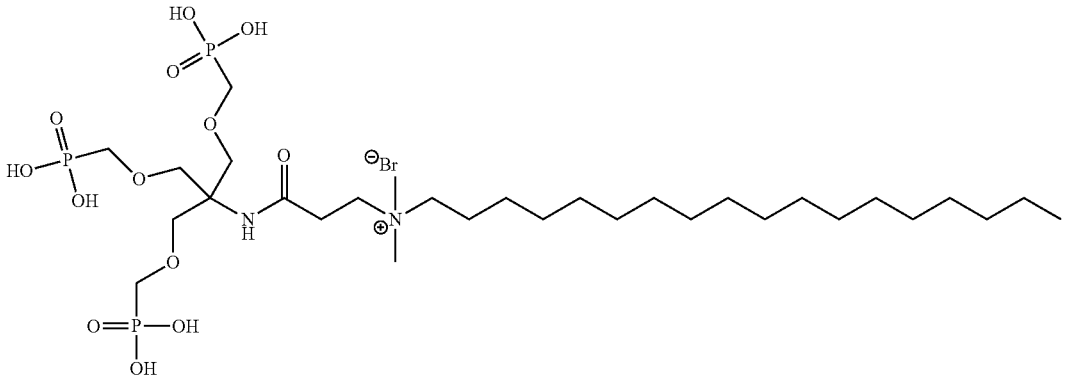

Tris ether phosphonic acid-1-N,N-dimethyloctadecan-1-aminium bromide. (26)
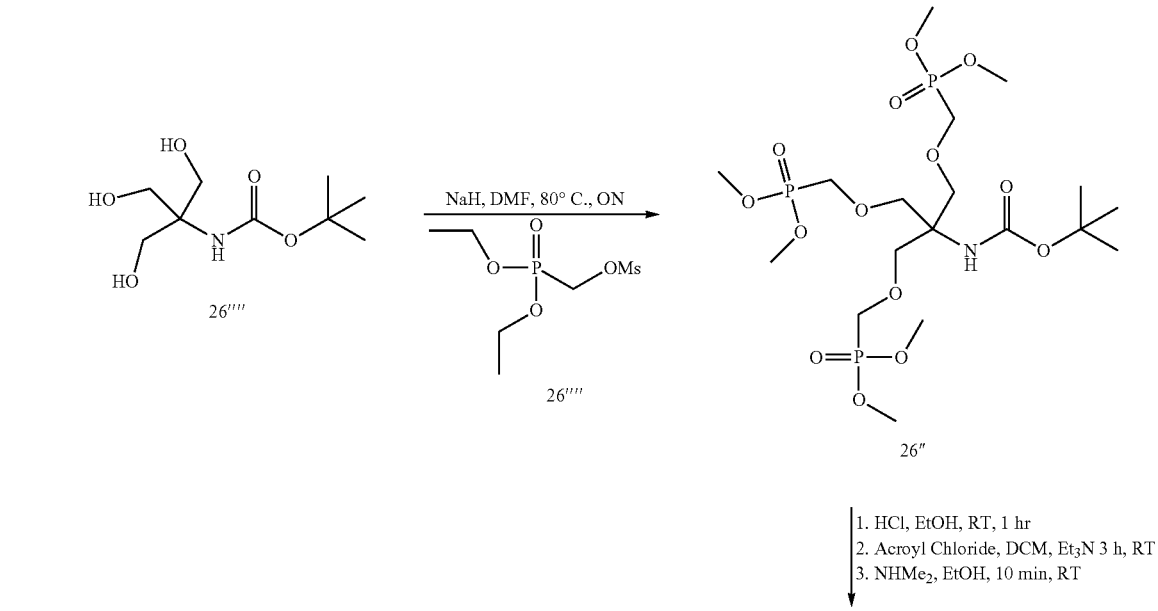
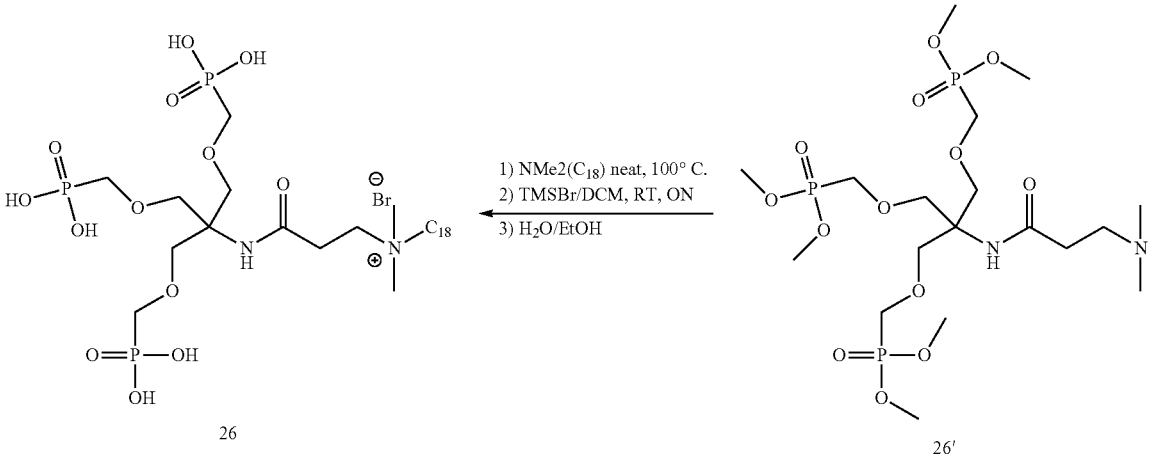

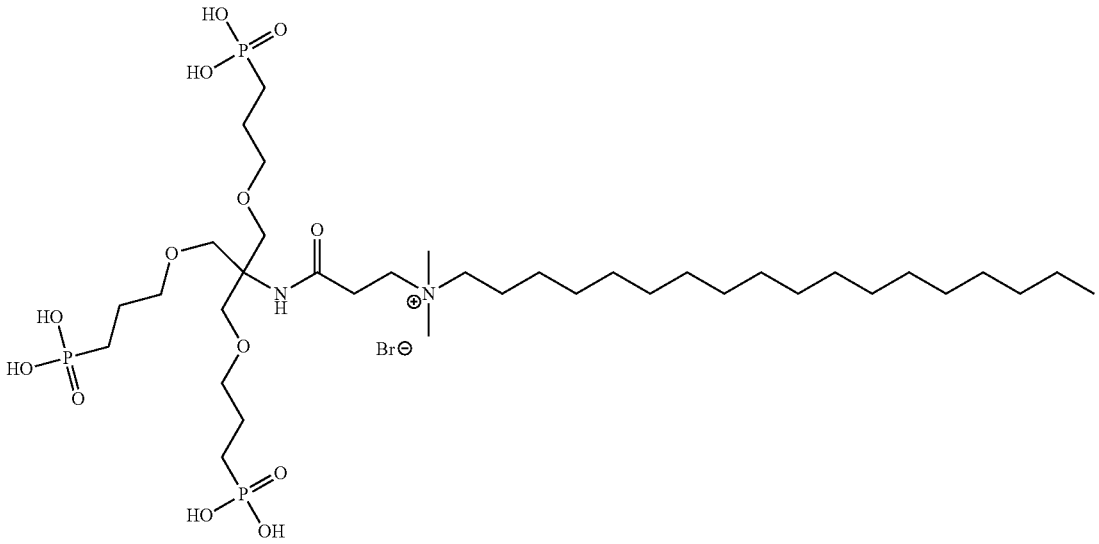
N-(3-((1,3-bis(3-phosphonopropoxy)-2-((3-phosphonopropoxy)methyl)propan-2-yl)amino)-3-oxopropyl)-N,N-dimethyloctadecan-1-aminium bromide. (27)
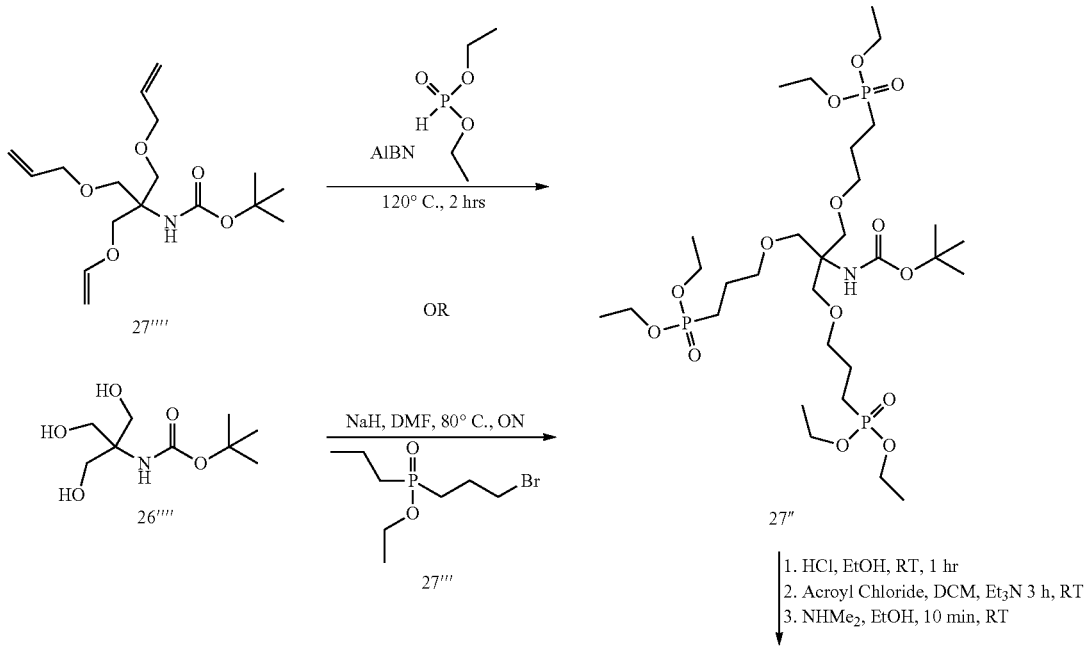

-continued
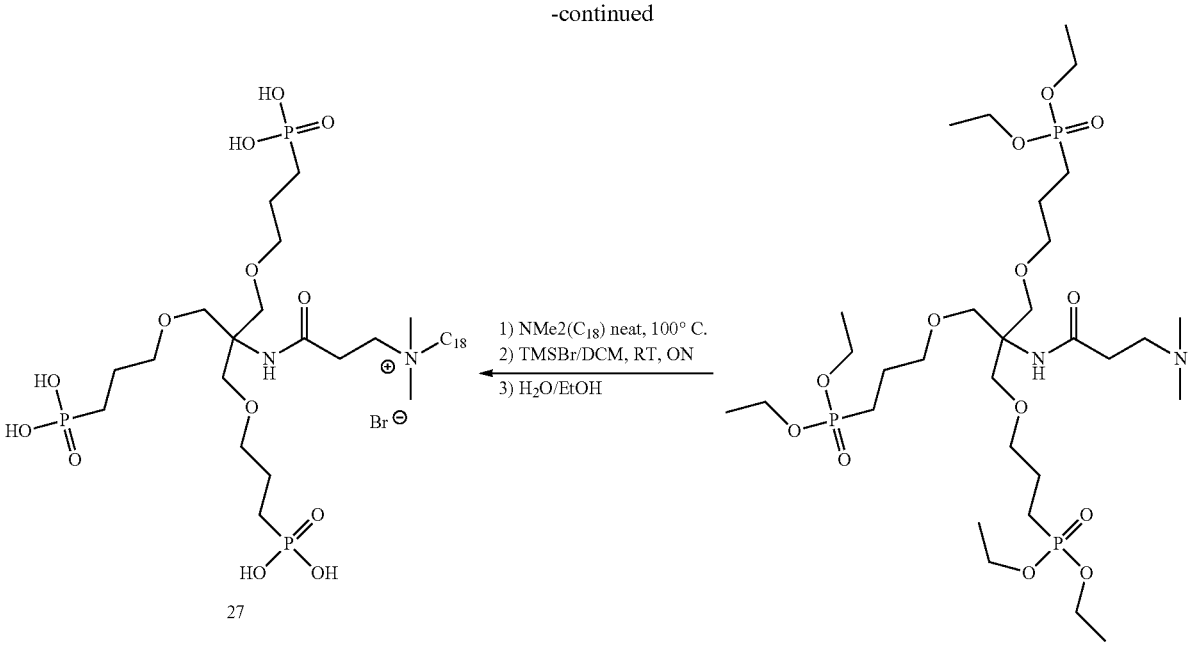
Tetraphosphonic Acid Antimicrobials:
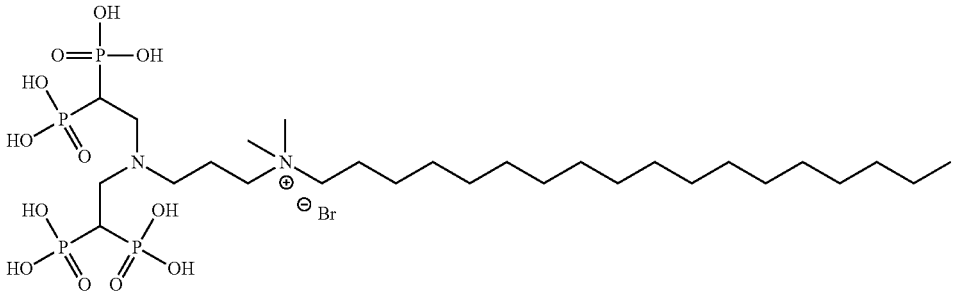
N-(3-(bis(2,2-diphosphonoethyl)amino)propyl)-N,N-dimethyloctadecan-1-aminium bromide. (28)
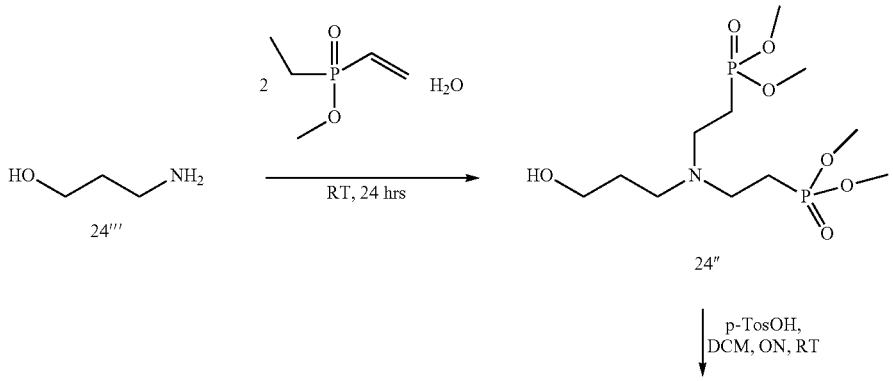

-continued
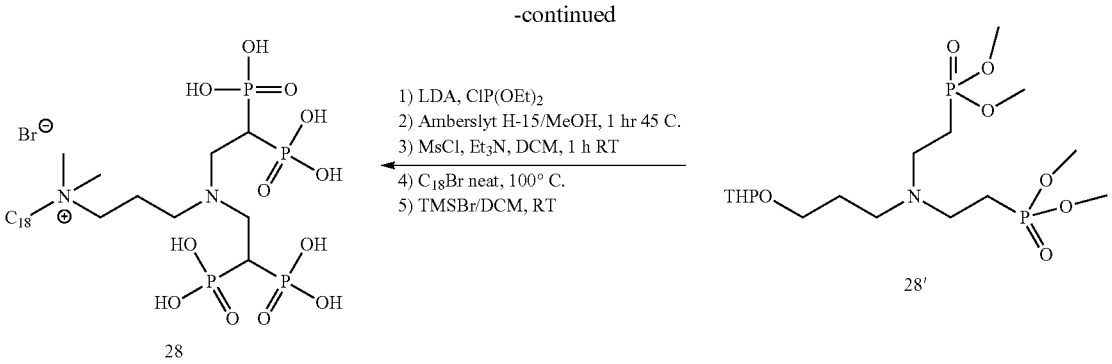
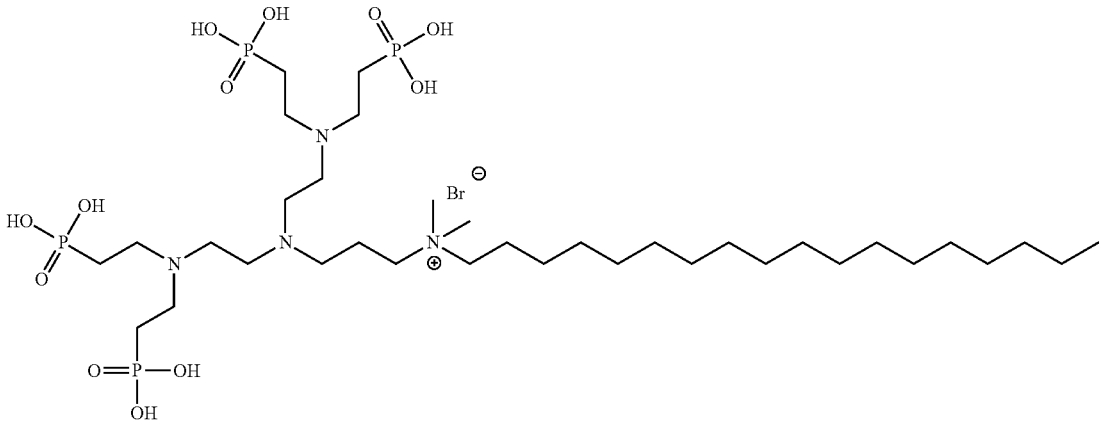
N-(3-(bis(2-(bis(2-phosphonoethyl)amino)ethyl)amino)propyl)-N,N-dimethyloctadecan-1-aminium bromide. (29)
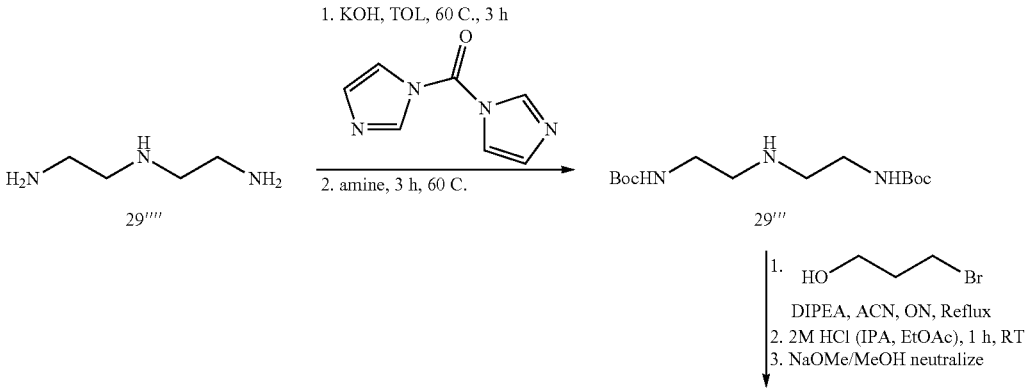

-continued
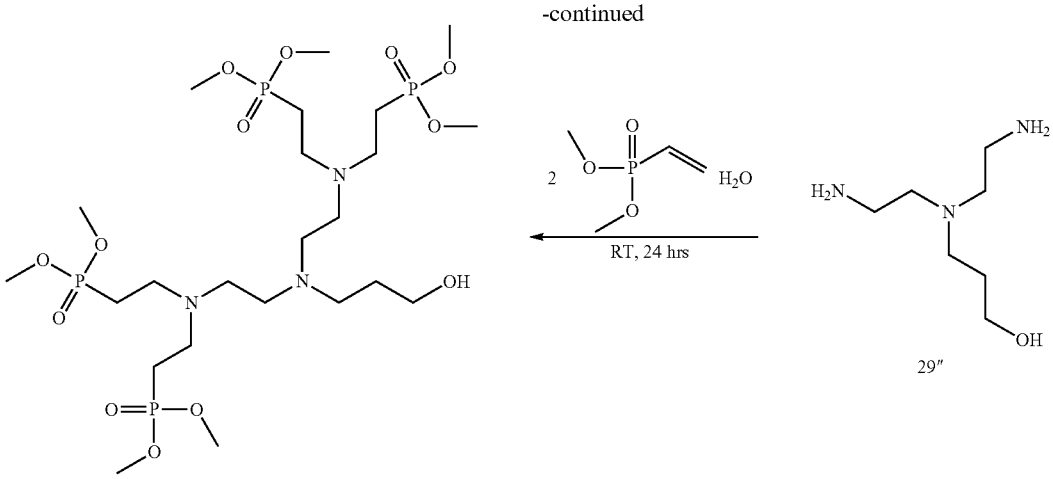
1) MsCl, $Et_3N$, DCM, 1 h RT
2) $NMe_2(C_{18})$ neat, 100° C.
3) TMSBr/DCM, RT, ON
4) $H_2O$/EtOH
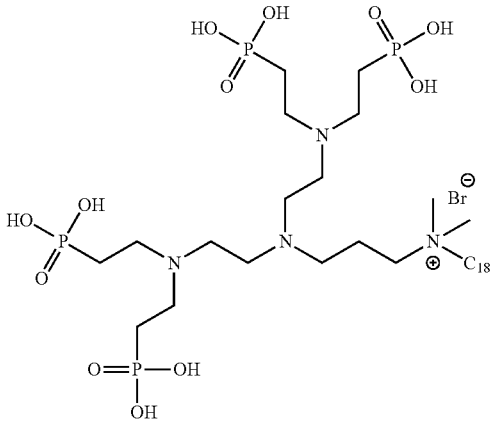
Dansyl-Phosphonic Acid Antimicrobials—UV Detection.
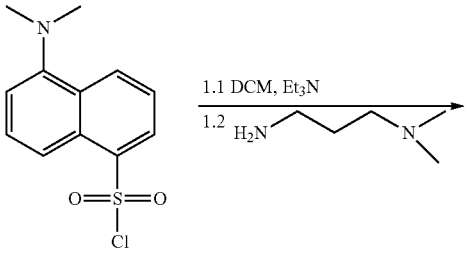

-continued

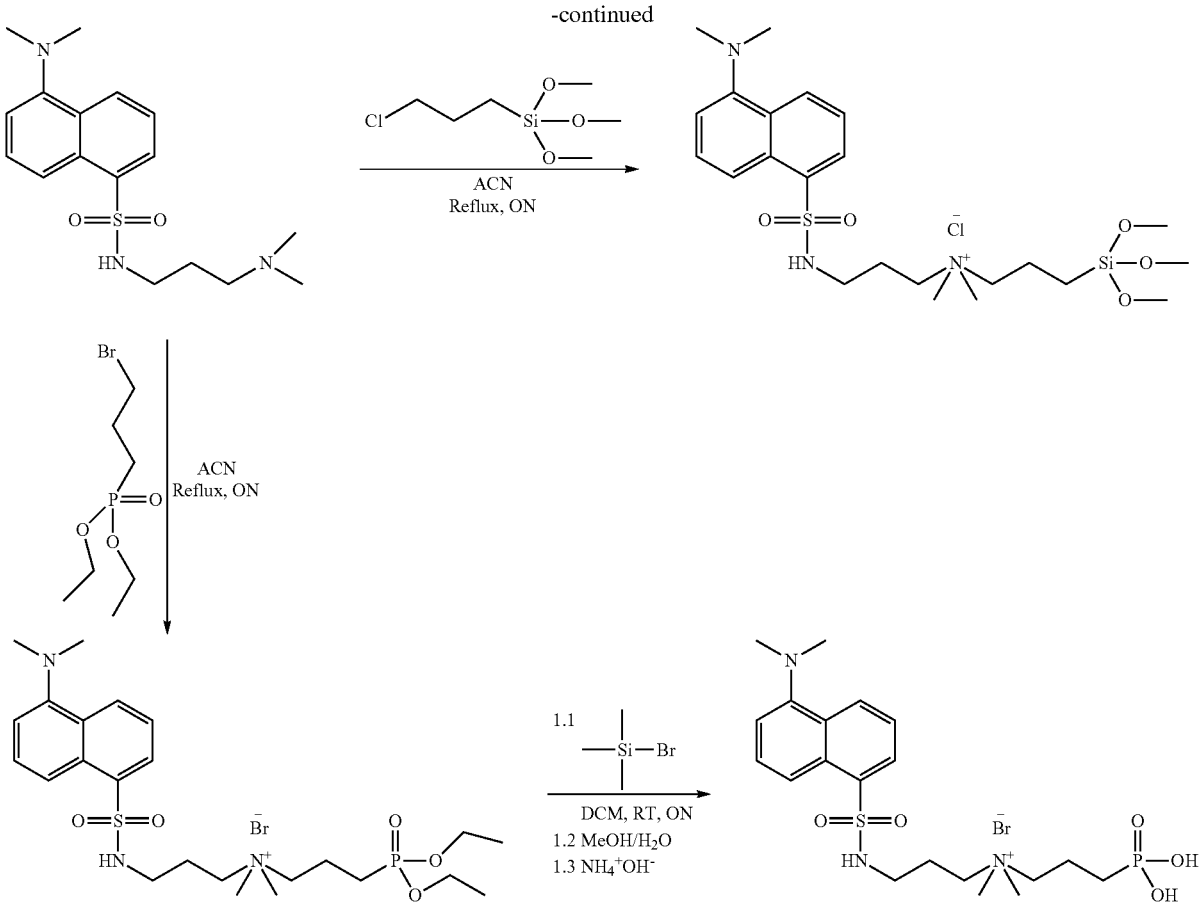

Synthesis of Dansylphosphonic Acid Quats (DPQ).

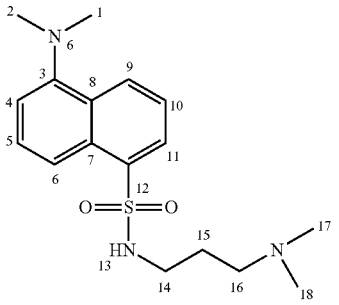

Example 21

5-(dimethylamino)-N-(3-(dimethylamino)propyl) naphthalene-1-sulfonamide (30)

This compound has been previously reported in: Wang, X. & Schneider, H. Binding of dansylamide derivatives to nucleotides and nucleic acids. J. Chem. Soc., Perkin Trans. 2, 1323-1328 (1998). To a flame dried 500 mL round bottom flask with a reflux condenser connected to an inert atmosphere manifold anhydrous DCM (300 mL) was added followed by dansyl chloride (10.0 g, 37.07 mmol), triethylamine (~8 mL, 55.61 mmol). While the solution was stirring at room temperature, 3-(dimethylamino)propylamine (7.0 ml, 55.61 mmol) was added drop wise via an inert syringe resulting in a colour change from orange to lime-green. After stirring for 1 h—HCl (g) was bubbled through the solution until pH 2 was reached. The resulting mixture was evaporated to dryness, then re-dissolved in saturated brine water (100 mL) and basified to pH 11 with 6N NaOH (15 mL) at 0° C. until white-yellow precipitate was observed. The mixture was refrigerated overnight enhancing further precipitation of product. The precipitate was filtered washing with water and the filtrate was extracted with DCM (500 mL) and evaporated to dryness to afford a white solid in 97% yield (12.1 g). (Recrystallized using 80% EtOH/$H_2O$). Mp=122-124° C.; TLC (5% $NH_4^+OH^-$:Acetone), $R_f$=0.72: $^1$H NMR (400 MHz, $CDCl_3$, δ): 8.52 (ddd, $^1$J=1.5 Hz, $^2$J=1.5 Hz, $^3$J=8.5 Hz, 1H, H9), 8.31 (ddd, $^1$J=1.0 Hz, $^2$J=1.0 Hz, $^3$J=8.5 Hz, 1H, H6), 8.23 (dd, $^1$J=1.5 Hz, $^2$J=7.0 Hz, 1H, H11), 7.50-7.58 (m, 2H, H(5, 10)), 7.18 (dd, $^1$J=1.0, $^2$J=7.5, 1H, H4), 2.97 (t, J=5.5 Hz, 2H, H14), 2.90 (s, 6H, H(1,2)), 2.22 (t, J=5.5 Hz, 2H, H16), 2.14 (s, 6H, H(17,18)), 1.57 (p, $^1$J=5.8 Hz, 2H, H15) ppm; $^{13}$C NMR (100 MHz, $CDCl_3$, δ): 151.9 (C3), 134.7 (C12), 129.98-129.65 (m, overlap, C5, C7, C9, C10, C11), 123.1 (C6), 119.0 (C8), 115.0 (C4), 59.6 (C16), 45.4 (C1, C2, C17, C18), 44.5 (C14), 24.6 (C15) ppm. HRMS-DART (m/z): [$M^+$] calculated for $C_{17}H_{26}N_3O_2S_1$, 336.1736. found, 336.1745.

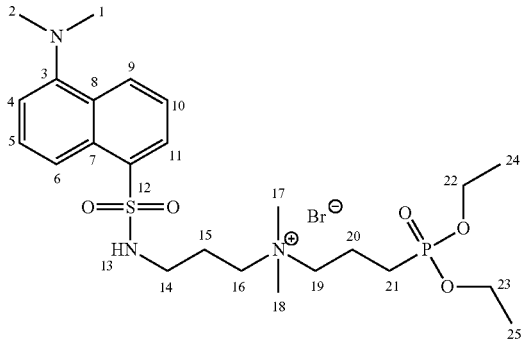

Example 22

3-(diethoxyphosphoryl)-N-(3-(5-(dimethylamino) naphthalene-1-sulfonamido)propyl)-N,N-dimethyl-propan-1-aminium bromide (31)

To a flame dried 20 mL glass vial, ACN (3 mL) was added followed by 5-(dimethylamino)-N-(3-(dimethylamino)propyl)-naphthalene-1-sulfonamide (335.46 mg, 1 mmol). While stirring diethyl(3-bromopropyl)phosphonate (=0.4 mL, 2 mmol) was added via an inert syringe, and the vial was capped. The solution was stirred for 48 hr at 110° C., after which the solution turned to pale-yellowish oil. The solution was cooled to room temperature, washed with $Et_2O$ (3×10 mL) to remove soluble impurities from the crude product. The product was further dried using rotary evaporator resulting in orange gummy oil in 70% yield (416.5 mg) Mp=34-36° C.; $^1$H NMR (400 MHz, $CDCl_3$, δ): 8.52 (ddd, $^1$J=1.5 Hz, $^2$J=1.5 Hz, $^3$J=8.5 Hz, 1H, H9), 8.31 (ddd, 1 J=1.0 Hz, 2J=1.0 Hz, $^3$J=8.5 Hz, 1H, H6), 8.23 (dd, $^1$J=1.5 Hz, $^2$J=7.0 Hz, 1H, H11), 7.50-7.58 (m, 2H, H(5, 10)), 7.18 (dd, $^1$J=1.0, $^2$J=7.5, 1H, H4), 4.12-4.03 (m, 4H, H(22,23)), 3.68-3.57 (m, 4H, H(16,19)), 3.18 (s, 6H, H(17, 18)), 3.10-3.03 (m, 2H, H14), 2.87 (s, 6H, H(1, 2)), 2.02 (brs, 4H, H(15,20)), 1.89-1.80 (m, 2H, H21), 1.29 (t, J=7.06 Hz, 6H, H(24,25)); $^{13}$C NMR (100 MHz, $CDCl_3$, δ): 151.79 (C3), 134.62 (C12), 129.79-128.60 (m, overlap, C5, C7, C9, C10, C11), 123.28 (C6), 119.28 (C8), 115.30 (C4), 62.23-62.16 (overlap, C16, C19, C22, C23), 51.31 (C17, C18), 45.43 (C1, C2), 39.73 (C14), 24.75-22.83 (C15, C20, C21), 16.45 ($^2$J=5.99, C24, C25) ppm; HRMS-DART (m/z): [M$^+$] calculated for $C_{24}H_{41}N_3O_5P_1S_1$, 514.250. found, 514.251.

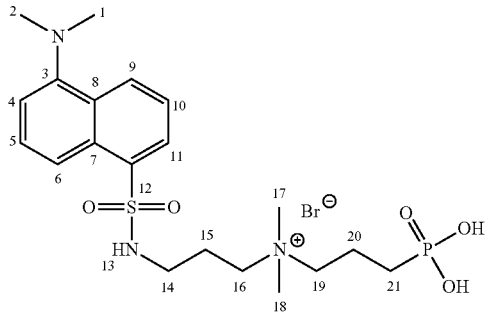

Example 23

3-(5-(dimethylamino)naphthalene-1-sulfonamido)-N,N-dimethyl-N-(3-phosphonopropyl)propan-1-aminium bromide (32)

Inside a flame dried and evacuated 20 mL screw cap vial N-(3-(diethoxyphosphoryl)propyl)-N,N-dimethyloctadecan-1-ammonium bromide (0.35 g, 0.58 mmol) was dissolved in anhydrous DCM (5 mL). To the clear stirred solution was added TMSBr (0.23 mL, 1.76 mmol, 3.0 eq.) through a rubber septum via syringe and the reaction was stirred at room temperature overnight. Completion of the reaction was followed by $^{31}$P after which the reaction was quenched with EtOH (10 mL) and stirred for 1 h followed by addition of $H_2O$ (1 mL). Volatiles were removed with a rotovap connected to a high vacuum Schlenk line and the crude product was triturated with $Et_2O$ (2×10 mL) to remove brown colored impurities. Further purification entailed extraction with $NH_4^+OH^-$:$H_2O$ (1:10, 10 mL) and washing with $Et_2O$ (1×5 mL). The aqueous fluorescent layer was evaporated from ACN (1×50 mL) to give the pure product. Yield (0.25 g, 79%). Light yellow solid. Mp=165-168° C.; $^1$H NMR (400 MHz, MeOD, δ): 8.52 (ddd, 1J=1.5 Hz, 2J=1.5 Hz, 3J=8.5 Hz, 1H, H9), 8.31 (ddd, $^1$J=1.0 Hz, $^2$J=1.0 Hz, $^3$J=8.5 Hz, 1H, H6), 8.23 (dd, $^1$J=1.5 Hz, $^2$J=7.0 Hz, 1H, H11), 7.50-7.58 (m, 2H, H(5, 10)), 7.18 (dd, $^1$J=1.0, $^2$J=7.5, 1H, H4), 3.36-3.26 (s, m overlap, 6H, H(17, 18,19)), 3.18-3.14 (m, 2H, H16), 2.97 (t, J=6.02 Hz, 2H, H14), 2.89 (s, 6H, H(1, 2)), 1.93-1.86 (m, 4H, H(15,20)), 1.57-1.49 (m, 2H, H21), ppm; $^{13}$C NMR (100 MHz, MeOD, δ): 133.80 (C3), 129.76-128.40 (m, overlap, C5, C7, C9, C10, C11, C12), 124.54 (C6), 119.81 (C8), 116.59 (C4), 64.13 (C19), 61.33 (C16), 45.08 (C17, C18), 34.04 (C1, C2), 24.77 (C14), 21.96 (C21), 16.85 ($^2$J=3.24, C15) ppm; $^{31}$P NMR (121.45 MHz, MeOD, δ): 26.92 ppm; HRMS-DART (m/z): [M$^+$]+ calculated for $C_{23}H_{51}NO_3P$, 420.3601. found, 420.3608.

Synthesis of Bisphosphonic Acid Dansylphosphonic Acid Quats (BPDPQ)

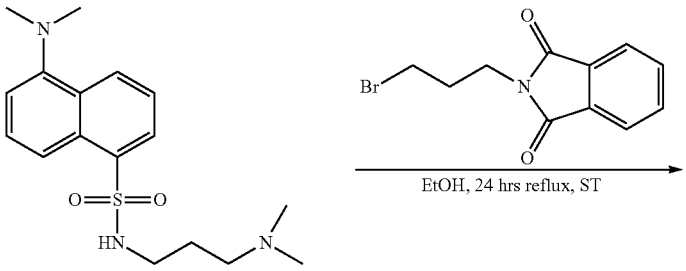

-continued

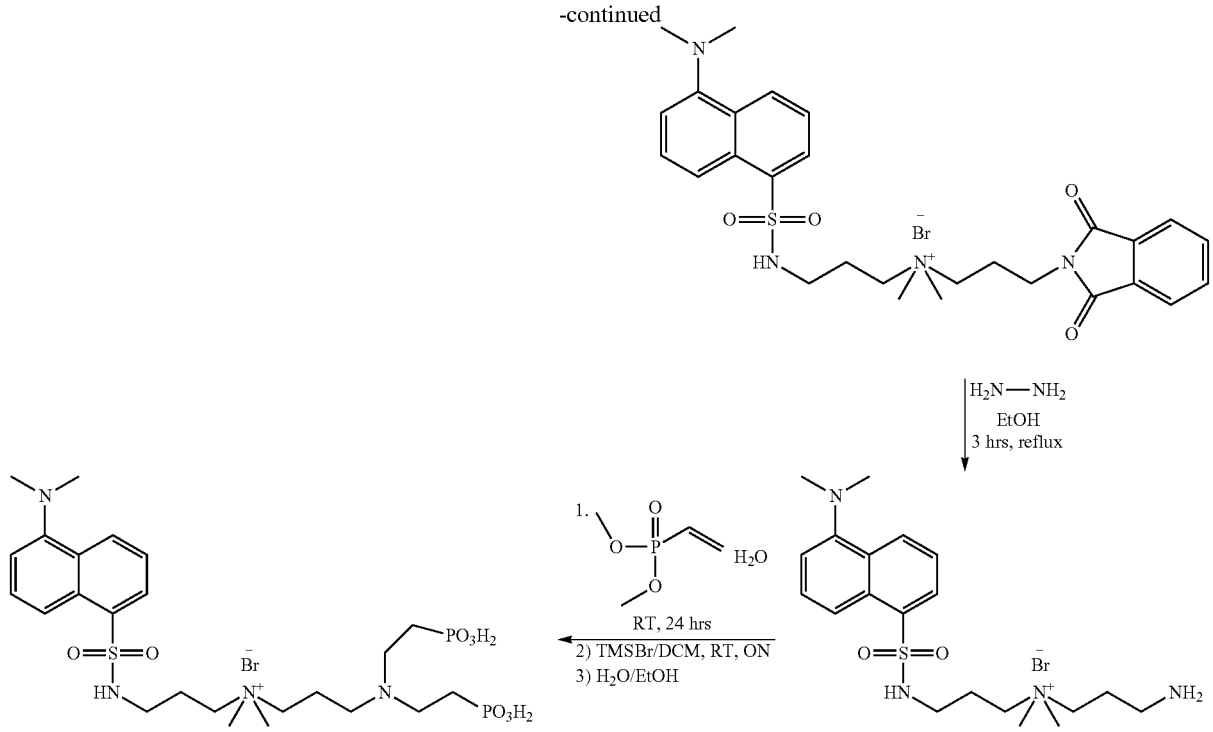

Example 24

Applying Phosphonate Antimicrobial Coatings

The following general procedure may be used to treat a surface with a phosphonate antimicrobial coating:

1) Surface Pretreatment/Passivation modifies a metal surface by creating a metal hydroxide layer to provide more binding sites on the surface of the material to which phosphonic acid compounds can bind can be achieved by mechanical means such as sanding, cleaning, or degreasing; chemical means such as treatment with piranha solution (a 3:1 $H_2SO_4/H_2O_2$ for about 10-30 minutes) or by activation by heating the surface (about 160° C. in air for about 1-2 hours).

2) Coating application by dip coating at room temperature to about 50° C. and about 1 to about 10 mM solution of phosphonate/phosphonic acid in water or alcohol; aerosol spraying an about 1 to about 10 mM solution of phosphonate/phosphonic acid in water or alcohol solution; or by vapor deposition of volatile phosphonate/phosphonic acid on the passivated surface.

3) Annealing to create strong molecule-material surface bonds by a thermal cure at about 100 to about 140° C. in an oven, or preferably, 120° C. for about 18 hours under about 0.1 Torr reduced pressure.

4) Washing the treated surface to remove unbound phosphonate/phosphonic acid material via immersion/dipping with alcohol or water often with the use of sonication.

5) Repeating steps 2, 3 and 4 until such time as the surface is sufficiently coated with the phosphonate antimicrobial coating The following are examples of pretreatment and coating procedures for a given substrate that may be applicable to the present invention:

Iron: grinding/polishing surface (600 grain size sand paper), dipping into a solution of 10% $HNO_3$ (4 min at room temperature), followed by degreasing in ethanol. Dip coating of phosphonate material (1 mM, 15 hrs, water). (Hanson, E. L., Schwartz, J., Nickel, B., Koch, N. & Danisman, M. F. Bonding Self-Assembled, Compact Organophosphonate Monolayers to the Native Oxide Surface of Silicon. J. Am. Chem. Soc. 125, 16074-16080 (2003); Harm et al., Novel protective coating for steel based on a combination of SAM and conducting polymers Macromolecular Symposia. 187, 65-72 (2002)) Novel protective coating for steel based on a combination of SAM and conducting polymers Titanium foil: sanded, rinsed with hot methanol, and stored at 160° C. in air, gives a surface coating of hydroxylated titanium dioxide. Aerosol sprayed (0.75 mM in THF), annealed 18 hrs at 120° C., immersion in (dry THF twice, for 5 min each). {{5016 Gawalt, Ellen S. 2001;}} Similarly titanium disks were wet-ground (220-4000 grit silicon carbide paper and further polished with OPChem polishing cloths using OP-S colloidal silica suspension) followed by ultrasonication (deionized water to eliminate silica particles). Rinsed (acetone then ultrapure water) and dried for a few minutes in an oven (80° C.). (Lecollinet, G. et al. Self-Assembled Monolayers of Bisphosphonates: Influence of Side Chain Steric Hindrance. Langmuir 25, 7828-7835 (2009))

Stainless Steel: Mechanically Polished (220, 400, 800, and 1200 grit silicon carbide paper followed by a 1 um diamond suspension). Ultrasonicated (MeOH, 15 min) or (DCM (10 min) then acetone (10 min)) and immersed (boiling MeOH to remove traces of organics and metallic dust), storage (120° C., oven). Dip coated (1 mM, dry tetrahydrofuran (THF)) and reduced pressure annealed (0.1 Torr). (Raman, A., Dubey, M., Gouzman, I. & Gawalt, E. S. Formation of Self-Assembled Monolayers of Alkylphosphonic Acid on the Native Oxide Surface of SS316L. Langmuir 22, 6469-6472 (2006)) Similarly, oxidized $SiO_2/Si$, $TiO_2/Ti$ and stainless steel samples were dip coated (10 min) wash cautiously with acetone followed by thermal annealing (24 hrs, 120 C). Weakly adsorbed molecules were removed from all coupons by 10 min sonication in acetone. Dipping, annealing, and sonicating steps were done twice. Water soluble coatings were dip coated (3 hours in water), no rinsing and annealed (120° C., 20 h) and sonicated for 10 min in ultrapure water. Dipping, drying, and sonicating were performed twice. (Lecollinet, G. et al. Self-Assembled Monolayers of Bisphosphonates: Influence of Side Chain Steric Hindrance. Langmuir 25, 7828-7835 (2009))

Silicon (100) wafer: cleaning by sonication in acetone (15 min). oxidized (3:1, 30% H2O2:98% H2SO4 for 30 min), and rinsed (ultrapure water) and immediately dip coated (25 μM solution in THF until the solvent evaporated at room temperature). Thermal annealed (140 C 48 hrs). Three cycles of depositions with multiple rinsing and sonication in THF and methanol was used to produce a monolayer film. The films were stored in glass containers filled with nitrogen until they were characterized. (Hanson, E. L., Schwartz, J., Nickel, B., Koch, N. & Danisman, M. F. Bonding Self-Assembled, Compact Organophosphonate Monolayers to the Native Oxide Surface of Silicon. J. Am. Chem. Soc. 125, 16074-16080 (2003))

Non thermal annealing: titanium samples dip coated (1 mM solution in acetone, 3 hrs) decant solvent and reduced pressure anneal (15 h at 50° C.). The samples were ultrasonically washed with acetone and then air-dried. (Lecollinet, G. et al. Self-Assembled Monolayers of Bisphosphonates: Influence of Side Chain Steric Hindrance. Langmuir 25, 7828-7835 (2009))

Example 25

Coating Composition of Compound (3) on $TiO_2$

A one inch by inch $TiO_2$ square was sanded with 600 grain size sand paper, followed by an ethanol (EtOH) rinse. Samples were stored in a 120° C. oven prior to use. A 10 mM solution of compound (3) in EtOH was aerosol spayed onto the $TiO_2$ square, allowed to air dry and placed into 120° C. oven overnight to anneal the compound followed by an EtOH rinse. Spaying, annealing and rinsing were repeated two more times.

The scope of the claims should not be limited by the preferred embodiments set forth in the examples, but should be given the broadest interpretation consistent with the description as a whole.

We claim:

1. A process for preparing a quaternary ammonium monophosphonate *acid free* compound of formula (I)

(I)

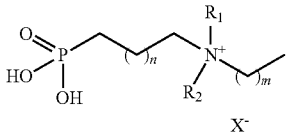

wherein $R_1$ and $R_2$ are independently methyl, ethyl, isopropyl or n-propyl; m is 15, 16, 17, 18 or 19; n is 0, 1, 2, 3, 4, 5 or 6; and X is chloro, bromo or iodo, comprising the steps of (a) reacting a compound of formula (II)

(II)

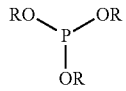

wherein R is independently methyl, ethyl, isopropyl, n-butyl or phenyl, with a compound of formula (III)

(III)

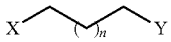

wherein X and n are as above and Y is a halogen selected from chloro or bromo to give a compound of formula (IV)

(IV)

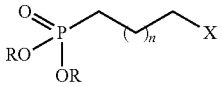

(b) reacting the compound of formula (IV) with a compound of formula (V)

(V)

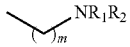

wherein $R_1$ and $R_2$ are independently methyl, ethyl, isopropyl or n-propyl, and m is 15, 16, 17, 18 or 19, to give a compound of formula (VI)

(VI)

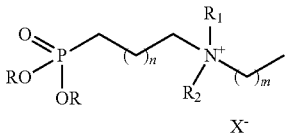

and (c) reacting a compound of formula (VI) with $SiR_3R_4R_5Z$ wherein $R_3$, $R_4$ and $R_5$ are independently methyl or ethyl and Z is chloro, bromo, iodo or triflate *in the presence of dichloromethane* (*DCM*) *between 8 to 12 hours at room temperature*, or a mineral acid selected from HCl, HBr or HI to give a compound of formula (I), *wherein the compound of formula* (*I*) *is isolated in pure form without chromatographic purification.*

2. The process of claim 1 wherein $R_1$ and $R_2$ are methyl.

3. The process of claim 1 wherein R is ethyl.

4. The process of claim 1 wherein n is 1 or 2.

5. The process of claim 1 wherein m is 17.

6. The process of claim 1 wherein $R_3$, $R_4$ and $R_5$ are the same and methyl.

7. The process of claim 1 wherein Z is chloro or triflate.

8. The process of claim 1 wherein X is bromo.

[9. A compound of formula

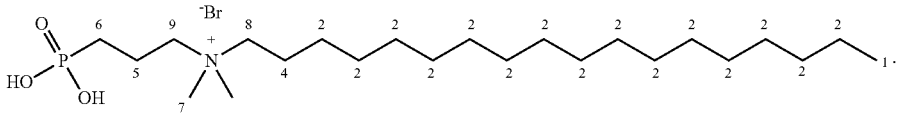

]

*10. The process of claim 1 further wherein the compound of formula (I) is purified by recrystallization.*

*11. The process of claim 1 wherein the compound of formula (I) is N,N-dimethyl-N-(3-phosphonopropyl) octadecan-1-ammonium bromide.*

*12. The process of claim 11 wherein the compound of formula (I) has the following characterization: Mp=118-120° C.; $^{1}H$ NMR (400 MHz, MeOD, δ): 3.38-3.33 (m, 2H, H8), 3.28-3.23 (m, 2H, H7), 3.02 (s, 6H, H6), 2.02-1.90 (m, 2H, H5), 1.75-1.65 (m, 4H, H4, H3), 1.20 (brs, 30H, H3), 0.82 (t, J=6.9 Hz, 3H, H1), ppm; $^{13}C$ NMR ($CDCl_3$, 100 MHz, δ): 64.26 (C7) 63.57 (C8), 49.94 (C6), 31.68 (C2 overlap), 29.41-28.86 (C2 overlap), 26.03 (C2 overlap), 22.45-22.17 (C3, C4), 16.47 (d, $^{1}J_{C-P}$=4.07 Hz, C5), 13.08 (C1) ppm; $^{31}P$ NMR (121.45 MHz, $CDCl_3$, δ): 26.92 ppm; HRMS-DART (m/z): [$M^{+}$] +calculated for $C_{23}H_{51}NO_3P$, 420.3601; found, 420.3608.*

* * * * *